United States Patent
Yeung et al.

(10) Patent No.: US 11,497,781 B2
(45) Date of Patent: Nov. 15, 2022

(54) METHODS OF TREATING BLADDER CANCER BY COMBINATION THERAPY COMPRISING THE ONCOLYTIC ADENOVIRUS CG0070 AND AN IMMUNE CHECKPOINT INHIBITOR

(71) Applicant: CG Oncology, Inc., Irvine, CA (US)

(72) Inventors: Alex Wah Hin Yeung, Irvine, CA (US); Arthur Kuan, Newport Coast, CA (US)

(73) Assignee: CG ONCOLOGY, INC., Irvine, CA (US)

( * ) Notice: Subject to any disclaimer, the term of this patent is extended or adjusted under 35 U.S.C. 154(b) by 0 days.

(21) Appl. No.: 16/083,709

(22) PCT Filed: Mar. 9, 2017

(86) PCT No.: PCT/US2017/021694
§ 371 (c)(1),
(2) Date: Sep. 10, 2018

(87) PCT Pub. No.: WO2017/156349
PCT Pub. Date: Sep. 14, 2017

(65) Prior Publication Data
US 2019/0070233 A1    Mar. 7, 2019

Related U.S. Application Data

(60) Provisional application No. 62/306,470, filed on Mar. 10, 2016.

(51) Int. Cl.
| *A61K 35/761* | (2015.01) |
| *A61K 39/395* | (2006.01) |
| *C07K 14/535* | (2006.01) |
| *C12N 7/00* | (2006.01) |
| *C12N 15/86* | (2006.01) |
| *A61P 35/02* | (2006.01) |

(52) U.S. Cl.
CPC ........ *A61K 35/761* (2013.01); *A61K 39/3955* (2013.01); *A61P 35/02* (2018.01); *C07K 14/535* (2013.01); *C12N 7/00* (2013.01); *C12N 15/86* (2013.01); *C12N 2710/10021* (2013.01); *C12N 2710/10032* (2013.01); *C12N 2710/10043* (2013.01); *C12N 2710/10343* (2013.01); *C12N 2830/008* (2013.01); *Y02A 50/30* (2018.01)

(58) Field of Classification Search
None
See application file for complete search history.

(56) References Cited

U.S. PATENT DOCUMENTS

| 4,590,071 A | 5/1986 | Scannon et al. |
| 6,432,700 B1 | 8/2002 | Henderson et al. |
| 6,495,130 B1 | 12/2002 | Henderson et al. |
| 6,682,736 B1 | 1/2004 | Hanson et al. |
| 6,692,736 B2 | 2/2004 | Yu et al. |
| 6,900,049 B2 | 5/2005 | Yu et al. |
| 6,984,720 B1 | 1/2006 | Korman et al. |
| 6,991,935 B2 | 1/2006 | Henderson et al. |
| 7,001,764 B2 | 2/2006 | Little et al. |
| 7,109,003 B2 | 9/2006 | Hanson et al. |
| 7,132,281 B2 | 11/2006 | Hanson et al. |
| 7,229,628 B1 | 6/2007 | Allison et al. |
| 7,267,815 B2 | 9/2007 | Ramesh et al. |
| 7,411,057 B2 | 8/2008 | Hanson et al. |
| 7,452,535 B2 | 11/2008 | Davis et al. |
| 7,459,154 B2 * | 12/2008 | Ramesh ............... A61K 9/0019 424/93.2 |
| 7,473,418 B2 | 1/2009 | Yu et al. |
| 7,575,919 B2 | 8/2009 | Yu et al. |
| 7,807,797 B2 | 10/2010 | Hanson et al. |
| 7,824,679 B2 | 11/2010 | Hanson et al. |
| 7,858,083 B2 | 12/2010 | Yu et al. |
| 7,928,074 B2 | 4/2011 | Khare |
| RE42,373 E | 5/2011 | Yu et al. |
| 7,959,925 B2 | 6/2011 | Weinberg et al. |
| 7,968,333 B2 | 6/2011 | Yu et al. |
| 8,017,114 B2 | 9/2011 | Korman et al. |
| 8,088,905 B2 | 1/2012 | Collins et al. |
| 8,142,778 B2 | 3/2012 | Davis et al. |
| 8,143,379 B2 | 3/2012 | Hanson et al. |
| 11,338,003 B2 | 5/2022 | Kuan |

(Continued)

FOREIGN PATENT DOCUMENTS

| AU | 2003252891 A1 | 11/2003 |
| EP | 2604110 A2 | 6/2013 |

(Continued)

OTHER PUBLICATIONS

Hemminki et al., Oncotarget, Feb. 2015, 6(6):4467-4481. (Year: 2015).*
Sistigu et al., Seminars in Immunopathology, Jul. 2011, 33(4):369-383. (Year: 2011).*
Rajani et al., Molecular Therapy, Jan. 2016, 24(1):166-174. (Year: 2016).*
Wang et al., Gene Therapy, 2012, 19:1065-1074. (Year: 2012).*
Burke et al., The Journal of Urology, Dec. 2012, 188:2391-2397. (Year: 2012).*
Savoia et al., Hum Vaccin Immunother, May 2016, 12(5):1092-1101; published online Feb. 18, 2016. (Year: 2016).*

(Continued)

*Primary Examiner* — Nicole Kinsey White
(74) *Attorney, Agent, or Firm* — Morrison & Foerster LLP

(57) ABSTRACT

The present invention provides methods for treating an individual having solid or lymphatic tumor comprising locally administering to the site of the tumor an oncolytic virus, and systemically administering an immunomodulator (including a combination of immunomodulators). The methods may further comprise local administration to the site of the tumor a second immunomodulator (including a combination of immunomodulators). Also provided are compositions and kits for the cancer therapy methods.

17 Claims, 1 Drawing Sheet
Specification includes a Sequence Listing.

(56) References Cited

U.S. PATENT DOCUMENTS

| | | |
|---|---|---|
| 2003/0039633 A1 | 2/2003 | Yu et al. |
| 2004/0197312 A1 | 10/2004 | Moskalenko et al. |
| 2005/0282280 A1 | 12/2005 | Ennist |
| 2006/0062764 A1 | 3/2006 | Police et al. |
| 2010/0040614 A1 | 2/2010 | Ahmed et al. |
| 2010/0150946 A1 | 6/2010 | Jooss et al. |
| 2010/0166799 A1 | 7/2010 | Hemminki et al. |
| 2010/0247440 A1 | 9/2010 | Moron |
| 2011/0044953 A1 | 2/2011 | Allison et al. |
| 2015/0190505 A1 | 7/2015 | Yeung |
| 2016/0108123 A1* | 4/2016 | Freeman ............ C07K 16/3069 424/85.2 |
| 2016/0289645 A1 | 10/2016 | Tufaro |
| 2018/0318365 A1 | 11/2018 | Yeung |
| 2020/0171151 A1 | 6/2020 | Yeung |
| 2021/0085734 A1 | 3/2021 | Kuan |
| 2022/0125864 A1 | 4/2022 | Yeung et al. |

FOREIGN PATENT DOCUMENTS

| | | |
|---|---|---|
| EP | 2 879 498 A2 | 6/2015 |
| JP | 2006-525995 A | 11/2006 |
| JP | 2008-510493 A | 4/2008 |
| JP | 2010-514791 A | 5/2010 |
| TW | 200607859 A | 3/2006 |
| WO | 199839464 A2 | 9/1998 |
| WO | 199839464 A3 | 9/1998 |
| WO | 200015820 A1 | 3/2000 |
| WO | 200039319 A2 | 7/2000 |
| WO | 200039319 A3 | 7/2000 |
| WO | 200173093 A2 | 10/2001 |
| WO | 200173093 A3 | 10/2001 |
| WO | 200200730 A2 | 1/2002 |
| WO | 200200730 A3 | 11/2002 |
| WO | 2004060303 A2 | 7/2004 |
| WO | 2094060303 A3 | 7/2004 |
| WO | WO-2005/030261 A1 | 4/2005 |
| WO | 2005103272 A2 | 11/2005 |
| WO | 2005103272 A3 | 11/2005 |
| WO | WO-2007/052029 A1 | 5/2007 |
| WO | WO-2007/123737 A2 | 11/2007 |
| WO | 2010072900 A1 | 7/2010 |
| WO | WO-2014/022138 A2 | 2/2014 |
| WO | WO-2014/022138 A3 | 2/2014 |
| WO | WO-2016/009017 A1 | 1/2016 |
| WO | 2016145354 A1 | 9/2016 |
| WO | WO-2017/070110 A1 | 4/2017 |
| WO | WO-2017/156349 A1 | 9/2017 |
| WO | WO-2007/126805 A2 | 11/2017 |
| WO | 2018191654 A1 | 10/2018 |

OTHER PUBLICATIONS

Shoyaib et al., PHarm Res, 2020, 37:12; published online Dec. 2019. (Year: 2019).*

Ramesh et al., Clin Cancer Res, 2006, 12(1):305-313. (Year: 2006).*

Anonymous: (Sep. 21, 2011). "Efficacy Study of Recombinant Adenovirus for Non Muscle Invasive Bladder Cancer (BOND)—NCT01438112", ClinicalTrials.gov, Sep. 21, 2011 (Sep. 21, 2011), XP055557337, Retrieved from the Internet: <URL:https://clinicaltrials.gov/ct2/show/NC101438112>. last visited on Feb. 15, 2019.

Bramante, S. (Oct. 2, 2015). "Oncolytic Adenovirus Coding For Gm-Csf In Treatment Of Cancer," *Faculty Of Medicine Of The University Of Helsinki Academic Dissertation*, pp. 1-101.

Bridle, B.W. et al. (Apr.-Jun. 2010, epub. Mar. 11, 2010). "Combining Oncolytic Virotherapy and Tumour Vaccination," *Cytokine & Growth Factor Reviews* 21(2-3):143-148.

Bristol, J.A. et al. (Jun. 2003). "In Vitro and In Vivo Activities of an Oncolytic Adenoviral Designed to Express GM-CSF," *Molecular Therapy* 7(6):755-784.

Burke, J.M. et al. (Dec. 2012). "A First in Human Phase 1 Study of CG0070, a GM-CSF Expressing Oncolytic Adenovirus, for the Treatment of Nonmuscle Invasive Bladder Cancer," *The Journal Of Urology* 188:2391-2397.

Carthon et al. (2010, e-pub. May 11, 2010). "Preoperative CTLA-4 Blockade: Tolerability and Immune Monitoring in the Setting of a Presurgical Clinical Trial," *Clin. Cancer Res.* 16(10):2861-2871.

Dong, Y.B. et al. (Mar. 15, 2002). "Adenovirus-Mediated E2F-1 Gene Transfer Sensitizes Melanoma Cells to Apoptosis Induced by Topoisomerase II Inhibitors," *Cancer Research* 62(6):1776-1783.

Dranoff, G. et al. (Apr. 1993). "Vaccination with Irradiated Tumor Cells Engineered to Secrete Murine Granulocyte-Macrophage Colony-Stimulationg Factor Stimulates Potent, Specific, and Long-Lasting Anti-Tumor Immunity," *Proc. Nat. Acad. Sci. USA* 90(8):3539-3543.

Fonseca, C. et al. (Feb. 19, 2009, e-pub. Nov. 13, 2008). "Protein Disulfide Isomerases are Antibody Targets During Immune-Mediated Tumor Destruction," *Blood* 113(8):1681-1688.

Hemminkio, O. et al. (Feb. 24, 2015). "Immunological Data from Cancer Patients Treated with Ad5/3-E2F-Δ24-GMCSF Suggests Utility for Tumor Immunotherapy," *Oncotarget* 6(6):4467-4481.

Hsu, S. et al. (2015). "Cold Genesys Annouces FDA Acceptance of a Phase I/II Clinical Trial Using CG0070 Plus an Anti-CTLA-4 Checkpoint Inhibitor as a NewAdjuvant Immunotherapy for Muscle Invasive Bladder Cancer," <http://www.businesswire.com/news/home/20151019005504/en/Cold-Genesys-Announces-FDA-Acceptance-Phase-III> retrieved from the internet Apr. 11, 2017, last visited on Jun. 23, 2017.

Ishihara, M. et al. (Aug. 8, 2014). "Systemic CD8+ T Cell-Mediated Tumoricidal Effects by Intratumoral Treatment of Oncolytic Herpes Simplex Virus with the Agonistic Monoclonal Antibody for Murine Glucocorticoid-Induced Tumor Necrosis Factor Receptor," *PLOS ONE*, 9(8):e104669, 13 pages.

Kaufman, H.L. et al. (Sep. 2015). "Oncolytic Viruses: A New Class Of Immunotherapy Drugs," *Nature Reviews. Drug Discovery* 14(9):642-662.

Kikuchi, J. et al. (2007, e-pub. Jun. 28, 2007). "E2F-6 Suppresses Growth-Associated Apoptosis Of Human Hematopoietic Progenitor Cells by Counteracting Proapoptotic Activity of E2F-1," *Stem Cells* 25:2439-2447.

Kwek, S.S. et al. (Apr. 2012). "Unmasking the Immune Recognition of Prostate Cancer with CTLA4 Blockage," *Nature Reviews* 12:289-297.

Mangsbo, S.M. et al. (Apr. 2010). "Enhanced Tumor Eradication by Combining CTLA-4 or PD-1 Blockade with CpG Therapy," *J. Immunother.* 33(3):225-235.

Melero, I. et al. (Sep. 2014, epub. Jul. 8, 2014). "Therapeutic Vaccines for Cancer: An Overview of Clinical Trials," *Nature Reviews Clinical Oncology* 11(9):509-524.

Packiam, V.T. et al. (Mary 6, 2016). "MP13-19: A Phase II/III Trial Of Cg0070, An Oncolytic Adenovirus, For Bcg-Refractory Non-Muscle-Invasive Bladder Cancer (NMIBC)," *Journal Of Urology*, 195(Supple. 4s):e142, 1 page.

ONCOS102 (Previously CGTG102) (Oct. 1, 2014). "Therapy of Advanced Cancers," NCT01598129, <https://clinicaltrials.gov/archive/NCT01598129/2014_10_01> retrieved from internet May 10, 2017, last visited Jun. 23, 2017.

Ramesh, N. et al. (Jan. 1, 2006). "CG0070, a Conditionally Replicating Granulocyte Macrophage Colony-Stimulating Factor—Armed Oncolytic Adenovirus for the Treatment of Bladder Cancer," *Clin. Cancer Res.* 12(1):305-313.

Senzer, N. et al. (May 2006). "A Phase 1 Dose-Escalation Trial of Intravesical CG0070 for Superficial Transitional Cell Carcinoma (TCC) of the Bladder After Bacillus Calmette-Guerin (BCG) Failure," *Molecular Therapy*, 13(Supple. 1):s22.

Simmons, A.D. et al. (2008, e-pub. Jan. 31, 2008). "Local Secretion of Anti-CTLA-4 Enhances the Therapeutic Efficacy of a Cancer Immunotherapy with Reduced Evidence of Systemic Autoimmunity," *Cancer Immunology, Immunotherapy* 57:1263-1270.

Sorensen, M.R. et al. (2010, e-pub. Aug. 2, 2010). "Adenoviral Vaccination Combined with CD40 Stimulation and CTLA-4 Blockage Can Lead to Complete Tumor Regression in a Murine Melanoma Model," *Vaccine* 28:6757-6764.

Van Den Eertwegh, A.J.M. et al. (May 2012). "Combined Immunotherapy with Granulocyte-Macrophage Colony-Stimulating Factor-Transduced Allogeneic Prostate Cancer Cells and Ipilimumab

(56) References Cited

OTHER PUBLICATIONS in Patients with Metastatic Castration-Resistant Prostate Cancer: A Phase 1 Dose-Escalation Trial," *Lancet Oncology* 13(5):509-517.

Weber, J. (2007). "Review: Anti-CTLA-4 Antibody Ipilimumab: Case Studies of Clinical Response and Immune-Related Adverse Events," *The Oncologist* 12(7):864-872.

Zhang, S.-N. et al. (Aug. 2011). "Optimizing DC Vaccination by Combination With Oncolytic Adenovirus Coexpressing IL-12 and GM-CSF," *Molecular Therapy*, 19(8):1558-1568.

European Extended Search Report, dated Jun. 19, 2019, for European Patent Application No. 16858069.4, 7 pages.

European Extended Search Report, dated Sep. 17, 2019, for European Patent Application No. 17764159.4, 12 pages.

International Preliminary Report On Patentability for PCT/US2013/51535 dated Oct. 30, 2014, filed on Jul. 22, 2013, 10 pages.

International Search Report for PCT/US2013/51535 dated Feb. 4, 2014, filed on Jul. 22, 2013, 5 pages.

International Preliminary Report on Patentability for PCT/US2017/021694 dated Sep. 11, 2018, on May 23, 2017, filed on Mar. 9, 2017, 5 pages.

International Search Report for PCT/US2017/021694 dated May 23, 2017, filed on Mar. 9, 2017, 5 pages.

International Preliminary Report on Patentability PCT/US2016/057526, dated Apr. 24, 2018, filed on Oct. 18, 2016, 6 pages.

International Search Report And Written Opinion for PCT/US2016/057526, dated Dec. 30, 2016, filed on Oct. 18, 2016, 39 pages.

Written Opinion Of The International Search Authority for PCT/US2013/51535 dated Feb. 4, 2014, filed on Jul. 22, 2013, 6 pages.

Written Opinion Of The International Search Authority for PCT/US2017/021694 dated May 23, 2017, filed on Mar. 9, 2017, 4 pages.

Anonymous (Jun. 19, 2014), "Immune Checkpoint-Modulating T-Cells Regulation," Epoch Times, 7 pages with English Translation.

Ao, J.-H. et al. (2013). "Optimal Management of Metastatic Melanoma," J. Pract. Dermatol. 6(4):219-223, English Abstract Only.

Dias, J.D. et al. (2012, e-pub. Nov. 10, 2011). "Target Cancer Immunotherapy With Oncolytic Adenovirus Coding For a Fully Human Monoclonal Antibody Specific For CTLA-4," Gene Therapy 19:988-998.

Hu, Z.-B. et al. (Apr. 2008). "Antitumor effect or Recombinant Oncolytic Adenovirus Ad-CD80-TPE-GM in Hep2 Xenograft Tumor Model," Chin. Med. Biotechnol. 3(2):116-120, English Abstract on p. 120.

Liu, B. et al. (Feb. 28, 2003). "ICP34.5 Deleted Herpes Simplex Virus With Enhanced Oncolytic, Immune Stimulating, and Anti-Tumour Properties," Gene Ther. 10(4):292-303.

Ohaegbulam, K.C. et al. (Jan. 2015). "Human Cancer Immunotherapy With Antibodies to the PD-1 and PD-L1 Pathway," Trends in Molecular Medicine 21(1):24-33.

Tang, L. et al. (Apr. 2015). "Progress in Drug Therapy For Small Cell Lung Cancer," Progress in Modern Biomedicine 15(10):1963-1970. English Abstract Only.

Anonymous: (Apr. 12, 2021). "History of Changes for Study: NCT01438112: Efficacy Study of Recombinant Adenovirus for Non Muscle Invasive Bladder Cancer (BOND)—NCT01438112", CiinicalTrials.gov, Retrieved from the Internet: URL:https://clinicaltrials.gov/ct2/history/NC101438112?V_17=View#StudyPageTop, last visited on May 17, 2022, 7 pages.

Bassi, P. et al. (May 1999). "Prognostic Factors Of Outcome After Radical Cystectomy For Bladder Cancer: A Retrospective Study Of A Homogeneous Patient Cohort," Urol. 161 (5):1494-1497.

Boehm, B.E. et al. (2015). "Novel Therapeutic Approaches for Recurrent Nonmuscle Invasive Bladder Cancer," Urol. Clin. N. Am. 42:159-168.

ClinicalTrials.gov (Sep. 2011). "Efficacy Study of Recombinant Adenovirus for Non Muscle Invasive Bladder Cancer (BOND)," ClinicalTrials.gov Identifier: NCT01438112, retrieved from internet URL:https://clinicaltrials.gov/ct2/show/NCT0 1438112, last visited Jun. 15, 2018, 10 pages.

ClinicalTrials.gov. (Feb. 19, 2019). "Safety and Efficacy of CG0070 Oncolytic Virus Regimen for High Grade NMIBC After BCG Failure—Full Text View—ClinicalTrials.gov," ClinicalTrials.gov Identifier: NCT02365818, Retrieved from the Internet: URL:https://clinicaltrials.gov/ct2/show/NCT02365818, last visited Nov. 26, 2020, 8 pages.

Extended European Search Report, dated Feb. 19, 2021, for European Patent Application No. 18784592.0, 8 pages.

Friedlander, T W et al. (May 20, 2012). "Activity of Intravesical CG0070 In Rb-Inactive Superficial Bladder Cancer After BCG Failure: Updated Results of a Phase I/II Trial," Journal of Clinical Oncology 30(15):Abstract No. 4593, 3 pages.

Fukuhara, H. et al. (Oct. 2016, e-pub. Sep. 9, 2016). "Oncolytic virus therapy: A new era of cancer treatment at dawn," Cancer Science 107(10):1373-1379.

GenBank Accession No. AF516106 (Jun. 5, 2002), "*Homo sapiens* E2F Transcription Factor 1 (E2F1) Gene, Complete Cds," 8 pages.

GenBank Accession No. AH006643.2 (Jun. 10, 2016). "*Homo sapiens* Chromosome 20 Transcription Factor E2F1 (E2F1) Gene, Complete Cds," 3 pages.

International Preliminary Report on Patentability, dated Oct. 15, 2019, for PCT Application No. PCT/US2018/02749, filed Apr. 13, 2018, 10 pages.

International Search Report and Written Opinion, dated Jun. 22, 2018, for PCT Application No. PCT/US2018/02749, filed Apr. 13, 2018, 16 pages.

Lamm, D. et al. (2006). A Phase 1 Dose-Escalation Trial of Intravesical CG0070 for Superficial Transitional Cell Carcinoma (TCC) of the Bladder After Bacillus Calmette-Guerin (BCG) Failure, retrieved from http://media.corporate-ir.net/media_files/IROL/98/98399/V0046_Oncoiytic_FINAL_Poster051806.pdf, last, visited May 18, 2006, 1 page.

Packiam, V.T. et al. (Oct. 2018, e-pub. Jul. 26, 2017). "An Open Label, Single-Arm, Phase II Multicenter Study Of The Safety and Efficacy Of CG0070 Oncolytic Vector Regimen In Patients With BCG-Unresponsive Non-Muscle-Invasive Bladder Cancer: Interim Results," Urologic Oncology: Seminars and Original Investigations 36(10):440-447.

Packiam, V.T. et al. "Interim Results from A Single-Arm Multicenter Phase II Trial of CG0070, an Oncolytic Adenovirus, for BCG-Unresponsive Non-Muscle-Invasive Bladder Cancer (NMIBC)," retrieved from https://university.auanet.org/abstract_detail.cfm?id=PNFLBA-13&meetingID=17BOS, last visited Apr. 1, 2017.

Ramesh, N et al. (May 2005). "CG0070, A Conditionally Replicating GM-CSF Armed Oncolytic Adenovirus For The Treatment Of Bladder Cancer," Proceedings of the American Association for Cancer Research Annual 46:1185, Abstract: 5019, 4 pages.

Witjes, J.A. (Feb. 2014). "Bladder Carcinoma In Situ In 2003: State Of The Art," European Urology 45 (2): 142-146.

Zamarin, D. et al. (Dec. 2014). "Potentiation of Immunomodulatory Antibody Therapy With Oncolytic Viruses For Treatment of Cancer," Molecular Therapy 1:14004, 10 pages.

\* cited by examiner

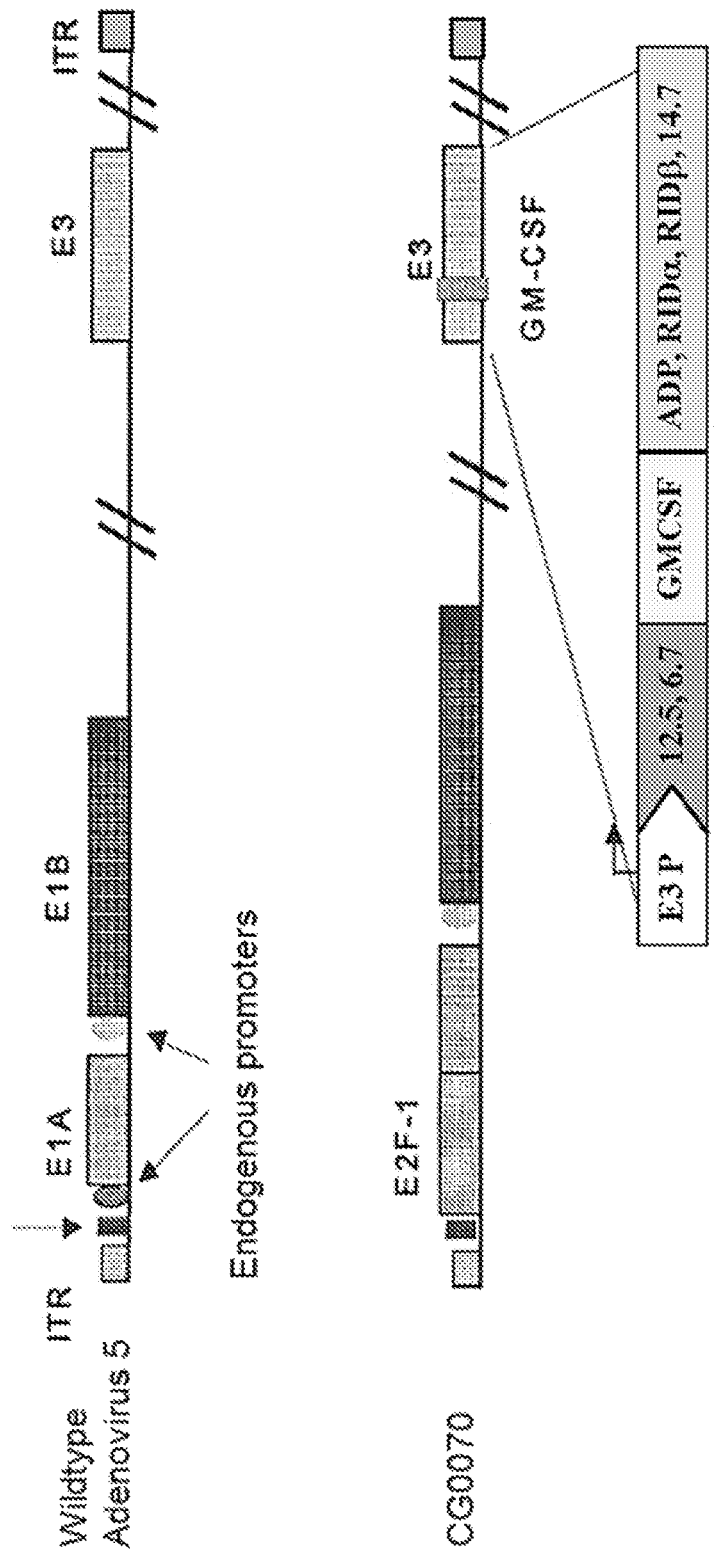

SEQUENCE LISTING

<160> NUMBER OF SEQ ID NOS: 1

<210> SEQ ID NO 1

```
<211> LENGTH: 1519
<212> TYPE: DNA
<213> ORGANISM: Homo sapiens

<400> SEQUENCE: 1
gggcccaaaa ttagcaagtg accacgtggt tctgaagcca gtggcctaag gaccaccctt     60
gcagaaccgt ggtctccttg tcacagtcta ggcagcctct ggcttagcct ctgtttcttt    120 cataacctttt ctcagcgcct gctctgggcc agaccagtgt tgggaggagt cgctactgag   180
ctcctagatt ggcaggggag gcagatggag aaaaggagtg tgtgtggtca gcattggagc    240
agaggcagca gtgggcaata gaggaagtga gtaaatcctt gggagggctc cctagaagtg    300
atgtgttttc tttttttgtt ttagagacag gatctcgctc tgtcgcccag gctggtgtgc    360
agtggcatga tcatagctca ctgcagcctc gacttctcgg gctcaagcaa tcctcccacc    420
tcagcctccc aagtagctgg gactacgggc acacgccacc atgcctggct aattttttgta   480 ttttttgtag agatgggtct tcaccatgtt gatcaggctg gtctcgaact cctgggctca    540
tgcgatccac cccgccagct gattacaggg attccgtgg tgagccaccg cgcccagacg     600
ccacttcatc gtattgtaaa cgtctgttac ctttctgttc ccctgtctac tggactgtga    660
gctccttagg gccacgaatt gaggatgggg cacagagcaa gctctccaaa cgtttgttga   720
atgagtgagg gaatgaatga gttcaagcag atgctatacg ttggctgttg gagattttgg    780
ctaaaatggg acttgcagga aagcccgacg tcccctcgc catttccagg caccgctctt    840
cagcttgggc tctgggtgag cgggatagg ctgggtgcag gattaggata atgtcatggg     900
tgaggcaagt tgaggatgga agaggtggct gatggctggg ctgtggaact gatgatcctg    960
aaaagaagag gggacagtct ctggaaatct aagctgaggc tgttggggc tacaggttga    1020 gggtcacgtg cagaagagag gctctgttct gaacctgcac tatagaaagg tcagtgggat   1080
gcgggagcgt cggggcgggg cggggcctat gttcccgtgt ccccacgcct ccagcagggg   1140
acgcccgggc tgggggcggg gagtcagacc gcgcctggta ccatccggac aaagcctgcg   1200
cgcgccccgc cccgccattg gccgtaccgc cccgcgccgc cgccccatcc cgccctcgc    1260 cgccgggtcc ggcgcgttaa agccaatagg aaccgccgcc gttgttccg tcacggacgg    1320 ggcagccaat tgtggcggcg ctcggcggct cgtggctctt tcgcggcaaa aaggattttgg   1380 cgcgtaaaag tggccgggac tttgcaggca gcggcggccg ggggcggagc gggatcgagc   1440
cctcgccgag gcctgccgcc atgggcccgc gccgccgccg ccgcctgtca cccgggccgc   1500
gcgggccgtg agcgtcatg                                                1519
```

METHODS OF TREATING BLADDER CANCER BY COMBINATION THERAPY COMPRISING THE ONCOLYTIC ADENOVIRUS CG0070 AND AN IMMUNE CHECKPOINT INHIBITOR

CROSS REFERENCE TO RELATED APPLICATIONS

This application is a U.S. national phase application under 35 U.S.C. § 371 of International Application No. PCT/US2017/021694, filed on Mar. 9, 2017, which claims priority benefit of U.S. Provisional Patent Application No. 62/306,470 filed on Mar. 10, 2016, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name 744442000300SEQLIST.txt, date recorded: Sep. 7, 2018, size: 3 KB).

FIELD OF THE INVENTION

The present invention relates to cancer immunotherapy comprising administration of oncolytic virus and one or more immunomodulators.

BACKGROUND OF THE INVENTION

The human immune system of innate and adaptive immunity is an extremely complex system which has not yet been successfully utilized to fight against cancer. One explanation is that, since cancers are usually developed within the later part of life, the development of an immunological response to counteract cancer is not vital to the survival of the fittest theory in the evolutionary process. In all likelihood, the different aspects of the human immune system are not designed specifically for that purpose, meaning to kill cells that are considered as "self". Even after extensive removal of the primary tumor it is still a problem to prevent the formation of metastases either due to growing out of micrometastases already present at the time of surgery, or to the formation of new metastases by tumor cells or tumor stem cells that have not been removed completely or being re-attached after surgery. In essence, for later stages of cancer, surgery and/or radiotherapy can only take care of the macroscopic lesions, while most patients will have their cancers recurring and not amenable to further therapies.

More recently FDA has approved two immunotherapeutic agents against prostate cancer and melanoma. The first agent, PROVENGE®, utilizes a GM-CSF fusion molecule with a prostatic antigen to activate the mononuclear or antigen presenting cells of late-stage cancer patients in vitro and is able to prolong the overall survival of these patients. The second agent is an anti-CTLA-4 monoclonal antibody, which was shown to produce a profoundly enhancing effect in T effector cell generation. An oncolytic virus CG0070 has also been shown to trigger a long-term complete response among bladder cancer patients after one series of six weekly intravesical treatments (see Burke J M, et al. Journal of Urology December 188 (6) 2391-7, 2012).

Current cancer immunotherapy methods face various fundamental challenges. For example, normally tumor-specific immune T lymphocytes in cancer patients, even when they are present, only occur at low frequency systemically. The likely reason is that the antigenicity and specific immunogenicity of common cancers' tumor antigens are generally weak, as well as the presence of an overwhelming amount of suppressor activities through cytokines and regulatory cells, such as Treg, tumor associated macrophages, etc. Additionally, the older concepts of using nonspecific components to boost immune response against specific components were found to have little success, as the ability for a human body to generate very specific immunological responses against its own cells is limited by nature. After all, most cancer cells are not immunogenic enough to be different from normal cells. Such an immune response derived from non-specific immunological components, even if generated, will also be short-lived.

For at least the reasons discussed above, in vitro and pre-formulated therapeutic cancer vaccines using available tumor antigens and adjuvants have been tried for decades without much success. There is a clear need for cancer immunotherapy methods with improved efficacy.

The disclosures of all publications, patents, patent applications and published patent applications referred to herein are hereby incorporated herein by reference in their entirety.

BRIEF SUMMARY OF THE INVENTION

The present application provides methods, compositions (including pharmaceutical compositions) and kits for treating a solid or lymphatic tumor in an individual comprising local administration to the site of the tumor an oncolytic virus, and systemic administration of an immunomodulator (including combination of immunomodulators). The methods, compositions, and kits may further comprise local administration of an immunomodulator (including combination of immunomodulators), inactivated tumor cells, pre-treatment and/or prior therapy.

Accordingly, one aspect of the present application provides a method of treating a solid or lymphatic tumor in an individual, comprising: a) locally administering to the site of the tumor an effective amount of an oncolytic virus; and b) systemically administering an effective amount of an immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule. In some embodiments, the oncolytic virus preferentially replicates in a cancer cell, such as a cancer cell that is defective in the Rb pathway. In some embodiments, the tumor-specific promoter is an E2F-1 promoter, such as a human E2F-1 promoter, for example, the human E2F-1 promoter comprises the nucleotide sequence set forth in SEQ ID NO: 1.

In some embodiments according to any of the methods described above, the immune-related molecule is selected from the group consisting of GM-CSF, IL-2, IL-12, interferon, CCL4, CCL9, CCL21, CXCL13, TLR1, TLR2, TLR3, TLR4, TLR5, TLR6, TLR7, TLR8, TLR9, TLR10, RIG-I, MDA5, LGP2, and LTαβ. In some embodiments, the immune-related molecule is GM-CSF.

In some embodiments according to any one of the methods provided above, the oncolytic virus is selected from the group consisting of adenovirus, herpes simplex virus, vaccinia virus, mumps virus, Newcastle disease virus, polio virus, measles virus, Seneca valley virus, coxsackie virus, reo virus, vesicular stomatitis virus, maraba and rhabdovirus, and parvovirus. In some embodiments, the oncolytic virus is an oncolytic adenovirus. In some embodiments, the viral gene essential for replication of the virus is selected from the group consisting of E1A, E1B, and E4. In some embodiments, the heterologous gene is operably linked to a viral promoter, such as an E1 promoter or an E3 promoter.

In some embodiments according to any one of the methods provided above, the oncolytic virus is an adenovirus serotype 5, wherein the endogenous E1a promoter of a native adenovirus is replaced by the human E2F-1 promoter, and the endogenous E3 19kD coding region of the native adenovirus is replaced by a heterologous gene encoding human GM-CSF. In some embodiments, the oncolytic virus is CG0070.

In some embodiments according to any one of the methods provided above, the oncolytic virus is administered at a dose of about $1\times10^8$ to about $1\times10^{14}$ viral particles. In some embodiments, the oncolytic virus is administered weekly. In some embodiments, the oncolytic virus is administered for about 1 week to about 6 weeks.

In some embodiments according to any one of the methods provided above, the oncolytic virus is administered directly into the tumor. In some embodiments, the oncolytic virus is administered to the tissue having the tumor.

In some embodiments according to any one of the methods provided above, the oncolytic virus and the immunomodulator are administered sequentially. In some embodiments, the oncolytic virus is administered prior to the administration of the immunomodulator. In some embodiments, the oncolytic virus is administered after the administration of the immunomodulator. In some embodiments, the oncolytic virus and the immunomodulator are administered simultaneously.

In some embodiments according to any one of the methods provided above, the immunomodulator is a modulator of an immune checkpoint molecule selected from the group consisting of CTLA-4, PD-1, PD-L1, PD-L2, TIM3, B7-H3, B7-H4, LAG-3, KIR, and ligands thereof. In some embodiments, the immunomodulator is an inhibitor of PD-L. In some embodiments, the inhibitor of PD-L1 is an anti-PD-L1 antibody, such as atezolizumab. In some embodiments, the immunomodulator is an immune-stimulating agent selected from the group consisting of activators of OX40, 4-1BB and CD40. In some embodiments, the immune-stimulating agent is an activator of OX40, such as an agonist antibody of OX40. In some embodiments, the immunomodulator is administered intravenously.

In some embodiments according to any one of the methods provided above, the method further comprises locally administering to the site of the tumor (such as directly into the tumor or to the tissue having the tumor) a second immunomodulator (including a combination of immunomodulators). In some embodiments, the second immunomodulator is a modulator of an immune checkpoint molecule selected from the group consisting of CTLA-4, PD-1, PD-L1, PD-L2, TIM3, B7-H3, B7-H4, LAG-3, KIR, and ligands thereof. In some embodiments, the second immunomodulator is an immune-stimulating agent selected from the group consisting of activators of OX40, 4-1BB and CD40. In some embodiments, the second immunomodulator is administered directly into the tumor. In some embodiments, the immunomodulator is administered prior to or after the administration of the second immunomodulator.

In some embodiments according to any one of the methods provided above further comprising locally administering to the site of the tumor a second immunomodulator, the method further comprises administering (such as systemically or locally to the site of the tumor) a third immunomodulator. In some embodiments, the third immunomodulator is a modulator of an immune checkpoint molecule selected from the group consisting of CTLA-4, PD-1, PD-L1, PD-L2. TIM3, B7-H3, B7-H4, LAG-3, KIR, and ligands thereof. In some embodiments, the third immunomodulator is an immune-stimulating agent selected from the group consisting of activators of OX40, 4-1BB and CD40. In some embodiments, the second immunomodulator and the third immunomodulator are administered simultaneously, such as in the same composition. In some embodiments, the second immunomodulator and the third immunomodulator are administered sequentially.

In some embodiments according to any one of the methods provided above, the method further comprises locally administering to the site of the tumor a pretreatment composition prior to the administration of the oncolytic virus. In some embodiments, the pretreatment composition comprises a transduction enhancing agent, such as N-Dodecyl-3-D-maltoside (DDM).

In some embodiments according to any one of the methods provided above, the individual is subject to a prior therapy prior to the administration of the oncolytic virus and the immunomodulator. In some embodiments, the prior therapy is radiation therapy. In some embodiments, the prior therapy comprises administration of a therapeutic agent, such as an agent that increases the level of cytokines involved an immunogenic pathway, and/or an agent that causes dysfunction or damage to a structural component of a tumor. In some embodiments, the therapeutic agent is selected from the group consisting of an anti-VEGF antibody, a hyaluronidase, CCL21, and N-dodecyl-β-maltoside. In some embodiments, the prior therapy is provided at a dose that is insufficient to treat the tumor.

In some embodiments according to any one of the methods provided above, the method further comprises locally administering to the site of the tumor an effective amount of inactivated tumor cells. In some embodiments, the inactivated tumor cells are autologous. In some embodiments, the inactivated tumor cells are allogenic. In some embodiments, the inactivated tumor cells are from a tumor cell line. In some embodiments, the inactivated tumor cells are inactivated by irradiation. In some embodiments, the oncolytic virus and the inactivated tumor cells are administered simultaneously, such as in a single composition. In some embodiments, the oncolytic virus and the inactivated tumor cells are admixed immediately prior to the administration.

In some embodiments according to any one of the methods provided above, the solid or lymphatic tumor is bladder cancer, such as muscle invasive bladder cancer or non-muscle invasive bladder cancer. In some embodiments, the oncolytic virus is administered intravesically.

In some embodiments according to any one of the methods provided above, the individual has high expression of one or more biomarkers in the tumor. In some embodiments, the one or more biomarkers are selected from PD-1, PD-L1, and PD-L2. In some embodiments, the one or more biomarkers are selected from CD80, CD83, CD86, and HLA-Class II antigens in tumor-derived mature dendritic cells. In some embodiments, the one or more biomarkers are selected from CXCL9, CXCL10, CXCL11, CCR7, CCL5, CCL8 SOD2. MT2A, OASL, GBP1, HES4, MTIB, MTIE, MTIG. MTIH, GADD45A, LAMP3 and miR-155.

In some embodiments according to any one of the methods provided above, the individual is a human individual.

Another aspect of the present application provides a kit for treating a solid or lymphatic tumor in an individual, comprising: a) an oncolytic virus, b) an immunomodulator, and c) a device for locally administering the oncolytic virus to a site of tumor, wherein the oncolytic virus comprises a viral vector comprising a tumor cell-specific promoter operably linked to a viral gene essential for replication of the virus, and a heterologous gene encoding an immune-related molecule, and wherein the immunomodulator is formulated for systemic administration. In some embodiments, the immune-related molecule is selected from the group consisting of GM-CSF. IL-2, IL12, interferon, CCL4, CCL19. CCL21, CXCL13, TLR1. TLR2, TLR3. TLR4, TLR5. TLR6, TLR7, TLR8, TLR9. TLR0, RIG-I. MDA5, LGP2, and LTαβ. In some embodiments, the oncolytic virus is an oncolytic adenovirus, such as an adenovirus serotype 5, wherein the endogenous E1a promoter of a native adenovirus is replaced by the human E2F-1 promoter, and the endogenous E3 19kD coding region of the native adenovirus is replaced by a heterologous gene encoding human GM-CSF. In some embodiments, the oncolytic virus is CG0070.

In some embodiments according to any of the kits provided above, the immunomodulator is a modulator of an immune checkpoint molecule selected from the group consisting of: CTLA-4, PD-1, PD-L1, PD-L2, TIM3, B7-H3, B7-H4, LAG-3, KIR, and ligands thereof. In some embodiments, the immunomodulator is an inhibitor of PD-L1, such as an anti-PD-L1 antibody, for example, atezolizumab.

In some embodiments according to any of the kits provided above, the immunomodulator is an immune-stimulating agent selected from the group consisting of activators of OX40, 4-1BB and CD40. In some embodiments, the immunomodulator is an agonist antibody of OX40.

In some embodiments according to any of the kits provided above, the kit further comprises a second immunomodulator (including combination of immunomodulators) formulated for local administration to the site of the tumor. In some embodiments, the kit further comprises a third immunomodulator (for example, for systemic administration or local administration to the site of the tumor).

In some embodiments according to any of the kits provided above, the kit further comprises a pretreatment composition comprising a transduction enhancing agent, such as N-Dodecyl-β-D-maltoside (DDM).

In some embodiments according to any of the kits provided above, the kit further comprises an immune-related molecule selected from the group consisting of GM-CSF, IL-2, IL12, interferon, CCL4, CCL19, CCL21. CXCL13, TLR1. TLR2, TLR3. TLR4, TLR5. TLR6, TLR7. TLR8. TLR9, TLR10. RIG-I, MDA5, LGP2. LTαβ, STING activators, PRRago, TLR stimulators, and RLR stimulators.

In some embodiments according to any of the kits provided above, the kit further comprises a plurality of inactivated tumor cells. In some embodiments, the kit further comprises instructions for admixing the oncolytic virus and the inactivated tumor cells prior to the administration. In some embodiments, the device for local administration is used for simultaneous administration of the plurality of inactivated tumor cells and the oncolytic virus.

In some embodiments according to any of the kits provided above, the device for local administration is for administrating the oncolytic virus directly into the tumor.

In some embodiments according to any of the kits provided above, the device for local administration is for administering the oncolytic virus to the tissue having the tumor.

Another aspect of the present application provides a method of treating a solid or lymphatic tumor in an individual, comprising: a) systemically (such as intravenously) administering to the site of the tumor an effective amount of an oncolytic virus; and b) systemically (such as intravenously) administering an effective amount of an immunomodulator (including combination of immunomodulators, such as antibody recognizing CTLA-4), wherein the oncolytic virus comprises a viral vector comprising a tumor cell-specific promoter operably linked to a viral gene essential for replication of the virus, and a heterologous gene encoding an immune-related molecule. The embodiments described above as being applicable to local administration of the oncolytic virus are also applicable to the method comprising systemic administration of the oncolytic virus.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF THE DRAWINGS

FIG. 1 is a schematic diagram of CG0070 and wild type (wt) adenovirus type 5. CG0070 is based on adenovirus serotype 5, but the endogenous E1a promoter and E3 19kD coding region have been replaced by the human E2F-1 promoter and a cDNA coding region of human GM-CSF, respectively.

DETAILED DESCRIPTION OF THE INVENTION

The present invention provides methods and compositions for treating a solid or lymphatic tumor in an individual by locally administering to the site of a tumor an effective amount of an oncolytic virus (such as CG0070), and systemically administering an effective amount of an immunomodulator (including combination of immunomodulators, such as an immune-stimulating agent and/or an immune checkpoint inhibitor). The methods and compositions may further comprise local administration of an immunomodulator (including combination of immunomodulators). For example, one exemplary tumor suitable for methods described herein is bladder cancer, and the oncolytic virus can be administered intravesically, while the immunomodulator can be administered intravenously.

The present invention provides a live and real time "in vivo" cancer vaccine system generated inside a human body by local (such as intratumoral) delivery of an oncolytic virus in combination with systemic (such as intravenous) delivery of an immunomodulator. A distinguishing feature of the present invention is the oncolytic virus, which has both a tumor cell-specific promoter operably linked to a viral gene essential for replication, and a heterologous gene encoding an immune-related molecule, such as GM-CSF. Thereby, local administration of the oncolytic virus allows both tumor-specific infections by the virus, and simultaneous local delivery of the immune-related molecule to the tumor site. Further combined with systemic delivery of an immunomodulator (including combination of immunomodulators) and optionally local administration of a second immunomodulator (including combination of immunomodulators), the cancer vaccine system may provide the therapeutic components at the right effective amounts, at the right timing, and in the right sequences to the tumor and the human body to elicit an enhanced immune response against the tumor.

It is thus believed that the combination described herein would allow full exploitation of the oncolytic and immunogenic reactions in the individual, and increase the therapeutic potential of the cancer immunotherapy. It is to be understood by a person of ordinary skill in the art that the combination therapy methods described herein requires that one agent or composition be administered in conjunction with another agent. The dosage, dosing schedule, routes of administration, and sequence of administration for each agent in the combination therapy provided herein (such as the oncolytic virus, and each immunomodulator) can be independently optimized to provide optimal therapeutic results. The methods may also be further combined with local administration of inactivated tumor cells, and/or pretreatment, such as local radiation, or local administration of cytokines, chemokines, or other beneficial therapeutic agent, to increase the chance of success for the therapy.

In one aspect, there is provided a method of treating a solid or lymphatic tumor in an individual, comprising: a) locally administering to the site of the tumor an effective amount of an oncolytic virus; and b) systemically administering an effective amount of an immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule. In some embodiments, there is provided a method of treating bladder cancer in an individual, comprising: a) intravesically administering an effective amount of an oncolytic virus; and b) systemically administering an effective amount of an immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule.

In some embodiments, there is provided a method of treating a solid or lymphatic tumor in an individual, comprising: a) locally administering to the site of the tumor an effective amount of an oncolytic virus; b) systemically administering an effective amount of an immunomodulator (including combination of immunomodulators); and c) locally administering to the site of the tumor an effective amount of an second immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule. In some embodiments, there is provided a method of treating bladder cancer in an individual, comprising: a) intravesically administering an effective amount of an oncolytic virus; b) systemically administering an effective amount of an immunomodulator (including combination of immunomodulators), and c) intravesically administering to the site of the tumor an effective amount of a second immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule.

Also provided are compositions (such as pharmaceutical compositions), kits, and articles manufacture useful for the methods described herein. In one aspect, there is provided a kit for treating a solid or lymphatic tumor in an individual, comprising: a) an oncolytic virus, b) an immunomodulator (including combination of immunomodulators), and c) a device for locally administering the oncolytic virus to a site of tumor, wherein the oncolytic virus comprises a viral vector comprising a tumor cell-specific promoter operably linked to a viral gene essential for replication of the virus, and a heterologous gene encoding an immune-related molecule.

Definitions

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, reducing recurrence rate of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the invention contemplate any one or more of these aspects of treatment.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. Treatment or administration in the "adjuvant setting" refers to a subsequent mode of treatment.

"Neoadjuvant setting" refers to a clinical setting in which the method is carried out before the primary/definitive therapy. Neoadjuvant setting herein also refers to any "tumor site preparation" therapy modality that is used in conjunction with, in a sequential manner, with the therapeutic components (e.g., oncolytic virus and immunomodulator(s); or oncolytic virus, immunomodulator(s) and inactivated tumor cells) as described in this invention.

The term "effective amount" used herein refers to an amount of a compound or composition sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation in cancer. In some embodiments, an effective amount is an amount sufficient to delay development of cancer. In some embodiments, an effective amount is an amount sufficient to prevent or delay recurrence. In some embodiments, an effective amount is an amount sufficient to reduce recurrence rate in the individual. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent occurrence and/or recurrence of tumor; (vii) delay occurrence and/or recurrence of tumor; (viii) reduce recurrence rate of tumor, and/or (ix) relieve to some extent one or more of the symptoms associated with the cancer. As is understood in the art, an "effective amount" may be in one or more doses, i.e., a single dose or multiple doses may be required to achieve the desired treatment endpoint.

"In conjunction with" or "in combination with" refers to administration of one treatment modality in addition to another treatment modality, such as administration of an oncolytic virus described herein in addition to administration of the other agent (such as immunomodulator(s), inactivated tumor cells, etc.) to the same individual under the same treatment plan. As such, "in conjunction with" or "in combination with" refers to administration of one treatment modality before, during or after delivery of the other treatment modality to the individual.

The term "simultaneous administration," as used herein, means that a first therapy and second therapy in a combination therapy are administered at the same time. When the first and second therapies are administered simultaneously, the first and second therapies may be contained in the same composition (e.g., a composition comprising both a first and second therapy) or in separate compositions (e.g., a first therapy is contained in one composition and a second therapy is contained in another composition).

As used herein, the term "sequential administration" or "in sequence" means that the first therapy and second therapy in a combination therapy are administered with a time separation, for example, of more than about 1 minute, such as more than about any of 5, 10, 15, 20, 30, 40, 50, 60, or more minutes. In some cases, the term "sequential administration" means that the first therapy and second therapy in a combination therapy are administered with a time separation of more than about 1 day, such as more than about any of 1 day to 1 week, 2 weeks, 3 weeks, 4 weeks, 8 weeks, 12 weeks, or more weeks. Either the first therapy or the second therapy may be administered first. The first and second therapies are contained in separate compositions, which may be contained in the same or different packages or kits.

The term "administered immediately prior to" means that the first therapy is administered no more than about 15 minutes, such as no more than about any of 10, 5 or 1 minutes before administration of the second therapy. The term "administered immediately after" means that the first therapy is administered no more than about 15 minutes, such as no more than about any of 15, 10 or 1 minutes after administration of the second therapy.

As used herein. "specific", "specificity", or "selective" or "selectivity" as used when describing a compound as an inhibitor, means that the compound preferably interacts with (e.g., binds to, modulates, and inhibits) a particular target (e.g., a protein and an enzyme) than a non-target.

The term "transduction" and "transfection" as used herein include all methods known in the art using an infectious agent (such as a virus) or other means to introduce DNA into cells for expression of a protein or molecule of interest. Besides a virus or virus-like agent, there are chemical-based transfection methods, such as those using calcium phosphate, dendrimers, liposomes, or cationic polymers (e.g., DEAE-dextran or polyethylenimine); non-chemical methods, such as electroporation, cell squeezing, sonoporation, optical transfection, impalefection, protoplast fusion, delivery of plasmids, or transposons; particle-based methods, such as using a gene gun, magnectofection or magnet assisted transfection, particle bombardment; and hybrid methods, such as nucleofection.

The term "tumor site preparation" as used herein, describes single treatment modality or combination of more than one treatment modalities to be used in conjunction with the therapeutic components (e.g., oncolytic virus and immunomodulator(s); or oncolytic virus, immunomodulator(s) and inactivated tumor cells) in a sequential manner, and in which the treatment modality or modalities are being applied directly or indirectly (e.g., through an IV therapy) to the tumor site (such as cancer cells or the tissue containing the cancer cells). Exemplary treatment modalities for tumor site preparations include, but are not limited to, administration of immune-related molecules, irradiation, and administration of therapeutic agents. All tumor site preparations described herein may include administration of a single molecule or agent, or a combination of more than one molecules and/or agents.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

Methods of Treating a Solid or Lymphatic Tumor

The present invention in one aspect provides methods of treating a solid or lymphatic tumor (such as bladder cancer) in an individual (such as a human), comprising: a) locally administering to the site of the tumor an effective amount of an oncolytic virus; and b) systemically administering an effective amount of an immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule. In some embodiments, the oncolytic virus is selected from the group consisting of adenovirus, herpes simplex virus, vaccinia virus, mumps virus, Newcastle disease virus, polio virus, measles virus, Seneca valley virus, coxsackie virus, reo virus, vesicular stomatitis virus, maraba and rhabdovirus, and parvovirus. In some embodiments, the oncolytic virus is attenuated (for example through multiple passages, inactivation or genetic modification). In some embodiments, the immunomodulator is an immune checkpoint inhibitor. In some embodiments, the immunomodulator is an immune-stimulating agent. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the oncolytic virus is administered directly into the tumor. In some embodiments, the oncolytic virus is administered to the tissue having the tumor. In some embodiments, the oncolytic virus is administered weekly. In some embodiments, the immunomodulator (including combination of immunomodulators) is administered intravenously. In some embodiments, the method further comprises local administration of a second immunomodulator (including combination of immunomodulators) to the site of the tumor.

Another aspect of the present application provides a method of treating a solid or lymphatic tumor in an individual, comprising: a) systemically (such as intravenously) administering to the site of the tumor an effective amount of an oncolytic virus; and b) systemically (such as intravenously) administering an effective amount of an immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule. The embodiments described herein as being applicable to local administration of the oncolytic virus are also applicable to the method comprising systemic administration of the oncolytic virus.

Exemplary viruses that are suitable for use as the oncolytic virus in the present invention include, but are not limited to, adenovirus, for example, H101 (ONCOCRINE®), CG-TG-102 (Ad5/3-D24-GM-CSF), and CG0070; herpes simplex virus, for example, Talimogene laherparapvec (T-VEC®) and HSV-1716 (SEPREHVIR®); reo virus, for example, REOLYSIN®; vaccinia virus, for example, JX-594; Seneca valley virus, for example, NTX-010 and SVV-001; Newcastle disease virus, for example, NDV-NS1 and GL-ONC1; polio virus, for example, PVS-RIPO; measles virus, for example, MV-NIS; coxsackie virus, for example, CAVATAK™; vesicular stomatitis virus; maraba and rhabdoviruses; parvovirus and mumps virus. In some embodiments, the oncolytic virus is oncolytic adenovirus. In some embodiments, the oncolytic virus is attenuated (for example through multiple passages, inactivation or genetic modification). In some embodiments, the oncolytic virus is only a part, or parts of the wild type oncolytic virus that can cause infection, inflammation or infection-like effects. In some embodiments, the virus is replication competent. In some embodiments, the virus replicates preferentially in a tumor cell. In some embodiments, the oncolytic virus preferentially replicates in a cancer cell that is defective in the Rb pathway.

In some embodiments, there is provided a method of treating a solid or lymphatic tumor (such as bladder cancer) in an individual (such as a human), comprising: a) locally administering to the site of the tumor an effective amount of an oncolytic virus (such as oncolytic adenovirus); and b) systemically administering an effective amount of an immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule. In some embodiments, the oncolytic virus is replication competent. In some embodiments, the oncolytic virus preferentially replicates in a cancer cell, such as an Rb-pathway defective cancer cell. In some embodiments, the immunomodulator is an immune checkpoint inhibitor. In some embodiments, the immunomodulator is an immune-stimulating agent. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the oncolytic virus is administered directly into the tumor. In some embodiments, the oncolytic virus is administered to the tissue having the tumor. In some embodiments, the oncolytic virus is administered weekly. In some embodiments, the immunomodulator (including combination of immunomodulators) is administered intravenously. In some embodiments, the method further comprises local administration of a second immunomodulator (including combination of immunomodulators) to the site of the tumor.

In some embodiments, there is provided a method of treating a solid or lymphatic tumor (such as bladder cancer) in an individual (such as a human), comprising: a) locally administering to the site of the tumor an effective amount of an oncolytic virus (such as oncolytic adenovirus); and b) systemically administering an effective amount of an immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule. In some embodiments, the tumor-specific promoter is an E2F-1 promoter, such as a human E2F-1 promoter, for example, an E2F-1 promoter comprising the nucleotide sequence set forth in SEQ ID NO: 1. In some embodiments, the viral gene essential for replication of the virus is selected from the group consisting of E1A, E1B, and E4. In some embodiments, the immunomodulator is an immune checkpoint inhibitor. In some embodiments, the immunomodulator is an immune-stimulating agent. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the oncolytic virus is administered directly into the tumor. In some embodiments, the oncolytic virus is administered to the tissue having the tumor. In some embodiments, the oncolytic virus is administered weekly. In some embodiments, the immunomodulator (including combination of immunomodulators) is administered intravenously. In some embodiments, the method further comprises local administration of a second immunomodulator (including combination of immunomodulators) to the site of the tumor.

In some embodiments, the methods described herein further comprise locally administering to the site of the tumor an immune-related molecule (such as cytokine, chemokine, or PRRago (i.e., pathogen recognition receptor agonist)). In some embodiments, the immune-related molecule is selected from the group consisting of GM-CSF, IL-2, IL-12, interferon (such as Type 1. Type 2 or Type 3 interferon. e.g., interferon γ), CCL4, CCL19, CCL21, CXCL13. TLR1, TLR2, TLR3, TLR4. TLR5, TLR6. TLR7, TLR8. TLR9, TLR10. RIG-I, MDA5, LGP2, and LTαβ. In some embodiments, the immune-related molecule is selected from the group consisting of STING (i.e., stimulator of interferon genes) activators (such as CDN, i.e., cyclic dinucleotides), PRRago (such as CpG, Imiquimod, or Poly I:C), TLR stimulators (such as GS-9620, AED-1419, CYT-003-QbG10, AVE-0675, or PF-7909), and RLR stimulators (such as RIG-I, Mda5, or LGP2 stimulators). In some embodiments, the immune-related molecule induces dendritic cells, T cells, B cells, and/or T follicular helper cells. In some embodiments, the immune-related molecule is administered separately from the oncolytic virus (e.g., in a separate composition or as a separate entity in the same composition). In some embodiments, the immune-related molecule is administered to the site of the tumor via transduction. Exemplary transduction methods known in the art include, but are not limited to, the use of calcium phosphate, dendrimers, liposomes, cationic polymers, electroporation, cell squeezing, sonoporation, optical transfection, protoplast fusion, impalefection, hydrodynamic delivery, gene gun, magnetofection, viral transfection and nucleofection. In some embodiments, the immune-related molecule is expressed by the oncolytic virus. For example, the oncolytic virus may comprise a nucleic acid encoding the immune-related molecule, and the nucleic acid can be in the viral vector or on a separate vector.

The present invention is based in part on unpublished results from our clinical trials. Without being bound by any theory or hypothesis, it is believed that the viral oncolytic virus, CG0070, which is specifically designed to replicate only in cancer cells, provides the "right amount" of GM-CSF at tumor sites and in "real time" during cancer cell death. This "at" tumor site delivery of GM-CSF by the oncolytic virus during cancer cell death is believed to be vital for antigen presenting cells to both mature and to cross present established antigens, neoantigens, and tolerance breaking antigens (TBA) from this cell death mixture to the activated T cells. The right amount of GM-CSF is needed at the tumor site in this therapeutic scenario, because a high dose of GM-CSF would render the immune system without a focus, and trigger an instantaneous increase of local and system suppressors; whereas a low dose of GM-CSF would not be enough for the activation of the inflammatory process and the related immune cells. A delicate balance at the tumor site involving the right amount of GM-CSF and the on-site "live" cancer cell death mixture is believed to elicit an adaptive immune response that is specific to cancer cells. Therefore, an oncolytic virus that is cancer specific and oncolytic, and in combination with the right amount of GM-CSF or other appropriate immune-related molecules either expressed by the oncolytic virus or secreted by body defense in response to any oncolytic virus during cell death, infection or inflammation, delivered "at" the tumor sites, are believed to be an ideal choice for effective cancer immunotherapy.

In some embodiments, the immune-related molecule enhances an immune response in the individual. Immune-related molecules may include, but are not limited to, a cytokine, a chemokine, a stem cell growth factor, a lymphotoxin, an hematopoietic factor, a colony stimulating factor (CSF), erythropoietin, thrombopoietin, tumor necrosis factor-alpha (TNF), TNF-beta, granulocyte-colony stimulating factor (G-CSF), granulocyte macrophage-colony stimulating factor (GM-CSF), interferon-alpha, interferon-beta, interferon-gamma, interferon-lambda, stem cell growth factor designated "SI factor", human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, mullerian-inhibiting substance, mouse gonadotropin-associated peptide, inhibin, activin, vascular endothelial growth factor, integrin, NGF-beta, platelet-growth factor. TGF-alpha, TGF-beta, insulin-like growth factor-I, insulin-like growth factor-II, macrophage-CSF (M-CSF). IL-1. IL-1a, IL-2, IL-3, IL-4, IL-5, IL-6, IL-7, IL-8, IL-9, IL-10, IL-11, IL-12, IL-13, IL-14. IL-15, IL-16, IL-17, IL-18. IL-21. IL-25. LIF, FLT-3, angiostatin, thrombospondin, endostatin, lymphotoxin, thalidomide, lenalidomide, or pomalidomide.

The immune-related molecule can be of any one of the molecular modalities known in the art, including, but not limited to, aptamer, mRNA, siRNA, microRNA, shRNA, peptide, antibody, anticalin, Spherical nucleic acid. TALEN, Zinc Finger Nuclease, CRISPR/Cas9, and small molecule.

The immune-related molecules can be used singly or in combination. For example, any number (such as any of 1, 2, 3, 4, 5, 6, or more) of immune-related molecules can be used simultaneously or sequentially.

The oncolytic virus of the present invention comprises a viral vector comprising nucleic acid sequence(s) encoding at least one (for example, 1, 2, 3, 4, 5, or more) immune-related molecule. In some embodiments, the oncolytic virus comprises a viral vector comprising a heterologous gene encoding an immune-related molecule. In some embodiments, the immune-related molecule is selected from the group consisting of GM-CSF, IL-2, IL-12, interferon. CCL4. CCL19, CCL21. CXCL13. TLR, TLR2. TLR3, TLR4. TLR5, TLR6. TLR7, TLR8. TLR9, TLR100, RIG-I, MDA5, LGP2, and LTαβ. In some embodiments, the immune-related molecule is GM-CSF. In some embodiments, the heterologous gene is operably linked to a viral promoter, such as an E1 promoter, or an E3 promoter.

Thus, in some embodiments, there is provided a method of treating a solid or lymphatic tumor (such as bladder cancer) in an individual (such as a human), comprising: a) locally administering to the site of the tumor an effective amount of an oncolytic virus (such as oncolytic adenovirus); and b) systemically administering an effective amount of an immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the tumor-specific promoter is an E2F-1 promoter, such as a human E2F-1 promoter or an E2F-1 promoter comprising the nucleotide sequence set forth in SEQ ID NO: 1. In some embodiments, the viral gene essential for replication of the oncolytic virus is selected from the group consisting of E1A. E1B, and E4. In some embodiments, the heterologous gene is operably linked to a viral promoter, such as an E3 promoter. In some embodiments, the immune-related molecule is GM-CSF. In some embodiments, the immunomodulator is an immune checkpoint inhibitor. In some embodiments, the immunomodulator is an immune-stimulating agent. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the oncolytic virus is administered directly into the tumor. In some embodiments, the oncolytic virus is administered to the tissue having the tumor. In some embodiments, the oncolytic virus is administered weekly. In some embodiments, the immunomodulator (including combination of immunomodulators) is administered intravenously. In some embodiments, the method further comprises local administration of a second immunomodulator (including combination of immunomodulators) to the site of the tumor.

In some embodiments, the oncolytic virus is an adenovirus serotype 5. In some embodiments, the endogenous E1a promoter of a native adenovirus is replaced by the human E2F-1 promoter, and the E3 19kD coding region of the native adenovirus is a nucleic acid sequence encoding human GM-CSF. In some embodiments, a polyadenylation signal (PA) is inserted 5' of the E2F-1 promoter. In some embodiments, the nucleic acid encoding human GM-CSF is operably linked to the E3 promoter. In some embodiments, the vector backbone of the adenovirus serotype 5 further comprises E2. E4, late protein regions or inverted terminal repeats (ITRs) identical to the wildtype adenovirus serotype 5 genome. In some embodiments, the oncolytic virus has the genomic structure as shown in FIG. 1. In some embodiments, the oncolytic virus is conditionally replicating. In some embodiments, the oncolytic virus preferentially replicates in cancer cells. In some embodiments, the cancer cells are Rb pathway-defective cancer cells. In some embodiments, the oncolytic virus is CG0070.

Thus, for example, in some embodiments, there is provided a method of treating a solid or lymphatic tumor in an individual, comprising: a) locally administering to the site of the tumor an effective amount of an adenovirus serotype 5; and b) systemically administering an effective amount of an immunomodulator (including combination of immunomodulators), wherein the endogenous E1a promoter of a native adenovirus is replaced by the human E2F-1 promoter, and the E3 19kD coding region of the native adenovirus is replaced by a heterologous gene encoding an immune-related molecule (such as cytokine or chemokine, for example, GM-CSF). In some embodiments, the tumor-specific promoter is an E2F-1 promoter, such as a human E2F-1 promoter or an E2F-1 promoter comprising the nucleotide sequence set forth in SEQ ID NO: 1. In some embodiments, the immunomodulator is an immune checkpoint inhibitor. In some embodiments, the immunomodulator is an immune-stimulating agent. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the adenovirus is administered directly into the tumor. In some embodiments, the adenovirus is administered to the tissue having the tumor. In some embodiments, the adenovirus is administered weekly. In some embodiments, the immunomodulator (including combination of immunomodulators) is administered intravenously. In some embodiments, the method further comprises local administration of a second immunomodulator (including combination of immunomodulators) to the site of the tumor.

In some embodiments, there is provided a method of treating a solid or lymphatic tumor in an individual, comprising: a) locally administering to the site of the tumor an effective amount of CG0070; and b) systemically administering an effective amount of an immunomodulator (including combination of immunomodulators). In some embodiments, the immunomodulator is an immune checkpoint inhibitor. In some embodiments, the immunomodulator is an immune-stimulating agent. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, CG0070 is administered directly into the tumor. In some embodiments, CG0070 is administered to the tissue having the tumor. In some embodiments, CG0070 is administered at a dose of about $1 \times 10^8$ to about $1 \times 10^{14}$ viral particles (vp) (such as any of about $1 \times 10^8$ to about $1 \times 10^{10}$, about $1 \times 10^{10}$ to about $1 \times 10^{12}$, or about $1 \times 10^{12}$ to about $1 \times 10^{14}$ vp). In some embodiments, CG0070 is administered weekly. In some embodiments, CG0070 is administered for about 1 week to about 6 weeks (such as at least about any of 3 weeks, 4 weeks or 5 weeks). In some embodiments, the immunomodulator (including combination of immunomodulators) is administered intravenously. In some embodiments, the method further comprises local administration of a second immunomodulator (including combination of immunomodulators) to the site of the tumor.

In some embodiments, the oncolytic virus and the immunomodulator (including combination of immunomodulators) discussed above are administered sequentially, i.e., the administration of the oncolytic virus is administered before or after the administration of the immunomodulator (including combination of immunomodulators). In some embodiments, the oncolytic virus is administered prior to the administration of the immunomodulator (including combination of immunomodulators). In some embodiments, the oncolytic virus is administered no more than about any of 15 minutes, 30 minutes, 1 hour, 2 hours, 3 hours, 4 hours, 5 hours, 6 hours, 12 hours, or 24 hours prior to the administration of the immunomodulator (including combination of immunomodulators). In some embodiments, the oncolytic virus is administered about days or weeks (such as about any of 1 day, 2 days, 3 days, 4 days, 5 days, 6 days, 1 week, 2 weeks, 3 weeks, 4 weeks, or more) prior to the administration of the immunomodulator (including combination of immunomodulators). In some embodiments, the oncolytic virus is administered after the administration of the immunomodulator (including combination of immunomodulators). In some embodiments, the oncolytic virus is administered no more than about any of 15 minutes, 30 minutes, 1 hour, 2 hours, 3 hours, 4 hours, 5 hours, 6 hours, 12 hours, or 24 hours after the administration of the immunomodulator (including combination of immunomodulators). In some embodiments, the oncolytic virus is administered about days or weeks (such as about any of 1 day, 2 days, 3 days, 4 days, 5 days, 6 days, 1 week, 2 weeks, 3 weeks, 4 weeks, or more) after the administration of the immunomodulator (including combination of immunomodulators). In some embodiments, the oncolytic virus and the immunomodulator (including combination of immunomodulators) are administered with one immediately after another (e.g., within 5 minutes or less between the two administrations). For example, in some embodiments, the oncolytic virus is administered immediately before the administration of the immunomodulator (including combination of immunomodulators). In some embodiments, the oncolytic virus is administered immediately after the administration of the immunomodulator (including combination of immunomodulators).

In some embodiments, the oncolytic virus and the immunomodulator (including combination of immunomodulators) are administered simultaneously. In some embodiments, the oncolytic virus and the immunomodulator (including combination of immunomodulators) are administered simultaneously via separate compositions.

The immunomodulators discussed herein include both immune-stimulating agents and immune checkpoint inhibitors. The immunomodulator can be of any one of the molecular modalities known in the art, including, but not limited to, aptamer, mRNA, siRNA, microRNA, shRNA, peptide, antibody, anticalin, Spherical nucleic acid, TALEN. Zinc Finger Nuclease, CRISPR/Cas9, and small molecule.

In some embodiments, the immunomodulator is an immune-stimulating agent. In some embodiments, the immune-stimulating agent is a natural or engineered ligand of an immune stimulatory molecule, including, for example, ligands of OX40 (e.g., OX40L), ligands of CD-28 (e.g., CD80. CD86), ligands of ICOS (e.g., B7RP1), ligands of 4-1BB (e.g., 4-1BBL, Ultra4-1BBL), ligands of CD27 (e.g., CD70), ligands of CD40 (e.g., CD40L), and ligands of TCR (e.g., MHC class I or class II molecules, IMCgp100). In some embodiments, the immune-stimulating agent is an antibody selected from the group consisting of anti-CD28 (e.g., TGN-1412), anti-OX40 (e.g., MEDI16469, MEDI-0562), anti-ICOS (e.g., MEDI-570), anti-GITR (e.g., TRX518, INBRX-110, NOV-120301), anti-41-BB (e.g., BMS-663513, PF-05082566), anti-CD27 (e.g., BION-1402. Varlilumab and hCD27.15), anti-CD40 (e.g., CP870,893, BI-655064, BMS-986090, APX005, APX005M), anti-CD3 (e.g., blinatumomab, muromonab), and anti-HVEM. In some embodiments, the antibody is an agonistic antibody. In some embodiments, the antibody is a monoclonal antibody. In some embodiments, the antibody is an antigen-binding fragment selected from the group consisting of Fab, Fab', F(ab')$_2$, Fv, scFv, and other antigen-binding subsequences of the full length antibody. In some embodiments, the antibody is a human, humanized, or chimeric antibody. In some embodiments, the antibody is a bispecific antibody, a multispecific antibody, a single domain antibody, a fusion protein comprising an antibody portion, or any other functional variants or derivatives thereof.

In some embodiments, the immunomodulator is an immune checkpoint inhibitor. In some embodiments, the immune checkpoint inhibitor is a natural or engineered ligand of an inhibitory immune checkpoint molecule, including, for example, ligands of CTLA-4 (e.g., B7.1, B7.2), ligands of TIM3 (e.g., Galectin-9), ligands of A2a Receptor (e.g., adenosine, Regadenoson), ligands of LAG3 (e.g., MHC class I or MHC class II molecules), ligands of BTLA (e.g., HVEM, B7-H4), ligands of KIR (e.g., MHC class I or MHC class II molecules), ligands of PD-1 (e.g., PD-L1, PD-L2), ligands of IDO (e.g., NKTR-218. Indoximod, NLG919), ligands of CD47 (e.g., SIRP-alpha receptor), and ligands of CSF1R. In some embodiments, the immune checkpoint inhibitor is an antibody that targets an inhibitory immune checkpoint protein. In some embodiments, the immunomodulator is an antibody selected from the group consisting of anti-CTLA-4 (e.g., Ipilimumab, Tremelimumab, KAHR-102), anti-TIM3 (e.g., F38-2E2. ENUM005), anti-LAG3 (e.g., BMS-986016, IMP701. IMP321, C9B7W), anti-KIR (e.g., Lirilumab, IPH2101, IPH4102), anti-PD-1 (e.g., Nivolumab, Pidilizumab, Pembrolizumab, BMS-936559, atezolizumab, Lambrolizumab, MK-3475. AMP-224, AMP-514, STI-A1110, TSR-042), anti-PD-L1 (e.g., KY-1003 (EP20120194977), MCLA-145, atezolizumab. BMS-936559, MEDI-4736, MSB0010718C, AUR-012, STI-A1010. PCT/US2001/020964, MPDL3280A, AMP-224, Dapirolizumab pegol (CDP-7657), MEDI-4920), anti-CD73 (e.g., AR-42 (OSU-HDAC42, HDAC-42, AR42, AR 42, OSU-HDAC 42, OSU-HDAC-42, NSC D736012, HDAC-42, HDAC 42, HDAC42, NSCD736012, NSC-D736012), MEDI-9447), anti-B7-H3 (e.g., MGA271, DS-5573a, 8H9), anti-CD47 (e.g., CC-90002, TTI-621, VLST-007), anti-BTLA, anti-VISTA, anti-A2aR, anti-B7-1, anti-B7-H4, anti-CD52 (such as alemtuzumab), anti-IL-10, anti-IL-35, anti-TGF-β (such as Fresolumimab), anti-CSF1R (e.g., FPA008), anti-NKG2A (e.g., monalizumab), anti-MICA (e.g., IPH43), and anti-CD39. In some embodiments, the antibody is an antagonistic antibody. In some embodiments, the antibody is a monoclonal antibody. In some embodiments, the antibody is a monoclonal antibody. In some embodiments, the antibody is an antigen-binding fragment selected from the group consisting of Fab, Fab', F(ab')$_2$, Fv, scFv, and other antigen-binding subsequences of the full length antibody. In some embodiments, the antibody is a human, humanized, or chimeric antibody. In some embodiments, the antibody is a bispecific antibody, a multispecific antibody, a single domain antibody, a fusion protein comprising an antibody portion, or any other functional variants or derivatives thereof.

In some embodiments, the method comprises systemic administration of a single immunomodulator. In some embodiments, the immunomodulator is an immune checkpoint inhibitor. In some embodiments, the immunomodulator is an immune-stimulating agent. In some embodiments, the immunomodulator is selected from the immunomodulators listed in Table 1, wherein the immunomodulator is administered with the same route of administration, and/or dose, and/or dosing frequency, and/or duration, and/or maintenance schedule as listed in Table 1. In some embodiments, the immunomodulator is selected from the immunomodulators listed in Table 1, wherein the immunomodulator is administered with the different route of administration, and/or dose, and/or dosing frequency, and/or duration, and/or maintenance schedule as listed in Table 1. In some embodiments, the immunomodulator is not a molecule selected from Table 1.

In some embodiments, the method comprises systemic administration of at least two (such as any of 2, 3, 4, 5, 6, or more) immunomodulators. In some embodiments, all or part of the at least two immunomodulators are administered simultaneously, such as in a single composition. In some embodiments, all or part of the at least two immunomodulators are administered sequentially. In some embodiments, the method comprises systemic administration of a combination of immunomodulators comprising an immune checkpoint inhibitor and an immune-stimulating agent. In some embodiments, the method comprises systemic administration of a combination of immunomodulators comprising two or more (such as any of 2, 3, 4, 5, 6, or more) checkpoint inhibitors. In some embodiments, the method comprises systemic administration of a combination of immunomodulators comprising two or more (such as any of 2, 3, 4, 5, 6, or more) immune-stimulating agents. In some embodiments, the method comprises systemic administration of a combination of immunomodulators comprising any number (such as any of 1, 2, 3, 4, 5, 6, or more) of immune checkpoint inhibitors and any number (such as any of 2, 3, 4, 5, 6, or more) of immune-stimulating agents. In some embodiments, the at least two immunomodulators comprise one or more immunomodulators selected from Table 1. For example, in some embodiment, the method comprises: a) locally administering to the site of the tumor an effective amount of an oncolytic virus (such as a virus, for example an oncolytic virus); and b) systemically administering to the individual an effective amount of a first systemic immunomodulator (such as an immune checkpoint inhibitor); and c) systemically administering an effective amount of a second systemic immunomodulator (such as an immune-stimulating agent).

In some embodiments, the method further comprises local administration of any number (such as 1, 2, 3, 4, or more) of additional immunomodulators (hereinafter referred to as the "second immunomodulator" or "local immunomodulator", while the immunomodulator in such context is referred herein as the "first" immunomodulator". "systemic immunomodulator", or "immunomodulator") to the site of the tumor. In some embodiments, the first immunomodulator and the second immunomodulator have the same target. In some embodiments, the first immunomodulator and the second immunomodulator are the same immunomodulator molecule. In some embodiments, the first immunomodulator and the second immunomodulator have the same target, but are of different modalities. In some embodiments, the first immunomodulator and the second immunomodulator are different immunomodulator molecules. In some embodiments, the first immunomodulator and the second immunomodulator do not have the same target. In some embodiments, the first immunomodulator is an immune checkpoint inhibitor, and the second immunomodulator is an immune-stimulating agent. In some embodiments, the first immunomodulator is an immune checkpoint inhibitor, and the second immunomodulator is an immune checkpoint inhibitor. In some embodiments, the first immunomodulator is an immune-stimulating agent, and the second immunomodulator is an immune-stimulating agent. In some embodiments, the first immunomodulator is an immune-stimulating agent, and the second immunomodulator is an immune checkpoint inhibitor. In some embodiments, the method comprises local administration of a combination of at least two local immunomodulators. In the cases that more than one systemic immunomodulators and more than one local immunomodulators are administered, any of the more than one systemic immunomodulator may have the same target, or be the same immunomodulator as a local immunomodulator.

The administration of the immunomodulators can be of any sequence, including simultaneous systemic administration of the first immunomodulator(s) and local administration of the second immunomodulator(s), and sequential administration of the immunomodulators, among which at least one immunomodulator is administered systemically, for example, first administering the second immunomodulator(s) locally (such as intratumorally) to the site of the tumor followed by systemic (such as intravenous) administration of the first immunomodulator(s), or first administering the first immunomodulator(s) systemically (such as intravenously) followed by local (such as intratumoral) administration of the second immunomodulator(s). Immunomodulators administered simultaneously via the same administration route may be administered as a single composition. For example, the immunomodulators can be admixed prior to (such as immediately prior to, e.g., within less than about 10, 5, or 1 minutes before) the administration of the single composition.

The local administration of the oncolytic virus and the local administration of the second immunomodulator (including combination of immunomodulators) can be simultaneous or sequential. In some embodiments, the oncolytic virus is administered before or after the local administration of the second immunomodulator (including combination of immunomodulators). In some embodiments, the oncolytic virus is administered prior to the local administration of the second immunomodulator (including combination of immunomodulators). In some embodiments, the oncolytic virus is administered no more than about any of 15 minutes, 30 minutes, 1 hour, 2 hours, 3 hours, 4 hours, 5 hours, 6 hours, 12 hours, or 24 hours prior to the local administration of the second immunomodulator (including combination of immunomodulators). In some embodiments, the oncolytic virus is administered about days or weeks (such as about any of 1 day, 2 days, 3 days, 4 days, 5 days, 6 days, 1 week, 2 weeks, 3 weeks, 4 weeks, or more) prior to the local administration of the second immunomodulator (including combination of immunomodulators). In some embodiments, the oncolytic virus is administered after the local administration of the second immunomodulator (including combination of immunomodulators). In some embodiments, the oncolytic virus is administered no more than about any of 15 minutes, 30 minutes, 1 hour, 2 hours, 3 hours, 4 hours, 5 hours, 6 hours, 12 hours, or 24 hours after the local administration of the second immunomodulator (including combination of immunomodulators). In some embodiments, the oncolytic virus is administered about days or weeks (such as about any of 1 day, 2 days, 3 days, 4 days, 5 days, 6 days, 1 week, 2 weeks, 3 weeks, 4 weeks, or more) after the local administration of the second immunomodulator (including combination of immunomodulators). In some embodiments, the oncolytic virus and the second immunomodulator (including combination of immunomodulators) are administered with one immediately after another (e.g., within 5 minutes or less between the two administrations). For example, in some embodiments, the oncolytic virus is administered immediately before the local administration of the second immunomodulator (including combination of immunomodulators). In some embodiments, the oncolytic virus is administered immediately after the local administration of the second immunomodulator (including combination of immunomodulators).

In some embodiments, the oncolytic virus and the second immunomodulator (including combination of immunomodulators) are administered simultaneously. In some embodiments, the oncolytic virus and the second immunomodulator (including combination of immunomodulators) are administered simultaneously via separate compositions. In some embodiments, the oncolytic virus and the second immunomodulator (including combination of immunomodulators) are administered as a single composition. In some embodiments, the oncolytic virus and the second immunomodulator (including combination of immunomodulators) are mixed prior to (such as immediately prior to, e.g., within less than about 10, 5, or 1 minutes before) the administration of the composition. In some embodiments, the composition comprising the oncolytic virus and the second immunomodulator (including combination of immunomodulators) is pre-made and stored for at least about 1 hours, 2 hours, 3 hours, 4 hours, 5 hours, 6 hours, 12 hours, 24 hours, 2 days, 3 days, 4 days, 5 days, 6 days, 7 days, 2 weeks, 3 weeks, or more prior to the administration.

Thus, in some embodiments, there is provided a method of treating a solid or lymphatic tumor in an individual, comprising: a) locally administering to the site of the tumor an effective amount of an oncolytic virus (such as oncolytic adenovirus, for example, CG0070): b) systemically administering an effective amount of an immunomodulator (including combination of immunomodulators); and c) locally administering to the site of the tumor an effective amount of an second immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule. In some embodiments, the tumor-specific promoter is an E2F-1 promoter, such as a human E2F-1 promoter or an E2F-1 promoter comprising the nucleotide sequence set forth in SEQ ID NO: 1. In some embodiments, the viral gene essential for replication of the virus is selected from the group consisting of E1A, E1B, and E4. In some embodiments, the heterologous gene is operably linked to a viral promoter, such as an E3 promoter. In some embodiments, the heterologous gene is GM-CSF. In some embodiments, the immunomodulator is an immune checkpoint inhibitor. In some embodiments, the immunomodulator is an immune-stimulating agent. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the second immunomodulator is an immune checkpoint inhibitor. In some embodiments, the second immunomodulator is an immune-stimulating agent. In some embodiments, the method comprises systemic administration of a combination of second immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the oncolytic virus is administered directly into the tumor. In some embodiments, the oncolytic virus is administered to the tissue having the tumor. In some embodiments, the oncolytic virus is administered weekly. In some embodiments, the immunomodulator (including combination of immunomodulators) is administered intravenously.

In some embodiments, there is provided a method of treating a solid or lymphatic tumor in an individual, comprising: a) locally administering to the site of the tumor an effective amount of an oncolytic virus (such as oncolytic adenovirus, for example, CG0070); b) systemically administering an effective amount of a first immunomodulator; and c) locally administering to the site of the tumor an effective amount of a second immunomodulator, wherein the oncolytic virus comprises a viral vector comprising a tumor cell-specific promoter operably linked to a viral gene essential for replication of the virus, and a heterologous gene encoding an immune-related molecule. In some embodiments, the tumor-specific promoter is an E2F-1 promoter, such as a human E2F-1 promoter or an E2F-1 promoter comprising the nucleotide sequence set forth in SEQ ID NO:1. In some embodiments, the viral gene essential for replication of the virus is selected from the group consisting of E1A. E1B, and E4. In some embodiments, the heterologous gene is operably linked to a viral promoter, such as an E3 promoter. In some embodiments, the heterologous gene is GM-CSF. In some embodiments, the first immunomodulator is an immune checkpoint inhibitor. In some embodiments, the first immunomodulator is an immune-stimulating agent. In some embodiments, the second immunomodulator is an immune checkpoint inhibitor. In some embodiments, the second immunomodulator is an immune-stimulating agent. In some embodiments, the oncolytic virus and/or the second immunomodulator are administered directly into the tumor. In some embodiments, the oncolytic virus the/or second immunomodulator are administered to the tissue having the tumor. In some embodiments, the oncolytic virus is administered weekly. In some embodiments, the first immunomodulator is administered intravenously. In some embodiments, the second immunomodulator and the oncolytic virus are administered simultaneously, such as in the same composition. In some embodiments, the second immunomodulator and the oncolytic virus are administered sequentially. In some embodiments, the first immunomodulator is administered after the administration of the second immunomodulator. In some embodiments, the first immunomodulator is administered before the administration of the second immunomodulator. In some embodiments, the sequence of the administration is as follows: local (such as intratumoral) administration of the oncolytic virus, followed by local (such as intratumoral) administration of the second immunomodulator, followed by systemic (such as intravenous) administration of the first immunomodulator.

In some embodiments, there is provided a method of treating a solid or lymphatic tumor in an individual, comprising: a) locally administering to the site of the tumor an effective amount of an oncolytic virus (such as oncolytic adenovirus, for example, CG0070); b) systemically administering an effective amount of a first immunomodulator; c) locally administering to the site of the tumor an effective amount of a second immunomodulator, and d) administering (such as systemically or locally to the site of the tumor) an effective amount of a third immunomodulator, wherein the oncolytic virus comprises a viral vector comprising a tumor cell-specific promoter operably linked to a viral gene essential for replication of the virus, and a heterologous gene encoding an immune-related molecule. In some embodiments, the tumor-specific promoter is an E2F-1 promoter, such as a human E2F-1 promoter or an E2F-1 promoter comprising the nucleotide sequence set forth in SEQ ID NO:1. In some embodiments, the viral gene essential for replication of the virus is selected from the group consisting of E1A, E1B, and E4. In some embodiments, the heterologous gene is operably linked to a viral promoter, such as an E3 promoter. In some embodiments, the heterologous gene is GM-CSF. In some embodiments, the first and/or second and/or third immunomodulator is an immune checkpoint inhibitor. In some embodiments, the first and/or second and/or third immunomodulator is an immune-stimulating agent. In some embodiments, the oncolytic virus and/or the second immunomodulator and/or the third immunomodulator are administered directly into the tumor. In some embodiments, the oncolytic virus the/or second immunomodulator are administered to the tissue having the tumor. In some embodiments, the oncolytic virus is administered weekly. In some embodiments, the first immunomodulator and/or the second immunomodulator is administered intravenously. In some embodiments, the second immunomodulator and and/or the third immunomodulator, and the oncolytic virus are administered simultaneously, such as in the same composition. In some embodiments, the second immunomodulator and/or the third immunomodulator, and the oncolytic virus are administered sequentially. In some embodiments, the first immunomodulator is administered after the administration of the second immunomodulator and/or the third immunomodulator. In some embodiments, the first immunomodulator is administered before the administration of the second immunomodulator and/or the third immunomodulator. In some embodiments, the sequence of the administration is as follows: local (such as intratumoral) administration of the oncolytic virus, followed by local (such as intratumoral) administration of the second immunomodulator, followed by local (such as intratumoral) administration of the third immunomodulator, followed by systemic (such as intravenous) administration of the first immunomodulator. In some embodiments, the sequence of the administration is as follows: local (such as intratumoral) administration of the oncolytic virus, followed by local (such as intratumoral) administration of the second immunomodulator and the third immunomodulator (e.g., in the same composition), followed by systemic (such as intravenous) administration of the first immunomodulator. In some embodiments, the sequence of the administration is as follows: local (such as intratumoral) administration of the oncolytic virus, followed by local (such as intratumoral) administration of the second immunomodulator, followed by systemic (such as intravenous)

administration of the first immunomodulator, followed by systemic (such as intravenous) administration of the third immunomodulator. In some embodiments, the sequence of the administration is as follows: local (such as intratumoral) administration of the oncolytic virus, followed by local (such as intratumoral) administration of the second immunomodulator, followed by systemic (such as intravenous) administration of the first immunomodulator and the third immunomodulator (e.g., in the same composition).

The third immunomodulator may be any of the immunomodulators described herein. In some embodiments, the third immunomodulator have the same target, such as being the same immunomodulator molecule as the first immunomodulator, wherein the third immunomodulator is administered locally to the site of the tumor. In some embodiments, the third immunomodulator have the same target, such as being the same immunomodulator molecule as the second immunomodulator, wherein the third immunomodulator is administered systemically. In some embodiments, the first immunomodulator, the second immunomodulator and the third immunomodulator are different, for example, having different targets, being different types of immunomodulators, and/or being different immunomodulator molecules.

In some embodiments, the immune checkpoint inhibitor is an inhibitor of CTLA-4. In some embodiments, the inhibitor of CTLA-4 is an anti-CTLA-4 antibody. Any of the anti-CTLA-4 antibodies that are known in the art may be used in the present invention, including, but not limited to, Ipilimumab. Tremelimumab, and KAHR-102. In some embodiments, the anti-CTLA-4 antibody is YERVOY® (Ipilimumab). In some embodiments, the anti-CTLA-4 antibody is a monoclonal antibody or a polyclonal antibody. In some embodiments, the anti-CTLA-4 antibody is an antigen-binding fragment selected from the group consisting of Fab, Fab', F(ab')$_2$, Fv, scFv, and other antigen-binding subsequences of the full length anti-CTLA-4 antibody. In some embodiments, the anti-CTLA-4 antibody is a human, humanized, or chimeric antibody. In some embodiments, the anti-CTLA-4 antibody is a bispecific antibody, a multispecific antibody, a single domain antibody, a fusion protein comprising an antibody portion, or any other functional variants or derivatives thereof. In some embodiments, the inhibitor of CTLA-4 is an engineered lipocalin protein specifically recognizing CTLA-4 (such as an anticalin molecule that specifically binds to CTLA-4). In some embodiments, the inhibitor of CTLA-4 is a natural or engineered ligand of CTLA-4, such as B7.1 or B7.2.

Thus, for example, in some embodiments, there is provided a method of treating a solid or lymphatic tumor in an individual (such as a human), comprising: a) locally administering to the site of the tumor an effective amount of an oncolytic virus (such as an oncolytic adenovirus); and b) systemically administering an effective amount of an inhibitor of CTLA-4 (such as an anti-CTLA-4 antibody, for example Ipilimumab, or an engineered lipocalin protein, for example an anticalin that specifically recognizes CTLA-4), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the oncolytic virus is attenuated (for example through multiple passages, inactivation or genetic modification). In some embodiments, the oncolytic virus preferentially replicates in a cancer cell, such as an Rb-pathway defective cancer cell. In some embodiments, the inhibitor of CTLA-4 is an anti-CTLA-4 antibody, for example Ipilimumab. In some embodiments, the inhibitor of CTLA-4 is an engineered lipocalin protein, for example an anticalin that specifically recognizes CTLA-4. In some embodiments, the oncolytic virus is administered directly into the tumor. In some embodiments, the oncolytic virus is administered to the tissue having the tumor. In some embodiments, the oncolytic virus is administered weekly. In some embodiments, the inhibitor of CTLA-4 is administered intravenously. In some embodiments, the oncolytic virus and the inhibitor of CTLA-4 are administered sequentially. In some embodiments, the oncolytic virus is administered prior to (such as immediately prior to) the administration of the inhibitor of CTLA-4. In some embodiments, the oncolytic virus is administered after (such as immediately after) the administration of the inhibitor of CTLA-4. In some embodiments, the oncolytic virus and the inhibitor of CTLA-4 are administered simultaneously. In some embodiments, the method further comprises local administration of a second immunomodulator, such as an immune checkpoint inhibitor or an immune-stimulating agent. In some embodiments, the method further comprises administration (such as systemic or local to the site of the tumor) of a third immunomodulator, such as an immune checkpoint inhibitor or an immune-stimulating agent.

In some embodiments, there is provided a method of treating a solid or lymphatic tumor in an individual, comprising: a) locally administering to the site of the tumor an effective amount of an oncolytic virus (such as oncolytic adenovirus); and b) systemically administering an effective amount of an inhibitor of CTLA-4 (such as an anti-CTLA-4 antibody, for example Ipilimumab, or an engineered lipocalin protein, for example an anticalin that specifically recognizes CTLA-4), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the tumor-specific promoter is an E2F-1 promoter, such as a human E2F-1 promoter or an E2F-1 promoter comprising the nucleotide sequence set forth in SEQ ID NO: 1. In some embodiments, the viral gene essential for replication of the virus is selected from the group consisting of E1A, E1B, and E4. In some embodiments, the heterologous gene is operably linked to a viral promoter, such as the E3 promoter. In some embodiments, the immune-related molecule is GM-CSF.

In some embodiments, there is provided a method of treating a solid or lymphatic tumor in an individual, comprising: a) locally administering to the site of the tumor an effective amount of an adenovirus serotype 5; and b) systemically administering an effective amount of an inhibitor of CTLA-4 (such as an anti-CTLA-4 antibody, for example Ipilimumab, or an engineered lipocalin protein, for example an anticalin that specifically recognizes CTLA-4), wherein the endogenous E1a promoter of a native adenovirus is replaced by the human E2F1-promoter, and E3 19kD coding region of the native adenovirus is replaced by a heterologous gene encoding an immune-related molecule (such as cytokine or chemokine, for example, GM-CSF). In some embodiments, the tumor-specific promoter is a human E2F-1 promoter or an E2F-1 promoter comprising the nucleotide sequence set forth in SEQ ID NO: 1.

In some embodiments, there is provided a method of treating a solid or lymphatic tumor in an individual, comprising: a) locally administering to the site of the tumor an effective amount of CG0070; and b) systemically administering an effective amount of an inhibitor of CTLA-4 (such as an anti-CTLA-4 antibody, for example Ipilimumab, or an engineered lipocalin protein, for example an anticalin that specifically recognizes CTLA-4). In some embodiments, the inhibitor of CTLA-4 is an anti-CTLA-4 antibody, for example Ipilimumab. In some embodiments, the inhibitor of CTLA-4 is an engineered lipocalin protein, for example an anticalin that specifically recognizes CTLA-4. In some embodiments, the CG0070 is administered directly into the tumor. In some embodiments, the CG0070 is administered to the tissue having the tumor. In some embodiments, the CG007 is administered at a dose of about $1\times10^8$ to about $1\times10^{14}$ viral particles (vp) (such as any of about $1\times10^8$ to about $1\times10^{10}$, about $1\times10^{10}$ to about $1\times10^{12}$, or about $1\times10^{12}$ to about $1\times10^{14}$ vp). In some embodiments, CG0070 is administered weekly. In some embodiments. CG0070 is administered for about 1 week to about 6 weeks (such as at least about any of 3 weeks, 4 weeks or 5 weeks). In some embodiments, the inhibitor of CTLA-4 is administered intravenously. In some embodiments, the CG0070 and the inhibitor of CTLA-4 are administered sequentially. In some embodiments, the CG0070 is administered prior to (such as immediately prior to) the administration of the inhibitor of CTLA-4. In some embodiments, the CG0070 is administered after (such as immediately after) the administration of the inhibitor of CTLA-4. In some embodiments, the CG0070 and the inhibitor of CTLA-4 are administered simultaneously. In some embodiments, the method further comprises local administration of a second immunomodulator, such as an immune checkpoint inhibitor or an immune-stimulating agent. In some embodiments, the method further comprises administration (such as systemic or local to the site of the tumor) of a third immunomodulator, such as an immune checkpoint inhibitor or an immune-stimulating agent.

In some embodiments, the immune checkpoint inhibitor is an inhibitor of PD-1. In some embodiments, the inhibitor of PD-1 is an anti-PD-1 antibody. Any of the anti-PD-1 antibodies known in the art may be used in the present invention, including, but not limited to, Nivolumab, pembrolizumab, pidilizumab, BMS-936559, and atezolizumab, Lambrolizumab, MK-3475, AMP-224, AMP-514. STI-A1110, and TSR-042. In some embodiments, the anti-PD-1 antibody is a monoclonal antibody or a polyclonal antibody. In some embodiments, the anti-PD-1 antibody is an antigen-binding fragment selected from the group consisting of Fab, Fab', F(ab')$_2$, Fv, scFv, and other antigen-binding subsequences of the full-length anti-PD-1 antibody. In some embodiments, the anti-PD-1 antibody is a human, humanized, or chimeric antibody. In some embodiments, the anti-PD-1 antibody is a bispecific antibody, a multispecific antibody, a single domain antibody, a fusion protein comprising an antibody portion, or any other variants or derivatives thereof. In some embodiments, the inhibitor of PD-1 is a natural or engineered ligand of PD-1, such as PD-L1 or PD-L2. In some embodiments, the inhibitor of PD-1 is an inhibitor of the interaction between PD-1 and its ligand, for example, an inhibitor of PD-1/PD-L1 interaction or an inhibitor of PD-1/PD-L2 interaction. In some embodiments, the inhibitor of PD-1 is an inhibitor of a PD-1 ligand, such as an inhibitor of PD-L (e.g., anti-PD-L1 antibody) or an inhibitor of PD-L2 (e.g., anti-PD-L2 antibody). Any of the inhibitors of interaction between PD-1 and its ligand may be used in the present invention, see, for example, U.S. Pat. Nos. 7,709,214, 7,432,059, 7,722,868, 8,217,149, 8,383,796, and 9,102,725. In some embodiments, the inhibitor of PD-1 is an Fc fusion protein comprising a PD-1 ligand, such as an Fc-fusion of PD-L2 (e.g., AMP-224).

Thus, for example, in some embodiments, there is provided a method of treating a solid or lymphatic tumor in an individual (such as a human), comprising: a) locally administering to the site of the tumor an effective amount of an oncolytic virus (such as an oncolytic adenovirus); and b) systemically administering an effective amount of an inhibitor of PD-1 (such as an anti-PD-1 antibody, for example, Nivolumab, Pembrolizumab, or Pidilizumab, or an Fc fusion protein of a PD-1 ligand, for example, AMP-224), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the oncolytic virus is attenuated (for example through multiple passages, inactivation or genetic modification). In some embodiments, the oncolytic virus preferentially replicates in a cancer cell, such as an Rb-pathway defective cancer cell. In some embodiments, the inhibitor of PD-1 is an anti-PD-1 antibody, for example, Nivolumab, Pembrolizumab, or Pidilizumab. In some embodiments, the inhibitor of PD-1 is an inhibitor of the interaction between PD-1 and its ligand, such as an inhibitor of PD-1/PD-L1 interaction or an inhibitor of PD-1/PD-L2 interaction. In some embodiments, the inhibitor of PD-1 is an Fc fusion protein comprising a PD-1 ligand, such as an Fc-fusion of PD-L2 (e.g., AMP-224). In some embodiments, the oncolytic virus is administered directly into the tumor. In some embodiments, the oncolytic virus is administered to the tissue having the tumor. In some embodiments, the oncolytic virus is administered weekly. In some embodiments, the inhibitor of PD-1 is administered intravenously. In some embodiments, the oncolytic virus and the inhibitor of PD-1 are administered sequentially. In some embodiments, the oncolytic virus is administered prior to (such as immediately prior to) the administration of the inhibitor of PD-1. In some embodiments, the oncolytic virus is administered after (such as immediately after) the administration of the inhibitor of PD-1. In some embodiments, the oncolytic virus and the inhibitor of PD-1 are administered simultaneously. In some embodiments, the method further comprises local administration of a second immunomodulator, such as an immune checkpoint inhibitor (such as a CTLA-4 inhibitor) or an immune-stimulating agent (e.g., a CD40 activator or a 4-1BB activator). In some embodiments, the method further comprises administration (such as systemic or local to the site of the tumor) of a third immunomodulator, such as an immune checkpoint inhibitor (such as a CTLA-4 inhibitor) or an immune-stimulating agent (e.g., a CD40 activator or a 4-1BB activator).

In some embodiments, there is provided a method of treating a solid or lymphatic tumor in an individual, comprising: a) locally administering to the site of the tumor an effective amount of an oncolytic virus (such as oncolytic adenovirus); and b) systemically administering an effective amount of an inhibitor of PD-1 (such as an anti-PD-1 antibody, for example, Nivolumab, Pembrolizumab, or Pidilizumab, or an Fc fusion protein of a PD-1 ligand, for example, AMP-224), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the tumor-specific promoter is an E2F-1 promoter, such as a human E2F-1 promoter or an E2F-1 promoter comprising the nucleotide sequence set forth in SEQ ID NO: 1. In some embodiments, the viral gene essential for replication of the virus is selected from the group consisting of E1A, E1B, and E4. In some embodiments, the heterologous gene is operably linked to a viral promoter, such as the E3 promoter. In some embodiments, the immune-related molecule is GM-CSF.

In some embodiments, there is provided a method of treating a solid or lymphatic tumor in an individual, comprising: a) locally administering to the site of the tumor an effective amount of an adenovirus serotype 5; and b) systemically administering an effective amount of an inhibitor of PD-1 (such as an anti-PD-1 antibody, for example, Nivolumab, Pembrolizumab, or Pidilizumab, or an Fc fusion protein of a PD-1 ligand, for example, AMP-224), wherein the endogenous E1a promoter of a native adenovirus is replaced by the human E2F1-promoter, and E3 19kD coding region of the native adenovirus is replaced by a heterologous gene encoding an immune-related molecule (such as cytokine or chemokine, for example, GM-CSF). In some embodiments, the tumor-specific promoter is a human E2F-1 promoter or an E2F-1 promoter comprising the nucleotide sequence set forth in SEQ ID NO:1.

In some embodiments, there is provided a method of treating a solid or lymphatic tumor in an individual, comprising: a) locally administering to the site of the tumor an effective amount of an adenovirus serotype 5, wherein the endogenous E1a promoter and E3 19kD coding region of a native adenovirus is replaced by the human E2F-1 promoter and a nucleic acid encoding an immune-related molecule (such as cytokine or chemokine, for example, GM-CSF); and b) locally administering to the site of the tumor an effective amount of an inhibitor of PD-1 (such as an anti-PD-1 antibody, for example, Nivolumab, Pembrolizumab, or Pidilizumab, or an Fc fusion protein of a PD-1 ligand, for example, AMP-224). In some embodiments, the tumor-specific promoter is a human E2F-1 promoter or an E2F-1 promoter comprising the nucleotide sequence set forth in SEQ ID NO:1.

In some embodiments, there is provided a method of treating a solid or lymphatic tumor in an individual, comprising: a) locally administering to the site of the tumor an effective amount of CG0070; and b) systemically administering an effective amount of an inhibitor of PD-1 (such as an anti-PD-1 antibody, for example, Nivolumab, Pembrolizumab, or Pidilizumab, or an Fc fusion protein of a PD-1 ligand, for example, AMP-224). In some embodiments, the inhibitor of PD-1 is an anti-PD-1 antibody, for example, Nivolumab, Pembrolizumab, or Pidilizumab. In some embodiments, the inhibitor of PD-1 is an inhibitor of the interaction between PD-1 and its ligand, such as an inhibitor of PD-1/PD-L1 interaction or an inhibitor of PD-1/PD-L2 interaction. In some embodiments, the inhibitor of PD-1 is an Fc fusion protein comprising a PD-1 ligand, such as an Fc-fusion of PD-L2 (e.g., AMP-224). In some embodiments, the CG0070 is administered directly into the tumor. In some embodiments, the CG0070 is administered to the tissue having the tumor. In some embodiments, the CG007 is administered at a dose of about $1 \times 10^8$ to about $1 \times 10^{14}$ viral particles (vp) (such as any of about $1 \times 10^8$ to about $1 \times 10^{10}$, about $1 \times 10^{10}$ to about $1 \times 10^{12}$, or about $1 \times 10^{12}$ to about $1 \times 10^{14}$ vp). In some embodiments, CG0070 is administered weekly. In some embodiments, CG0070 is administered for about 1 week to about 6 weeks (such as at least about any of 3 weeks, 4 weeks or 5 weeks). In some embodiments, the inhibitor of PD-1 is administered intravenously. In some embodiments, the CG0070 and the inhibitor of PD-1 are administered sequentially. In some embodiments, the CG0070 is administered prior to (such as immediately prior to) the administration of the inhibitor of PD-1. In some embodiments, the CG0070 is administered after (such as immediately after) the administration of the inhibitor of PD-1. In some embodiments, the CG0070 and the inhibitor of PD-1 are administered simultaneously. In some embodiments, the method further comprises local administration of a second immunomodulator, such as an immune checkpoint inhibitor or an immune-stimulating agent. In some embodiments, the method further comprises administration (such as systemic or local to the site of the tumor) of a third immunomodulator, such as an immune checkpoint inhibitor or an immune-stimulating agent.

In some embodiments, the immune checkpoint inhibitor is an inhibitor of PD-1 ligand (e.g., PD-L and/or PD-L2). In some embodiments, the inhibitor of PD-1 ligand is an anti-PD-L1 antibody. In some embodiments, the inhibitor of PD-1 ligand is an anti-PD-L2 antibody. Exemplary anti-PD-L1 antibodies include, but are not limited to, KY-1003. MCLA-145, RG7446 (also known as atezolizumab), BMS935559 (also known as MDX-1105), MPDL3280A, MEDI4736. Avelumab (also known as MSB0010718C), and STI-A1010. In some embodiments, the anti-PD-L1 or anti-PD-L2 is a monoclonal antibody or a polyclonal antibody. In some embodiments, the anti-PD-L1 or anti-PD-L2 is an antigen-binding fragment selected from the group consisting of Fab. Fab', $F(ab')_2$, Fv, scFv, and other antigen-binding subsequences of the full-length anti-PD-L1 or anti-PD-L2 antibody. In some embodiments, the anti-PD-L or anti-PD-L2 antibody is a human, humanized, or chimeric antibody. In some embodiments, the anti-PD-L1 or anti-PD-L2 antibody is a bispecific antibody, a multispecific antibody, a single domain antibody, a fusion protein comprising an antibody portion, or any other variants or derivatives thereof. In some embodiments, the inhibitor of PD-1 ligand is an inhibitor (e.g., peptide, protein or small molecule) of both PD-L1 and PD-L2. Exemplary inhibitors of both PD-L1 and PD-L2 include, but are not limited to, AUR-012, and AMP-224. In some embodiments, the inhibitor of PD-L1 and the inhibitor of PD-L2 can be used interchangeably in any of the methods of treatment described herein.

In some embodiments, there is provided a method of treating a solid or lymphatic tumor in an individual (such as a human), comprising: a) locally administering to the site of the tumor an effective amount of an oncolytic virus (such as an oncolytic adenovirus); and b) systemically administering an effective amount of an inhibitor of PD-1 ligand (such as an anti-PD-L1 or anti-PD-L2 antibody, or an inhibitor of both PD-L and PD-L2), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the oncolytic virus is attenuated (for example through multiple passages, inactivation or genetic modification). In some embodiments, the oncolytic virus preferentially replicates in a cancer cell, such as an Rb-pathway defective cancer cell. In some embodiments, the inhibitor of PD-1 ligand is an anti-PD-L1 antibody, for example, KY-1003, MCLA-145, atezolizumab, BMS935559, MPDL3280A, MEDI4736, Avelumab, or STI-A1010. In some embodiments, the inhibitor of PD-1 ligand is an anti-PD-L2 antibody. In some embodiments, the inhibitor of PD-1 ligand is an inhibitor (e.g., peptide, protein or small molecule) of both PD-L1 and PD-L2, such as AUR-012, and AMP-224. In some embodiments, the oncolytic virus is administered directly into the tumor. In some embodiments, the oncolytic virus is administered to the tissue having the tumor. In some embodiments, the oncolytic virus is administered weekly. In some embodiments, the inhibitor of PD-1 ligand is administered intravenously. In some embodiments, the oncolytic virus and the inhibitor of PD-1 ligand are administered sequentially. In some embodiments, the oncolytic virus is administered prior to (such as immediately prior to) the administration of the inhibitor of PD-1 ligand. In some embodiments, the oncolytic virus is administered after (such as immediately after) the administration of the inhibitor of PD-1 ligand. In some embodiments, the oncolytic virus and the inhibitor of PD-1 ligand are administered simultaneously. In some embodiments, the method further comprises local administration of a second immunomodulator, such as an immune checkpoint inhibitor or an immune-stimulating agent. In some embodiments, the method further comprises administration (such as systemic or local to the site of the tumor) of a third immunomodulator, such as an immune checkpoint inhibitor or an immune-stimulating agent.

In some embodiments, there is provided a method of treating a solid or lymphatic tumor in an individual, comprising: a) locally administering to the site of the tumor an effective amount of an oncolytic virus (such as oncolytic adenovirus); and b) systemically administering an effective amount of an inhibitor of PD-1 ligand (such as an anti-PD-L1 or anti-PD-L2 antibody, or an inhibitor of both PD-L and PD-L2), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the tumor-specific promoter is an E2F-1 promoter, such as a human E2F-1 promoter or an E2F-1 promoter comprising the nucleotide sequence set forth in SEQ ID NO: 1. In some embodiments, the viral gene essential for replication of the virus is selected from the group consisting of E1A. E1B, and E4. In some embodiments, the heterologous gene is operably linked to a viral promoter, such as the E3 promoter. In some embodiments, the immune-related molecule is GM-CSF.

In some embodiments, there is provided a method of treating a solid or lymphatic tumor in an individual, comprising: a) locally administering to the site of the tumor an effective amount of an adenovirus serotype 5; and b) systemically administering an effective amount of an inhibitor of PD-1 ligand (such as an anti-PD-L1 or anti-PD-L2 antibody, or an inhibitor of both PD-L and PD-L2), wherein the endogenous E1a promoter of a native adenovirus is replaced by the human E2F1-promoter, and E3 19kD coding region of the native adenovirus is replaced by a heterologous gene encoding an immune-related molecule (such as cytokine or chemokine, for example, GM-CSF). In some embodiments, the tumor-specific promoter is a human E2F-1 promoter or an E2F-1 promoter comprising the nucleotide sequence set forth in SEQ ID NO: 1.

In some embodiments, there is provided a method of treating a solid or lymphatic tumor in an individual, comprising: a) locally administering to the site of the tumor an effective amount of CG0070; and b) systemically administering an effective amount of an inhibitor of PD-1 ligand (such as an anti-PD-L1 or anti-PD-L2 antibody, or an inhibitor of both PD-L1 and PD-L2). In some embodiments, the inhibitor of PD-1 ligand is an anti-PD-L1 antibody, for example, KY-1003, MCLA-145, atezolizumab, BMS935559, MPDL3280A, MEDI4736, Avelumab, or STI-A1010. In some embodiments, the inhibitor of PD-1 ligand is an anti-PD-L2 antibody. In some embodiments, the inhibitor of PD-1 ligand is an inhibitor (e.g., peptide, protein or small molecule) of both PD-L1 and PD-L2, such as AUR-012, and AMP-224. In some embodiments, the CG0070 is administered directly into the tumor. In some embodiments, the CG0070 is administered to the tissue having the tumor. In some embodiments, the CG007 is administered at a dose of about $1\times10^8$ to about $1\times10^{14}$ viral particles (vp) (such as any of about $1\times10^8$ to about $1\times10^{10}$, about $1\times10^{10}$ to about $1\times10^{12}$, or about $1\times10^{12}$ to about $1\times10^{14}$ vp). In some embodiments, CG0070 is administered weekly. In some embodiments, CG0070 is administered for about 1 week to about 6 weeks (such as at least about any of 3 weeks, 4 weeks or 5 weeks). In some embodiments, the inhibitor of PD-1 ligand is administered intravenously. In some embodiments, the CG0070 and the inhibitor of PD-1 ligand are administered sequentially. In some embodiments, the CG0070 is administered prior to (such as immediately prior to) the administration of the inhibitor of PD-1 ligand. In some embodiments, the CG0070 is administered after (such as immediately after) the administration of the inhibitor of PD-1 ligand. In some embodiments, the CG0070 and the inhibitor of PD-1 ligand are administered simultaneously. In some embodiments, the method further comprises local administration of a second immunomodulator, such as an immune checkpoint inhibitor or an immune-stimulating agent. In some embodiments, the method further comprises administration (such as systemic or local to the site of the tumor) of a third immunomodulator, such as an immune checkpoint inhibitor or an immune-stimulating agent.

In some embodiments, there is provided a method of treating a solid or lymphatic tumor in an individual, comprising: a) intratumorally administering an effective amount of CG0070; b) intravenously administering an effective amount of an inhibitor of PD-L1 (such as an antagonist anti-PD-L1 antibody, for example, atezolizumab); and c) intratumorally administering an effective amount of an inhibitor of CTLA-4 (such as an anti-CTLA-4 antibody, for example Ipilimumab). In some embodiments, the CG0070 is administered at a dose of about $1\times10^8$ to about $1\times10^{14}$ viral particles (vp) (such as any of about $1\times10^8$ to about $1\times10^{10}$, about $1\times10^{10}$ to about $1\times10^{12}$, or about $1\times10^{12}$ to about $1\times10^{14}$ vp). In some embodiments, CG0070 is administered weekly. In some embodiments, the inhibitor of PD-L1 is administered at a dose of about 1 mg/kg to about 20 mg/kg, or about 750 mg to about 1200 mg. In some embodiments, the inhibitor of PD-L1 is administered about monthly to about biweekly (such as about once every 2 weeks, about once every 3 weeks, or about once every 4 weeks). In some embodiments, the inhibitor of CTLA-4 is administered at a dose of about 0.1 mg/Kg to about 10 mg/Kg (such as any of about 0.1 mg/Kg to about 1 mg/Kg, about 1 mg/Kg to about 5 mg/Kg, or about 5 mg/Kg to about 10 mg/Kg weekly). In some embodiments, the inhibitor of CTLA-4 is administered weekly. In some embodiments, the inhibitor of CTLA-4 is administered immediately after (e.g., no more than 5 minutes after) administration of CG0070. In some embodiments, the inhibitor of PD-L1 is an antagonist antibody of PD-L1, such as atezolizumab. In some embodiments, the inhibitor of CTLA-4 is an anti-CTLA-4 antibody, for example Ipilimumab (e.g., YERVOY®). In some embodiments, the inhibitor of CTLA-4 is an engineered lipocalin protein, for example an anticalin that specifically recognizes CTLA-4. In some embodiments, the individual is further administered intratumorally an effective amount of DDM as a transduction enhancing agent in combination with the CG0070 administration. In some embodiments, CG0070 and the inhibitor of CTLA-4 are administered by injection into the tissue having the tumor. In some embodiments. CG0070 and the inhibitor of CTLA-4 are administered by injection directly into the tumor. In some embodiments, the CG0070 and the inhibitor of PD-L1 are administered sequentially. In some embodiments, the CG0070 is administered prior to (such as immediately prior to) the administration of the inhibitor of PD-L1. In some embodiments, the CG0070 is administered after (such as immediately after) the administration of the inhibitor of PD-L1. In some embodiments, the CG0070 and the inhibitor of PD-L1 are administered simultaneously. In some embodiments. CG0070 is administered for about 1 to about 6 weeks as one treatment course. In some embodiments, the treatment course is repeated every about two to about three months. In some embodiments, the solid or lymphatic tumor is selected from the group consisting of head and neck cancer, breast cancer, colorectal cancer, liver cancer, pancreatic adenocarcinoma, gallbladder and bile duct cancer, ovarian cancer, cervical cancer, small cell lung cancer, non-small cell lung cancer, renal cell carcinoma, bladder cancer, prostate cancer, bone cancer, mesothelioma, brain cancer, soft tissue sarcoma, uterine cancer, thyroid cancer, nasopharyngeal carcinoma, and melanoma. In some embodiments, the solid or lymphatic tumor has been refractory to prior therapy. In some embodiments, the method further comprises local administration of a second immunomodulator, such as an immune-stimulating agent. In some embodiments, the second immunomodulator is a CD40 activator, such as an agonist anti-CD40 antibody (e.g., APX005M). In some embodiments, the second immunomodulator is a 4-1BB activator, such as an agonist anti-4-1BB antibody (e.g., PF-05082566).

In some embodiments, the immune-stimulating agent is an activator of CD40. In some embodiments, the activator of CD40 is an agonistic anti-CD40 antibody. Any of the known anti-CD40 antibodies may be used in the present invention, including, but not limited to, CP-870.893, Dacetuzumab (also known as SGN-40), ChiLob 7/4, APX005, and APX005M. BI-655064, and BMS-986090. In some embodiments, the agonistic anti-CD40 antibody is a monoclonal antibody or a polyclonal antibody. In some embodiments, the agonistic anti-CD40 antibody is an antigen-binding fragment selected from the group consisting of Fab, Fab', F(ab')$_2$, Fv, scFv, and other antigen-binding subsequences of the full-length anti-CD40 antibody. In some embodiments, the agonistic anti-CD40 antibody is a human, humanized, or chimeric antibody. In some embodiments, the agonistic anti-CD40 antibody is a bispecific antibody, a multispecific antibody, a single domain antibody, a fusion protein comprising an antibody portion, or any other variants or derivatives thereof. In some embodiments, the activator of CD40 is a natural or engineered CD40 ligand, such as CD40L. In some embodiments, the activator of CD40 is an inhibitor of the interaction between CD40 and CD40L. In some embodiments, the activator of CD40 increases the signaling of CD40.

Thus, for example, in some embodiments, there is provided a method of treating a solid or lymphatic tumor in an individual (such as a human), comprising: a) locally administering to the site of the tumor an effective amount of an oncolytic virus (such as an oncolytic adenovirus); and b) systemically administering an effective amount of an activator of CD40 (such as an agnostic anti-CD40 antibody, for example, CP-870,893, Dacetuzumab. ChiLob 7/4 or APX005M), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the oncolytic virus is attenuated (for example through multiple passages, inactivation or genetic modification). In some embodiments, the oncolytic virus preferentially replicates in a cancer cell, such as an Rb-pathway defective cancer cell. In some embodiments, the activator of CD40 is an agnostic anti-CD40 antibody, for example, CP-870,893, Dacetuzumab, ChiLob 7/4 or APX005M. In some embodiments, the oncolytic virus is administered directly into the tumor. In some embodiments, the oncolytic virus is administered to the tissue having the tumor. In some embodiments, the oncolytic virus is administered weekly. In some embodiments, the activator of CD40 is administered intravenously. In some embodiments, the oncolytic virus and the activator of CD40 are administered sequentially. In some embodiments, the oncolytic virus is administered prior to (such as immediately prior to) the administration of the activator of CD40. In some embodiments, the oncolytic virus is administered after (such as immediately after) the administration of the activator of CD40. In some embodiments, the oncolytic virus and the activator of CD40 are administered simultaneously. In some embodiments, the method further comprises local administration of a second immunomodulator, such as an immune checkpoint inhibitor or an immune-stimulating agent. In some embodiments, the method further comprises administration (such as systemic or local to the site of the tumor) of a third immunomodulator, such as an immune checkpoint inhibitor or an immune-stimulating agent.

In some embodiments, there is provided a method of treating a solid or lymphatic tumor in an individual, comprising: a) locally administering to the site of the tumor an effective amount of an oncolytic virus (such as oncolytic adenovirus); and b) systemically administering an effective amount of an activator of CD40 (such as an agnostic anti-CD40 antibody, for example, CP-870,893. Dacetuzumab, ChiLob 7/4 or APX005M), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the tumor-specific promoter is an E2F-1 promoter, such as a human E2F-1 promoter or an E2F-1 promoter comprising the nucleotide sequence set forth in SEQ ID NO: 1. In some embodiments, the viral gene essential for replication of the virus is selected from the group consisting of E1A, E1B, and E4. In some embodiments, the heterologous gene is operably linked to a viral promoter, such as the E3 promoter. In some embodiments, the immune-related molecule is GM-CSF.

In some embodiments, there is provided a method of treating a solid or lymphatic tumor in an individual, comprising: a) locally administering to the site of the tumor an effective amount of an adenovirus serotype 5; and b) systemically administering an effective amount of an activator of CD40 (such as an agnostic anti-CD40 antibody, for example, CP-870,893, Dacetuzumab. ChiLob 7/4 or APX005M), wherein the endogenous E1a promoter of a native adenovirus is replaced by the human E2F1-promoter, and E3 19kD coding region of the native adenovirus is replaced by a heterologous gene encoding an immune-related molecule (such as cytokine or chemokine, for example, GM-CSF). In some embodiments, the tumor-specific promoter is a human E2F-1 promoter or an E2F-1 promoter comprising the nucleotide sequence set forth in SEQ ID NO: 1.

In some embodiments, there is provided a method of treating a solid or lymphatic tumor in an individual, comprising: a) locally administering to the site of the tumor an effective amount of CG0070; and b) systemically administering an effective amount of an activator of CD40 (such as an agnostic anti-CD40 antibody, for example, CP-870,893, Dacetuzumab, ChiLob 7/4 or APX005M). In some embodiments, the activator of CD40 is an agnostic anti-CD40 antibody, for example, CP-870.893. Dacetuzumab, ChiLob 7/4 or APX005M. In some embodiments, the CG0070 is administered directly into the tumor. In some embodiments, the CG0070 is administered to the tissue having the tumor. In some embodiments, the CG007 is administered at a dose of about $1 \times 10^8$ to about $1 \times 10^{14}$ viral particles (vp) (such as any of about $1 \times 10^8$ to about $1 \times 10^{10}$, about $1 \times 10^{10}$ to about $1 \times 10^{12}$, or about $1 \times 10^{12}$ to about $1 \times 10^{14}$ vp). In some embodiments, CG0070 is administered weekly. In some embodiments, CG0070 is administered for about 1 week to about 6 weeks (such as at least about any of 3 weeks, 4 weeks or 5 weeks). In some embodiments, the activator of CD40 is administered intravenously. In some embodiments, the CG0070 and the activator of CD40 are administered sequentially. In some embodiments, the CG0070 is administered prior to (such as immediately prior to) the administration of the activator of CD40. In some embodiments, the CG0070 is administered after (such as immediately after) the administration of the activator of CD40. In some embodiments, the CG0070 and the activator of CD40 are administered simultaneously. In some embodiments, the method further comprises local administration of a second immunomodulator, such as an immune checkpoint inhibitor or an immune-stimulating agent. In some embodiments, the method further comprises administration (such as systemic or local to the site of the tumor) of a third immunomodulator, such as an immune checkpoint inhibitor or an immune-stimulating agent.

In some embodiments, the immune-stimulating agent is an activator of OX40. In some embodiments, the activator of OX40 is an agonistic anti-OX40 antibody. Any of the known anti-OX40 antibodies may be used in the present invention, including, but not limited to, MEDI6469, MEDI0562, MEDI6383, GSK3174998, KHK4083 and InVivoMAb clone OX-86. In some embodiments, the agonistic anti-OX40 antibody is a monoclonal antibody or a polyclonal antibody. In some embodiments, the agonistic anti-OX40 antibody is an antigen-binding fragment selected from the group consisting of Fab, Fab', F(ab')$_2$, Fv, scFv, and other antigen-binding subsequences of the full-length anti-OX40 antibody. In some embodiments, the agonistic anti-OX40 antibody is a human, humanized, or chimeric antibody. In some embodiments, the agonistic anti-OX40 antibody is a bispecific antibody, a multispecific antibody, a single domain antibody, a fusion protein comprising an antibody portion, or any other variants or derivatives thereof. In some embodiments, the activator of OX40 is a natural or engineered OX40 ligand, such as OX40L. In some embodiments, the activator of OX40 is an inhibitor of the interaction between OX40 and OX40L. Any of the inhibitors of interaction between OX40 and OX40L may be used in the present invention, see, for example, U.S. Pat. No. 8,283,450, U.S. Ser. No. 11/867,621, U.S. Pat. Nos. 7,547,438, 7,063, 845, 7,537,763 and 5,801,227. In some embodiments, the activator of OX40 increases the signaling of OX40.

Thus, for example, in some embodiments, there is provided a method of treating a solid or lymphatic tumor in an individual (such as a human), comprising: a) locally administering to the site of the tumor an effective amount of an oncolytic virus (such as an oncolytic adenovirus); and b) systemically administering an effective amount of an activator of OX40 (such as an agnostic anti-OX40 antibody, for example, MEDI6469, MEDI0562, MEDI6383. GSK3174998, KHK4083 or InVivoMAb clone OX-86), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the oncolytic virus is attenuated (for example through multiple passages, inactivation or genetic modification). In some embodiments, the oncolytic virus preferentially replicates in a cancer cell, such as an Rb-pathway defective cancer cell. In some embodiments, the activator of OX40 is an agnostic anti-OX40 antibody, for example, MEDI6469, MEDI0562, MEDI6383, GSK3174998. KHK4083 or InVivoMAb clone OX-86. In some embodiments, the oncolytic virus is administered directly into the tumor. In some embodiments, the oncolytic virus is administered to the tissue having the tumor. In some embodiments, the oncolytic virus is administered weekly. In some embodiments, the activator of OX40 is administered intravenously. In some embodiments, the oncolytic virus and the activator of OX40 are administered sequentially. In some embodiments, the oncolytic virus is administered prior to (such as immediately prior to) the administration of the activator of OX40. In some embodiments, the oncolytic virus is administered after (such as immediately after) the administration of the activator of OX40. In some embodiments, the oncolytic virus and the activator of OX40 are administered simultaneously. In some embodiments, the method further comprises local administration of a second immunomodulator, such as an immune checkpoint inhibitor or an immune-stimulating agent. In some embodiments, the method further comprises administration (such as systemic or local to the site of the tumor) of a third immunomodulator, such as an immune checkpoint inhibitor or an immune-stimulating agent.

In some embodiments, there is provided a method of treating a solid or lymphatic tumor in an individual, comprising: a) locally administering to the site of the tumor an effective amount of an oncolytic virus (such as oncolytic adenovirus); and b) systemically administering an effective amount of an activator of OX40 (such as an agnostic anti-OX40 antibody, for example, MEDI6469. MEDI0562, MEDI6383. GSK3174998. KHK4083 or InVivoMAb clone OX-86), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the tumor-specific promoter is an E2F-1 promoter, such as a human E2F-1 promoter or an E2F-1 promoter comprising the nucleotide sequence set forth in SEQ ID NO: 1. In some embodiments, the viral gene essential for replication of the virus is selected from the group consisting of E1A, E1B, and E4. In some embodiments, the heterologous gene is operably linked to a viral promoter, such as the E3 promoter. In some embodiments, the immune-related molecule is GM-CSF.

In some embodiments, there is provided a method of treating a solid or lymphatic tumor in an individual, comprising: a) locally administering to the site of the tumor an effective amount of an adenovirus serotype 5; and b) systemically administering an effective amount of an activator of OX40 (such as an agnostic anti-OX40 antibody, for example, MEDI6469, MEDI0562, MEDI6383, GSK3174998, KHK4083 or InVivoMAb clone OX-86), wherein the endogenous E1a promoter of a native adenovirus is replaced by the human E2F1-promoter, and E3 19kD coding region of the native adenovirus is replaced by a heterologous gene encoding an immune-related molecule (such as cytokine or chemokine, for example, GM-CSF). In some embodiments, the tumor-specific promoter is a human E2F-1 promoter or an E2F-1 promoter comprising the nucleotide sequence set forth in SEQ ID NO: 1.

In some embodiments, there is provided a method of treating a solid or lymphatic tumor in an individual, comprising: a) locally administering to the site of the tumor an effective amount of CG0070; and b) systemically administering an effective amount of an activator of OX40 (such as an agnostic anti-OX40 antibody, for example, MEDI6469, MEDI0562, MEDI6383, GSK3174998, KHK4083 or InVivoMAb clone OX-86). In some embodiments, the activator of OX40 is an agnostic anti-OX40 antibody, for example, MEDI6469, MEDI0562, MEDI6383, GSK3174998. KHK4083 or InVivoMAb clone OX-86. In some embodiments, CG0070 is administered directly into the tumor. In some embodiments. CG0070 is administered to the tissue having the tumor. In some embodiments, the CG0070 is administered at a dose of about $1\times10^8$ to about $1\times10^{14}$ viral particles (vp) (such as any of about $1\times10^8$ to about $1\times10^{10}$, about $1\times10^{10}$ to about $1\times10^{12}$, or about $1\times10^{12}$ to about $1\times10^{14}$ vp). In some embodiments, CG0070 is administered weekly. In some embodiments, CG0070 is administered for about 1 week to about 6 weeks (such as at least about any of 3 weeks, 4 weeks or 5 weeks). In some embodiments, the activator of OX40 is administered at a dose of about 0.001 mg/kg to about 10 mg/kg (such as such as any of about 0.003 mg/Kg to about 0.01 mg/Kg, about 0.01 mg/Kg to about 0.1 mg/Kg, about 0.1 mg/Kg to about 1 mg/Kg, about 1 mg/Kg to about 5 mg/Kg, or about 5 mg/Kg to about 10 mg/Kg). In some embodiments, the activator of OX40 is administered about monthly to about weekly (such as about weekly, about once every 2 weeks, or about once every 3 weeks). In some embodiments, the CG0070 and the activator of OX40 are administered sequentially. In some embodiments, the CG0070 is administered prior to (such as immediately prior to) the administration of the activator of OX40. In some embodiments, the CG0070 is administered after (such as immediately after) the administration of the activator of OX40. In some embodiments, CG0070 and the activator of OX40 are administered simultaneously. In some embodiments, the method further comprises local administration of a second immunomodulator, such as an immune checkpoint inhibitor or an immune-stimulating agent. In some embodiments, the method further comprises administration (such as systemic or local to the site of the tumor) of a third immunomodulator, such as an immune checkpoint inhibitor or an immune-stimulating agent.

In some embodiments, there is provided a method of treating a solid or lymphatic tumor in an individual, comprising: a) intratumorally administering an effective amount of CG0070; b) intravenously administering an effective amount of an OX40 activator (such as an agnostic anti-OX40 antibody, for example, MEDI6469, MEDI0562, MEDI6383. GSK3174998, KHK4083 or InVivoMAb clone OX-86); and c) intratumorally administering an effective amount of an inhibitor of CTLA-4 (such as an anti-CTLA-4 antibody, for example Ipilimumab). In some embodiments, the CG0070 is administered at a dose of about $1\times10^8$ to about $1\times10^{14}$ viral particles (vp) (such as any of about $1\times10^8$ to about $1\times10^{10}$, about $1\times10^{10}$ to about $1\times10^{12}$, or about $1\times10^{12}$ to about $1\times10^{14}$ vp). In some embodiments, CG0070 is administered weekly. In some embodiments, the OX40 activator is administered at a dose of about 0.001 mg/kg to about 10 mg/kg (such as such as any of about 0.003 mg/Kg to about 0.01 mg/Kg, about 0.01 mg/Kg to about 0.1 mg/Kg, about 0.1 mg/Kg to about 1 mg/Kg, about 1 mg/Kg to about 5 mg/Kg, or about 5 mg/Kg to about 10 mg/Kg). In some embodiments, the activator of OX40 is administered about monthly to about weekly (such as about weekly, about once every 2 weeks, or about once every 3 weeks). In some embodiments, the inhibitor of CTLA-4 is administered at a dose of about 0.1 mg/Kg to about 10 mg/Kg (such as any of about 0.1 mg/Kg to about 1 mg/Kg, about 1 mg/Kg to about 5 mg/Kg, or about 5 mg/Kg to about 10 mg/Kg weekly). In some embodiments, the inhibitor of CTLA-4 is administered weekly. In some embodiments, the inhibitor of CTLA-4 is administered immediately after (e.g., no more than 5 minutes after) administration of CG0070. In some embodiments, the OX40 activator is an agonistic antibody of OX40, such as GSK3174998. In some embodiments, the inhibitor of CTLA-4 is an anti-CTLA-4 antibody, for example Ipilimumab (e.g., YERVOY®). In some embodiments, the inhibitor of CTLA-4 is an engineered lipocalin protein, for example an anticalin that specifically recognizes CTLA-4. In some embodiments, the individual is further administered intratumorally an effective amount of DDM as a transduction enhancing agent in combination with the CG0070 administration. In some embodiments, the CG0070 and the activator of OX40 are administered sequentially. In some embodiments, the CG0070 is administered prior to (such as immediately prior to) the administration of the activator of OX40. In some embodiments, the CG0070 is administered after (such as immediately after) the administration of the activator of OX40. In some embodiments, CG0070 and the activator of OX40 are administered simultaneously. In some embodiments, CG0070 and the inhibitor of CTLA-4 are administered by injection into the tissue having the tumor. In some embodiments. CG0070 and the inhibitor of CTLA-4 are administered by injection directly into the tumor. In some embodiments, CG0070 is administered for about 1 to about 6 weeks as one treatment course. In some embodiments, the treatment course is repeated every about two to about three months. In some embodiments, the solid or lymphatic tumor is selected from the group consisting of head and neck cancer, breast cancer, colorectal cancer, liver cancer, pancreatic adenocarcinoma, gallbladder and bile duct cancer, ovarian cancer, cervical cancer, small cell lung cancer, non-small cell lung cancer, renal cell carcinoma, bladder cancer, prostate cancer, bone cancer, mesothelioma, brain cancer, soft tissue sarcoma, uterine cancer, thyroid cancer, nasopharyngeal carcinoma, and melanoma. In some embodiments, the solid or lymphatic tumor has been refractory to prior therapy. In some embodiments, the method further comprises intratumoral administration of a second immunomodulator, such as an immune-stimulating agent. In some embodiments, the second immunomodulator is a CD40 activator, such as an agonist anti-CD40 antibody (e.g., APX005M). In some embodiments, the second immunomodulator is a 4-1BB activator, such as an agonist anti-4-1BB antibody (e.g., PF-05082566).

The methods described herein may further comprise a step of locally administering to the site of the tumor a pretreatment composition prior to the administration of the oncolytic virus. In some embodiments, the pretreatment composition comprises a transduction enhancing agent, such as N-Dodecyl-β-D-maltoside (DDM). DDM is a nonionic surfactant comprised of a maltose derivatized with a single twelve-carbon chain, and acts as a mild detergent and solubilizing agent. It has been used as a food additive and is known to enhance mucosal surface permeation in rodents, probably due to its effect on membrane associated GAG and tight junctions.

The pretreatment composition can be administered directly into the tumor or to a tissue having the tumor. In some embodiments, the pretreatment composition comprises a solution of the transduction enhancing agent (such as DDM). Suitable concentration of the pretreatment composition (such as DDM solution) include, but are not limited to, about any one of 0.01%, 0.05%, 0.1%, 0.2%, 0.3%, 0.4%, 0.5%, 1%, 2%, 3%, 4%, or 5% of the transducing enchanting agent (such as DDM). In some embodiments, the pretreatment composition comprises any of about 0.01% to about 0.05%, about 0.05% to about 0.1%, about 0.1% to about 0.5%, about 0.5% to about 1%, about 1% to about 2%, about 2% to about 3%, about 3% to about 4%, about 4% to about 5%, about 0.01% to about 1%, about 0.05% to about 2%, about 1% to about 5%, or about 0.1% to about 5% of the transduction enhancing agent (such as DDM).

In some embodiments, the pretreatment (such as DDM) is administered immediately (such as no more than 5 minutes) prior to the administration of the oncolytic virus. In some embodiments, the pretreatment (such as DDM) is administered no more than about any of 5 minutes, 10 minutes, 15 minutes, 20 minutes, 30 minutes, 45 minutes, 1 hour, 90 minutes, 2 hours, 3 hours or 4 hours before the administration of the oncolytic virus. In some embodiments, the pretreatment (such as DDM) is administered no more than about 2 hours before the administration of the oncolytic virus.

Suitable dosages for the pretreatment composition (such as DDM) include, but are not limited to, about any of 0.1 mg/kg, 0.5 mg/kg, 1 mg/kg, 1.5 mg/kg, 2 mg/kg, 2.5 mg/kg, 5 mg/kg, 10 mg/kg, 25 mg/kg, 50 mg/kg, 100 mg/kg, 150 mg/kg, 200 mg/kg, 250 mg/kg, 300 mg/kg, 400 mg/kg, 500 mg/kg, 0.1 mg/kg to 0.5 mg/kg, 0.5 mg/kg to 1 mg/kg, 1 mg/kg to 2 mg/kg, 2 mg/kg to 5 mg/kg, 5 mg/kg to 10 mg/kg, 10 mg/kg to 25 mg/kg, 25 mg/kg to 50 mg/kg, 50 mg/kg to 100 mg/kg, 100 mg/kg to 150 mg/kg, 150 mg/kg to 200 mg/kg, 200 mg/kg to 250 mg/kg, 250 mg/kg to 500 mg/kg, or 0.5 mg/kg to about 5 mg/kg. In some embodiments, a suitable dosage for the pretreatment composition is about any one of 0.1 g, 0.2 g, 0.5 g, 0.75 g, 1 g, 1.5 g, 2 g, 2.5 g, 5 g, or 10 g of the transduction enhancing agent (such as DDM).

In some embodiments, the individual (e.g., wholly or only at the site of the tumor) is subject to a prior therapy prior to the administration of the oncolytic virus and the immunomodulator (including combination of immunomodulators). In some embodiments, the prior therapy is tumor site preparation using one or more (such as 1, 2, 3, 4, 5, or more) treatment modalities, including, but are not limited to radiation therapy, administration of one or more immune-related molecules, administration of other therapeutic agents, and combinations thereof. It is believed that adding other pretreatment preparations can increase the chance of success for the methods described above. Without being bound by any theory or hypothesis, for example, local radiation, with or without lymphodepletion effects, or chemotherapy, may increase the chance of the infectious process, and may deplete the more sensitive Treg cells at the tumor sites, thereby reviving the exhausted or telorized T memory cells. Similarly, tumor site preparations prior to or in concomitant with the administration of the invention combination at the tumor site can involve cytokines, chemokines, small molecules and other well-known beneficial immunomodulators, such as IL2, IL12, OX40, CD40 and 4-1BB agonist. These tumor site preparation modalities can be given in conjunction with or in sequence depending on needs.

In some embodiments, the prior therapy is radiation therapy (e.g., with or without chemotherapy). In some embodiments, the radiation therapy is in combination with chemotherapy. In some embodiments, the prior therapy is radiation therapy to the whole body. In some embodiments, the prior therapy is radiation therapy to only tumor sites. In some embodiments, the prior therapy is radiation therapy to tissues having the tumor. In some embodiments, the prior therapy is radiation therapy to only the site of the tumor selected for local administration of the oncolytic virus. In some embodiments, the prior therapy is radiation therapy to only a tissue having the tumor selected for local administration of the oncolytic virus. In some embodiments, the dose of the radiation therapy is insufficient to treat the tumor cells. For example, a suitable dosage of the radiation therapy is about any one of 1 Gy, 5 Gy, 10 Gy, 15 Gy, 20 Gy, 25 Gy, 30 Gy, 35 Gy, 40 Gy, 45 Gy, 50 Gy, 55 Gy, 60 Gy, 65 Gy, 70 Gy, 75 Gy, 80 Gy, 90 Gy or 100 Gy. In some embodiments, the dose of the radiation therapy is no more than about any one of 1 Gy, 5 Gy, 10 Gy, 15 Gy, 20 Gy, 25 Gy, 30 Gy, 35 Gy, 40 Gy, 45 Gy, 50 Gy, 55 Gy, 60 Gy, 65 Gy, 70 Gy, 75 Gy, 80 Gy, 90 Gy or 100 Gy. In some embodiments, the dose of the radiation therapy is any one of about 1 Gy to about 5 Gy, about 5 Gy to about 10 Gy, about 10 Gy to about 15 Gy, about 15 Gy to about 20 Gy, about 20 Gy to about 25 Gy, about 25 Gy to about 30 Gy, about 30 Gy to about 35 Gy, about 5 Gy to about 15 Gy, about 10 Gy to about 20 Gy, about 20 Gy to about 30 Gy, about 30 Gy to about 40 Gy, about 40 Gy to about 50 Gy, about 50 Gy to about 60 Gy, about 60 Gy to about 70 Gy, about 70 Gy to about 80 Gy, about 80 Gy to about 100 Gy, about 10 Gy to about 30 Gy, about 20 Gy to about 40 Gy, about 1Gy to about 25 Gy, about 25 Gy to about 50 Gy, about 30 Gy to about 60 Gy, about 60 Gy to about 80 Gy, or about 10 Gy to about 60 Gy. The suitable dosage of the radiation therapy may also depend on the type, stage and location of the tumor.

In some embodiments, the radiation therapy is administered in more than one fraction, such as about any one of 2, 3, 4, 5, 6, 7, 8, 9, 10, 12, 15, 16, 18, 20 or more fractions. In some embodiments, the radiation therapy fractions are administered over the course of about any one of 1 day, 2 days, 3 days, 4 days, 5 days, 6 days, 1 week, 2 weeks, 3 weeks, 4 weeks, 5 weeks, 6 weeks, 7 weeks or more. In some embodiments, the radiation therapy fractions are administered over the course of any one of about 1 day to about 5 days, about 1 week to about 2 weeks, about 2 weeks to about 3 weeks, about 3 weeks to about 4 weeks, about 4 weeks to about 5 weeks, about 5 weeks to about 6 weeks, about 6 weeks to about 7 weeks, about 2 weeks to about 4 weeks, about 4 weeks to about 6 weeks, or about 1 week to about 6 weeks. In some embodiments, the radiation therapy is administered about two fractions per day. In some embodiments, each fraction of the radiation therapy is about 1.8 Gy to about 2 Gy per day, five days a week, for an adult, or about 1.5 Gy to about 1.8 Gy per day, five days a week for a child. In some embodiments, each fraction of the radiation therapy is about any one of 1 Gy, 1.5 Gy, 2 Gy, 2.5 Gy, 5 Gy, 10 Gy, 15 Gy, 20 Gy, 30 Gy, 40 Gy, 50 Gy or more. In some embodiments, each fraction of the radiation therapy is any one of about 1 Gy to about 1.5 Gy, about 1.5 Gy to about 2 Gy, about 1 Gy to about 2.5 Gy, about 2.5 Gy to about 5 Gy, about 5 Gy to about 10 Gy, about 10 Gy to about 15 Gy, about 15 Gy to about 20 Gy, about 20 Gy to about 30 Gy, about 25 Gy to about 50 Gy, about 1 Gy to about 10 Gy, or about 2 Gy to about 20 Gy. In some embodiments, the radiation therapy is administered in a single fraction.

In some embodiments, the radiation therapy is aim at lymphodepletion, either as a single dose fraction per day or in multiple fractions over days to weeks. In some embodiments, the lymphodepletion radiation therapy is given as a total body irradiation. In some embodiments, the lymphodepletion is only given to local tumor sites, or to tissues with the tumor. In some embodiments, the lymphodepletion radiation therapy is administered two fractions per day. In some embodiments, each fraction of the lymphodepletion radiation therapy is about 1 Gy to about 2 Gy per day, five days a week, for an adult, or about 0.5 Gy to about 1.8 Gy per day, five days a week for a child. In some embodiments, each fraction of the radiation therapy is about any one of 1 Gy, 1.5 Gy, 2 Gy, 2.5 Gy, 5 Gy, 10 Gy, 15 Gy, 20 Gy, 30 Gy, 40 Gy, 50 Gy or more. In some embodiments, each fraction of the radiation therapy is any one of about 1 Gy to about 1.5 Gy, about 1.5 Gy to about 2 Gy, about 1 Gy to about 2.5 Gy, about 2.5 Gy to about 5 Gy, about 5 Gy to about 10 Gy, about 10 Gy to about 15 Gy, about 15 Gy to about 20 Gy, about 20 Gy to about 30 Gy, about 25 Gy to about 50 Gy, about 1 Gy to about 10 Gy, or about 2 Gy to about 20 Gy. In some embodiments, lymphodepletion radiation therapy is administered with or without the use of a chemotherapeutic agent, such as but not limited to, cyclophosphamide and fludarabine.

Any of the known methods of radiation therapy may be used in the present invention, including, but not limited to external beam radiation therapy (EBRT or XRT), tele therapy, brachytherapy, sealed source radiation therapy, systemic radioisotope therapy (RIT), unsealed source radiation therapy, intraoperative radiation therapy (IORT), targeted intraoperative radiation therapy (TARGIT), intensity-modulated radiation therapy (IMRT), volumetric modulated arc therapy (VMAT), particle therapy, and auger therapy.

In some embodiments, the method for treating an individual having a solid or lymphatic tumor, comprising (a) locally administering a radiation therapy; b) locally administering to the site of the tumor an effective amount of an oncolytic virus (such as an oncolytic adenovirus, for example, CG0070); and c) systemically administering an effective amount of an immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the tumor-specific promoter is an E2F-1 promoter, such as a human E2F-1 promoter or an E2F-1 promoter comprising the nucleotide sequence set forth in SEQ ID NO: 1. In some embodiments, the viral gene essential for replication of the oncolytic virus is selected from the group consisting of E1A, E1B, and E4. In some embodiments, the heterologous gene is operably linked to a viral promoter, such as an E3 promoter. In some embodiments, the immune-related molecule is GM-CSF. In some embodiments, the radiation therapy is administered prior to the administration of the oncolytic virus and/or the immunomodulator (including combination of immunomodulators). In some embodiments, the radiation therapy is administered about 1 day to about 1 week (e.g., about 2 days) prior to the administration of the oncolytic virus and the immunomodulator (including combination of immunomodulators). In some embodiments, the radiation therapy, and/or the oncolytic virus are administered directly to the solid or lymphatic tumor. In some embodiments, the radiation therapy, and/or the oncolytic virus are administered to the tissue having the solid or lymphatic tumor. In some embodiments, the immunomodulator is a modulator of an immune checkpoint molecule selected from the group consisting of CTLA-4, PD-1, PD-L1, PD-L2, TIM3, B7-H3, B7-H4. LAG-3, KIR, and ligands thereof. In some embodiments, the immunomodulator is an immune-stimulating agent selected from the group consisting of activators of OX40, 4-1BB and CD40. In some embodiments, the method further comprises local administration of a second immunomodulator, such as an immune checkpoint inhibitor or an immune-stimulating agent. In some embodiments, the method further comprises administration (such as systemic or local to the site of the tumor) of a third immunomodulator, such as an immune checkpoint inhibitor or an immune-stimulating agent.

In some embodiments, the prior therapy comprises administration of a therapeutic agent. In some embodiments, the dosage of the therapeutic agent is sufficient to treat the tumor. In some embodiments, the dosage of the therapeutic agent is insufficient to treat the tumor. In some embodiments, the therapeutic agent is any one or combination of chemotherapeutic agents known in the art, for example, cyclosphamide. In some embodiments, the therapeutic agent is any one or combination of agents targeting or blocking a cellular signaling pathway known in the art, for example, a BRAF inhibitor. In some embodiments, the therapeutic agent is any one or combination of cell therapies known in the art, for example, TIL cells, CAR/T cells, and/or TCR/T cells. In some embodiments, the therapeutic agent is an agent that increases the level of cytokines involved an immunogenic pathway. Any of the immune-related molecules described herein may be used as the therapeutic agent, including, but are not limited to, cytokines such as IL6, IL8 and IL18 (these cytokines can either have pro and/or anti-inflammatory actions, or some may promote new blood vessels formation and tumor growth), chemokines (such as CCL21 that can promote tumor spread by increase of lymphatic structures), growth factors (such as FLT3L), heat shock proteins, small molecule kinase inhibitors (such as JAK2 inhibitor), IAP inhibitors, STING activators (such as CDN). PRRago (such as CpG ODN (oligodeoxynucleotides). Imiquimod, or Poly I:C), TLR stimulators (such as GS-9620, AED-1419, CYT-003-QbG10, AVE-0675, or PF-7909), and RLR stimulators (such as RIG-I, Mda5, or LGP2 stimulators). In some embodiments, the therapeutic agent is an agent that causes dysfunction or damage to a structural component of a tumor. Exemplary agents include, but are not limited to, anti-VEGF antibody, a hyaluronidase, and n-dodecyl-β-maltoside. In some embodiments, the therapeutic agent induces immune cells, such as dendritic cells, B cells, and T cells (such as follicular T helper cells).

Any of the therapeutic agent/s described herein, e.g. chemotherapeutic agents, agents targeting or blocking cell signaling pathways, cytokines, chemokines, cell therapies, etc., can be administered directly or indirectly (e.g. through intravenous administration) to the tumor sites, either singly or in combination.

In some embodiments, the method for treating an individual having a solid or lymphatic tumor, comprising: (a) locally administering a therapeutic agent (such as a chemokine, or a PRRago); b) locally administering to the site of the tumor an effective amount of an oncolytic virus (such as an oncolytic adenovirus, for example, CG0070); and c) systemically administering an effective amount of an immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the tumor-specific promoter is an E2F-1 promoter, such as a human E2F-1 promoter or an E2F-1 promoter comprising the nucleotide sequence set forth in SEQ ID NO: 1. In some embodiments, the viral gene essential for replication of the oncolytic virus is selected from the group consisting of E1A, E1B, and E4. In some embodiments, the heterologous gene is operably linked to a viral promoter, such as an E3 promoter. In some embodiments, the immune-related molecule is GM-CSF. In some embodiments, the therapeutic agent comprises a chemokine, such as CCL21. In some embodiments, the therapeutic agent is a PRRago, such as a CpG ODN (for example, CpG 7909CCL21). In some embodiments, the therapeutic agent is in a nanocapsule. In some embodiments, the therapeutic agent is administered prior to the administration of the oncolytic virus. In some embodiments, the therapeutic agent is administered prior to the administration of the oncolytic virus and/or the immunomodulator (including combination of immunomodulators). In some embodiments, the therapeutic agent is administered about 1 day to about 1 week (e.g., about 2 days) prior to the administration of the oncolytic virus and the immunomodulator (including combination of immunomodulators). In some embodiments, the therapeutic agent, and/or the oncolytic virus are administered directly to the solid or lymphatic tumor. In some embodiments, the therapeutic agent, and/or the oncolytic virus are administered to the tissue having the solid or lymphatic tumor. In some embodiments, the immunomodulator is a modulator of an immune checkpoint molecule selected from the group consisting of CTLA-4, PD-1, PD-L1. PD-L2, TIM3, B7-H3. B7-H4, LAG-3, KIR, and ligands thereof. In some embodiments, the immunomodulator is an immune-stimulating agent selected from the group consisting of activators of OX40, 4-1BB and CD40. In some embodiments, the method further comprises local administration of a second immunomodulator, such as an immune checkpoint inhibitor or an immune-stimulating agent. In some embodiments, the method further comprises administration (such as systemic or local to the site of the tumor) of a third immunomodulator, such as an immune checkpoint inhibitor or an immune-stimulating agent.

Suitable dosages for the oncolytic virus depend on factors such as the nature of the oncolytic virus, type of the solid or lymphatic tumor being treated, and routes of administration. As used herein, "particles" as related to an oncolytic virus mean the collective number of physical singular units of the oncolytic virus (such as a virus or bacterium). This number can be converted to, or is equivalent to, another number meaning infectious titer units, e.g., plaque forming unit (pfu) or international unit, by infectivity assays as known in the art. In some embodiments, the oncolytic virus is administered at a dose of about any one of $1\times10^5$ particles, $1\times10^6$ particles, $1\times10^7$ particles, $1\times10^8$ particles, $1\times10^9$ particles, $1\times10^{10}$ particles, $2\times10^{10}$ particles, $5\times10^{10}$ particles, $1\times10^{11}$ particles, $2\times10^{11}$ particles, $5\times10^{11}$ particles, $1\times10^{12}$ particles, $2\times10^{12}$ particles, $5\times10^{12}$ particles, $1\times10^{13}$ particles, $2\times10^{13}$ particles, $5\times10^{13}$ particles, $1\times10^{14}$ particles, or $1\times10^{15}$ particles. In some embodiments, the oncolytic virus is administered at a dose of any one of about $1\times10^5$ particles to about $1\times10^6$ particles, about $1\times10^6$ particles to about $1\times10^7$ particles, about $1\times10^7$ particles to about $1\times10^8$ particles, about $1\times10^8$ particles to about $1\times10^9$ particles, about $1\times10^9$ particles to about $1\times10^{10}$ particles, about $1\times10^{10}$ particles to about $1\times10^{11}$ particles, about $1\times10^{11}$ particles to about $5\times10^{11}$ particles, about $5\times10^{11}$ particles to about $1\times10^{12}$ particles, about $1\times10^{12}$ particles to about $2\times10^{12}$ particles, about $2\times10^{12}$ particles to about $5\times10^{12}$ particles, about $5\times10^{12}$ particles to about $1\times10^{13}$ particles, about $1\times10^{13}$ particles to about $1\times10^{14}$ particles, or about $1\times10^{14}$ particles to about $1\times10^{15}$ particles.

In some embodiments, the oncolytic virus is administered daily. In some embodiments, the oncolytic virus is administered is administered at least about any one of 1×, 2×, 3×, 4×, 5×, 6×, or 7× (i.e., daily) a week. In some embodiments, the oncolytic virus is administered weekly. In some embodiments, the oncolytic virus is administered weekly without break; weekly, two out of three weeks; weekly three out of four weeks; once every two weeks; once every 3 weeks; once every 4 weeks; once every 6 weeks; once every 8 weeks, monthly, or every two to 12 months. In some embodiments, the intervals between each administration are less than about any one of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any one of 1 month, 2 months, 3 months, 4 months, 5 months, 6 months, 8 months, or 12 months. In some embodiments, there is no break in the dosing schedule. In some embodiments, the interval between each administration is no more than about a week.

The administration of the oncolytic virus can be over an extended period of time, such as from about a month up to about seven years. In some embodiments, the oncolytic virus is administered over a period of at least about any one of 1, 2, 3, 4, 5, 6, 7, 8, 9, 10, 11, 12, 18, 24, 30, 36, 48, 60, 72, or 84 months. In some embodiments, the oncolytic virus is administered over a period of at least 4 weeks or 6 weeks. In some embodiments, the oncolytic virus is administered weekly for four weeks every 3 months. In some embodiments, the oncolytic virus is administered weekly for 6 weeks every 3 months.

Suitable dosages for the immunomodulator (including the first, second and third immunomodulator, and combination of immunomodulators) depend on factors such as the nature of the immunomodulator or combination of immunomodulators, type of the solid or lymphatic tumor being treated, and the routes of administration. Exemplary doses of the immunomodulator (including the first, second and third immunomodulator, and combination of immunomodulators) include, but are not limited to, about any one of 1 mg/m$^2$, 5 mg/m$^2$. 10 mg/m$^2$, 20 mg/m$^2$, 50 mg/m$^2$. 100 mg/m$^2$, 200 mg/m$^2$, 300 mg/m$^2$, 400 mg/m$^2$, 500 mg/m$^2$, 750 mg/m$^2$, 1000 mg/m$^2$, or more. In some embodiments, the dose of the immunomodulator (including the first, second and third immunomodulator, and combination of immunomodulators) is included in any one of the following ranges: about 1 to about 5 mg/m$^2$, about 5 to about 10 mg/m$^2$, about 10 to about 20 mg/m$^2$, about 20 to about 50 mg/m$^2$, about 50 to about 100 mg/m$^2$, about 100 mg/m$^2$ to about 200 mg/m$^2$, about 200 to about 300 mg/m$^2$, about 300 to about 400 mg/m$^2$, about 400 to about 500 mg/m$^2$, about 500 to about 750 mg/m$^2$, or about 750 to about 1000 mg/m$^2$. In some embodiments, the dose of the immunomodulator (including the first, second and third immunomodulator, and combination of immunomodulators) is about any one of 1 µg/kg, 2 µg/kg, 5 µg/kg, 10 µg/kg, 20 µg/kg, 50 µg/kg, 0.1 mg/kg, 0.2 mg/kg, 0.3 mg/kg, 0.4 mg/kg, 0.5 mg/kg, 1 mg/kg, 2 mg/kg, 5 mg/kg, 10 mg/kg, 20 mg/kg, 50 mg/kg, 100 mg/kg, or more. In some embodiments, the dose of the immunomodulator (including the first, second and third immunomodulator, and combination of immunomodulators) is any one of about 1 µg/kg to about 5 µg/kg, about 5 µg/kg to about 10 µg/kg, about 10 µg/kg to about 50 µg/kg, about 50 µg/kg to about 0.1 mg/kg, about 0.1 mg/kg to about 0.2 mg/kg, about 0.2 mg/kg to about 0.3 mg/kg, about 0.3 mg/kg to about 0.4 mg/kg, about 0.4 mg/kg to about 0.5 mg/kg, about 0.5 mg/kg to about 1 mg/kg, about 1 mg/kg to about 5 mg/kg, about 5 mg/kg to about 10 mg/kg, about 10 mg/kg to about 20 mg/kg, about 20 mg/kg to about 50 mg/kg, about 50 mg/kg to about 100 mg/kg, or about 1 mg/kg to about 100 mg/kg. In some embodiments, the dose of the immunomodulator (including the first, second and third immunomodulator, and combination of immunomodulators) is about any one of 1 μg, 10 μg, 50 μg, 100 μg, 500 μg, 1 mg, 2 mg, 4 mg, 6 mg, 12 mg, 18 mg, 24 mg, 50 mg, 100 mg, 500 mg or 1000 mg. In some embodiments, the dose of the immunomodulator (including the first, second and third immunomodulator, and combination of immunomodulators) is any one of about 1 lag to about 10 g, about 10 lag to about 50 10 μg, about 50 μg to about 100 μg, about 100 μg to about 500 μg, about 500 g to about 1 mg, about 1 mg to about 5 mg, about 5 mg to about 10 mg, about 10 mg to about 25 mg, about 25 mg to about 50 mg, about 50 mg to about 100 mg, about 100 mg to about 500 mg, about 500 mg to about 1000 mg, about 1 μg to about 1 mg, about 1 mg to about 1000 mg, or about 1 μg to about 1000 mg.

When administered locally to the tumor site, in some embodiments, the dose of the immunomodulator (including the second and third immunomodulator, and combination of immunomodulators) administered per tumor site is no more than about any of 10 μg, 50 μg, 100 μg, 500 μg, 1 mg, 2 mg, 4 mg, 6 mg, 12 mg, 18 mg, 24 mg, 50 mg, or 100 mg. In some embodiments, the dose of the immunomodulator (including the second and third immunomodulator, and combination of immunomodulators) administered locally per tumor site is any one of about 10 μg to about 50 μg, about 50 μg to about 100 μg, about 100 μg to about 500 μg, about 100 μg to about 1 mg, about 1 mg to about 2 mg, about 2 mg to about 5 mg, about 5 mg to about 10 mg, about 10 mg to about 15 mg, about 10 mg to about 25 mg, about 25 mg to about 50 mg, about 50 mg to about 100 mg, about 1 mg to about 50 mg, or about 100 μg to about 10 mg. In some embodiments, the dose of the immunomodulator (including the second and third immunomodulator, and combination of immunomodulators) administered locally per tumor site is based on the size of the tumor.

In some embodiments, the immunomodulator (including the first, second and third immunomodulator, and combination of immunomodulators) is administered daily. In some embodiments, the immunomodulator (including the first, second and third immunomodulator, and combination of immunomodulators) is administered is administered at least about any one of 1×, 2×, 3×, 4×, 5×, 6×, or 7× (i.e., daily) a week. In some embodiments, the immunomodulator (including the first, second and third immunomodulator, and combination of immunomodulators) is administered weekly without break; weekly, two out of three weeks; weekly three out of four weeks; once every two weeks; once every 3 weeks; once every 4 weeks; once every 6 weeks; once every 8 weeks, monthly, or every two to 12 months. In some embodiments, the intervals between each administration are less than about any one of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any one of 1 month, 2 months, 3 months, 4 months, 5 months, 6 months, 8 months, or 12 months. In some embodiments, there is no break in the dosing schedule. In some embodiments, the interval between each administration is no more than about a week. In some embodiments, the immunomodulator (including the first, second and third immunomodulator, and combination of immunomodulators) is administered with the same dosing schedule as the oncolytic virus. In some embodiments, the immunomodulator (including the first, second and third immunomodulator, and combination of immunomodulators) is administered with a different dosing schedule as the oncolytic virus. In some embodiments, the oncolytic virus is administered weekly for four weeks.

The administration of the immunomodulator (including the first, second and third immunomodulator, and combination of immunomodulators) can be over an extended period of time, such as from about a month up to about seven years. In some embodiments, the immunomodulator (including the first, second and third immunomodulator, and combination of immunomodulators) is administered over a period of at least about any one of 1, 2, 3, 4, 5, 6, 7, 8, 9, 10, 11, 12, 18, 24, 30, 36, 48, 60, 72, or 84 months. In some embodiments, the immunomodulator (including the first, second and third immunomodulator, and combination of immunomodulators) is administered over a period of at least 3 weeks or 6 weeks.

Exemplary routes of administration of the oncolytic virus, the immunomodulator (including the first, second and third immunomodulator, and combination of immunomodulators), prior therapy, and/or the pretreatment compositions include, but are not limited to, intratumoral, intravesical, intramuscular, intraperitoneal, intravenous, intra-arterial, intracranial, intrapleural, subcutaneous, and epidermal routes, or be delivered into lymph glands, body spaces, organs or tissues known to contain such live cancer cells (such as intrahepatic or intrapancreatic injections). In some embodiments, the local administration is carried out by direct injection of the agent(s) into the tumor. In some embodiments, the local administration is carried out by direct injection of the agent(s) to a site close to the tumor cells. In some embodiments, the systemic administration is via intravenous infusion. The specific route of the administration depends on the nature of the solid or lymphatic tumor and is discussed further below in the context of different types of solid or lymphatic tumor.

In some embodiments, wherein the oncolytic virus and/or optionally the second immunomodulator (including combinations of immunomodulators) are administered intratumorally (e.g., intratumoral injection), the total volume administered is no more than about any one of 0.5 mL, 1 mL, 1.5 mL, 2 mL, 2.5 mL, 5 mL or 10 mL. In some embodiments, the volume of the oncolytic virus and/or optionally the second immunomodulator (including combinations of immunomodulators) for intratumoral administration (such as intratumoral injection) per tumor site is dependent on the size of the tumor site. Tumor size can be measured as the tumor volume or the longest dimension of the tumor. For example, for a tumor with the longest dimension greater than about 5 cm, the intratumoral administration volume is no more than about 2 mL; for a tumor with the longest dimension of about 2 cm to about 5 cm, the intratumoral administration volume is about 1 mL; for a tumor with the longest dimension of about 0.75 cm to about 2 cm, the intratumoral administration volume is about 0.5 mL; and for a tumor with the longest dimension of smaller than about 0.75 cm, the intratumoral administration volume is about 0.1 mL. In some embodiments, the oncolytic virus and/or optionally the second immunomodulator (including combinations of immunomodulators) are administered to all tumor sites. In some embodiments, the oncolytic virus and/or optionally the s second immunomodulator (including combinations of immunomodulators) are administered to about any one of 1, 2, 3, 4, 5, 6, or more tumor sites. In some embodiments, the oncolytic virus and/or optionally the second immunomodulator (including combinations of immunomodulators) are administered to the tumor site with the largest size.

Solid or lymphatic tumors discussed herein include, but is not limited to, Hodgkin lymphoma, non-Hodgkin lymphoma, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma. Kaposi's sarcoma, soft tissue sarcoma, uterine sacronomasynovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma melanoma, neuroblastoma, and retinoblastoma.

In some embodiments, the solid or lymphatic tumor is selected from the group consisting of head and neck squamous cell cancer, breast cancer, colorectal cancer, pancreatic adenocarcinoma, ovarian cancer, non-small cell lung cancer, prostate cancer, and melanoma. The methods are applicable to solid or lymphatic tumors of all stages, including stages. I, II, III, and IV, according to the American Joint Committee on Cancer (AJCC) staging groups. In some embodiments, the solid or lymphatic tumor is an/a: early stage cancer, non-metastatic cancer, primary cancer, advanced cancer, locally advanced cancer, metastatic cancer, cancer in remission, cancer in an adjuvant setting, or cancer in a neoadjuvant setting. In some embodiments, the solid or lymphatic tumor is localized resectable, localized unresectable, or unresectable. In some embodiments, the solid or lymphatic tumor is localized resectable or borderline resectable. In some embodiments, the cancer has been refractory to prior therapy.

In some embodiments, the solid or lymphatic tumor is head and neck cancer. In some embodiments, the head and neck cancer is a squamous cell carcinoma in the head and neck. In some embodiments, the head and neck cancer is a hypopharyngeal cancer, laryngeal cancer, lip and oral cavity cancer, metastatic squamous neck cancer with occult primary, nasopharyngeal cancer, oropharyngeal cancer, paranasal sinus and nasal cavity cancer, or salivary gland cancer. In some embodiments, the head and neck squamous cell cancer is an early stage head and neck cancer, non-metastatic head and neck cancer, advanced head and neck cancer, locally advanced head and neck cancer, metastatic head and neck cancer, head and neck cancer in remission, head and neck cancer in adjuvant setting, or head and neck cancer in neoadjuvant setting. In some embodiments, the head and neck cancer is in a neoadjuvant setting. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by injection into the head and neck tissue having the head and neck tumor. In some embodiments, the administration of the oncolytic virus, and/or the second (including combination of immunomodulators), and/or the pretreatment composition is carried out by injection directly into the head and neck tumor. In some embodiments, the administration of the oncolytic virus, and/or the second (including combination of immunomodulators), and/or the pretreatment composition is carried out by injection directly into metastatic sites of the head and neck tumor. In some embodiments, the administration of the oncolytic virus, and/or the second (including combination of immunomodulators), and/or the pretreatment composition is carried out by injection into the head and neck tissue close to the head and neck tumor.

In some embodiments, the solid or lymphatic tumor is breast cancer. In some embodiments, the breast cancer is early stage breast cancer, non-metastatic breast cancer, advanced breast cancer, stage IV breast cancer, locally advanced breast cancer, metastatic breast cancer, breast cancer in remission, breast cancer in an adjuvant setting, or breast cancer in a neoadjuvant setting. In some embodiments, the breast cancer is in a neoadjuvant setting. In some embodiments, the breast cancer is at an advanced stage. In some embodiments, the breast cancer (which may be HER2 positive or HER2 negative) includes, for example, advanced breast cancer, stage IV breast cancer, locally advanced breast cancer, and metastatic breast cancer. In some embodiments, the breast cancer is a triple negative breast cancer. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by intramammary injection into the mammary tissue having the breast tumor. In some embodiments, the administration of the oncolytic virus, and/or the second immunomodulator (including combination of immunomodulators), and/or the pretreatment composition is carried out by intramammary injection directly into the breast tumor. In some embodiments, the administration of the oncolytic virus, and/or the second immunomodulator (including combination of immunomodulators), and/or the pretreatment composition is carried out by injection directly into metastatic sites of the breast tumor. In some embodiments, the administration of the oncolytic virus, and/or the second immunomodulator (including combination of immunomodulators), and/or the pretreatment composition is carried out by intramammary injection into the mammary tissue close to the breast tumor.

In some embodiments, the cancer is renal cell carcinoma. In some embodiments, the renal cell carcinoma is an adenocarcinoma. In some embodiments, the renal cell carcinoma is a clear cell renal cell carcinoma, papillary renal cell carcinoma (also called chromophilic renal cell carcinoma), chromophobe renal cell carcinoma, collecting duct renal cell carcinoma, granular renal cell carcinoma, mixed granular renal cell carcinoma, renal angiomyolipomas, or spindle renal cell carcinoma. In some embodiments, the renal cell carcinoma is at any of stage I, II, III, or IV, according to the American Joint Committee on Cancer (AJCC) staging groups. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by intrarenal injection into the renal tissue having the renal tumor. In some embodiments, the administration of the oncolytic virus, and/or the second immunomodulator (including combination of immunomodulators), and/or the pretreatment composition is carried out by intrarenal injection directly into the renal tumor. In some embodiments, the administration of the oncolytic virus, and/or the second immunomodulator (including combination of immunomodulators), and/or the pretreatment composition is carried out by injection directly into metastatic sites of the renal tumor. In some embodiments, the administration of the oncolytic virus, and/or the second immunomodulator (including combination of immunomodulators), and/or the pretreatment composition is carried out by intrarenal injection into the renal tissue close to the renal tumor.

In some embodiments, the solid or lymphatic tumor is prostate cancer. In some embodiments, the prostate cancer is an adenocarcinoma. In some embodiments, the prostate cancer is a sarcoma, neuroendocrine tumor, small cell cancer, ductal cancer, or a lymphoma. In some embodiments, the prostate cancer is at any of the four stages. A, B, C, or D, according to the Jewett staging system. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by intraprostatic injection into the prostate tissue having the prostate tumor. In some embodiments, the administration of the oncolytic virus, and/or the second immunomodulator (including combination of immunomodulators), and/or the pretreatment composition is carried out by intraprostatic injection directly into the prostate tumor. In some embodiments, the administration of the oncolytic virus, and/or the second immunomodulator (including combination of immunomodulators), and/or the pretreatment composition is carried out by injection directly into metastatic sites of the prostate tumor. In some embodiments, the administration of the oncolytic virus, and/or the second immunomodulator (including combination of immunomodulators), and/or the pretreatment composition is carried out by intraprostatic injection into the prostate tissue close to the prostate tumor.

In some embodiments, the solid or lymphatic tumor is lung cancer. In some embodiments, the lung cancer is a non-small cell lung cancer (NSCLC). Examples of NSCLC include, but are not limited to, large-cell carcinoma, adenocarcinoma, neuroendocrine lung tumors, and squamous cell carcinoma. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by intrapulmonary injection into the lung tissue having the lung tumor. In some embodiments, the lung cancer is small cell lung cancer (SCLC). In some embodiments, the administration of the oncolytic virus, and/or the second immunomodulator (including combination of immunomodulators), and/or the pretreatment composition is carried out by intrapulmonary injection directly into the lung tumor. In some embodiments, the administration of the oncolytic virus, and/or the second immunomodulator (including combination of immunomodulators), and/or the pretreatment composition is carried out by injection directly into metastatic sites of the lung tumor. In some embodiments, the administration of the oncolytic virus, and/or the second immunomodulator (including combination of immunomodulators), and/or the pretreatment composition is carried out by intrapulmonary injection into the lung tissue close to the lung tumor.

In some embodiments, the solid or lymphatic tumor is melanoma. In some embodiments, the melanoma is superficial spreading melanoma, lentigo maligna melanoma, nodular melanoma, mucosal melanoma, polypoid melanoma, desmoplastic melanoma, amelanotic melanoma, soft-tissue melanoma, or acral lentiginous melanoma. In some embodiments, the melanoma is at any of stage I, II, III, or IV, according to the American Joint Committee on Cancer (AJCC) staging groups. In some embodiments, the melanoma is recurrent. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by injection into the skin tissue having the melanoma tumor. In some embodiments, the administration of the oncolytic virus, and/or the second immunomodulator (including combination of immunomodulators), and/or the pretreatment composition is carried out by injection directly into the melanoma tumor. In some embodiments, the administration of the oncolytic virus, and/or the second immunomodulator (including combination of immunomodulators), and/or the pretreatment composition is carried out by injection directly into metastatic sites of the melanoma tumor. In some embodiments, the administration of the oncolytic virus, and/or the second immunomodulator (including combination of immunomodulators), and/or the pretreatment composition is carried out by injection into the lung tissue close to the melanoma tumor.

In some embodiments, the solid or lymphatic tumor is ovarian cancer. In some embodiments, the ovarian cancer is ovarian epithelial cancer. In some embodiments, the ovarian cancer is stage I (e.g., stage IA, IB, or IC), stage II (e.g., stage IIA, IIB, or IIC), stage III (e.g., stage IIIA, IIIB, or IIIC), or stage IV. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by intraovarian injection into the ovarian tissue having the ovarian tumor. In some embodiments, the administration of the oncolytic virus, and/or the second immunomodulator (including combination of immunomodulators), and/or the pretreatment composition is carried out by intraovarian injection directly into the ovarian tumor. In some embodiments, the administration of the oncolytic virus, and/or the second immunomodulator (including combination of immunomodulators), and/or the pretreatment composition is carried out by injection directly into metastatic sites of the ovarian tumor. In some embodiments, the administration of the oncolytic virus, and/or the second immunomodulator (including combination of immunomodulators), and/or the pretreatment composition is carried out by intraovarian injection into the ovarian tissue close to the ovarian tumor.

In some embodiments, according to any of the methods described above, the solid or lymphatic tumor is pancreatic cancer. In some embodiments, the pancreatic cancer is a seous cystic neoplasm, mucinous cystic neoplasm, intraductal papillary mucinous neoplasm, pancreatic adenocarcinoma, adenosquamous carcinoma, squamous cell carcinoma, signet ring cell carcinoma, undifferentiated carcinoma, undifferentiated carcinoma with giant cells, solid pseudopapillary neoplasm, ampullary cancer, or pancreatic neuroendocrine tumor. In some embodiments, the pancreatic cancer is a pancreatic adenocarcinoma. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by intrapancreatic injection into the pancreatic tissue having the pancreatic tumor. In some embodiments, the administration of the oncolytic virus, and/or the second immunomodulator (including combination of immunomodulators), and/or the pretreatment composition is carried out by intrapancreatic injection directly into the pancreatic tumor. In some embodiments, the administration of the oncolytic virus, and/or the second immunomodulator (including combination of immunomodulators), and/or the pretreatment composition is carried out by injection directly into metastatic sites of the pancreatic tumor. In some embodiments, the administration of the oncolytic virus, and/or the second immunomodulator (including combination of immunomodulators), and/or the pretreatment composition is carried out by intrapancreatic injection into the pancreatic tissue close to the pancreatic tumor.

In some embodiments, the solid or lymphatic tumor is endometrial cancer. In some embodiments, the endometrial cancer is adenocarcinoma, carcinosarcoma, squamous cell carcinoma, undifferentiated carcinoma, small cell carcinoma, or transitional carcinoma. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by intraendometrial injection into the endometrial tissue having the endometrial tumor. In some embodiments, the administration of the oncolytic virus, and/or the second immunomodulator (including combination of immunomodulators), and/or the pretreatment composition is carried out by intraendometrial injection directly into the endometrial tumor. In some embodiments, the administration of the oncolytic virus, and/or the second immunomodulator (including combination of immunomodulators), and/or the pretreatment composition is carried out by injection directly into metastatic sites of the endometrial tumor. In some embodiments, the administration of the oncolytic virus, and/or the second immunomodulator (including combination of immunomodulators), and/or the pretreatment composition is carried out by intraendometrial injection into the endometrial tissue close to the endometrial tumor.

In some embodiments, according to any of the methods described above, the solid or lymphatic tumor is colorectal cancer. In some embodiments, the colorectal cancer is adenocarcinoma, gastrointestinal carcinoid tumor, gastrointestinal stromal tumor, leiomysarcoma, melanoma, or squamous cell carcinoma. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by injection into the colorectal tissue having the colorectal tumor. In some embodiments, the administration of the oncolytic virus, and/or the second immunomodulator (including combination of immunomodulators), and/or the pretreatment composition is carried out by injection directly into the colorectal tumor. In some embodiments, the administration of the oncolytic virus, and/or the second immunomodulator (including combination of immunomodulators), and/or the pretreatment composition is carried out by injection directly into metastatic sites of the colorectal tumor. In some embodiments, the administration of the oncolytic virus, and/or the second immunomodulator (including combination of immunomodulators), and/or the pretreatment composition is carried out by injection into the colorectal tissue close to the colorectal tumor.

In some embodiments, according to any of the methods described above, the solid or lymphatic tumor is hepatocellular carcinoma (HCC). In some embodiments, the HCC is early stage HCC, non-metastatic HCC, primary HCC, advanced HCC, locally advanced HCC, metastatic HCC, HCC in remission, or recurrent HCC. In some embodiments, the HCC is localized resectable (i.e., tumors that are confined to a portion of the liver that allows for complete surgical removal), localized unresectable (i.e., the localized tumors may be unresectable because crucial blood vessel structures are involved or because the liver is impaired), or unresectable (i.e., the tumors involve all lobes of the liver and/or has spread to involve other organs (e.g., lung, lymph nodes, bone). In some embodiments, the HCC is, according to TNM classifications, a stage I tumor (single tumor without vascular invasion), a stage II tumor (single tumor with vascular invasion, or multiple tumors, none greater than 5 cm), a stage III tumor (multiple tumors, any greater than 5 cm, or tumors involving major branch of portal or hepatic veins), a stage IV tumor (tumors with direct invasion of adjacent organs other than the gallbladder, or perforation of visceral peritoneum), N1 tumor (regional lymph node metastasis), or M1 tumor (distant metastasis). In some embodiments, the HCC is, according to AJCC (American Joint Commission on Cancer) staging criteria, stage T1, T2, T3, or T4 HCC. In some embodiments, the HCC is any one of liver cell carcinomas, fibrolamellar variants of HCC, and mixed hepatocellular cholangiocarcinomas. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by intrahepatic injection into the liver tissue having the HCC. In some embodiments, the administration of the oncolytic virus, and/or the second immunomodulator (including combination of immunomodulators), and/or the pretreatment composition is carried out by intrahepatic injection directly into the HCC. In some embodiments, the administration of the oncolytic virus, and/or the second immunomodulator (including combination of immunomodulators), and/or the pretreatment composition is carried out by injection directly into metastatic sites of the HCC. In some embodiments, the administration of the oncolytic virus, and/or the second immunomodulator (including combination of immunomodulators), and/or the pretreatment composition is carried out by intrahepatic injection into the tissue close to the HCC.

In some embodiments, according to any of the methods described above, the solid or lymphatic tumor is lymphoma. In some embodiments, the lymphoma is a B-cell neoplasm, a T-cell neoplasm, and/or a putative NK-cell neoplasm. Examples of B-cell neoplasms include, but are not limited to, precursor B-cell neoplasms (e.g., precursor B-lymphoblastic leukemia/lymphoma) and peripheral B-cell neoplasms (e.g., B-cell chronic lymphocytic leukemia/prolymphocytic leukemia/small lymphocytic lymphoma (small lymphocytic (SL) NHL), lymphoplasmacytoid lymphoma/immunocytoma, mantel cell lymphoma, follicle center lymphoma, follicular lymphoma (e.g., cytologic grades: I (small cell), II (mixed small and large cell), III (large cell) and/or subtype: diffuse and predominantly small cell type), low grade/follicular non-Hodgkin's lymphoma (NHL), intermediate grade/follicular NHL, marginal zone B-cell lymphoma (e.g., extranodal (e.g., MALT-type+/−monocytoid B cells) and/or Nodal (e.g., +/−monocytoid B cells)), splenic marginal zone lymphoma (e.g., +/−villous lymphocytes). Hairy cell leukemia, plasmacytoma/plasma cell myeloma (e.g., myeloma and multiple myeloma), diffuse large B-cell lymphoma (e.g., primary mediastinal (thymic) B-cell lymphoma), intermediate grade diffuse NHL, Burkitt's lymphoma, High-grade B-cell lymphoma, Burkitt-like, high grade immunoblastic NHL, high grade lymphoblastic NHL, high grade small non-cleaved cell NHL, bulky disease NHL, AIDS-related lymphoma, and Waldenstrom's macroglobulinemia). Examples of T-cell and/or putative NK-cell neoplasms include, but are not limited to, precursor T-cell neoplasm (precursor T-lymphoblastic lymphoma/leukemia) and peripheral T-cell and NK-cell neoplasms (e.g., T-cell chronic lymphocytic leukemia/prolymphocytic leukemia, and large granular lymphocyte leukemia (LGL) (e.g., T-cell type and/or NK-cell type), cutaneous T-cell lymphoma (e.g., mycosis fungoides/Sezary syndrome), primary T-cell lymphomas unspecified (e.g., cytological categories (e.g., medium-sized cell, mixed medium and large cell), large cell, lymphoepitheloid cell, subtype hepatosplenic γδ T-cell lymphoma, and subcutaneous panniculitic T-cell lymphoma), angioimmunoblastic T-cell lymphoma (AILD), angiocentric lymphoma, intestinal T-cell lymphoma (e.g., +/−enteropathy associated), adult T-cell lymphoma/leukemia (ATL), anaplastic large cell lymphoma (ALCL) (e.g., CD30+, T- and null-cell types), anaplastic large-cell lymphoma, and Hodgkin's like). In some embodiments, the lymphoma is Hodgkin's disease or Non-Hodgkin Lymphoma (NHL). For example, the Hodgkin's disease may be lymphocyte predominance, nodular sclerosis, mixed cellularity, lymphocyte depletion, and/or lymphocyte-rich. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by intralymphatic injection into the lymph node having the lymphatic tumor. In some embodiments, the administration of the oncolytic virus, and/or the second immunomodulator (including combination of immunomodulators), and/or the pretreatment composition is carried out by intralymphatic injection directly into the lymphatic tumor. In some embodiments, the administration of the oncolytic virus, and/or the second immunomodulator (including combination of immunomodulators), and/or the pretreatment composition is carried out by injection directly into metastatic sites of the lymphatic tumor. In some embodiments, the administration of the oncolytic virus, and/or the second immunomodulator (including combination of immunomodulators), and/or the pretreatment composition is carried out by intralymphatic injection into the tissue close to the lymphatic tumor.

In some embodiments, according to any of the methods described above, the solid or lymphatic tumor is mesothelioma. In some embodiments, the mesothelioma is pleural mesothelioma, peritoneal mesothelioma, pericardial mesothelioma, or mesothelioma affecting mesothelial tissue covering other organs. In some embodiments, the mesothelioma is benign mesothelioma or malignant mesothelioma. In some embodiments, the mesothelioma is epithelial mesothelioma, sarcomatoid mesothelioma, biphasic mesothelioma, or papillary mesothelioma. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by injection into the mesothelial tissue having the mesothelioma. In some embodiments, the administration of the oncolytic virus, and/or the second immunomodulator (including combination of immunomodulators), and/or the pretreatment composition is carried out by injection directly into the mesothelioma. In some embodiments, the administration of the oncolytic virus, and/or the second immunomodulator (including combination of immunomodulators), and/or the pretreatment composition is carried out by injection directly into metastatic sites of the mesothelioma. In some embodiments, the administration of the oncolytic virus, and/or the second immunomodulator (including combination of immunomodulators), and/or the pretreatment composition is carried out by injection into the mesothelial tissue close to the mesothelioma.

In some embodiments, according to any of the methods described above, the solid or lymphatic tumor is brain tumor. In some embodiments, the brain tumor is primary brain tumor or secondary (or metastatic) brain tumor. In some embodiments, the brain tumor is glioma (such as astrocytoma, oligodendroglioma, or ependymoma), meningioma. Schwannoma, craniopharyngioma, germ cell tumor, or pineal region tumor. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by injection into the brain tissue having the brain tumor. In some embodiments, the administration of the oncolytic virus, and/or the second immunomodulator (including combination of immunomodulators), and/or the pretreatment composition is carried out by injection directly into the brain tumor. In some embodiments, the administration of the oncolytic virus, and/or the second immunomodulator (including combination of immunomodulators), and/or the pretreatment composition is carried out by injection directly into metastatic sites of the brain tumor. In some embodiments, the administration of the oncolytic virus, and/or the second immunomodulator (including combination of immunomodulators), and/or the pretreatment composition is carried out by injection into the brain tissue close to the brain tumor.

In some embodiments, according to any of the methods described above, the solid or lymphatic tumor is gallbladder and bile duct tumor. In some embodiments, the gallbladder and bile duct tumor is carcinoma, adenocarcinoma, cholangiocarcinoma, papillary tumor, small cell (neuroendocrine) carcinoma, adenosquamous carcinoma, or rhabdomyosarcoma. In some embodiments, the gallbladder and bile duct tumor is gallbladder carcinoma, carcinoma of extrahepatic bile duct, or carcinoma of intrahepatic bile duct. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by injection into the gallbladder or bile duct tissue having the gallbladder and bile duct tumor. In some embodiments, the administration of the oncolytic virus, and/or the second immunomodulator (including combination of immunomodulators), and/or the pretreatment composition is carried out by injection directly into the gallbladder and bile duct tumor. In some embodiments, the administration of the oncolytic virus, and/or the second immunomodulator (including combination of immunomodulators), and/or the pretreatment composition is carried out by injection directly into metastatic sites of the gallbladder and bile duct tumor. In some embodiments, the administration of the oncolytic virus, and/or the second immunomodulator (including combination of immunomodulators), and/or the pretreatment composition is carried out by injection into the gallbladder or bile duct tissue close to the gallbladder and bile duct tumor.

In some embodiments, according to any of the methods described above, the solid or lymphatic tumor is soft tissue sarcoma. In some embodiments, the soft tissue sarcoma is adult fibrosarcoma, alveolar soft-part sarcoma, angiosarcoma, clear cell sarcoma, desmoplastic small round cell tumor, epitheloid sarcoma, fibromyxoid sarcoma, liposarcoma, malignant mesenchymoma, malignant peripheral nerve sheath tumor (e.g., neurofibrosarcoma, malignant schwannoma, or neurogenic sarcoma), myxofibrosarcoma, synovial sarcoma, undifferentiated pleomorphic sarcoma, dermatofibrosarcoma protuberan, fibromatosis, hemangioendothelioma, infantile fibrosarcoma, solitary fibrous tumor, elastofibroma, fibroma, fibrous histiocytoma, glomus tumor, granular cell tumor, hemangioma, hibernoma, lipoma, leiomyoma, leiomyoma, lipoblastoma, lymphangioma, myxoma, neurofibroma, neuroma, PEComa, rhabdomyoma, schwannoma, tenosynovial giant cell tumor, spindle cell tumor, or tumor-like conditions of soft tissue. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by injection into the tissue having the soft tissue sarcoma. In some embodiments, the administration of the oncolytic virus, and/or the second immunomodulator (including combination of immunomodulators), and/or the pretreatment composition is carried out by injection directly into the soft tissue sarcoma. In some embodiments, the administration of the oncolytic virus, and/or the second immunomodulator (including combination of immunomodulators), and/or the pretreatment composition is carried out by injection directly into metastatic sites of the soft tissue sarcoma. In some embodiments, the administration of the oncolytic virus, and/or the second immunomodulator (including combination of immunomodulators), and/or the pretreatment composition is carried out by injection into the tissue close to the soft tissue sarcoma.

In some embodiments, according to any of the methods described above, the solid or lymphatic tumor is uterine tumor. In some embodiments, the uterine tumor is uterine carcinoma, uterine sarcoma (such as endometrial stromal sarcoma, undifferentiated sarcoma, or uterine leiomyosarcoma), or uterine carcinosarcoma (such as malignant mixed mesodermal tumor, or malignant mixed mullerian tumor). In some embodiments, the uterine tumor is a fibroid tumor, such as leiomyoma, adenofibroma, or adenomyoma. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by intrauterine injection into the uterine tissue having the uterine tumor. In some embodiments, the administration of the oncolytic virus, and/or the second immunomodulator (including combination of immunomodulators), and/or the pretreatment composition is carried out by intrauterine injection directly into the uterine tumor. In some embodiments, the administration of the oncolytic virus, and/or the second immunomodulator (including combination of immunomodulators), and/or the pretreatment composition is carried out by injection directly into metastatic sites of the uterine tumor. In some embodiments, the administration of the oncolytic virus, and/or the second immunomodulator (including combination of immunomodulators), and/or the pretreatment composition is carried out by intrauterine injection into the uterine tissue close to the uterine tumor.

In some embodiments, according to any of the methods described above, the solid or lymphatic tumor is cervical tumor. In some embodiments, the cervical tumor is squamous cell carcinoma, adenocarcinoma, or adenosquamous carcinoma. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by intracervical injection into the cervical tissue having the cervical tumor. In some embodiments, the administration of the oncolytic virus, and/or the second immunomodulator (including combination of immunomodulators), and/or the pretreatment composition is carried out by intracervical injection directly into the cervical tumor. In some embodiments, the administration of the oncolytic virus, and/or the second immunomodulator (including combination of immunomodulators), and/or the pretreatment composition is carried out by injection directly into metastatic sites of the cervical tumor. In some embodiments, the administration of the oncolytic virus, and/or the second immunomodulator (including combination of immunomodulators), and/or the pretreatment composition is carried out by intracervical injection into the cervical tissue close to the cervical tumor.

In some embodiments, according to any of the methods described above, the solid or lymphatic tumor is thyroid tumor. In some embodiments, the thyroid tumor is differentiated thyroid tumor (such as papillary carcinoma, follicular carcinoma, or Hurthle cell carcinoma), medullary thyroid carcinoma, anaplastic carcinoma, thyroid lymphoma, thyroid sarcoma, or parathyroid tumor. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by injection into the thyroid tissue having the thyroid tumor. In some embodiments, the administration of the oncolytic virus, and/or the second immunomodulator (including combination of immunomodulators), and/or the pretreatment composition is carried out by injection directly into the thyroid tumor. In some embodiments, the administration of the oncolytic virus, and/or the second immunomodulator (including combination of immunomodulators), and/or the pretreatment composition is carried out by injection directly into metastatic sites of the thyroid tumor. In some embodiments, the administration of the oncolytic virus, and/or the second immunomodulator (including combination of immunomodulators), and/or the pretreatment composition is carried out by injection into the thyroid tissue close to the thyroid tumor.

In some embodiments, according to any of the methods described above, the solid or lymphatic tumor is nasopharyngeal carcinoma. In some embodiments, the nasopharyngeal carcinoma is keratinizing squamous cell carcinoma, non-keratinizing differentiated carcinoma, or undifferentiated carcinoma (e.g., lymphoepithelioma), oral cavity and oropharyngeal tumor, nasal cavity and paranasal sinus tumor, or salivary gland tumor. In some embodiments, the immunomodulator (including combination of immunomodulators) is administered intravenously. In some embodiments, the administration of the oncolytic virus, and/or the second immunomodulator (including combination of immunomodulators), and/or the pretreatment composition is carried out by injection into the nasopharyngeal tissue having the nasopharyngeal carcinoma. In some embodiments, the administration of the oncolytic virus, and/or the second immunomodulator (including combination of immunomodulators), and/or the pretreatment composition is carried out by injection directly into the nasopharyngeal carcinoma. In some embodiments, the administration of the oncolytic virus, and/or the second immunomodulator (including combination of immunomodulators), and/or the pretreatment composition is carried out by injection directly into metastatic sites of the nasopharyngeal carcinoma. In some embodiments, the administration of the oncolytic virus, and/or the second immunomodulator (including combination of immunomodulators), and/or the pretreatment composition is carried out by injection into the nasopharyngeal tissue close to the nasopharyngeal carcinoma.

In some embodiments, the individual is a human individual. In some embodiments, the individual being treated for solid or lymphatic tumor has been identified as having one or more of the conditions described herein. Identification of the conditions as described herein by a skilled physician is routine in the art (e.g., via blood tests, X-rays, ultrasound, CT scans, PET scans, PET/CT scans. MRI scans, PET/MRI scans, nuclear medicine radioisotope scans, endoscopy, biopsy, angiography, CT-angiography, etc.) and may also be suspected by the individual or others, for example, due to tumor growth, hemorrhage, ulceration, pain, enlarged lymph nodes, cough, jaundice, swelling, weight loss, cachexia, sweating, anemia, paraneoplastic phenomena, thrombosis, etc. In some embodiments, the individual is selected for any one of the treatment methods described herein based on any one or more of a number of risk factors and/or diagnostic approaches appreciated by the skilled artisan, including, but not limited to, genetic profiling, family history, medical history (e.g., appearance of related conditions and viral infection history), lifestyle or habits.

In some embodiments, the individual is selected for any one of the treatment methods described herein based on the expression level of one or more biomarkers, including, but not limited to, immune checkpoint molecules, co-stimulatory molecules, cytokines, chemokines, other immune-related molecules, and HLA-Class II antigens. In some embodiments, the individual is selected for the treatment based on the expression level (e.g., high expression level) of one or more inhibitory immune checkpoint molecules, including, but not limited to, CTLA-4, PD-1. PD-L1, PD-L2, TIM3, B7-H3, B7-H4, LAG-3, KIR, 2B4 and ligands thereof. In some embodiments, the individual is selected for the treatment methods based on the expression level (e.g., low expression level) of one or more stimulatory immune checkpoint molecules or co-stimulatory molecules, including, but not limited to, OX40, 4-1BB, CD40, and ligands thereof. In some embodiments, the individual is selected for the treatment based on the expression level (e.g., high expression level) of one or more biomarkers selected from the group consisting of PD-1, PD-L1, and PD-L2 in the tumor (such as tumor cells and/or immune cells inside the tumor). In some embodiments, the individual is selected for the treatment based on the expression level (e.g., high expression level) of one or more biomarkers selected from the group consisting of CD80, CD83, CD86 and HLA-Class II antigens in tumor-derived mature dendritic cells. In some embodiments, the individual is selected for the treatment based on the expression level (e.g., high expression level) of one or more biomarkers selected from the group consisting of CXCL9, CXCL10, CXCL11, CCR7, CCL5, CCL8, SOD2, MT2A, OASL, GBP1, HES4, MTIB, MTIE, MTIG, MTIH, GADD45A, LAMP3 and miR-155.

In some embodiments, the individual has high expression of one or more inhibitory immune checkpoint molecules. In some embodiments, the individual has low expression of one or more stimulatory immune checkpoint molecule and/or co-stimulatory molecules. In some embodiments, the individual has high expression of one or more biomarkers selected from the group consisting of PD-1, PD-L1, and PD-L2 in the tumor (such as tumor cells and/or immune cells inside the tumor). In some embodiments, PD-L1 and PD-L2 can be used interchangeably as a biomarker for selecting patients or as a ligand for inhibiting PD-1. In some embodiments, the individual has high expression of one or more biomarkers selected from the group consisting of CD80, CD83, CD86 and HLA-Class II antigens in tumor-derived mature dendritic cells. Exemplary HLA-Class II antigens include, but are not limited to, tumor-specific antigens and tumor-associated antigens expressed in the solid or lymphatic tumor, such as PSA for prostate tumor, alpha fetoprotein for HCC, CEA for adenocarcinoma. In some embodiments, the individual has high expression of one or more biomarkers selected from the group consisting of CXCL9, CXCL0, CXCL11, CCR7, CCL5, CCL8, SOD2, MT2A. OASL, GBP1, HES4. MTIB, MTIE. MTIG, MTIH, GADD45A. LAMP3 and miR-155. In some embodiments, the method further comprises assessing the expression level of one or more biomarkers in the individual. In some embodiments, the method is adjusted based on the expression level of the one or more biomarkers.

Expression level of a biomarker may be measured at the nucleic acid level (e.g., gene copy number, DNA methylation or chromatin remodeling level, mRNA level), or protein level, including post-translational modification level of the protein, such as phosphorylation level of the protein corresponding to the biomarker. Expression level can be determined using any of the known methods in the art. For example, suitable methods for determining the mRNA expression level of a biomarker include, but are not limited to, Reverse Transcription Polymerase Chain Reaction (RT-PCR), quantitative PCR, microarray, and RNA sequencing. For example, suitable methods for determining the protein expression level of a biomarker include, but are not limited to, immunohistochemistry, Western blotting, and mass spectroscopy methods.

The expression level of the biomarker may be determined using a fresh or archived sample from the individual, including, but not limited to, the solid or lymphatic tumor tissue, a normal tissue adjacent to the solid or lymphatic tumor tissue, a normal tissue distal to the solid or lymphatic tumor tissue, or peripheral blood lymphocytes. In some embodiments, the sample is solid or lymphatic tumor tissue. In some embodiments, the sample is a biopsy containing tumor cells, such as fine needle aspiration of tumor cells. In some embodiments, the biopsied cells are centrifuged into a pellet, fixed, and embedded in paraffin prior to the analysis. In some embodiments, the biopsied cells are flash frozen prior to the analysis. In some embodiments, the sample is a bodily fluid, such as a blood sample or a plasma sample. In some embodiments, the sample comprises a circulating metastatic cancer cell. In some embodiments, the sample is obtained by sorting circulating tumor cells (CTCs) from blood.

In some embodiments, the expression levels of the one or more biomarkers in a specific cell population of the individual are determined using a sample from the individual. In some embodiments, the sample comprises immune cells isolated or derived from the solid or lymphatic tumor. Exemplary immune cells that are relevant for biomarker expression determination include, but are not limited to, dendritic cells (such as immature or mature dendritic cells), B cells, T cells (such as Th1 cells, Th2 cells, Th17 cells. NK T cells. Treg cells, etc.), Natural Killer (NK) cells, monocytes, macrophages, neutrophils, and combinations thereof. In some embodiments, the sample comprises tumor infiltrating lymphocytes. In some embodiments, the sample comprises tumor-derived mature dendritic cells. The specific cell population can be isolated from a sample, such as a tumor sample (e.g., tumor biopsy or resection) or a body fluid (e.g., blood sample), using methods known in the art, such as flow cytometry methods based on expression of specific cell surface molecules in the cell population.

High or low expression level of a biomarker is determined as compared to a standard expression level of the biomarker known in the art (e.g., a clinically accepted normal level in a standardized test), or as compared to the expression level of the biomarker in a control sample. In some embodiments, the expression level of the biomarker in an individual is compared to the expression level of the biomarker in multiple control samples. In some embodiments, multiple control samples are used to generate a statistic that is used to classify the level of the biomarker in an individual with the solid or lymphatic tumor. Control samples can be obtained from the same sources (e.g., individual and tissue) and methods as non-control samples. In some embodiments, the control sample is obtained from a different individual (for example an individual not having the solid or lymphatic tumor; an individual having a benign or less advanced form of the solid or lymphatic tumor; and/or an individual sharing similar ethnic, age, and gender). In some embodiments, the control sample is a cultured tissue or cell that has been determined to be a proper control. In some embodiments, wherein the sample is solid or lymphatic tumor tissue sample, the control sample may be a non-cancerous sample from the same individual. In some embodiments, multiple control samples (for example from different individuals) are used to determine a range of levels of the biomarker in a particular tissue, organ, or cell population. In some embodiments, the expression level of the biomarker in a sample of the individual is classified as high, medium or low according to a scoring system, such as an immunohistochemistry-based scoring system. In some embodiments, high expression of the biomarker is at least about any one of 1.5 times, 2 times, 3 times, 5 times, 10 times, 20 times, 50 times, 100 times, 200 times, 500 times, 1000 times or more than the expression level of the biomarker in a sample from the individual as compared to a control sample. In some embodiments, low expression of the biomarker is no more than about any one of 90%, 80%, 70%, 60%, 50%, 40%, 30%, 20%, 10%, 5%, 1%, 0.1%, 0.01%, 0.001% or less than the expression level of the biomarker in a sample from the individual as compared to a control sample. In some embodiments, the expression levels of two or more biomarkers are combined, for example, using a statistic model to determine an expression score, for selecting or recommending the individual for the treatment.

Methods of Treating Bladder Cancer by Intravesical Administrations

Any of the methods described above may be used to treat a bladder cancer. In this context, local administration of the oncolytic virus may encompass intravesical administration of the oncolytic virus. Systemic administration of the immunomodulator (including combination of immunomodulators) may encompass intravenous administration of the immunomodulator (including combination of immunomodulators). Furthermore, local administration of the second immunomodulator (including combination of immunomodulators) may encompass intravenous administration of the second immunomodulator (including combination of immunomodulators).

In some embodiments, there is provided a method of treating bladder cancer in an individual, comprising: a) intravesically administering an effective amount of an oncolytic virus; and b) systemically administering an effective amount of an immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule. In some embodiments, the oncolytic virus is selected from the group consisting of adenovirus, herpes simplex virus, vaccinia virus, mumps virus. Newcastle disease virus, polio virus, measles virus, Seneca valley virus, coxsackie virus, reo virus, vesicular stomatitis virus, maraba and rhabdovirus, and parvovirus. In some embodiments, the oncolytic virus is attenuated (for example through multiple passages, inactivation or genetic modification). In some embodiments, the immunomodulator is an immune checkpoint inhibitor. In some embodiments, the immunomodulator is an immune-stimulating agent. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the oncolytic virus is administered weekly. In some embodiments, the immunomodulator (including combination of immunomodulators) is administered intravenously. In some embodiments, the method further comprises intravesical administration of a second immunomodulator (including combination of immunomodulators). In some embodiments, the method further comprises administration (such as intravesical or systemic) of a third immunomodulator (including combination of immunomodulators). In some embodiments, the immunomodulator, and/or the second immunomodulator, and/or the third immunomodulator is a modulator of an immune checkpoint molecule selected from the group consisting of CTLA-4, PD-1, PD-L1, PD-L2, TIM3, B7-H3. B7-H4. LAG-3, KIR, and ligands thereof. In some embodiments, the immunomodulator, and/or the second immunomodulator, and/or the third immunomodulator is an immune-stimulating agent. In some embodiments, the immune-stimulating agent is an activator of OX40, 4-1BB or CD40.

In some embodiments, there is provided a method of treating bladder cancer in an individual, comprising: a) intravesically administering an effective amount of an oncolytic virus (such as oncolytic adenovirus); and b) systemically administering an effective amount of an immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule. In some embodiments, the oncolytic virus is replication competent. In some embodiments, the oncolytic virus preferentially replicates in a cancer cell, such as an Rb-pathway defective cancer cell. In some embodiments, the immunomodulator is an immune checkpoint inhibitor. In some embodiments, the immunomodulator is an immune-stimulating agent. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the oncolytic virus is administered weekly. In some embodiments, the immunomodulator (including combination of immunomodulators) is administered intravenously. In some embodiments, the method further comprises intravesical administration of a second immunomodulator (including combination of immunomodulators). In some embodiments, the method further comprises administration (such as intravesical or systemic) of a third immunomodulator (including combination of immunomodulators). In some embodiments, the immunomodulator, and/or the second immunomodulator, and/or the third immunomodulator is a modulator of an immune checkpoint molecule selected from the group consisting of CTLA-4, PD-1, PD-L1, PD-L2, TIM3, B7-H3, B7-H4. LAG-3, KIR, and ligands thereof. In some embodiments, the immunomodulator, and/or the second immunomodulator, and/or the third immunomodulator is an immune-stimulating agent. In some embodiments, the immune-stimulating agent is an activator of OX40, 4-1BB or CD40.

In some embodiments, there is provided a method of treating bladder cancer in an individual, comprising: a) intravesically administering an effective amount of an oncolytic virus (such as oncolytic adenovirus); and b) systemically administering an effective amount of an immunomodulator (including combination of immunomodulators), wherein the oncolytic virus comprises a viral vector comprising a tumor cell-specific promoter operably linked to a viral gene essential for replication of the virus, and a heterologous gene encoding an immune-related molecule. In some embodiments, the tumor-specific promoter is an E2F-1 promoter, such as a human E2F-1 promoter or an E2F-1 promoter comprising the nucleotide sequence set forth in SEQ ID NO:1. In some embodiments, the viral gene essential for replication of the oncolytic virus is selected from the group consisting of E1A, E1B, and E4. In some embodiments, the heterologous gene is operably linked to a viral promoter, such as an E3 promoter. In some embodiments, the immune-related molecule is GM-CSF. In some embodiments, the immunomodulator is an immune checkpoint inhibitor. In some embodiments, the immunomodulator is an immune-stimulating agent. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the oncolytic virus is administered weekly. In some embodiments, the immunomodulator (including combination of immunomodulators) is administered intravenously. In some embodiments, the method further comprises intravesical administration of a second immunomodulator (including combination of immunomodulators). In some embodiments, the method further comprises administration (such as intravesical or systemic) of a third immunomodulator (including combination of immunomodulators). In some embodiments, the immunomodulator, and/or the second immunomodulator, and/or the third immunomodulator is a modulator of an immune checkpoint molecule selected from the group consisting of CTLA-4. PD-1, PD-L, PD-L2, TIM3, B7-H3, B7-H4, LAG-3. KIR, and ligands thereof. In some embodiments, the immunomodulator, and/or the second immunomodulator, and/or the third immunomodulator is an immune-stimulating agent. In some embodiments, the immune-stimulating agent is an activator of OX40, 4-1BB or CD40.

In some embodiments, there is provided a method of treating bladder cancer in an individual, comprising: a) intravesically administering an effective amount of an adenovirus serotype 5; and b) systemically administering an effective amount of an immunomodulator (including combination of immunomodulators), wherein the endogenous E1a promoter of a native adenovirus is replaced by the human E2F-1 promoter, and the E3 19kD coding region of the native adenovirus is replaced by a heterologous gene encoding an immune-related molecule (such as cytokine or chemokine, for example, GM-CSF). In some embodiments, the tumor-specific promoter is an E2F-1 promoter, such as a human E2F-1 promoter or an E2F-1 promoter comprising the nucleotide sequence set forth in SEQ ID NO: 1. In some embodiments, the immunomodulator is an immune checkpoint inhibitor. In some embodiments, the immunomodulator is an immune-stimulating agent. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the adenovirus is administered weekly. In some embodiments, the immunomodulator (including combination of immunomodulators) is administered intravenously. In some embodiments, the method further comprises intravesical administration of a second immunomodulator (including combination of immunomodulators). In some embodiments, the method further comprises administration (such as intravesical or systemic) of a third immunomodulator (including combination of immunomodulators). In some embodiments, the immunomodulator, and/or the second immunomodulator, and/or the third immunomodulator is a modulator of an immune checkpoint molecule selected from the group consisting of CTLA-4, PD-1. PD-L1, PD-L2, TIM3. B7-H3, B7-H4, LAG-3. KIR, and ligands thereof. In some embodiments, the immunomodulator, and/or the second immunomodulator, and/or the third immunomodulator is an immune-stimulating agent. In some embodiments, the immune-stimulating agent is an activator of OX40, 4-1BB or CD40.

In some embodiments, there is provided a method of treating bladder cancer in an individual, comprising: a) intravesically administering an effective amount of CG0070; and b) systemically administering an effective amount of an immunomodulator (including combination of immunomodulators). In some embodiments, the immunomodulator is an immune checkpoint inhibitor. In some embodiments, the immunomodulator is an immune-stimulating agent. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, CG0070 is administered at a dose of about $1 \times 10^8$ to about $1 \times 10^{14}$ viral particles (vp) (such as any of about $1 \times 10^8$ to about $1 \times 10^{10}$, about $1 \times 10^{10}$ to about $1 \times 10^{12}$, or about $1 \times 10^{12}$ to about $1 \times 10^{14}$ vp). In some embodiments, CG0070 is administered weekly. In some embodiments, CG0070 is administered for about 1 week to about 6 weeks (such as at least about any of 3 weeks, 4 weeks or 5 weeks). In some embodiments, the immunomodulator (including combination of immunomodulators) is administered intravenously. In some embodiments, the method further comprises intravesical administration of a second immunomodulator (including combination of immunomodulators). In some embodiments, the method further comprises administration (such as intravesical or systemic) of a third immunomodulator (including combination of immunomodulators). In some embodiments, the immunomodulator, and/or the second immunomodulator, and/or the third immunomodulator is a modulator of an immune checkpoint molecule selected from the group consisting of CTLA-4. PD-1. PD-L1, PD-L2, TIM3. B7-H3, B7-H4. LAG-3. KIR, and ligands thereof. In some embodiments, the immunomodulator, and/or the second immunomodulator, and/or the third immunomodulator is an immune-stimulating agent. In some embodiments, the immune-stimulating agent is an activator of OX40, 4-1BB or CD40.

The methods described herein can be used to treat a variety of bladder cancer conditions. In some embodiments, the bladder cancer is a low grade bladder cancer. In some embodiments, the bladder cancer is a high grade bladder cancer. In some embodiments, the bladder cancer is muscle invasive (e.g., T2, T3 or T4). In some embodiments, the bladder cancer is non-invasive (e.g., Ta, T1 Cis, Cis with Ta and/or T1).

In some embodiments, the bladder cancer is transitional cell carcinoma or urothelial carcinoma (such as metastatic urothelial carcinoma), including, but not limited to, papillary tumors and flat carcinomas. In some embodiments, the bladder cancer is metastatic urothelial carcinoma. In some embodiments, the bladder cancer is urothelial carcinoma of the bladder. In some embodiments, the bladder cancer is urothelial carcinoma of the ureter. In some embodiments, the bladder cancer is urothelial carcinoma of the urethra. In some embodiments, the bladder cancer is urothelial carcinoma of the renal pelvis.

In some embodiments, the bladder cancer is squamous cell carcinoma. In some embodiments, the bladder cancer is non-squamous cell carcinoma. In some embodiments, the bladder cancer is adenocarcinoma. In some embodiments, the bladder cancer is small cell carcinoma.

In some embodiments, the bladder cancer is early stage bladder cancer, non-metastatic bladder cancer, non-invasive bladder cancer, non-muscle-invasive bladder cancer, primary bladder cancer, advanced bladder cancer, locally advanced bladder cancer (such as unresectable locally advanced bladder cancer), metastatic bladder cancer, or bladder cancer in remission. In some embodiments, the bladder cancer is localized resectable, localized unresectable, or unresectable. In some embodiments, the bladder cancer is a high grade, non-muscle-invasive cancer that has been refractory to standard intra-bladder infusion (intravesical) therapy.

The methods provided herein can be used to treat an individual (e.g., human) who has been diagnosed with or is suspected of having bladder cancer. In some embodiments, the individual has undergone a tumor resection. In some embodiments, the individual has refused surgery. In some embodiments, the individual is medically inoperable. In some embodiments, the individual is at a clinical stage of Ta, Tis, T1, T2, T3a, T3b, or T4 bladder cancer. In some embodiments, the individual is at a clinical stage of Tis, CIS, Ta, or T1.

In some embodiments, the individual has been previously treated for bladder cancer (also referred to as the "prior therapy"). In some embodiments, individual has been previously treated with a standard therapy for bladder cancer. In some embodiments, the prior standard therapy is treatment with BCG. In some embodiments, the prior standard therapy is treatment with mitomycin C. In some embodiments, the prior standard therapy is treatment with interferon (such as interferon-α). In some embodiments, the individual has bladder cancer in remission, progressive bladder cancer, or recurrent bladder cancer. In some embodiments, the individual is resistant to treatment of bladder cancer with other agents (such as platinum-based agents, BCG, mitomycin C, and/or interferon). In some embodiments, the individual is initially responsive to treatment of bladder cancer with other agents (such as platinum-based agents, or BCG) but has progressed after treatment.

In some embodiments, the individual has recurrent bladder cancer (such as a bladder cancer at the clinical stage of Ta, Tis, T1, T2, T3a, T3b, or T4) after a prior therapy (such as prior standard therapy, for example treatment with BCG). For example, the individual may be initially responsive to the treatment with the prior therapy, but develops bladder cancer after about any of about 2, 3, 4, 5, 6, 7, 8, 9, 10, 11, 12, 24, 36, 48, or 60 months upon the cessation of the prior therapy.

Any of the immunomodulators described herein, including immune-stimulating agents and immune checkpoint inhibitors, may be used in the combination therapy for systemic or intravesical administration. The immunomodulator (including the first, second and third immunomodulator, and combination of immunomodulators) can be of any one of the molecular modalities known in the art, including, but not limited to, aptamer, mRNA, siRNA, microRNA, shRNA, peptide, antibody, anticalin, Spherical nucleic acid, TALEN, Zinc Finger Nuclease, CRISPR/Cas9, and small molecule.

In some embodiments, the immunomodulator (including the first, second and third immunomodulator, and combination of immunomodulators) is an immune-stimulating agent. In some embodiments, the immune-stimulating agent is a natural or engineered ligand of an immune stimulatory molecule, including, for example, ligands of OX40 (e.g., OX40L), ligands of CD-28 (e.g., CD80, CD86), ligands of ICOS (e.g., B7RP1), ligands of 4-1BB (e.g., 4-1BBL. Ultra4-1BBL), ligands of CD27 (e.g., CD70), ligands of CD40 (e.g., CD40L), and ligands of TCR (e.g., MHC class I or class II molecules. IMCgp100). In some embodiments, the immune-stimulating agent is an antibody selected from the group consisting of anti-CD28 (e.g., TGN-1412), anti-OX40 (e.g., MEDI6469, MEDI-0562), anti-ICOS (e.g., MEDI-570), anti-GITR (e.g., TRX518, INBRX-110, NOV-120301), anti-41-BB (e.g., BMS-663513. PF-05082566), anti-CD27 (e.g., BION-1402, Varlilumab and hCD27.15), anti-CD40 (e.g., CP870,893, BI-655064. BMS-986090. APX005, APX005M), anti-CD3 (e.g., blinatumomab, muromonab), and anti-HVEM. In some embodiments, the antibody is an agonistic antibody. In some embodiments, the antibody is a monoclonal antibody. In some embodiments, the antibody is an antigen-binding fragment selected from the group consisting of Fab, Fab', F(ab')$_2$, Fv, scFv, and other antigen-binding subsequences of the full length antibody. In some embodiments, the antibody is a human, humanized, or chimeric antibody. In some embodiments, the antibody is a bispecific antibody, a multispecific antibody, a single domain antibody, a fusion protein comprising an antibody portion, or any other functional variants or derivatives thereof.

In some embodiments, the immunomodulator (including the first, second and third immunomodulator, and combination of immunomodulators) is an immune checkpoint inhibitor. In some embodiments, the immune checkpoint inhibitor is a natural or engineered ligand of an inhibitory immune checkpoint molecule, including, for example, ligands of CTLA-4 (e.g., B7.1, B7.2), ligands of TIM3 (e.g., Galectin-9), ligands of A2a Receptor (e.g., adenosine, Regadenoson), ligands of LAG3 (e.g., MHC class I or MHC class II molecules), ligands of BTLA (e.g., HVEM, B7-H4), ligands of KIR (e.g., MHC class I or MHC class II molecules), ligands of PD-1 (e.g., PD-L1, PD-L2), ligands of IDO (e.g., NKTR-218, Indoximod, NLG919), ligands of CD47 (e.g., SIRP-alpha receptor), and ligands of CSF1R. In some embodiments, the immune checkpoint inhibitor is an antibody that targets an inhibitory immune checkpoint protein. In some embodiments, the immunomodulator is an antibody selected from the group consisting of anti-CTLA-4 (e.g., Ipilimumab, Tremelimumab, KAHR-102), anti-TIM3 (e.g., F38-2E2, ENUM005), anti-LAG3 (e.g., BMS-986016, IMP701, IMP321. C9B7W), anti-KIR (e.g., Lirilumab, IPH2101, IPH4102), anti-PD-1 (e.g., Nivolumab, Pidilizumab, Pembrolizumab, BMS-936559, atezolizumab, Lambrolizumab, MK-3475, AMP-224, AMP-514, STI-A1110, TSR-042), anti-PD-L1 (e.g., KY-1003 (EP20120194977). MCLA-145, atezolizumab, BMS-936559, MEDI-4736, MSB0010718C, AUR-012, STI-A1010, PCT/US2001/020964, MPDL3280A. AMP-224. Dapirolizumab pegol (CDP-7657), MEDI-4920), anti-CD73 (e.g., AR-42 (OSU-HDAC42, HDAC-42, AR42, AR 42, OSU-HDAC 42, OSU-HDAC-42, NSC D736012, HDAC-42, HDAC 42, HDAC42, NSCD736012, NSC-D736012), MEDI-9447), anti-B7-H3 (e.g., MGA271, DS-5573a, 8H9), anti-CD47 (e.g., CC-90002, TTI-621. VLST-007), anti-BTLA, anti-VISTA, anti-A2aR, anti-B7-1, anti-B7-H4, anti-CD52 (such as alemtuzumab), anti-IL-10, anti-IL-35, anti-TGF-β (such as Fresolumimab), anti-CSF1R (e.g., FPA008), anti-NKG2A (e.g., monalizumab), anti-MICA (e.g., IPH43), and anti-CD39. In some embodiments, the antibody is an antagonistic antibody. In some embodiments, the antibody is a monoclonal antibody. In some embodiments, the antibody is a monoclonal antibody. In some embodiments, the antibody is an antigen-binding fragment selected from the group consisting of Fab, Fab', F(ab')$_2$, Fv, scFv, and other antigen-binding subsequences of the full length antibody. In some embodiments, the antibody is a human, humanized, or chimeric antibody. In some embodiments, the antibody is a bispecific antibody, a multispecific antibody, a single domain antibody, a fusion protein comprising an antibody portion, or any other functional variants or derivatives thereof.

In some embodiments, the method comprises systemic (such as intravenous) administration of a single immunomodulator. In some embodiments, the immunomodulator is an immune checkpoint inhibitor. In some embodiments, the immunomodulator is an immune-stimulating agent.

In some embodiments, the method comprises systemic (such as intravenous) administration of at least two (such as any of 2, 3, 4, 5, 6, or more) immunomodulators. In some embodiments, all or part of the at least two immunomodulators are administered simultaneously, such as in a single composition. In some embodiments, all or part of the at least two immunomodulators are administered sequentially. In some embodiments, the method comprises systemic (such as intravenous) administration of a combination of immunomodulators comprising an immune checkpoint inhibitor and an immune-stimulating agent. In some embodiments, the method comprises systemic (such as intravenous) administration of a combination of immunomodulators comprising two or more (such as any of 2, 3, 4, 5, 6, or more) checkpoint inhibitors. In some embodiments, the method comprises systemic (such as intravenous) administration of a combination of immunomodulators comprising two or more (such as any of 2, 3, 4, 5, 6, or more) immune-stimulating agents. In some embodiments, the method comprises systemic (such as intravenous) administration of a combination of immunomodulators comprising any number (such as any of 1, 2, 3, 4, 5, 6, or more) of immune checkpoint inhibitors and any number (such as any of 2, 3, 4, 5, 6, or more) of immune-stimulating agents. In some embodiments, the method comprises systemic (such as intravenous) administration of an OX40 inhibitor (such as an agnostic anti-OX40 antibody, for example, MEDI6469, MEDI0562, MEDI6383, GSK3174998. KHK4083 or InVivoMAb clone OX-86).

In some embodiments, the method further comprises intravesical administration of a second immunomodulator (including combination of immunomodulators).

In some embodiments, the method further comprises intravesical administration of a single immunomodulator. In some embodiments, the immunomodulator is an immune checkpoint inhibitor. In some embodiments, the immunomodulator is an immune-stimulating agent.

In some embodiments, the method further comprises intravesical administration of at least two (such as any of 2, 3, 4, 5, 6, or more) immunomodulators. In some embodiments, all or part of the at least two immunomodulators are administered simultaneously, such as in a single composition. In some embodiments, all or part of the at least two immunomodulators are administered sequentially. In some embodiments, the method comprises intravesical administration of a combination of immunomodulators comprising an immune checkpoint inhibitor and an immune-stimulating agent. In some embodiments, the method comprises intravesical administration of a combination of immunomodulators comprising two or more (such as any of 2, 3, 4, 5, 6, or more) checkpoint inhibitors. In some embodiments, the method comprises intravesical administration of a combination of immunomodulators comprising two or more (such as any of 2, 3, 4, 5, 6, or more) immune-stimulating agents. In some embodiments, the method comprises intravesical administration of a combination of immunomodulators comprising any number (such as any of 1, 2, 3, 4, 5, 6, or more) of immune checkpoint inhibitors and any number (such as any of 2, 3, 4, 5, 6, or more) of immune-stimulating agents.

In some embodiments, the method comprises intravesical administration of a CTLA-4 inhibitor (such as an anti-CTLA-4 antibody, for example Ipilimumab, or an engineered lipocalin protein, for example an anticalin that specifically recognizes CTLA-4) and a CD40 agonist (such as an agnostic anti-CD40 antibody, for example, APX005M). In some embodiments, the method comprises intravesical administration of a CTLA-4 inhibitor (such as an anti-CTLA-4 antibody, for example Ipilimumab, or an engineered lipocalin protein, for example an anticalin that specifically recognizes CTLA-4) and a 4-1BB agonist (such as an agonistic anti-4-1BB antibody, e.g., PF-05082566).

Thus, for example, in some embodiments, there is provided a method of treating a bladder cancer in an individual (such as a human), comprising: a) intravesically administering an effective amount of an oncolytic virus (such as an oncolytic adenovirus); and b) systemically administering an effective amount of an inhibitor of CTLA-4 (such as an anti-CTLA-4 antibody, for example Ipilimumab, or an engineered lipocalin protein, for example an anticalin that specifically recognizes CTLA-4), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the oncolytic virus is attenuated (for example through multiple passages, inactivation or genetic modification). In some embodiments, the oncolytic virus preferentially replicates in a cancer cell, such as an Rb-pathway defective cancer cell. In some embodiments, the inhibitor of CTLA-4 is an anti-CTLA-4 antibody, for example Ipilimumab. In some embodiments, the inhibitor of CTLA-4 is an engineered lipocalin protein, for example an anticalin that specifically recognizes CTLA-4. In some embodiments, the oncolytic virus is administered weekly. In some embodiments, the inhibitor of CTLA-4 is administered intravenously. In some embodiments, the oncolytic virus and the inhibitor of CTLA-4 are administered sequentially. In some embodiments, the oncolytic virus is administered prior to (such as immediately prior to) the administration of the inhibitor of CTLA-4. In some embodiments, the oncolytic virus is administered after (such as immediately after) the administration of the inhibitor of CTLA-4. In some embodiments, the oncolytic virus and the inhibitor of CTLA-4 are administered simultaneously. In some embodiments, the method further comprises intravesical administration of a second immunomodulator, such as an immune checkpoint inhibitor or an immune-stimulating agent. In some embodiments, the method further comprises administration (such as systemic or intravesical) of a third immunomodulator, such as an immune checkpoint inhibitor or an immune-stimulating agent.

In some embodiments, there is provided a method of treating a bladder cancer in an individual, comprising: a) intravesically administering an effective amount of an oncolytic virus (such as oncolytic adenovirus); and b) systemically administering an effective amount of an inhibitor of CTLA-4 (such as an anti-CTLA-4 antibody, for example Ipilimumab, or an engineered lipocalin protein, for example an anticalin that specifically recognizes CTLA-4), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the tumor-specific promoter is an E2F-1 promoter, such as a human E2F-1 promoter or an E2F-1 promoter comprising the nucleotide sequence set forth in SEQ ID NO:1. In some embodiments, the viral gene essential for replication of the virus is selected from the group consisting of E1A, E1B, and E4. In some embodiments, the heterologous gene is operably linked to a viral promoter, such as the E3 promoter. In some embodiments, the immune-related molecule is GM-CSF.

In some embodiments, there is provided a method of treating a bladder cancer in an individual, comprising: a) intravesically administering an effective amount of an adenovirus serotype 5; and b) systemically administering an effective amount of an inhibitor of CTLA-4 (such as an anti-CTLA-4 antibody, for example Ipilimumab, or an engineered lipocalin protein, for example an anticalin that specifically recognizes CTLA-4), wherein the endogenous E1a promoter of a native adenovirus is replaced by the human E2F1-promoter, and E3 19kD coding region of the native adenovirus is replaced by a heterologous gene encoding an immune-related molecule (such as cytokine or chemokine, for example, GM-CSF). In some embodiments, the tumor-specific promoter is a human E2F-1 promoter or an E2F-1 promoter comprising the nucleotide sequence set forth in SEQ ID NO: 1.

In some embodiments, there is provided a method of treating a bladder cancer in an individual, comprising: a) intravesically administering an effective amount of CG0070; and b) systemically administering an effective amount of an inhibitor of CTLA-4 (such as an anti-CTLA-4 antibody, for example Ipilimumab, or an engineered lipocalin protein, for example an anticalin that specifically recognizes CTLA-4). In some embodiments, the inhibitor of CTLA-4 is an anti-CTLA-4 antibody, for example Ipilimumab. In some embodiments, the inhibitor of CTLA-4 is an engineered lipocalin protein, for example an anticalin that specifically recognizes CTLA-4. In some embodiments, the CG007 is administered at a dose of about $1 \times 10^8$ to about $1 \times 10^{14}$ viral particles (vp) (such as any of about $1 \times 10^8$ to about $1 \times 10^{10}$, about $1 \times 10^{10}$ to about $1 \times 10^{12}$, or about $1 \times 10^{12}$ to about $1 \times 10^{14}$ vp). In some embodiments, CG0070 is administered weekly. In some embodiments, CG0070 is administered for about 1 week to about 6 weeks (such as at least about any of 3 weeks, 4 weeks or 5 weeks). In some embodiments, the inhibitor of CTLA-4 is administered intravenously. In some embodiments, the CG0070 and the inhibitor of CTLA-4 are administered sequentially. In some embodiments, the CG0070 is administered prior to (such as immediately prior to) the administration of the inhibitor of CTLA-4. In some embodiments, the CG0070 is administered after (such as immediately after) the administration of the inhibitor of CTLA-4. In some embodiments, the CG0070 and the inhibitor of CTLA-4 are administered simultaneously. In some embodiments, the method further comprises intravesical administration of a second immunomodulator, such as an immune checkpoint inhibitor or an immune-stimulating agent. In some embodiments, the method further comprises administration (such as systemic or intravesical) of a third immunomodulator, such as an immune checkpoint inhibitor or an immune-stimulating agent.

In some embodiments, there is provided a method of treating a bladder cancer in an individual (such as a human), comprising: a) intravesically administering an effective amount of an oncolytic virus (such as an oncolytic adenovirus); and b) systemically administering an effective amount of an inhibitor of PD-1 (such as an anti-PD-1 antibody, for example, Nivolumab. Pembrolizumab, or Pidilizumab, or an Fc fusion protein of a PD-1 ligand, for example, AMP-224), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the oncolytic virus is attenuated (for example through multiple passages, inactivation or genetic modification). In some embodiments, the oncolytic virus preferentially replicates in a cancer cell, such as an Rb-pathway defective cancer cell. In some embodiments, the inhibitor of PD-1 is an anti-PD-1 antibody, for example, Nivolumab, Pembrolizumab, or Pidilizumab. In some embodiments, the inhibitor of PD-1 is an inhibitor of the interaction between PD-1 and its ligand, such as an inhibitor of PD-1/PD-L1 interaction or an inhibitor of PD-1/PD-L2 interaction. In some embodiments, the inhibitor of PD-1 is an Fc fusion protein comprising a PD-1 ligand, such as an Fc-fusion of PD-L2 (e.g., AMP-224). In some embodiments, the oncolytic virus is administered weekly. In some embodiments, the inhibitor of PD-1 is administered intravenously. In some embodiments, the oncolytic virus and the inhibitor of PD-1 are administered sequentially. In some embodiments, the oncolytic virus is administered prior to (such as immediately prior to) the administration of the inhibitor of PD-1. In some embodiments, the oncolytic virus is administered after (such as immediately after) the administration of the inhibitor of PD-1. In some embodiments, the oncolytic virus and the inhibitor of PD-1 are administered simultaneously. In some embodiments, the method further comprises intravesical administration of a second immunomodulator, such as an immune checkpoint inhibitor (such as a CTLA-4 inhibitor) or an immune-stimulating agent (e.g., a CD40 activator or a 4-1BB activator). In some embodiments, the method further comprises administration (such as systemic or intravesical) of a third immunomodulator, such as an immune checkpoint inhibitor (such as a CTLA-4 inhibitor) or an immune-stimulating agent (e.g., a CD40 activator or a 4-1BB activator).

In some embodiments, there is provided a method of treating a bladder cancer in an individual, comprising: a) intravesically administering an effective amount of an oncolytic virus (such as oncolytic adenovirus); and b) systemically administering an effective amount of an inhibitor of PD-1 (such as an anti-PD-1 antibody, for example, Nivolumab, Pembrolizumab, or Pidilizumab, or an Fc fusion protein of a PD-1 ligand, for example, AMP-224), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the tumor-specific promoter is an E2F-1 promoter, such as a human E2F-1 promoter or an E2F-1 promoter comprising the nucleotide sequence set forth in SEQ ID NO:1. In some embodiments, the viral gene essential for replication of the virus is selected from the group consisting of E1A, E1B, and E4. In some embodiments, the heterologous gene is operably linked to a viral promoter, such as the E3 promoter. In some embodiments, the immune-related molecule is GM-CSF.

In some embodiments, there is provided a method of treating a bladder cancer in an individual, comprising: a) intravesically administering an effective amount of an adenovirus serotype 5; and b) systemically administering an effective amount of an inhibitor of PD-1 (such as an anti-PD-1 antibody, for example, Nivolumab, Pembrolizumab, or Pidilizumab, or an Fc fusion protein of a PD-1 ligand, for example, AMP-224), wherein the endogenous E1a promoter of a native adenovirus is replaced by the human E2F1-promoter, and E3 19kD coding region of the native adenovirus is replaced by a heterologous gene encoding an immune-related molecule (such as cytokine or chemokine, for example, GM-CSF). In some embodiments, the tumor-specific promoter is a human E2F-1 promoter or an E2F-1 promoter comprising the nucleotide sequence set forth in SEQ ID NO:1.

In some embodiments, there is provided a method of treating a bladder cancer in an individual, comprising: a) intravesically administering an effective amount of an adenovirus serotype 5, wherein the endogenous E1a promoter and E3 19kD coding region of a native adenovirus is replaced by the human E2F-1 promoter and a nucleic acid encoding an immune-related molecule (such as cytokine or chemokine, for example, GM-CSF); and b) intravesically administering an effective amount of an inhibitor of PD-1 (such as an anti-PD-1 antibody, for example, Nivolumab, Pembrolizumab, or Pidilizumab, or an Fc fusion protein of a PD-1 ligand, for example, AMP-224). In some embodiments, the tumor-specific promoter is a human E2F-1 promoter or an E2F-1 promoter comprising the nucleotide sequence set forth in SEQ ID NO: 1.

In some embodiments, there is provided a method of treating a bladder cancer in an individual, comprising: a) intravesically administering an effective amount of CG0070; and b) systemically administering an effective amount of an inhibitor of PD-1 (such as an anti-PD-1 antibody, for example, Nivolumab. Pembrolizumab, or Pidilizumab, or an Fc fusion protein of a PD-1 ligand, for example, AMP-224). In some embodiments, the inhibitor of PD-1 is an anti-PD-1 antibody, for example, Nivolumab, Pembrolizumab, or Pidilizumab. In some embodiments, the inhibitor of PD-1 is an inhibitor of the interaction between PD-1 and its ligand, such as an inhibitor of PD-1/PD-L1 interaction or an inhibitor of PD-1/PD-L2 interaction. In some embodiments, the inhibitor of PD-1 is an Fc fusion protein comprising a PD-1 ligand, such as an Fc-fusion of PD-L2 (e.g., AMP-224). In some embodiments, the CG007 is administered at a dose of about $1\times10^8$ to about $1\times10^{14}$ viral particles (vp) (such as any of about $1\times10^8$ to about $1\times10^{10}$, about $1\times10^{10}$ to about $1\times10^{12}$, or about $1\times10^{12}$ to about $1\times10^{14}$ vp). In some embodiments, CG0070 is administered weekly. In some embodiments, CG0070 is administered for about 1 week to about 6 weeks (such as at least about any of 3 weeks, 4 weeks or 5 weeks). In some embodiments, the inhibitor of PD-1 is administered intravenously. In some embodiments, the CG0070 and the inhibitor of PD-1 are administered sequentially. In some embodiments, the CG0070 is administered prior to (such as immediately prior to) the administration of the inhibitor of PD-1. In some embodiments, the CG0070 is administered after (such as immediately after) the administration of the inhibitor of PD-1. In some embodiments, the CG0070 and the inhibitor of PD-1 are administered simultaneously. In some embodiments, the method further comprises intravesical administration of a second immunomodulator, such as an immune checkpoint inhibitor or an immune-stimulating agent. In some embodiments, the method further comprises administration (such as systemic or intravesical) of a third immunomodulator, such as an immune checkpoint inhibitor or an immune-stimulating agent.

In some embodiments, there is provided a method of treating a bladder cancer in an individual (such as a human), comprising: a) intravesically administering an effective amount of an oncolytic virus (such as an oncolytic adenovirus); and b) systemically administering an effective amount of an inhibitor of PD-1 ligand (such as an anti-PD-L1 or anti-PD-L2 antibody, or an inhibitor of both PD-L1 and PD-L2), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the oncolytic virus is attenuated (for example through multiple passages, inactivation or genetic modification). In some embodiments, the oncolytic virus preferentially replicates in a cancer cell, such as an Rb-pathway defective cancer cell. In some embodiments, the inhibitor of PD-1 ligand is an anti-PD-L1 antibody, for example, KY-1003. MCLA-145, atezolizumab, BMS935559, MPDL3280A, MEDI4736, Avelumab, or STI-A1010. In some embodiments, the inhibitor of PD-1 ligand is an anti-PD-L2 antibody. In some embodiments, the inhibitor of PD-1 ligand is an inhibitor (e.g., peptide, protein or small molecule) of both PD-L and PD-L2, such as AUR-012, and AMP-224. In some embodiments, the oncolytic virus is administered weekly. In some embodiments, the inhibitor of PD-1 ligand is administered intravenously. In some embodiments, the oncolytic virus and the inhibitor of PD-1 ligand are administered sequentially. In some embodiments, the oncolytic virus is administered prior to (such as immediately prior to) the administration of the inhibitor of PD-1 ligand. In some embodiments, the oncolytic virus is administered after (such as immediately after) the administration of the inhibitor of PD-1 ligand. In some embodiments, the oncolytic virus and the inhibitor of PD-1 ligand are administered simultaneously. In some embodiments, the method further comprises intravesical administration of a second immunomodulator, such as an immune checkpoint inhibitor or an immune-stimulating agent. In some embodiments, the method further comprises administration (such as systemic or intravesical) of a third immunomodulator, such as an immune checkpoint inhibitor or an immune-stimulating agent.

In some embodiments, there is provided a method of treating a bladder cancer in an individual, comprising: a) intravesically administering an effective amount of an oncolytic virus (such as oncolytic adenovirus); and b) systemically administering an effective amount of an inhibitor of PD-1 ligand (such as an anti-PD-L1 or anti-PD-L2 antibody, or an inhibitor of both PD-L1 and PD-L2), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the tumor-specific promoter is an E2F-1 promoter, such as a human E2F-1 promoter or an E2F-1 promoter comprising the nucleotide sequence set forth in SEQ ID NO: 1. In some embodiments, the viral gene essential for replication of the virus is selected from the group consisting of E A, E1B, and E4. In some embodiments, the heterologous gene is operably linked to a viral promoter, such as the E3 promoter. In some embodiments, the immune-related molecule is GM-CSF.

In some embodiments, there is provided a method of treating a bladder cancer in an individual, comprising: a) intravesically administering an effective amount of an adenovirus serotype 5; and b) systemically administering an effective amount of an inhibitor of PD-1 ligand (such as an anti-PD-L1 or anti-PD-L2 antibody, or an inhibitor of both PD-L1 and PD-L2), wherein the endogenous E1a promoter of a native adenovirus is replaced by the human E2F1-promoter, and E3 19kD coding region of the native adenovirus is replaced by a heterologous gene encoding an immune-related molecule (such as cytokine or chemokine, for example, GM-CSF). In some embodiments, the tumor-specific promoter is a human E2F-1 promoter or an E2F-1 promoter comprising the nucleotide sequence set forth in SEQ ID NO: 1.

In some embodiments, there is provided a method of treating a bladder cancer in an individual, comprising: a) intravesically administering an effective amount of CG0070; and b) systemically administering an effective amount of an inhibitor of PD-1 ligand (such as an anti-PD-L1 or anti-PD-L2 antibody, or an inhibitor of both PD-L and PD-L2). In some embodiments, the inhibitor of PD-1 ligand is an anti-PD-L1 antibody, for example, KY-1003, MCLA-145, atezolizumab, BMS935559, MPDL3280A, MEDI4736, Avelumab, or STI-A1010. In some embodiments, the inhibitor of PD-1 ligand is an anti-PD-L2 antibody. In some embodiments, the inhibitor of PD-1 ligand is an inhibitor (e.g., peptide, protein or small molecule) of both PD-L1 and PD-L2, such as AUR-012, and AMP-224. In some embodiments, the CG007 is administered at a dose of about $1\times10^8$ to about $1\times10^{14}$ viral particles (vp) (such as any of about $1\times10^8$ to about $1\times10^{10}$, about $1\times10^{10}$ to about $1\times10^{12}$, or about $1\times10^{12}$ to about $1\times10^{14}$ vp). In some embodiments. CG0070 is administered weekly. In some embodiments, CG0070 is administered for about 1 week to about 6 weeks (such as at least about any of 3 weeks, 4 weeks or 5 weeks). In some embodiments, the inhibitor of PD-1 ligand is administered intravenously. In some embodiments, the CG0070 and the inhibitor of PD-1 ligand are administered sequentially. In some embodiments, the CG0070 is administered prior to (such as immediately prior to) the administration of the inhibitor of PD-1 ligand. In some embodiments, the CG0070 is administered after (such as immediately after) the administration of the inhibitor of PD-1 ligand. In some embodiments, the CG0070 and the inhibitor of PD-1 ligand are administered simultaneously. In some embodiments, the method further comprises intravesical administration of a second immunomodulator, such as an immune checkpoint inhibitor or an immune-stimulating agent. In some embodiments, the method further comprises administration (such as systemic or intravesical) of a third immunomodulator, such as an immune checkpoint inhibitor or an immune-stimulating agent.

In some embodiments, there is provided a method of treating a bladder cancer in an individual, comprising: a) intravesically administering an effective amount of CG0070; b) intravenously administering an effective amount of an inhibitor of PD-L1 (such as an antagonist anti-PD-L1 antibody, for example, atezolizumab); and c) intravesically administering an effective amount of an inhibitor of CTLA-4 (such as an anti-CTLA-4 antibody, for example Ipilimumab). In some embodiments, the CG0070 is administered at a dose of about $1\times10^8$ to about $1\times10^{14}$ viral particles (vp) (such as any of about $1\times10^8$ to about $1\times10^{10}$, about $1\times10^{10}$ to about $1\times10^{12}$, or about $1\times10^{12}$ to about $1\times10^{14}$ vp). In some embodiments, CG0070 is administered weekly. In some embodiments, the inhibitor of PD-L is administered at a dose of about 1 mg/kg to about 20 mg/kg, or about 750 mg to about 1200 mg. In some embodiments, the inhibitor of PD-L is administered about monthly to about biweekly (such as about once every 2 weeks, about once every 3 weeks, or about once every 4 weeks). In some embodiments, the inhibitor of CTLA-4 is administered at a dose of about 0.1 mg/Kg to about 10 mg/Kg (such as any of about 0.1 mg/Kg to about 1 mg/Kg, about 1 mg/Kg to about 5 mg/Kg, or about 5 mg/Kg to about 10 mg/Kg weekly). In some embodiments, the inhibitor of CTLA-4 is administered weekly. In some embodiments, the inhibitor of CTLA-4 is administered immediately after (e.g., no more than 5 minutes after) administration of CG0070. In some embodiments, the inhibitor of PD-L1 is an antagonist antibody of PD-L1, such as atezolizumab. In some embodiments, the inhibitor of CTLA-4 is an anti-CTLA-4 antibody, for example Ipilimumab (e.g., YERVOY®). In some embodiments, the inhibitor of CTLA-4 is an engineered lipocalin protein, for example an anticalin that specifically recognizes CTLA-4. In some embodiments, the CG0070 and the inhibitor of PD-L1 are administered sequentially. In some embodiments, the CG0070 is administered prior to (such as immediately prior to) the administration of the inhibitor of PD-L1. In some embodiments, the CG0070 is administered after (such as immediately after) the administration of the inhibitor of PD-L1. In some embodiments, the CG0070 and the inhibitor of PD-L1 are administered simultaneously. In some embodiments, the individual is further administered intravesically an effective amount of DDM as a transduction enhancing agent in combination with the CG0070 administration. In some embodiments, CG0070 is administered for about 1 to about 6 weeks as one treatment course. In some embodiments, the treatment course is repeated every about two to about three months. In some embodiments, the method further comprises intravesically administration of a second immunomodulator, such as an immune-stimulating agent. In some embodiments, the second immunomodulator is a CD40 activator, such as an agonist anti-CD40 antibody (e.g., APX005M). In some embodiments, the second immunomodulator is a 4-1BB activator, such as an agonist anti-4-1BB antibody (e.g., PF-05082566).

In some embodiments, there is provided a method of treating a bladder cancer in an individual (such as a human), comprising: a) intravesically administering an effective amount of an oncolytic virus (such as an oncolytic adenovirus); and b) systemically administering an effective amount of an activator of CD40 (such as an agnostic anti-CD40 antibody, for example, CP-870,893, Dacetuzumab. ChiLob 7/4 or APX005M), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the oncolytic virus is attenuated (for example through multiple passages, inactivation or genetic modification). In some embodiments, the oncolytic virus preferentially replicates in a cancer cell, such as an Rb-pathway defective cancer cell. In some embodiments, the activator of CD40 is an agnostic anti-CD40 antibody, for example, CP-870.893. Dacetuzumab, ChiLob 7/4 or APX005M. In some embodiments, the oncolytic virus is administered weekly. In some embodiments, the activator of CD40 is administered intravenously. In some embodiments, the oncolytic virus and the activator of CD40 are administered sequentially. In some embodiments, the oncolytic virus is administered prior to (such as immediately prior to) the administration of the activator of CD40. In some embodiments, the oncolytic virus is administered after (such as immediately after) the administration of the activator of CD40. In some embodiments, the oncolytic virus and the activator of CD40 are administered simultaneously. In some embodiments, the method further comprises intravesical administration of a second immunomodulator, such as an immune checkpoint inhibitor or an immune-stimulating agent. In some embodiments, the method further comprises administration (such as systemic or intravesical) of a third immunomodulator, such as an immune checkpoint inhibitor or an immune-stimulating agent.

In some embodiments, there is provided a method of treating a bladder cancer in an individual, comprising: a) intravesically administering an effective amount of an oncolytic virus (such as oncolytic adenovirus); and b) systemically administering an effective amount of an activator of CD40 (such as an agnostic anti-CD40 antibody, for example, CP-870.893, Dacetuzumab, ChiLob 7/4 or APX005M), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the tumor-specific promoter is an E2F-1 promoter, such as a human E2F-1 promoter or an E2F-1 promoter comprising the nucleotide sequence set forth in SEQ ID NO: 1. In some embodiments, the viral gene essential for replication of the virus is selected from the group consisting of E1A, E1B, and E4. In some embodiments, the heterologous gene is operably linked to a viral promoter, such as the E3 promoter. In some embodiments, the immune-related molecule is GM-CSF.

In some embodiments, there is provided a method of treating a bladder cancer in an individual, comprising: a) intravesically administering an effective amount of an adenovirus serotype 5; and b) systemically administering an effective amount of an activator of CD40 (such as an agnostic anti-CD40 antibody, for example, CP-870,893, Dacetuzumab, ChiLob 7/4 or APX005M), wherein the endogenous E1a promoter of a native adenovirus is replaced by the human E2F1-promoter, and E3 19kD coding region of the native adenovirus is replaced by a heterologous gene encoding an immune-related molecule (such as cytokine or chemokine, for example, GM-CSF). In some embodiments, the tumor-specific promoter is a human E2F-1 promoter or an E2F-1 promoter comprising the nucleotide sequence set forth in SEQ ID NO: 1.

In some embodiments, there is provided a method of treating a bladder cancer in an individual, comprising: a) intravesically administering an effective amount of CG0070; and b) systemically administering an effective amount of an activator of CD40 (such as an agnostic anti-CD40 antibody, for example, CP-870,893, Dacetuzumab, ChiLob 7/4 or APX005M). In some embodiments, the activator of CD40 is an agnostic anti-CD40 antibody, for example, CP-870.893. Dacetuzumab. ChiLob 7/4 or APX005M. In some embodiments, the CG007 is administered at a dose of about $1 \times 10^8$ to about $1 \times 10^{14}$ viral particles (vp) (such as any of about $1 \times 10^8$ to about $1 \times 10^{10}$, about $1 \times 10^{10}$ to about $1 \times 10^{12}$, or about $1 \times 10^{12}$ to about $1 \times 10^{14}$ vp). In some embodiments. CG0070 is administered weekly. In some embodiments, CG0070 is administered for about 1 week to about 6 weeks (such as at least about any of 3 weeks, 4 weeks or 5 weeks). In some embodiments, the activator of CD40 is administered intravenously. In some embodiments, the CG0070 and the activator of CD40 are administered sequentially. In some embodiments, the CG0070 is administered prior to (such as immediately prior to) the administration of the activator of CD40. In some embodiments, the CG0070 is administered after (such as immediately after) the administration of the activator of CD40. In some embodiments, the CG0070 and the activator of CD40 are administered simultaneously. In some embodiments, the method further comprises intravesical administration of a second immunomodulator, such as an immune checkpoint inhibitor or an immune-stimulating agent. In some embodiments, the method further comprises administration (such as systemic or intravesical) of a third immunomodulator, such as an immune checkpoint inhibitor or an immune-stimulating agent.

In some embodiments, there is provided a method of treating a bladder cancer in an individual (such as a human), comprising: a) intravesically administering an effective amount of an oncolytic virus (such as an oncolytic adenovirus); and b) systemically administering an effective amount of an activator of OX40 (such as an agnostic anti-OX40 antibody, for example, MEDI6469, MEDI0562, MEDI6383, GSK3174998, KHK4083 or InVivoMAb clone OX-86), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the oncolytic virus is attenuated (for example through multiple passages, inactivation or genetic modification). In some embodiments, the oncolytic virus preferentially replicates in a cancer cell, such as an Rb-pathway defective cancer cell. In some embodiments, the activator of OX40 is an agnostic anti-OX40 antibody, for example, MEDI6469, MEDI0562, MEDI6383, GSK3174998, KHK4083 or In VivoMAb clone OX-86. In some embodiments, the oncolytic virus is administered weekly. In some embodiments, the activator of OX40 is administered intravenously. In some embodiments, the oncolytic virus and the activator of OX40 are administered sequentially. In some embodiments, the oncolytic virus is administered prior to (such as immediately prior to) the administration of the activator of OX40. In some embodiments, the oncolytic virus is administered after (such as immediately after) the administration of the activator of OX40. In some embodiments, the oncolytic virus and the activator of OX40 are administered simultaneously. In some embodiments, the method further comprises intravesical administration of a second immunomodulator, such as an immune checkpoint inhibitor or an immune-stimulating agent. In some embodiments, the method further comprises administration (such as systemic or intravesical) of a third immunomodulator, such as an immune checkpoint inhibitor or an immune-stimulating agent.

In some embodiments, there is provided a method of treating a bladder cancer in an individual, comprising: a) intravesically administering an effective amount of an oncolytic virus (such as oncolytic adenovirus); and b) systemically administering an effective amount of an activator of OX40 (such as an agnostic anti-OX40 antibody, for example, MEDI6469, MEDI0562, MEDI6383, GSK3174998, KHK4083 or InVivoMAb clone OX-86), wherein the oncolytic virus comprises a viral vector comprising a tumor cell-specific promoter operably linked to a viral gene essential for replication of the virus, and a heterologous gene encoding an immune-related molecule (such as cytokine or chemokine). In some embodiments, the tumor-specific promoter is an E2F-1 promoter, such as a human E2F-1 promoter or an E2F-1 promoter comprising the nucleotide sequence set forth in SEQ ID NO: 1. In some embodiments, the viral gene essential for replication of the virus is selected from the group consisting of E1A, E1B, and E4. In some embodiments, the heterologous gene is operably linked to a viral promoter, such as the E3 promoter. In some embodiments, the immune-related molecule is GM-CSF.

In some embodiments, there is provided a method of treating a bladder cancer in an individual, comprising: a) intravesically administering an effective amount of an adenovirus serotype 5; and b) systemically administering an effective amount of an activator of OX40 (such as an agnostic anti-OX40 antibody, for example, MEDI6469, MEDI0562, MEDI6383, GSK3174998, KHK4083 or InVivoMAb clone OX-86), wherein the endogenous E1a promoter of a native adenovirus is replaced by the human E2F1-promoter, and E3 19kD coding region of the native adenovirus is replaced by a heterologous gene encoding an immune-related molecule (such as cytokine or chemokine, for example, GM-CSF). In some embodiments, the tumor-specific promoter is a human E2F-1 promoter or an E2F-1 promoter comprising the nucleotide sequence set forth in SEQ ID NO:1.

In some embodiments, there is provided a method of treating a bladder cancer in an individual, comprising: a) intravesically administering an effective amount of CG0070; and b) systemically administering an effective amount of an activator of OX40 (such as an agnostic anti-OX40 antibody, for example, MEDI6469, MEDI0562, MEDI6383. GSK3174998, KHK4083 or InVivoMAb clone OX-86). In some embodiments, the activator of OX40 is an agnostic anti-OX40 antibody, for example, MEDI6469, MEDI0562, MEDI6383, GSK3174998, KHK4083 or n VivoMAb clone OX-86. In some embodiments, the CG0070 is administered at a dose of about $1\times10^8$ to about $1\times10^{14}$ viral particles (vp) (such as any of about $1\times10^8$ to about $1\times10^{10}$, about $1\times10^{10}$ to about $1\times10^{12}$, or about $1\times10^{12}$ to about $1\times10^{14}$ vp). In some embodiments, CG0070 is administered weekly. In some embodiments, CG0070 is administered for about 1 week to about 6 weeks (such as at least about any of 3 weeks, 4 weeks or 5 weeks). In some embodiments, the activator of OX40 is administered at a dose of about 0.001 mg/kg to about 10 mg/kg (such as such as any of about 0.003 mg/Kg to about 0.01 mg/Kg, about 0.01 mg/Kg to about 0.1 mg/Kg, about 0.1 mg/Kg to about 1 mg/Kg, about 1 mg/Kg to about 5 mg/Kg, or about 5 mg/Kg to about 10 mg/Kg). In some embodiments, the activator of OX40 is administered about monthly to about weekly (such as about weekly, about once every 2 weeks, or about once every 3 weeks). In some embodiments, the CG0070 and the activator of OX40 are administered sequentially. In some embodiments, the CG0070 is administered prior to (such as immediately prior to) the administration of the activator of OX40. In some embodiments, the CG0070 is administered after (such as immediately after) the administration of the activator of OX40. In some embodiments, CG0070 and the activator of OX40 are administered simultaneously. In some embodiments, the method further comprises intravesically administration of a second immunomodulator, such as an immune checkpoint inhibitor or an immune-stimulating agent. In some embodiments, the method further comprises administration (such as systemic or intravesical) of a third immunomodulator, such as an immune checkpoint inhibitor or an immune-stimulating agent.

In some embodiments, there is provided a method of treating a bladder cancer in an individual, comprising: a) intravesically administering an effective amount of CG0070; b) intravenously administering an effective amount of an OX40 activator (such as an agnostic anti-OX40 antibody, for example, MEDI6469, MEDI0562, MEDI6383, GSK3174998, KHK4083 or InVivoMAb clone OX-86); and c) intravesically administering an effective amount of an inhibitor of CTLA-4 (such as an anti-CTLA-4 antibody, for example Ipilimumab, or an engineered lipocalin protein, for example an anticalin that specifically recognizes CTLA-4). In some embodiments, the CG0070 is administered at a dose of about $1\times10^8$ to about $1\times10^{14}$ viral particles (vp) (such as any of about $1\times10^8$ to about $1\times10^{10}$, about $1\times10^{10}$ to about $1\times10^{12}$, or about $1\times10^{12}$ to about $1\times10^{114}$ vp). In some embodiments, CG0070 is administered weekly. In some embodiments, the OX40 activator is administered at a dose of about 0.001 mg/kg to about 10 mg/kg (such as such as any of about 0.003 mg/Kg to about 0.01 mg/Kg, about 0.01 mg/Kg to about 0.1 mg/Kg, about 0.1 mg/Kg to about 1 mg/Kg, about 1 mg/Kg to about 5 mg/Kg, or about 5 mg/Kg to about 10 mg/Kg). In some embodiments, the activator of OX40 is administered about monthly to about weekly (such as about weekly, about once every 2 weeks, or about once every 3 weeks). In some embodiments, the inhibitor of CTLA-4 is administered at a dose of about 0.1 mg/Kg to about 10 mg/Kg (such as any of about 0.1 mg/Kg to about 1 mg/Kg, about 1 mg/Kg to about 5 mg/Kg, or about 5 mg/Kg to about 10 mg/Kg weekly). In some embodiments, the inhibitor of CTLA-4 is administered weekly. In some embodiments, the inhibitor of CTLA-4 is administered immediately after (e.g., no more than 5 minutes after) administration of CG0070. In some embodiments, the OX40 activator is an agonistic antibody of OX40, such as GSK3174998. In some embodiments, the inhibitor of CTLA-4 is an anti-CTLA-4 antibody, for example Ipilimumab (e.g., YERVOY®). In some embodiments, the inhibitor of CTLA-4 is an engineered lipocalin protein, for example an anticalin that specifically recognizes CTLA-4. In some embodiments, the CG0070 and the OX40 activator are administered sequentially. In some embodiments, the CG0070 is administered prior to (such as immediately prior to) the administration of the OX40 activator. In some embodiments, the CG0070 is administered after (such as immediately after) the administration of the OX40 activator. In some embodiments, the CG0070 and the OX40 activator are administered simultaneously. In some embodiments, the individual is further administered intravesically an effective amount of DDM as a transduction enhancing agent in combination with the CG0070 administration. In some embodiments, CG0070 is administered for about 1 to about 6 weeks as one treatment course. In some embodiments, the treatment course is repeated every about two to about three months. In some embodiments, the method further comprises intravesically administration of a second immunomodulator, such as an immune-stimulating agent. In some embodiments, the second immunomodulator is a CD40 activator, such as an agonist anti-CD40 antibody (e.g., APX005M). In some embodiments, the second immunomodulator is a 4-1BB activator, such as an agonist anti-4-1BB antibody (e.g., PF-05082566).

The intravesical administration of the oncolytic virus and/or optionally the second immunomodulator (including combination of immunomodulators) provide a unique opportunity of a relatively convenient yet effective intravesical tumor exposure to the oncolytic virus and/or optional the second immunomodulator (including combination of immunomodulators), as well as a potentially reduced toxicity to other tissues. Suitable dosages and dosing frequency of the oncolytic virus and the immunomodulator (including the first, second, third immunomodulators, and combination of immunomodulators) are within the same ranges as those described for local administration of the oncolytic virus and the immunomodulator (including the first, second, third immunomodulator, and combination of immunomodulators) respectively in the previous section.

In some embodiments, the oncolytic virus and/or optionally the second immunomodulator (including combination of immunomodulators) are administered by instillation as a solution via a catheter. In some embodiments, the total volume of the solution used for the intravesical installation is about any of 1 mL, 10 mL, 50 mL, 75 mL, 100 mL, 125 mL, 150 mL, 200 mL, 250 mL, 300 mL, 400 mL or 500 mL. In some embodiments, the total volume of the solution used for the intravesical installation is any of about 1 mL to about 10 mL, about 10 mL to about 50 mL, about 50 mL to about 75 mL, about 75 mL to about 100 mL, about 100 mL to about 125 mL, about 75 mL to about 125 mL, about 100 mL to about 150 mL, about 150 mL to about 200 mL, about 200 mL to about 300 mL, about 300 mL to about 400 mL, about 400 mL to about 500 mL, about 50 mL to about 500 mL, about 50 mL to about 250 mL, or about 100 mL to about 250 mL.

In some embodiments, the oncolytic virus is administered at a dose of about $1\times10^8$ to about $1\times10^{15}$ particles (such as about $1\times10^{11}$ to about $1\times10^{14}$ particles, for example about $1\times10^{12}$ particles). In some embodiments, the oncolytic virus is administered at a volume of about 50 to about 500 mL (such as about 100 mL) by instillation.

In some embodiments, the second immunomodulator (including combination of immunomodulators) is administered intravesically at a dose of about 0.1 mg/Kg to about 100 mg/Kg (such as about 0.1 mg/Kg to about 0.3 mg/Kg, about 0.1 mg/Kg to about 0.5 mg/Kg, about 0.5 mg/Kg to about 1 mg/Kg, about 1 mg/Kg to about 10 mg/Kg, about 10 mg/Kg to about 50 mg/Kg, about 50 mg/Kg to about 100 mg/Kg, or about 1 mg/Kg to about 100 mg/Kg). In some embodiments, the second immunomodulator (including combination of immunomodulators) is administered intravesically at a dose no more than about any of 500 mg, 400 mg, 300 mg, 200 mg, 100 mg, 80 mg, 60 mg, 40 mg, 20 mg, or 10 mg per administration. In some embodiments, the second immunomodulator (including combination of immunomodulators) is administered intravesically at a volume of about 1 mL to about 500 mL (such as about 100 mL) by instillation.

The solution of the oncolytic virus and/or optionally the second immunomodulator (including combination of immunomodulators) may be retained in the bladder for a certain amount of time before voiding, in order to achieve uniform distribution or sufficient exposure of the oncolytic virus optionally the second immunomodulator (including combination of immunomodulators) among the bladder tumor cells. In some embodiments, the solution is retained in the bladder of the individual for at least about any of 5 minutes, 10 minutes, 15 minutes, 20 minutes, 30 minutes, 45 minutes, 1 hour, 2 hours, or more. In some embodiments, the solution is retained in the bladder of the individual for any of about 5 minutes to about 10 minutes, about 10 minutes to about 15 minutes, about 10 minutes to about 20 minutes, about 20 minutes to about 30 minutes, about 30 minutes to about 45 minutes, about 45 minutes to about 50 minutes, about 50 minutes to about 1 hour, about 5 minutes to about 15 minutes, about 10 minutes to about 30 minutes, about 30 minutes to about 1 hour, or about 1 hour to about 2 hours. In some embodiments, the oncolytic virus (such as the oncolytic virus, e.g., CG0070) is retained in the bladder of the individual for about 45 minutes to about 50 minutes. In some embodiments, the second immunomodulator (including combination of immunomodulators) is retained in the bladder for about 45 minutes to 1 hour. In some embodiments, the efficiency of the intravesical administration of the oncolytic virus is further enhanced by a pretreatment comprising intravesical administration of an effective amount of a transduction enhancing agent, such as DDM.

In some embodiments, the pretreatment step is carried out by contacting the luminal surface of the bladder in the individual with the pretreatment composition prior to the administration of the oncolytic virus. For example, the pretreatment composition may comprise about 0.01% to about 0.5% (such as 0.05 to about 0.2%, for example about 0.1%) of the transduction enhancing agent (such as DDM).

In some embodiments, the total volume of the pretreatment composition (such as DDM) is about 10 mL to about 1000 mL (such as about 10 mL to about 100 mL, about 100 mL to about 500 mL, or about 500 mL to about 1000 mL). In some embodiments, a suitable dosage for the pretreatment composition is about any one of 0.1 g, 0.2 g, 0.5 g, 0.75 g, 1 g, 1.5 g, 2 g, 2.5 g, 5 g, or 10 g of the transduction enhancing agent (such as DDM). In some embodiments, the effective amount of the pretreatment composition is about 1 g of DDM (e.g., 100 mL of 0.1% DDM solution).

In some embodiments, the pretreatment composition (such as DDM) is administered immediately (such as no more than 5 minutes) prior to the administration of the oncolytic virus. In some embodiments, the pretreatment composition (such as DDM) is administered no more than about any of 5 minutes, 10 minutes, 15 minutes, 20 minutes, 30 minutes, 45 minutes, 1 hour, 90 minutes, 2 hours, 3 hours or 4 hours before the administration of the oncolytic virus. In some embodiments, the pretreatment composition (such as DDM) is administered no more than about 2 hours before the administration of the oncolytic virus. In some embodiments, the pretreatment composition (such as DDM solution) is retained in the bladder for at least about any one of 5 minutes, 10 minutes, 15 minutes, or 20 minutes. In some embodiments, the pretreatment composition (such as DDM solution) is retained in the bladder for any of about 5 minutes to about 10 minutes, about 10 minutes to about 15 minutes, about 12 minutes to about 15 minutes, about 15 minutes to about 20 minutes, or about 10 minutes to about 20 minutes. In some embodiments, the pretreatment composition (such as DDM solution) is retained in the bladder for about 12 minutes to about 15 minutes.

In some embodiments, the pretreatment step is carried out by contacting the luminal surface of the bladder in the individual with the pretreatment composition prior to the administration of the oncolytic virus.

In some embodiments, the method further comprises washing the luminal surface of the bladder contact with the pretreatment composition In some embodiments, the method further comprises washing the luminal surface of the bladder after contacting the bladder with the pretreatment composition prior to the administration of the oncolytic virus.

In some embodiments, the pretreatment step comprises one or more tumor site preparation steps as described in the "Methods of treating a solid or lymphatic tumor" section.

In some embodiments, the pretreatment comprises intravesical administration of an effective amount of an immune-related molecule (such as cytokine, chemokine or PRRago). In some embodiments, the immune-related molecule is selected from the group consisting of GM-CSF, IL-2, IL12, interferon (such as Type 1, Type 2 or Type 3 interferon, e.g., interferonγ), CCL4, CCL19, CCL21. CXCL3. TLR1, TLR2. TLR3, TLR4. TLR5, TLR6. TLR7, TLR8. TLR9, TLR10, RIG-I, MDA5, LGP2, LTαβ, STING activators (such as CDN), PRRago (such as CpG. Imiquimod, or Poly I:C), TLR stimulators (such as GS-9620, AED-1419. CYT-003-QbG10, AVE-0675, or PF-7909), and RLR stimulators (such as RIG-1, Mda5, or LGP2 stimulators). In some embodiments, the immune-related molecule is administered directly in its native format. In some embodiments, the immune-related molecule is administered in a format that would include an excipient or any compound known to the art that can delay its metabolism, release and/or decay within the tumor site. In some embodiments, the immune-related molecule can be combined with one or more additional immune-related molecules. In some embodiments, the immune-related molecules of two or more in combinations are administered in a format that would include an excipient or any compound known to the art that can affect its metabolism, release and/or decay within the tumor site. In some embodiments, the immune-related molecule induces dendritic cells. T cells. B cells, and/or T follicular helper cells. In some embodiments, the immune-related molecule is administered separately from the oncolytic virus (e.g., in a separate composition or as a separate entity in the same composition). In some embodiments, the immune-related molecule is administered to the site of the tumor via transduction. Exemplary transduction methods known in the art include, but are not limited to, the use of calcium phosphate, dendrimers, liposomes, cationic polymers, electroporation, cell squeezing, sonoporation, optical transfection, protoplast fusion, impalefection, hydrodynamic delivery, gene gun, magnetofection, viral transfection and nucleofection. In some embodiments, the immune-related molecule is expressed by the oncolytic virus. For example, the oncolytic virus may comprise a nucleic acid encoding the immune-related molecule, and the nucleic acid can be in the viral vector or on a separate vector. In some embodiments, the oncolytic virus comprises a viral vector, and wherein the viral vector comprises the nucleic acid encoding the immune-related molecule. In some embodiments, the nucleic acid encoding the immune-related molecule is operably linked to a viral promoter, such as an E1 promoter, or an E3 promoter.

In some embodiments, the pretreatment step comprises administering an effective amount of radiation therapy to the bladder of the individual prior to the administration of the oncolytic virus and the immunomodulator (including combination of immunomodulators). In some embodiments, the radiation therapy is in combination with chemotherapy. In some embodiments, the radiation therapy is administered without chemotherapy. In some embodiments, the radiation therapy comprises irradiation to the whole body. In some embodiments, the radiation therapy is irradiation to only tumor sites. In some embodiments, the radiation therapy is irradiation to tissues having the tumor. In some embodiments, the radiation therapy is irradiation to only the site of the tumor selected for local administration of the oncolytic virus. In some embodiments, the radiation therapy is irradiation to only a tissue having the tumor selected for local administration of the oncolytic virus. In some embodiments, the dose of the radiation therapy is insufficient to treat the tumor. For example, a suitable dosage of the radiation therapy is about any one of 1 Gy, 5 Gy, 10 Gy, 15 Gy, 20 Gy, 25 Gy, 30 Gy, 35 Gy, 40 Gy, 45 Gy, 50 Gy, 55 Gy, 60 Gy, 65 Gy, 70 Gy, 75 Gy, 80 Gy, 90 Gy or 100 Gy. In some embodiments, the dose of the radiation therapy is no more than about any one of 1 Gy, 5 Gy, 10 Gy, 15 Gy, 20 Gy, 25 Gy, 30 Gy, 35 Gy, 40 Gy, 45 Gy, 50 Gy, 55 Gy, 60 Gy, 65 Gy, 70 Gy, 75 Gy, 80 Gy, 90 Gy or 100 Gy. In some embodiments, the dose of the radiation therapy is any one of about 1 Gy to about 5 Gy, about 5 Gy to about 10 Gy, about 10 Gy to about 15 Gy, about 15 Gy to about 20 Gy, about 20 Gy to about 25 Gy, about 25 Gy to about 30 Gy, about 30 Gy to about 35 Gy, about 5 Gy to about 15 Gy, about 10 Gy to about 20 Gy, about 20 Gy to about 30 Gy, about 30 Gy to about 40 Gy, about 40 Gy to about 50 Gy, about 50 Gy to about 60 Gy, about 60 Gy to about 70 Gy, about 70 Gy to about 80 Gy, about 80 Gy to about 100 Gy, about 10 Gy to about 30 Gy, about 20 Gy to about 40 Gy, about 1Gy to about 25 Gy, about 25 Gy to about 50 Gy, about 30 Gy to about 60 Gy, about 60 Gy to about 80 Gy, or about 10 Gy to about 60 Gy. In some embodiments, the radiation therapy is administered in more than one fraction, such as about any one of 2, 3, 4, 5, 6, 7, 8, 9, 10, 12, 15, 16, 18, 20 or more fractions. In some embodiments, the radiation therapy fractions are administered over the course of about any one of 1 day, 2 days, 3 days, 4 days, 5 days, 6 days, 1 week, 2 weeks, 3 weeks, 4 weeks, 5 weeks, 6 weeks, 7 weeks or more. In some embodiments, the radiation therapy fractions are administered over the course of any one of about 1 day to about 5 days, about 1 week to about 2 weeks, about 2 weeks to about 3 weeks, about 3 weeks to about 4 weeks, about 4 weeks to about 5 weeks, about 5 weeks to about 6 weeks, about 6 weeks to about 7 weeks, about 2 weeks to about 4 weeks, about 4 weeks to about 6 weeks, or about 1 week to about 6 weeks. In some embodiments, the radiation therapy is administered about two fractions per day. In some embodiments, each fraction of the radiation therapy is about 1.8 Gy to about 2 Gy per day, five days a week, for an adult, or about 1.5 Gy to about 1.8 Gy per day, five days a week for a child. In some embodiments, each fraction of the radiation therapy is about any one of 1 Gy, 1.5 Gy, 2 Gy, 2.5 Gy, 5 Gy, 10 Gy, 15 Gy, 20 Gy, 30 Gy, 40 Gy, 50 Gy or more. In some embodiments, each fraction of the radiation therapy is any one of about 1 Gy to about 1.5 Gy, about 1.5 Gy to about 2 Gy, about 1 Gy to about 2.5 Gy, about 2.5 Gy to about 5 Gy, about 5 Gy to about 10 Gy, about 10 Gy to about 15 Gy, about 15 Gy to about 20 Gy, about 20 Gy to about 30 Gy, about 25 Gy to about 50 Gy, about 1 Gy to about 10 Gy, or about 2 Gy to about 20 Gy.

In some embodiments, the radiation therapy is administered in a single fraction. In some embodiments, the radiation therapy is aim at lymphodepletion, either as a single dose fraction per day or in multiple fractions over days to weeks. In some embodiments, the lymphodepletion radiation therapy is given as a total body irradiation. In some embodiments, the lymphodepletion is only given to local tumor sites, or to tissues with the tumor. In some embodiments, the lymphodepletion radiation therapy is administered two fractions per day. In some embodiments, each fraction of the lymphodepletion radiation therapy is about 1 Gy to about 2 Gy per day, five days a week, for an adult, or about 0.5 Gy to about 1.8 Gy per day, five days a week for a child. In some embodiments, each fraction of the radiation therapy is about any one of 1 Gy, 1.5 Gy, 2 Gy, 2.5 Gy, 5 Gy, 10 Gy, 15 Gy, 20 Gy, 30 Gy, 40 Gy, 50 Gy or more. In some embodiments, each fraction of the radiation therapy is any one of about 1 Gy to about 1.5 Gy, about 1.5 Gy to about 2 Gy, about 1 Gy to about 2.5 Gy, about 2.5 Gy to about 5 Gy, about 5 Gy to about 10 Gy, about 10 Gy to about 15 Gy, about 15 Gy to about 20 Gy, about 20 Gy to about 30 Gy, about 25 Gy to about 50 Gy, about 1 Gy to about 10 Gy, or about 2 Gy to about 20 Gy. In some embodiments, lymphodepletion radiation therapy is administered with or without the use of a chemotherapeutic agent, such as but not limited to, cyclophosphamide and fludarabine.

Any of the known methods of radiation therapy may be used in the present invention, including, but not limited to external beam radiation therapy (EBRT or XRT), tele therapy, brachytherapy, sealed source radiation therapy, systemic radioisotope therapy (RIT), unsealed source radiation therapy, intraoperative radiation therapy (IORT), targeted intraoperative radiation therapy (TARGIT), intensity-modulated radiation therapy (IMRT), volumetric modulated arc therapy (VMAT), particle therapy, and auger therapy.

In some embodiments, the pretreatment step comprises administrating directly or indirectly (e.g. through an intravenous route) to the luminal surface of the bladder in the individual an effective amount of a therapeutic agent prior to the administration of the oncolytic virus and the immunomodulator (including combination of immunomodulators). In some embodiments, the therapeutic agent is any one or combination of chemotherapeutic agents known in the art, for example, cyclosphamide. In some embodiments, the therapeutic agent is any one or combination of agents targeting or blocking a cellular signaling pathway known in the art, for example, a BRAF inhibitor. In some embodiments, the therapeutic agent is any one or combination of cell therapies known in the art, for example, TIL cells, CAR/T cells, and/or TCR/T cells. In some embodiments, the therapeutic agent is an agent that increases the level of cytokines involved an immunogenic pathway. Any of the immune-related molecules described herein may be used as the therapeutic agent, including, but are not limited to, cytokines such as IL6, IL8 and IL18 (these cytokines can either have pro and/or anti-inflammatory actions, or some may promote new blood vessels formation and tumor growth), chemokines (such as CCL21 that can promote tumor spread by increase of lymphatic structures), growth factors (such as FLT3L), heat shock proteins, small molecule kinase inhibitors (such as JAK2 inhibitor), and IAP inhibitors. In some embodiments, the therapeutic agent is an agent that causes dysfunction or damage to a structural component of a tumor. Exemplary agents include, but are not limited to, anti-VEGF antibody, a hyaluronidase, and n-dodecyl-β-maltoside. In some embodiments, the therapeutic agent induces immune cells, such as dendritic cells, B cells, and T cells (such as follicular T helper cells).

Combination Therapy with Tumor Cells

Any of the methods described above can be combined with local administration to the tumor site a plurality of inactivated tumor cells.

Accordingly, one aspect of the present application relates to methods of treating a solid or lymphatic tumor in an individual (such as a human), comprising: a) locally administering to the site of the tumor an effective amount of an oncolytic virus; b) systemically administering an effective amount of an immunomodulator (including combination of immunomodulators); and c) locally administering to the site of the tumor an effective amount of inactivated tumor cells, wherein the oncolytic virus comprises a viral vector comprising a tumor cell-specific promoter operably linked to a viral gene essential for replication of the virus, and a heterologous gene encoding an immune-related molecule. In some embodiments, there is provided a method of treating a solid or lymphatic tumor in an individual (such as a human), comprising: a) locally administering to the site of the tumor an effective amount of an oncolytic virus; b) systemically administering an effective amount of an immunomodulator (including combination of immunomodulators); c) locally administering to the site of the tumor an effective amount of a second immunomodulator (including combination of immunomodulators); and d) locally administering to the site of the tumor an effective amount of inactivated tumor cells, wherein the oncolytic virus comprises a viral vector comprising a tumor cell-specific promoter operably linked to a viral gene essential for replication of the virus, and a heterologous gene encoding an immune-related molecule. This at least three-component combination therapy method may comprise any embodiment of the methods described above for the combination therapy comprising the oncolytic virus and the immunomodulator (including combination of immunomodulators). The present combination therapy method comprising the inactivated tumor cells is advantageous over other cancer immunotherapy methods involving similar components, because administration parameters, such as dosage, dosing frequency and/or route of administration, for each of the three components, namely, the oncolytic virus (such as oncolytic virus, for example, oncolytic adenovirus), the immunomodulator (including combination of immunomodulators), and the inactivated tumor cells can be independently adjusted to optimize the efficacy and minimize the toxicity of the therapy to the individual.

Without being bound by any theory or hypothesis, it is believed that in this three-component combination therapy, an outside source of inactivated but live tumor cells (also referred herein as "live cancer cells" or "live tumor cells"), whether they are autologous or allogeneic in origin, could provide an additional, yet important source of new antigens when administered at the site of the tumor. Outside source in this context means that these tumor cells have already been removed previously, from the same individual or from another individual. The cells may have further been subjected to in vitro culture for expansion, cryopreservation, thawing and characterization. It is believed that this outside source of inactivated tumor cells can sometimes stimulate not only a T cell response, but may also solicit a B cell, and sometimes trigger a massive antibody response that is synergistic with the oncolytic virus (such as virus), and the immunomodulator (including combination of immunomodulators) as described previously.

Thus, in some embodiments, there is provided a method of treating a solid or lymphatic tumor in an individual, comprising: a) locally administering to the site of the tumor an effective amount of an oncolytic virus; b) systemically administering an effective amount of an immunomodulator (including combination of immunomodulators); and c) locally administering to the site of the tumor an effective amount of inactivated tumor cells, wherein the oncolytic virus comprises a viral vector comprising a tumor cell-specific promoter operably linked to a viral gene essential for replication of the virus, and a heterologous gene encoding an immune-related molecule. In some embodiments, the oncolytic virus is selected from the group consisting of adenovirus, herpes simplex virus, vaccinia virus, mumps virus, Newcastle disease virus, polio virus, measles virus. Seneca valley virus, coxsackie virus, reo virus, vesicular stomatitis virus, maraba and rhabdovirus, and parvovirus. In some embodiments, the oncolytic virus is attenuated (for example through multiple passages, inactivation or genetic modification). In some embodiments, the immunomodulator is an immune checkpoint inhibitor. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the inactivated tumor cells are autologous. In some embodiments, the inactivated tumor cells are allogenic. In some embodiments, the inactivated tumor cells are from a tumor cell line. In some embodiments, the inactivated tumor cells are inactivated by irradiation. In some embodiments, the oncolytic virus and the inactivated tumor cells are administered simultaneously (for example, in a single composition). In some embodiments, the oncolytic virus and the inactivated tumor cells are admixed immediately prior to the administration. In some embodiments, the oncolytic virus and the inactivated tumor cells are administered in sequentially. In some embodiments, the oncolytic virus and the inactivated tumor cells are admixed at the administration site immediately after the administration. In some embodiments, the oncolytic virus, and/or the inactivated tumor cells are administered to the tissue having the tumor. In some embodiments, the oncolytic virus, and/or the inactivated tumor cells are administered directly into the tumor. In some embodiments, the immunomodulator, and/or the second immunomodulator, and/or the third immunomodulator is a modulator of an immune checkpoint molecule selected from the group consisting of CTLA-4, PD-1, PD-L. PD-L2. TIM3, B7-H3, B7-H4, LAG-3, KIR, and ligands thereof. In some embodiments, the immunomodulator, and/or the second immunomodulator, and/or the third immunomodulator is an immune-stimulating agent. In some embodiments, the immune-stimulating agent is an activator of OX40, 4-1BB or CD40.

In some embodiments, there is provided a method of treating a solid or lymphatic tumor in an individual, comprising: a) locally administering to the site of the tumor an effective amount of an oncolytic virus (such as oncolytic adenovirus); b) systemically administering an effective amount of an immunomodulator (including combination of immunomodulators); and c) locally administering to the site of the tumor an effective amount of inactivated tumor cells, wherein the oncolytic virus comprises a viral vector comprising a tumor cell-specific promoter operably linked to a viral gene essential for replication of the virus, and a heterologous gene encoding an immune-related molecule. In some embodiments, the oncolytic virus is replication competent. In some embodiments, the oncolytic virus preferentially replicates in a cancer cell, such as an Rb-pathway defective cancer cell. In some embodiments, the immunomodulator is an immune checkpoint inhibitor. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the inactivated tumor cells are autologous. In some embodiments, the inactivated tumor cells are allogenic. In some embodiments, the inactivated tumor cells are from a tumor cell line. In some embodiments, the inactivated tumor cells are inactivated by irradiation. In some embodiments, the oncolytic virus and the inactivated tumor cells are administered simultaneously (for example, in a single composition). In some embodiments, the oncolytic virus and the inactivated tumor cells are admixed immediately prior to the administration. In some embodiments, the oncolytic virus and the inactivated tumor cells are administered in sequentially. In some embodiments, the oncolytic virus and the inactivated tumor cells are admixed at the administration site immediately after the administration. In some embodiments, the oncolytic virus, and/or the inactivated tumor cells are administered to the tissue having the tumor. In some embodiments, the oncolytic virus, and/or the inactivated tumor cells are administered directly into the tumor. In some embodiments, the immunomodulator, and/or the second immunomodulator, and/or the third immunomodulator is a modulator of an immune checkpoint molecule selected from the group consisting of CTLA-4. PD-1, PD-L, PD-L2, TIM3. B7-H3, B7-H4. LAG-3, KIR, and ligands thereof. In some embodiments, the immunomodulator, and/or the second immunomodulator, and/or the third immunomodulator is an immune-stimulating agent. In some embodiments, the immune-stimulating agent is an activator of OX40, 4-1BB or CD40.

In some embodiments, there is provided a method of treating a solid or lymphatic tumor in an individual, comprising: a) locally administering to the site of the tumor an effective amount of an oncolytic virus (such as oncolytic adenovirus); b) systemically administering an effective amount of an immunomodulator (including combination of immunomodulators); and c) locally administering to the site of the tumor an effective amount of inactivated tumor cells, wherein the oncolytic virus comprises a viral vector comprising a tumor cell-specific promoter operably linked to a viral gene essential for replication of the virus, and a heterologous gene encoding an immune-related molecule. In some embodiments, the tumor-specific promoter is an E2F-1 promoter, such as a human E2F-1 promoter or an E2F-1 promoter comprising the nucleotide sequence set forth in SEQ ID NO: 1. In some embodiments, the viral gene essential for replication of the oncolytic virus is selected from the group consisting of E1A. E1B, and E4. In some embodiments, the heterologous gene is operably linked to a viral promoter, such as an E3 promoter. In some embodiments, the immune-related molecule is GM-CSF. In some embodiments, the immunomodulator is an immune checkpoint inhibitor. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the inactivated tumor cells are autologous. In some embodiments, the inactivated tumor cells are allogenic. In some embodiments, the inactivated tumor cells are from a tumor cell line. In some embodiments, the inactivated tumor cells are inactivated by irradiation. In some embodiments, the oncolytic virus and the inactivated tumor cells are administered simultaneously (for example, in a single composition). In some embodiments, the oncolytic virus and the inactivated tumor cells are admixed immediately prior to the administration. In some embodiments, the oncolytic virus and the inactivated tumor cells are administered in sequentially. In some embodiments, the oncolytic virus and the inactivated tumor cells are admixed at the administration site immediately after the administration. In some embodiments, the oncolytic virus, and/or the inactivated tumor cells are administered to the tissue having the tumor. In some embodiments, the oncolytic virus, and/or the inactivated tumor cells are administered directly into the tumor. In some embodiments, the immunomodulator, and/or the second immunomodulator, and/or the third immunomodulator is a modulator of an immune checkpoint molecule selected from the group consisting of CTLA-4. PD-1, PD-L. PD-L2, TIM3. B7-H3, B7-H4. LAG-3, KIR, and ligands thereof. In some embodiments, the immunomodulator, and/or the second immunomodulator, and/or the third immunomodulator is an immune-stimulating agent. In some embodiments, the immune-stimulating agent is an activator of OX40, 4-1BB or CD40.

In some embodiments, there is provided a method of treating a solid or lymphatic tumor in an individual, comprising: a) locally administering to the site of the tumor an effective amount of an adenovirus serotype 5; b) systemically administering an effective amount of an immunomodulator (including combination of immunomodulators); and c) locally administering to the site of the tumor an effective amount of inactivated tumor cells, wherein the endogenous E1a promoter of a native adenovirus is replaced by the human E2F-1 promoter, and the E3 19kD coding region of the native adenovirus is replaced by a heterologous gene encoding an immune-related molecule (such as cytokine or chemokine, for example, GM-CSF). In some embodiments, the tumor-specific promoter is an E2F-1 promoter, such as a human E2F-1 promoter or an E2F-1 promoter comprising the nucleotide sequence set forth in SEQ ID NO:1. In some embodiments, the immunomodulator is an immune checkpoint inhibitor. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, the inactivated tumor cells are autologous. In some embodiments, the inactivated tumor cells are allogenic. In some embodiments, the inactivated tumor cells are from a tumor cell line. In some embodiments, the inactivated tumor cells are inactivated by irradiation. In some embodiments, the adenovirus and the inactivated tumor cells are administered simultaneously (for example, in a single composition). In some embodiments, the adenovirus and the inactivated tumor cells are admixed immediately prior to the administration. In some embodiments, the adenovirus and the inactivated tumor cells are administered in sequentially. In some embodiments, the adenovirus and the inactivated tumor cells are admixed at the administration site immediately after the administration. In some embodiments, the adenovirus, and/or the inactivated tumor cells are administered to the tissue having the tumor. In some embodiments, the adenovirus, and/or the inactivated tumor cells are administered directly into the tumor. In some embodiments, the immunomodulator, and/or the second immunomodulator, and/or the third immunomodulator is a modulator of an immune checkpoint molecule selected from the group consisting of CTLA-4. PD-1. PD-L1, PD-L2, TIM3. B7-H3, B7-H4. LAG-3, KIR, and ligands thereof. In some embodiments, the immunomodulator, and/or the second immunomodulator, and/or the third immunomodulator is an immune-stimulating agent. In some embodiments, the immune-stimulating agent is an activator of OX40, 4-1BB or CD40.

In some embodiments, there is provided a method of treating a solid or lymphatic tumor in an individual, comprising: a) locally administering to the site of the tumor an effective amount of CG0070; and b) systemically administering to the site of the tumor an effective amount of an immunomodulator (including combination of immunomodulators); and c) locally administering to the site of the tumor an effective amount of inactivated tumor cells. In some embodiments, the immunomodulator is an immune checkpoint inhibitor. In some embodiments, the method comprises systemic administration of a combination of immunomodulators comprising one or more immune checkpoint inhibitors and/or one or more immune-stimulating agents (such as at least two immune checkpoint inhibitors, at least two immune-stimulating agents, or a combination of at least one immune checkpoint inhibitor and at least one immune-stimulating agent). In some embodiments, CG0070 is administered at a dose of about $1\times10^8$ to about $1\times10^{14}$ viral particles (vp) (such as any of about $1\times10^8$ to about $1\times10^{10}$, about $1\times10^{10}$ to about $1\times10^{12}$, or about $1\times10^{12}$ to about $1\times10^{14}$ vp). In some embodiments, CG0070 is administered weekly. In some embodiments, CG0070 is administered for about 1 week to about 6 weeks (such as at least about any of 3 weeks, 4 weeks or 5 weeks). In some embodiments, the inactivated tumor cells are autologous. In some embodiments, the inactivated tumor cells are allogenic. In some embodiments, the inactivated tumor cells are from a tumor cell line. In some embodiments, the inactivated tumor cells are inactivated by irradiation. In some embodiments, the CG0070 and the inactivated tumor cells are administered simultaneously (for example, in a single composition). In some embodiments, the CG0070 and the inactivated tumor cells are admixed immediately prior to the administration. In some embodiments, the CG0070 and the inactivated tumor cells are administered in sequentially. In some embodiments, the CG0070 and the inactivated tumor cells are admixed at the administration site immediately after the administration. In some embodiments, the CG0070, and/or the inactivated tumor cells are administered to the tissue having the tumor. In some embodiments, the CG0070, and/or the inactivated tumor cells are administered directly into the tumor. In some embodiments, the immunomodulator, and/or the second immunomodulator, and/or the third immunomodulator is a modulator of an immune checkpoint molecule selected from the group consisting of CTLA-4, PD-1, PD-L1, PD-L2, TIM3, B7-H3, B7-H4, LAG-3, KIR, and ligands thereof. In some embodiments, the immunomodulator, and/or the second immunomodulator, and/or the third immunomodulator is an immune-stimulating agent. In some embodiments, the immune-stimulating agent is an activator of OX40, 4-1BB or CD40.

In some embodiments, there is provided a method of treating a solid or lymphatic tumor in an individual, comprising: a) intratumorally administering an effective amount of CG0070; b) intravenously administering an effective amount of a PD-L1 inhibitor (such as an antagonist anti-PD-L1 antibody, for example, atezolizumab); c) intratumorally administering an effective amount of an inhibitor of CTLA-4 (such as an anti-CTLA-4 antibody, for example Ipilimumab, or an engineered lipocalin protein, for example an anticalin that specifically recognizes CTLA-4); d) optionally intratumorally administering an effective amount of a 4-1BB activator (such as an agonistic anti-4-1BB antibody, for example, PF-05082566); and e) intratumorally administering to the site of the tumor an effective amount of inactivated tumor cells (such as allogenic inactivated tumor cells). In some embodiments, the CG0070 is administered at a dose of about $1\times10^8$ to about $1\times10^{114}$ viral particles (vp) (such as any of about $1\times10^8$ to about $1\times10^{10}$, about $1\times10^{10}$ to about $1\times10^{12}$, or about $1\times10^{12}$ to about $1\times10^{14}$ vp). In some embodiments, CG0070 is administered weekly. In some embodiments, the inhibitor of PD-L1 is administered at a dose of about 1 mg/kg to about 20 mg/kg, or about 750 mg to about 1200 mg. In some embodiments, the inhibitor of PD-L1 is administered about monthly to about biweekly (such as about once every 2 weeks, about once every 3 weeks, or about once every 4 weeks). In some embodiments, the 4-1BB activator is administered at a dose of about 0.1 mg to about 100 mg (such as no more than about any of 1 mg, 3 mg, 6 mg, 12 mg, or 24 mg). In some embodiments, the 4-1BB activator is administered intravenously. In some embodiments, the effective amount of the inactivated tumor cells is at least about $10^4$ the effective amount of CG0070. In some embodiments, the inhibitor of CTLA-4 and the 4-1BB activator are administered immediately after (e.g., no more than 5 minutes after) administration of CG0070 and the inactivated tumor cells. In some embodiments, the inhibitor of PD-L1 is an antagonist antibody of PD-L1, such as atezolizumab. In some embodiments, the inhibitor of CTLA-4 is an anti-CTLA-4 antibody, for example Ipilimumab (e.g., YERVOY®). In some embodiments, the inhibitor of CTLA-4 is an engineered lipocalin protein, for example an anticalin that specifically recognizes CTLA-4.

In some embodiments, the 4-1BB activator is an agonistic anti-4-1BB antibody, such as PF-05082566. In some embodiments, the individual is further administered intratumorally an effective amount of DDM as a transduction enhancing agent in combination with the CG0070 administration. In some embodiments, the inactivated tumor cells are inactivated by irradiation. In some embodiments, CG0070 and the inactivated tumor cells are administered simultaneously (for example, in a single composition). In some embodiments, CG0070 and the inactivated tumor cells are admixed immediately prior to the administration. In some embodiments. CG0070, the inhibitor of CTLA-4, the 41-BB activator, and the inactivated tumor cells are administered by injection into the tissue having the tumor. In some embodiments, CG0070, the inhibitor of CTLA-4, the 41-BB activator, and the inactivated tumor cells are administered by injection directly into the tumor. In some embodiments, CG0070, the inhibitor of CTLA-4, the 41-BB activator, and the inactivated tumor cells are administered weekly for about 1 week to about 8 weeks (such as about 4 weeks or about 6 weeks) as one treatment course. In some embodiments, the treatment course is repeated every about two months to about three months. In some embodiments, the solid or lymphatic tumor is selected from the group consisting of head and neck cancer, breast cancer, colorectal cancer, liver cancer, pancreatic adenocarcinoma, gallbladder and bile duct cancer, ovarian cancer, cervical cancer, small cell lung cancer, non-small cell lung cancer, renal cell carcinoma, bladder cancer, prostate cancer, bone cancer, mesothelioma, brain cancer, soft tissue sarcoma, uterine cancer, thyroid cancer, nasopharyngeal carcinoma, and melanoma. In some embodiments, the solid or lymphatic tumor has been refractory to prior therapy.

In some embodiments, there is provided a method of treating a solid or lymphatic tumor in an individual, comprising: a) intratumorally administering an effective amount of CG0070; b) intravenously administering an effective amount of OX40 activator (such as an agnostic anti-OX40 antibody, for example, MEDI6469, MEDI0562, MEDI6383, GSK3174998, KHK4083 or In VivoMAb clone OX-86); c) intratumorally administering an effective amount of an inhibitor of CTLA-4 (such as an anti-CTLA-4 antibody, for example Ipilimumab, or an engineered lipocalin protein, for example an anticalin that specifically recognizes CTLA-4); d) optionally intratumorally administering an effective amount of a 4-1BB activator (such as an agonistic anti-4-1BB antibody, for example, PF-05082566); and e) intratumorally administering to the site of the tumor an effective amount of inactivated tumor cells (such as allogenic inactivated tumor cells). In some embodiments, the CG0070 is administered at a dose of about $1\times10^8$ to about $1\times10^{14}$ viral particles (vp) (such as any of about $1\times10^8$ to about $1\times10^{10}$, about $1\times10^{10}$ to about $1\times10^{12}$, or about $1\times10^{12}$ to about $1\times10^{14}$ vp). In some embodiments, CG0070 is administered weekly. In some embodiments, the OX40 activator is administered at a dose of about 0.001 mg/kg to about 10 mg/kg (such as such as any of about 0.003 mg/Kg to about 0.01 mg/Kg, about 0.01 mg/Kg to about 0.1 mg/Kg, about 0.1 mg/Kg to about 1 mg/Kg, about 1 mg/Kg to about 5 mg/Kg, or about 5 mg/Kg to about 10 mg/Kg). In some embodiments, the activator of OX40 is administered about monthly to about weekly (such as about weekly, about once every 2 weeks, or about once every 3 weeks). In some embodiments, the 4-1BB activator is administered at a dose of about 0.1 mg to about 100 mg (such as no more than about any of 1 mg, 3 mg, 6 mg, 12 mg, or 24 mg). In some embodiments, the 4-1BB activator is administered intravenously. In some embodiments, the effective amount of the inactivated tumor cells is at least about $10^4$ the effective amount of CG0070. In some embodiments, the inhibitor of CTLA-4 and the 4-1BB activator are administered immediately after (e.g., no more than 5 minutes after) administration of CG0070 and the inactivated tumor cells. In some embodiments, the OX40 activator is an agonistic antibody of OX40, such as GSK3174998. In some embodiments, the inhibitor of CTLA-4 is an anti-CTLA-4 antibody, for example Ipilimumab (e.g., YERVOY®). In some embodiments, the inhibitor of CTLA-4 is an engineered lipocalin protein, for example an anticalin that specifically recognizes CTLA-4. In some embodiments, the 4-1 BB activator is an agonistic anti-4-1BB antibody, such as PF-05082566. In some embodiments, the individual is further administered intratumorally an effective amount of DDM as a transduction enhancing agent in combination with the CG0070 administration. In some embodiments, the inactivated tumor cells are inactivated by irradiation. In some embodiments, CG0070 and the inactivated tumor cells are administered simultaneously (for example, in a single composition). In some embodiments, CG0070 and the inactivated tumor cells are admixed immediately prior to the administration. In some embodiments. CG0070, the inhibitor of CTLA-4, the 41-BB activator, and the inactivated tumor cells are administered by injection into the tissue having the tumor. In some embodiments. CG0070, the inhibitor of CTLA-4, the 41-BB activator, and the inactivated tumor cells are administered by injection directly into the tumor. In some embodiments, CG0070, the inhibitor of CTLA-4, the 41-BB activator, and the inactivated tumor cells are administered weekly for about 1 week to about 8 weeks (such as about 4 weeks or about 6 weeks) as one treatment course. In some embodiments, the treatment course is repeated every about two months to about three months. In some embodiments, the solid or lymphatic tumor is selected from the group consisting of head and neck cancer, breast cancer, colorectal cancer, liver cancer, pancreatic adenocarcinoma, gallbladder and bile duct cancer, ovarian cancer, cervical cancer, small cell lung cancer, non-small cell lung cancer, renal cell carcinoma, bladder cancer, prostate cancer, bone cancer, mesothelioma, brain cancer, soft tissue sarcoma, uterine cancer, thyroid cancer, nasopharyngeal carcinoma, and melanoma. In some embodiments, the solid or lymphatic tumor has been refractory to prior therapy.

The inactivated tumor cells may be obtained from a variety of sources, including, but not limited to, autologous source, allogenic source, a tumor cell line and combinations thereof. Typically, the inactivated tumor cells are of the same type, or express one or more of the same tumor antigens and the solid or lymphatic tumor being treated. In some embodiments, the inactivated tumor cells consist of a single population of tumor cells. In some embodiments, the inactivated tumor cells comprise a plurality (such as 2, 3, 4, 5, 6, or more) of population of tumor cells.

In some embodiments, the inactivated tumor cells are derived from an allogenic source. In some embodiments, the inactivated tumor cells are derived from a different individual having a tumor (such as solid or lymphatic tumor of the same type). In some embodiments, the inactivated tumor cells and the solid or lymphatic tumor of the individual being treated express at least one common tumor antigen (such as tumor associated antigen and/or tumor specific antigen).

In some embodiments, the inactivated tumor cells are derived from a tumor cell line sharing the same or similar origin or genetic profile (such as tumor antigen expression profile) as the solid or lymphatic tumor of the individual. In some embodiments, the inactivated tumor cells and the individual having a tumor express at least one common tumor antigen (such as tumor associated antigen and/or tumor specific antigen). For example, when the solid or lymphatic tumor being treated is prostate cancer, the prostate tumor cell line may be selected from the group consisting of DU145, PC-3, and LnCaP.

In some embodiments, the inactivated tumor cells are derived from the same individual having the solid or lymphatic tumor. In some embodiments, the inactivated tumor cells are derived from the tissue having the solid or lymphatic tumor. In some embodiments, the inactivated tumor cells are derived from the solid or lymphatic tumor (e.g., from tumor biopsy or a resected tumor). In some embodiments, the inactivated tumor cells are derived from a metastatic site of the solid or lymphatic tumor from the individual. In some embodiments, the inactivated tumor cells provide one or more cellular, cytokine, chemokine, and/or antigenic components during death of the inactivated tumor cells in vivo, wherein the one or more components is sampled and cross-presented by the antigen presenting cells (such as dendritic cells) of the individual to stimulate an immune response against the solid or lymphatic tumor.

In some embodiments, the inactivated tumor cells are modified, such as genetically modified, for example, via transduction by an infectious agent harboring a vector encoding a transgene. The inactivated tumor cells may be transduced or transfected by the infectious agent in vitro, or in vivo. In some embodiments, the inactivated tumor cells are modified to express or secrete an immune-related molecule. In some embodiments, the immune-related molecule is a cytokine, a chemokine, or another immune-related molecule. In some embodiments, the immune-related molecule is selected from the group consisting of IL-2, IL-12, interferon (such as Type 1, Type 2 or Type 3 interferon, e.g., interferon γ), CCL4. CCL19, CCL21, CXCL13, TLR1, TLR2, TLR3, TLR4, TLR5. TLR6, TLR7. TLR8, TLR9, TLR10. RIG-I, MDA5, LGP2, and LTαβ. In some embodiments, the immune-related molecule is selected from the group consisting of STING activators (such as CDN), PRRago (such as CpG, Imiquimod, or Poly I:C), TLR stimulators (such as GS-9620, AED-1419, CYT-003-QbG10, AVE-0675, or PF-7909), and RLR stimulators (such as RIG-I, Mda5, or LGP2 stimulators).

In some embodiments, the inactivated tumor cells are modified to express or secrete one or more immunomodulators. In some embodiments, the one or more immunomodulators comprise an immune-stimulating agent. In some embodiments, the immune-stimulating agent is a natural or engineered ligand of an immune stimulatory molecule, including, for example, ligands of OX40 (e.g., OX40L), ligands of CD-28 (e.g., CD80, CD86), ligands of ICOS (e.g., B7RP1), ligands of 4-1BB (e.g., 4-1BBL, Ultra4-1BBL), ligands of CD27 (e.g., CD70), ligands of CD40 (e.g., CD40L), and ligands of TCR (e.g., MHC class I or class II molecules. IMCgp100). In some embodiments, the immune-stimulating agent is an antibody selected from the group consisting of anti-CD28 (e.g., TGN-1412), anti-OX40 (e.g., MEDI6469, MEDI-0562), anti-ICOS (e.g., MEDI-570), anti-GITR (e.g., TRX518. INBRX-110, NOV-120301), anti-41-BB (e.g., BMS-663513, PF-05082566), anti-CD27 (e.g., BION-1402. Varlilumab and hCD27.15), anti-CD40 (e.g., CP870,893, BI-655064, BMS-986090, APX005, APX005M), anti-CD3 (e.g., blinatumomab, muromonab), and anti-HVEM. In some embodiments, the antibody is an agonistic antibody. In some embodiments, the antibody is a monoclonal antibody. In some embodiments, the antibody is an antigen-binding fragment selected from the group consisting of Fab, Fab', F(ab')$_2$, and Fv, scFv, or other antigen-binding subsequences of the full length antibody. In some embodiments, the antibody is a human, humanized, or chimeric antibody. In some embodiments, the antibody is a bispecific antibody, a multispecific antibody, a single domain antibody, a fusion protein comprising an antibody portion, or any other functional variants or derivatives thereof.

In some embodiments, the immunomodulator (including the first, second, third immunomodulator, and combination of immunomodulators) comprise an immune checkpoint inhibitor. In some embodiments, the immune checkpoint inhibitor is a natural or engineered ligand of an inhibitory immune checkpoint molecule, including, for example, ligands of CTLA-4 (e.g., B7.1, B7.2), ligands of TIM3 (e.g., Galectin-9), ligands of A2a Receptor (e.g., adenosine. Regadenoson), ligands of LAG3 (e.g., MHC class I or MHC class II molecules), ligands of BTLA (e.g., HVEM, B7-H4), ligands of KIR (e.g., MHC class I or MHC class II molecules), ligands of PD-1 (e.g., PD-L1, PD-L2), ligands of IDO (e.g., NKTR-218, Indoximod, NLG919), ligands of CD47 (e.g., SIRP-alpha receptor), and ligands of CSF1R. In some embodiments, the immune checkpoint inhibitor is an antibody that targets an inhibitory immune checkpoint protein. In some embodiments, the immunomodulator is an antibody selected from the group consisting of anti-CTLA-4 (e.g., Ipilimumab, Tremelimumab, KAHR-102), anti-TIM3 (e.g., F38-2E2, ENUM005), anti-LAG3 (e.g., BMS-986016, IMP701, IMP321, C9B7W), anti-KIR (e.g., Lirilumab, IPH2101, 1PH4102), anti-PD-1 (e.g., Nivolumab, Pidilizumab, Pembrolizumab, BMS-936559, atezolizumab, Lambrolizumab, MK-3475, AMP-224, AMP-514, STI-A1110, TSR-042), anti-PD-L1 (e.g., KY-1003 (EP20120194977), MCLA-145, atezolizumab. BMS-936559, MEDI-4736, MSB0010718C, AUR-012, STI-A1010, PCT/US2001/020964. MPDL3280A, AMP-224. Dapirolizumab pegol (CDP-7657), MEDI-4920), anti-CD73 (e.g., AR-42 (OSU-HDAC42, HDAC-42, AR42, AR 42, OSU-HDAC 42, OSU-HDAC-42, NSC D736012, HDAC-42, HDAC 42, HDAC42, NSCD736012, NSC-D736012), MEDI-9447), anti-B7-H3 (e.g., MGA271, DS-5573a, 8H9), anti-CD47 (e.g., CC-90002, TTI-621, VLST-007), anti-BTLA, anti-VISTA, anti-A2aR, anti-B7-1, anti-B7-H4, anti-CD52 (such as alemtuzumab), anti-IL-10, anti-IL-35, anti-TGF-β (such as Fresolumimab), anti-CSF1R (e.g., FPA008), anti-NKG2A (e.g., monalizumab), anti-MICA (e.g., IPH43), and anti-CD39. In some embodiments, the antibody is an antagonistic antibody. In some embodiments, the antibody is a monoclonal antibody. In some embodiments, the antibody is a monoclonal antibody. In some embodiments, the antibody is an antigen-binding fragment selected from the group consisting of Fab, Fab', F(ab')$_2$, and Fv, scFv, or other antigen-binding subsequences of the full length antibody. In some embodiments, the antibody is a human, humanized, or chimeric antibody. In some embodiments, the antibody is a bispecific antibody, a multispecific antibody, a single domain antibody, a fusion protein comprising an antibody portion, or any other functional variants or derivatives thereof.

In some embodiments, the inactivated tumor cells are transduced and genetically modified by the oncolytic virus used in the combination therapy.

Tumor cells may be isolated from a tissue, a resected tumor, or a tumor biopsy by any of the methods known in the art, including, but not limited to mechanical, enzymatic separation methods, and combinations thereof. For example, a mixture of collagenase. DNase and hyaluronidase can be used to incubate tumor specimen to obtain the inactivated tumor cells. In some embodiments, multiple batches of isolated autologous tumor cells are obtained from the solid or lymphatic tumor or metastatic sites of the individual during the course of treatment. In some embodiments, the inactivated tumor cells are cryopreserved prior to inactivation.

Since cancer cells, particular in metastatic sites, are heterogeneous mixtures of different clones of cells undergoing rapid replications and frequent mutations, it is sometimes preferable to have a specific component that may adapt to these changes while or when they do occur. Autologous tumor cells can be prepared from the original surgical specimen, biopsies or from removal of metastatic lesions later on. One of the advantages of this method is that the autologous tumor cells can be changed according to the patient's response and the availability of tumor samples. For example, a tumor-oncolytic virus (e.g. virus) live and in vivo vaccine system generated in the primary tumor phase may be different from the one generated later on, using tumor cells from metastatic sites. The ultimate goal, in some embodiments, is to adapt the immunotherapeutic response according to the prevailing tumor types, an advantage that cannot be found in recent development of pathway-targeted therapy or monoclonal antibody-directed therapy.

The inactivated tumor cells are inactivated prior to the administration. Typically, the inactivated tumor cells are proliferation incompetent. Tumor cells can be inactivated with any of the known method in the art. In some embodiments, the inactivated tumor cells are inactivated by irradiation. In some embodiments, the inactivated tumor cells are irradiated at a dose of from about 50 to about 200 rads/min, or from about 120 to about 140 rads/min prior to administration to the patient. In some embodiments, the inactivated tumor cells are irradiated with a total dose of about any one of 2,500 rads, 5,000 rads, 10,000 rads, 15,000 rads or 20.000 rads. In some embodiments, the inactivated tumor cells are irradiated with a total dose of from about 10,000 to about 20.000 rads. In some embodiments, the inactivated tumor cells are irradiated with a total dose sufficient to inhibit substantially 100% of the cells, from further proliferation. In some embodiments, wherein the inactivated tumor cells are genetically modified, the total dose of irradiation is insufficient to inhibit expression or secretion of the immune-related molecule, such as GM-CSF. In some embodiments, the total dose of irradiation is insufficient to inhibit transduction or genetic modification of the inactivated tumor cells by the oncolytic virus upon administration. In some embodiments, the inactivated tumor cells are cryopreserved prior to the administration.

The inactivated tumor cells are administered intratumorally, for example, by intratumoral injection. Suitable dosage of the inactivated tumor cells for administration depends on the status (e.g., microenvironment, type, stage etc.) of the solid or lymphatic tumor and other diagnostic and risk factors of the individual. In some embodiments, a suitable dosage of the inactivated tumor cells is about any one of $1\times10^3$, $1\times10^4$, $1\times10^5$, $2\times10^5$, $5\times10^5$, $1\times10^6$, $2\times10^6$, $5\times10^6$. $1\times10^7$, $5\times10^7$, or $1\times10^8$ cells. In some embodiments, a suitable dosage of the inactivated tumor cells is any one of about $1\times10^3$ to about $1\times10^4$, about $1\times10^4$ to about $1\times10^5$, about $1\times10^5$ to about $2\times10^5$, about $2\times10^5$ to about $5\times10^5$, about $5\times10^5$ to about $10^6$, about $10^6$ to about $2\times10^6$, about $2\times10^6$ to about $5\times10^6$, about $5\times10^6$ to about $1\times10^7$, about $1\times10^7$ to about $5\times10^7$, or about $5\times10^7$ to about $1\times10^8$ tumor cells. In some embodiments, the dosage of the inactivated tumor cells is calculated as cells/Kg of body weight.

In some embodiments, the relative ratio of the oncolytic virus (such as virus) to the inactivated tumor cells is based on the multiplicity of infection (MOI) index calculated using the number of oncolytic virus particles to the number of the inactivated tumor cells alone or to the total number of live tumor cells including the inactivated tumor cells and the estimated number of live tumor cells at the administration site. In some embodiments, the MOI is at least about any one of 1, 2, 5, 10, 50, 100, 200, 500, 1000, 5000, $10^4$, $10^5$, $10^6$, or more. In some embodiments, the oncolytic virus is provided in an amount proportional to the volume of the estimated tumor sites. In some embodiments, the inactivated tumor cells are provided in an amount limited by preparations from tumor biopsy, tumor resection, tumor cell culture and other methods for isolating tumor cells known to the art. In some embodiments, the oncolytic virus is provided in the composition at about $1\times10^5$ particles to about $1\times10^{14}$ particles (for example, about $1\times10^{12}$ particles). In some embodiments, the inactivated tumor cells are provided in the composition at about $1\times10^3$ cells to about $1\times10^8$ cells (for example, about $1\times10^5$ inactivated tumor cells).

In some embodiments, the inactivated tumor cells are administered daily. In some embodiments, the inactivated tumor cells are at least about any one of 1×, 2×, 3×, 4×, 5×, 6×, or 7× (i.e., daily) a week. In some embodiments, the inactivated tumor cells are administered weekly. In some embodiments, the inactivated tumor cells are administered biweekly; weekly without break; weekly, two out of three weeks; weekly three out of four weeks; once every two weeks; once every 3 weeks; once every 4 weeks; once every 6 weeks; once every 8 weeks, monthly, or every two to 12 months. In some embodiments, the intervals between each administration are less than about any one of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any one of 1 month, 2 months, 3 months, 4 months, 5 months, 6 months, 8 months, or 12 months. In some embodiments, there is no break in the dosing schedule. In some embodiments, the interval between each administration is no more than about a week. In some embodiments, the inactivated tumor cells are administered with the same dosing schedule as the oncolytic virus. In some embodiments, the inactivated tumor cells are administered with a different dosing schedule as the oncolytic virus.

The administration of the inactivated tumor cells can be over an extended period of time, such as from about a month up to about seven years. In some embodiments, the inactivated tumor cells are administered over a period of at least about any one of 1, 2, 3, 4, 5, 6, 7, 8, 9, 10, 11, 12, 18, 24, 30, 36, 48, 60, 72, or 84 months. In some embodiments, the inactivated tumor cells are administered over a period of at least 3 weeks or 6 weeks. In some embodiments, the inactivated tumor cells are administered weekly for three out of four weeks every 3 months. In some embodiments, the inactivated tumor cells are administered weekly for 6 weeks every 3 months.

In some embodiments, the oncolytic virus is administered weekly. In some embodiments, the immunomodulator (including the first, second and third immunomodulator, and combination of immunomodulators) is administered about monthly to about weekly. In some embodiments, the inactivated tumor cells are administered weekly.

In some embodiments, the oncolytic virus is administered daily. In some embodiments, the immunomodulator (including the first, second and third immunomodulator, and combination of immunomodulators) is administered daily. In some embodiments, the inactivated tumor cells are administered daily.

In some embodiments, the oncolytic virus is administered first daily or weekly for a number of times (such as any of 1, 2, 3, 4, 5, 6, 7, 10, or more) in a first treatment course, followed by a second treatment course of daily or weekly administration for a number of times (such as any of 1, 2, 3, 4, 5, 6, 7, 10, or more), and then followed by maintenance treatment courses every month or every few (such as any of 2, 3, 4, 5, 6, or more) months. In some embodiments, the immunomodulator (including the first, second and third immunomodulator, and combination of immunomodulators) is administered first daily or weekly for a number of times (such as any of 1, 2, 3, 4, 5, 6, 7, 10, or more) in a first treatment course, followed by a second treatment course of daily or weekly administration for a number of times (such as any of 1, 2, 3, 4, 5, 6, 7, 10, or more), and then followed by maintenance treatment courses every month or every few (such as any of 2, 3, 4, 5, 6, or more) months. In some embodiments, the inactivated tumor cells are administered first daily or weekly for a number of times (such as any of 1, 2, 3, 4, 5, 6, 7, 10, or more) in a first treatment course, followed by a second treatment course of daily or weekly administration for a number of times (such as any of 1, 2, 3, 4, 5, 6, 7, 10, or more), and then followed by maintenance treatment courses every month or every few (such as any of 2, 3, 4, 5, 6, or more) months.

In some embodiments, the oncolytic virus, the immunomodulator (including the first, second and third immunomodulator, and combination of immunomodulators) and the inactivated cells are administered with any combination of the dosing schedules described above. Each treatment course may comprise administration over the course of days, weeks, or months. The treatment course may be repeated for as long as needed.

In some embodiments, the oncolytic virus and the inactivated tumor cells discussed above are administered sequentially, i.e., the administration of the oncolytic virus is administered before or after the administration of the inactivated tumor cells. In some embodiments, the oncolytic virus is administered prior to the administration of the inactivated tumor cells. In some embodiments, the oncolytic virus is administered no more than about any of 15 minutes, 30 minutes, 1 hour, 2 hours, 3 hours, 4 hours, 5 hours, 6 hours, 12 hours, or 24 hours prior to the administration of the inactivated tumor cells. In some embodiments, the oncolytic virus is administered about days or weeks (such as about any of 1 day, 2 days, 3 days, 4 days, 5 days, 6 days, 1 week, 2 weeks, 3 weeks, 4 weeks, or more) prior to the administration of the inactivated tumor cells. In some embodiments, the oncolytic virus is administered after the administration of the inactivated tumor cells. In some embodiments, the oncolytic virus is administered no more than about any of 15 minutes, 30 minutes, 1 hour, 2 hours, 3 hours, 4 hours, 5 hours, 6 hours, 12 hours, or 24 hours after the administration of the inactivated tumor cells. In some embodiments, the oncolytic virus is administered about days or weeks (such as about any of 1 day, 2 days, 3 days, 4 days, 5 days, 6 days, 1 week, 2 weeks, 3 weeks, 4 weeks, or more) after the administration of the inactivated tumor cells. In some embodiments, the oncolytic virus and the inactivated tumor cells are administered with one immediately after another (i.e., within 5 minutes or less between the two administrations). For example, in some embodiments, the oncolytic virus is administered immediately before the administration of the inactivated tumor cells. In some embodiments, the oncolytic virus is administered immediately after the administration of the inactivated tumor cells.

In some embodiments, the oncolytic virus and the inactivated tumor cells are administered simultaneously. In some embodiments, the oncolytic virus and the inactivated tumor cells are administered simultaneously via separate compositions. In some embodiments, the oncolytic virus and the inactivated tumor cells are administered as a single composition. In some embodiments, the oncolytic virus and the inactivated tumor cells are mixed prior to (such as immediately prior to, e.g., within less than about 10, 5, or 1 minutes before) the administration of the composition. In some embodiments, the composition comprising the oncolytic virus and the inactivated tumor cells is pre-made and stored for at least about any of 1 hours, 2 hours, 3 hours, 4 hours, 5 hours, 6 hours, 12 hours, 24 hours, 2 days, 3 days, 4 days, 5 days, 6 days, 7 days, 2 weeks, 3 weeks, or more prior to the administration. In some embodiments, the inactivated tumor cells and the oncolytic virus are completely separated until the moment of administration to the individual. In some embodiments, the oncolytic virus and the inactivated tumor cells do not need to be pre-incubated prior to the administration.

Kits and Pharmaceutical Compositions

In another aspect, there are provided kits, unit dosages, and articles of manufacture useful for any one of the methods described herein.

For example, in some embodiments, there is provided a kit for treating a solid or lymphatic tumor in an individual, comprising: a) an oncolytic virus, b) an immunomodulator (including combination of immunomodulators), and c) a device for locally administering the oncolytic virus to a site of tumor, wherein the oncolytic virus comprises a viral vector comprising a tumor cell-specific promoter operably linked to a viral gene essential for replication of the virus, and a heterologous gene encoding an immune-related molecule. In some embodiments, the oncolytic virus is an oncolytic adenovirus. In some embodiments, the oncolytic virus is attenuated (for example through multiple passages, inactivation or genetic modification). In some embodiments, the oncolytic virus preferentially replicates in a cancer cell, such as an Rb-pathway defective cancer cell. In some embodiments, the immune-related molecule is selected from the group consisting of GM-CSF, IL-2, IL12, interferon (such as Type 1, Type 2 or Type 3 interferon, e.g., interferonγ). CCL4, CCL19, CCL21, CXCL13. TLR1, TLR2. TLR3, TLR4. TLR5, TLR6. TLR7, TLR8. TLR9, TLR10, RIG-I. MDA5, LGP2, and LTαβ. In some embodiments, the immune-related molecule is GM-CSF. In some embodiments, the kit further comprises a second immunomodulator (including combination of immunomodulators) formulated for local administration to the site of the tumor. In some embodiments, the kit further comprises a third immunomodulator (including combination of immunomodulators). In some embodiments, the third immunomodulator is formulated for systemic administration. In some embodiments, the third immunomodulator is formulated for local administration to the site of the tumor. In some embodiments, the immunomodulator (such as the first, second or third immunomodulator) is an immune-stimulating agent, for example, an activator (such as an agonist antibody) of OX40, 4-1BB or CD40. In some embodiments, the immunomodulator (such as the first, second or third immunomodulator) is a modulator (such as an antibody) of an immune checkpoint molecule selected from the group consisting of CTLA-4. PD-1. PD-L1, PD-L2. TIM3. B7-H3, B7-H4, LAG-3. KIR, and ligands thereof. In some embodiments, the kit comprises a combination of immunomodulators comprising one or more immune checkpoint inhibitors and/or one or more immune-stimulating agents (such as a combination of a CTLA-4 inhibitor and an OX40 activator). In some embodiments, the kit comprises at least two immune checkpoint inhibitors, such as a CTLA-4 inhibitor and a PD-L1 inhibitor. In some embodiments, the kit further comprises an immune-related molecule selected from the group consisting of GM-CSF, IL-2, IL12, interferon (such as Type 1, Type 2 or Type 3 interferon, e.g., interferonγ), CCL4, CCL19, CCL21. CXCL13, TLR1, TLR2. TLR3, TLR4. TLR5, TLR6. TLR7, TLR8. TLR9, TLR10, RIG-I. MDA5, LGP2, LTαβ, STING activators (such as CDN), PRRago (such as CpG, Imiquimod, or Poly I:C), TLR stimulators (such as GS-9620, AED-1419, CYT-003-QbG10. AVE-0675, or PF-7909), and RLR stimulators (such as RIG-I, Mda5, or LGP2 stimulators). In some embodiments, the kit further comprises a pretreatment composition comprising a transduction enhancing agent, such as N-Dodecyl-β-D-maltoside (DDM). In some embodiments, the kit further comprises a plurality of inactivated tumor cells. In some embodiments, the plurality of inactivated tumor cells is autologous, allogenic, from a tumor cell line, or combinations thereof. In some embodiments, the plurality of inactivated tumor cells is inactivated by irradiation. In some embodiments, the kit further comprises devices, materials, and/or instructions for admixing the oncolytic virus and the plurality of inactivated tumor cells prior to administration. In some embodiments, the device for local administration is used for simultaneous administration of the plurality of inactivated tumor cells and the oncolytic virus. In some embodiments, the device for local administration is for administrating the oncolytic virus, and/or the inactivated tumor cells directly into the tumor. In some embodiments, the device for local administration is for administering the oncolytic virus, and/or the inactivated tumor cells to the tissue having the tumor. In some embodiments, the local administration is intravesical administration. In some embodiments, the systemic administration is intravenous administration. In some embodiments, the kit further comprises an instruction for carrying out any one of the methods described above.

In some embodiments, there is provided a kit for treating a solid or lymphatic tumor in an individual, comprising: a) an oncolytic virus (such as oncolytic adenovirus), b) an immunomodulator (including combination of immunomodulators), and c) a device for locally administering the oncolytic virus to a site of tumor, wherein the oncolytic virus comprises a viral vector comprising a tumor cell-specific promoter operably linked to a viral gene essential for replication of the virus, and a heterologous gene encoding an immune-related molecule. In some embodiments, the oncolytic virus is attenuated (for example through multiple passages, inactivation or genetic modification). In some embodiments, the tumor-specific promoter is an E2F-1 promoter, such as a human E2F-1 promoter or an E2F-1 promoter comprising the nucleotide sequence set forth in SEQ ID NO: 1. In some embodiments, the viral gene essential for replication of the oncolytic virus is selected from the group consisting of E1A, E1B, and E4. In some embodiments, the heterologous gene is operably linked to a viral promoter, such as an E3 promoter. In some embodiments, the immune-related molecule is GM-CSF. In some embodiments, the kit further comprises a second immunomodulator (including combination of immunomodulators) formulated for local administration to the site of the tumor. In some embodiments, the kit further comprises a third immunomodulator (including combination of immunomodulators). In some embodiments, the third immunomodulator is formulated for systemic administration. In some embodiments, the third immunomodulator is formulated for local administration to the site of the tumor. In some embodiments, the immunomodulator (such as the first, second or third immunomodulator) is an immune-stimulating agent, for example, an activator (such as an agonist antibody) of OX40, 4-1BB or CD40. In some embodiments, the immunomodulator (such as the first, second or third immunomodulator) is a modulator (such as an antibody) of an immune checkpoint molecule selected from the group consisting of CTLA-4, PD-1, PD-L1, PD-L2. TIM3, B7-H3, B7-H4, LAG-3, KIR, and ligands thereof. In some embodiments, the kit comprises a combination of immunomodulators comprising one or more immune checkpoint inhibitors and/or one or more immune-stimulating agents (such as a combination of a CTLA-4 inhibitor and an OX40 activator). In some embodiments, the kit comprises at least two immune checkpoint inhibitors, such as a CTLA-4 inhibitor and a PD-L1 inhibitor. In some embodiments, the kit further comprises an immune-related molecule selected from the group consisting of GM-CSF. IL-2. IL12, interferon (such as Type 1, Type 2 or Type 3 interferon, e.g., interferonγ), CCL4, CCL19, CCL21, CXCL13, TLR1, TLR2. TLR3, TLR4. TLR5, TLR6. TLR7, TLR8. TLR9, TLR10, RIG-I, MDA5, LGP2, LTαβ, STING activators (such as CDN), PRRago (such as CpG, Imiquimod, or Poly I:C). TLR stimulators (such as GS-9620, AED-1419, CYT-003-QbG10. AVE-0675, or PF-7909), and RLR stimulators (such as RIG-I, Mda5, or LGP2 stimulators). In some embodiments, the kit further comprises a pretreatment composition comprising a transduction enhancing agent, such as N-Dodecyl-β-D-maltoside (DDM). In some embodiments, the kit further comprises a plurality of inactivated tumor cells. In some embodiments, the plurality of inactivated tumor cells is autologous, allogenic, from a tumor cell line, or combinations thereof. In some embodiments, the plurality of inactivated tumor cells is inactivated by irradiation. In some embodiments, the kit further comprises devices, materials, and/or instructions for admixing the oncolytic virus and the plurality of inactivated tumor cells prior to administration. In some embodiments, the device for local administration is used for simultaneous administration of the plurality of inactivated tumor cells and the oncolytic virus. In some embodiments, the device for local administration is for administrating the oncolytic virus, and/or the inactivated tumor cells directly into the tumor. In some embodiments, the device for local administration is for administering the oncolytic virus, and/or the inactivated tumor cells to the tissue having the tumor. In some embodiments, the local administration is intravesical administration. In some embodiments, the systemic administration is intravenous administration. In some embodiments, the kit further comprises an instruction for carrying out any one of the methods described above.

In some embodiments, there is provided a kit for treating a solid or lymphatic tumor in an individual, comprising: a) an adenovirus serotype 5, wherein the endogenous E1a promoter of a native adenovirus is replaced by the human E2F-1 promoter, and E3 19kD coding region of the native adenovirus is replaced by a nucleic acid encoding an immune-related molecule (such as cytokine or chemokine, for example, GM-CSF), b) an immunomodulator (including combination of immunomodulators), and c) a device for locally administering the adenovirus to a site of tumor. In some embodiments, the kit further comprises a second immunomodulator (including combination of immunomodulators) formulated for local administration to the site of the tumor. In some embodiments, the kit further comprises a third immunomodulator (including combination of immunomodulators). In some embodiments, the third immunomodulator is formulated for systemic administration. In some embodiments, the third immunomodulator is formulated for local administration to the site of the tumor. In some embodiments, the immunomodulator (such as the first, second or third immunomodulator) is an immune-stimulating agent, for example, an activator (such as an agonist antibody) of OX40, 4-1BB or CD40. In some embodiments, the immunomodulator (such as the first, second or third immunomodulator) is a modulator (such as an antibody) of an immune checkpoint molecule selected from the group consisting of CTLA-4, PD-1, PD-L, PD-L2. TIM3. B7-H3, B7-H4. LAG-3, KIR, and ligands thereof. In some embodiments, the kit comprises a combination of immunomodulators comprising one or more immune checkpoint inhibitors and/or one or more immune-stimulating agents (such as a combination of a CTLA-4 inhibitor and an OX40 activator). In some embodiments, the kit comprises at least two immune checkpoint inhibitors, such as a CTLA-4 inhibitor and a PD-L1 inhibitor. In some embodiments, the kit further comprises an immune-related molecule selected from the group consisting of GM-CSF, IL-2, IL12, interferon (such as Type 1, Type 2 or Type 3 interferon, e.g., interferonγ), CCL4, CCL19, CCL21. CXCL13. TLR, TLR2. TLR3, TLR4. TLR5, TLR6. TLR7, TLR8. TLR9, TLR10, RIG-I, MDA5, LGP2, LTαβ, STING activators (such as CDN), PRRago (such as CpG, Imiquimod, or Poly I:C), TLR stimulators (such as GS-9620, AED-1419. CYT-003-QbG10, AVE-0675, or PF-7909), and RLR stimulators (such as RIG-1, Mda5, or LGP2 stimulators). In some embodiments, the kit further comprises a pretreatment composition comprising a transduction enhancing agent, such as N-Dodecyl-β-D-maltoside (DDM). In some embodiments, the kit further comprises a plurality of inactivated tumor cells. In some embodiments, the plurality of inactivated tumor cells is autologous, allogenic, from a tumor cell line, or combinations thereof. In some embodiments, the plurality of inactivated tumor cells is inactivated by irradiation. In some embodiments, the kit further comprises devices, materials, and/or instructions for admixing the adenovirus and the plurality of inactivated tumor cells prior to administration. In some embodiments, the device for local administration is used for simultaneous administration of the plurality of inactivated tumor cells and the adenovirus. In some embodiments, the device for local administration is for administrating the adenovirus, and/or the inactivated tumor cells directly into the tumor. In some embodiments, the device for local administration is for administering the adenovirus, and/or the inactivated tumor cells to the tissue having the tumor. In some embodiments, the local administration is intravesical administration. In some embodiments, the systemic administration is intravenous administration. In some embodiments, the kit further comprises an instruction for carrying out any one of the methods described above.

In some embodiments, there is provided a kit for treating a solid or lymphatic tumor in an individual, comprising: a) CG0070, b) an immunomodulator (including combination of immunomodulators), and c) a device for locally administering the CG0070 to a site of tumor. In some embodiments, the kit further comprises a second immunomodulator (including combination of immunomodulators) formulated for local administration to the site of the tumor. In some embodiments, the kit further comprises a third immunomodulator (including combination of immunomodulators). In some embodiments, the third immunomodulator is formulated for systemic administration. In some embodiments, the third immunomodulator is formulated for local administration to the site of the tumor. In some embodiments, the immunomodulator (such as the first, second or third immunomodulator) is an immune-stimulating agent, for example, an activator (such as an agonist antibody) of OX40, 4-1BB or CD40. In some embodiments, the immunomodulator (such as the first, second or third immunomodulator) is a modulator (such as an antibody) of an immune checkpoint molecule selected from the group consisting of CTLA-4, PD-1, PD-L1, PD-L2. TIM3, B7-H3, B7-H4. LAG-3, KIR, and ligands thereof. In some embodiments, the kit comprises a combination of immunomodulators comprising one or more immune checkpoint inhibitors and/or one or more immune-stimulating agents (such as a combination of a CTLA-4 inhibitor and an OX40 activator). In some embodiments, the kit comprises at least two immune checkpoint inhibitors, such as a CTLA-4 inhibitor and a PD-L1 inhibitor. In some embodiments, the kit further comprises an immune-related molecule selected from the group consisting of GM-CSF, IL-2, IL12, interferon (such as Type 1, Type 2 or Type 3 interferon, e.g., interferonγ), CCL4, CCL19, CCL21. CXCL3. TLR1, TLR2. TLR3, TLR4. TLR5, TLR6. TLR7, TLR8. TLR9, TLR10, RIG-I, MDA5, LGP2, LTαβ, STING activators (such as CDN), PRRago (such as CpG. Imiquimod, or Poly I:C), TLR stimulators (such as GS-9620. AED-1419. CYT-003-QbG10, AVE-0675, or PF-7909), and RLR stimulators (such as RIG-I, Mda5, or LGP2 stimulators). In some embodiments, the kit further comprises a pretreatment composition comprising a transduction enhancing agent, such as N-Dodecyl-1-D-maltoside (DDM). In some embodiments, the kit further comprises a plurality of inactivated tumor cells. In some embodiments, the plurality of inactivated tumor cells is autologous, allogenic, from a tumor cell line, or combinations thereof. In some embodiments, the plurality of inactivated tumor cells is inactivated by irradiation. In some embodiments, the kit further comprises devices, materials, and/or instructions for admixing the CG0070 and the plurality of inactivated tumor cells prior to administration. In some embodiments, the device for local administration is used for simultaneous administration of the plurality of inactivated tumor cells and the CG0070. In some embodiments, the device for local administration is for administrating the CG0070, and/or the inactivated tumor cells directly into the tumor. In some embodiments, the device for local administration is for administering the CG0070, and/or the inactivated tumor cells to the tissue having the tumor. In some embodiments, the local administration is intravesical administration. In some embodiments, the systemic administration is intravenous administration. In some embodiments, the kit further comprises an instruction for carrying out any one of the methods described above.

The kit may further comprise a description of selection of individuals suitable for treatment. For example, the kit may comprise a description of selection of individuals based on the expression of one or more biomarkers, such as PD-1, PD-L1, or PD-L2. In some embodiments, the kit further comprises reagents for assessing the expression level of the biomarkers, such as PD-1. PD-L1, or PD-L2. Instructions supplied in the kits of the invention are typically written instructions on a label or package insert (e.g., a paper sheet included in the kit), but machine-readable instructions (e.g., instructions carried on a magnetic or optical storage disk) are also acceptable.

Further provided is a tumor cell preparation kit comprising materials and instructions to conduct tumor dissociation and preparation, enzymatic and/or virus vector transduction agents, cryopreservation vials, etc., and a packaging insert containing directions for use. The tumor cell preparation kit may be used to provide the inactivated tumor cells, and the kit may be combined with any one of the kits for treating a solid or lymphatic tumor described above for carrying out a combination therapy comprising the oncolytic virus, the immunomodulator (including combination of immunomodulators), and the isolated and inactivated tumor cells.

The instructions relating to the use of the oncolytic virus (such as the oncolytic adenovirus, for example CG0070) and the immunomodulator (including combination of immunomodulators) generally include information as to dosage, dosing schedule, and route of administration for the intended treatment. The containers may be unit doses, bulk packages (e.g., multi-dose packages) or sub-unit doses. For example, kits may be provided that contain sufficient dosages of the oncolytic virus and the immunomodulator (including combination of immunomodulators) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the oncolytic virus and the immunomodulator (including combination of immunomodulators) and instructions for use, packaged in quantities sufficient for storage and use in pharmacies, for example, hospital pharmacies and compounding pharmacies.

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). At least one active agent in the composition is a) an oncolytic virus; or b) an immunomodulator (including combination of immunomodulators). The label or package insert indicates that the composition is used for treating the particular condition in an individual. The label or package insert will further comprise instructions for administering the composition to the individual. Articles of manufacture and kits comprising combination therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating a solid or lymphatic tumor (such as bladder cancer, renal cell carcinoma, or melanoma).

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Medical devices for local administration (such as intravesical or intratumoral injection) of the oncolytic virus, and/or optionally the second immunomodulator (including combination of immunomodulators), and/or inactivated tumor cells are known in the art. For example, medical device for intravesical delivery may include a catheter, for example, a Rusch 173430 Foley Catheter & BARD LUBRI-SIL Foley Catheter #70516SI. Medical devices for intratumoral injection may include a syringe, a needle or needle arrays, and a plurality of outlets. The intratumoral injection device may be specially designed to ensure uniform distribution of the oncolytic virus, the second immunomodulator (including combination of immunomodulators), and/or inactivated tumor cells in the tumor site. In some embodiments, the intratumoral injection device comprises a forced air jet.

Further provided are compositions (such as pharmaceutical compositions) useful for any of the methods described herein. The pharmaceutical composition may comprise the oncolytic virus, the immunomodulator (including combination of immunomodulators), or the inactivated tumor cells. In some embodiments, the pharmaceutical composition comprises the oncolytic virus formulated for local (such as intratumoral) administration to the site of the tumor. In some embodiments, the pharmaceutical composition comprises the second immunomodulator (including combination of immunomodulators) formulated for local (such as intratumoral) administration to the site of the tumor. In some embodiments, the pharmaceutical composition comprises the plurality of inactivated tumor cells formulated for local (such as intratumoral) administration to the site of the tumor. In some embodiments, the pharmaceutical composition comprises a combination of the oncolytic virus, the second immunomodulator, and/or the inactivated tumor cells formulated for local (such as intratumoral) administration to the site of the tumor. In some embodiments, the pharmaceutical composition comprises the immunomodulator (including combination of immunomodulators) formulated for systemic (such as intravenous) administration.

The pharmaceutical composition may comprise any suitable excipient, including active or passive excipients for drug delivery, such as polymer and non-polymer systems. In some embodiments, the excipient is a natural polysaccharide, such as an exopolysaccharide hydrogel. Exemplary polymers suitable for use as an excipient for the pharmaceutical composition include, but are not limited to, no biodegradable polymers, such as silicone, cross-linked PVA, and EVA; biodegradable natural polymers, such as gelatin, collagen, atelocollagen, scleroglucan, Gellan and Guar gum; biodegradable synthetic polymers, such as PLA, PGA, PLGA, polycaprolactone, polyparadioxane, polyphosphoesters, polyanhydride, and polyphosphazenes. Other systems that can be used as excipients include microspheres and nanospheres with or without polymers, including "smart" polymer systems comprising pH responsive dendrimers, such as poly-amidoamine (PAMAM), dendrimers, poly(propyleneimine) dendrimers, Poly(L-lisine) ester, Poly(hydroxyproline). Poly(propyl acrylic acid). Poly(methacrylic acid), CARBOPOL®, Polysilamine, EUDRAGIT® S-100, EUDRAGIT® L-100, Chitosan, Poly(methacrylic acid) (PMMA), PMAA-PEG copolymer, Maleic anhydride (MA), N,N-dimethylaminoethyl methacrylate (DMAEMA); temperature responsive polymers, such as Poloxamers (PLURONICS®). Prolastin, Poly(N-substituted acrylamide). Poly(organophosphazene), cyclotriphosphazenes with poly(ethyleneglycol) and amino acid esters, block copolymers of poly(ethylene glycol)/poly(lactic-co-glycolic acid), Poly(ethylene glycol) (PEG), Poly(propylene glycol) (PPG), PMAA, Poly(vinyl alcohol) (PVA), various silk-elastin-like polymers, Poly(silamine), Poly(vinyl methyl ether) (PVME), Poly(vinyl methyl oxazolidone) (PVMO), Poly (vinyl pyrrolidone) (PVP), Poly(N-vinylcaprolactam), poly (N-vinyl isobutyl amid), poly(vinyl methyl ether), poly(N-vinylcaprolactam) (PVCL), Poly(siloxyethylene glycol), poly(dimethylamino ethyl methacrylate), triblock copolymer poly(DL-lactide-co-glycolide-b-ethylene glycol-b-DL-lactide-co-glycolide) (PLGA-PEG-PLGA). Cellulose derivatives. Alginate, Gellan, Xyloglucan; magnetic field sensitive polymers, such as Poly(N-isopropylacrylamide) (PNIPAAm); hydrogels comprising ferromagnetic material PNIPAAm-co-acrylamide; electric signals sensitive polymers, such as Chitosan. Sulfonated polystyrenes, Poly(thiophene)s, Poly(ethyloxazoline); ionic polymers, such as Sodium alginate ($Ca^{2+}$). Chitosan ($Mg^{2+}$); and photosensitive polymers, such as modified poly(acrylamide)s.

In some embodiments, the oncolytic virus, the second immunomodulator (including combination of immunomodulators), and the inactivated tumor cells may be independently or together formulated in a polymer (e.g., hydrogel) in the pharmaceutical composition. The polymer (e.g., hydrogel) may enable delayed release of one or more component (i.e. any one or combinations of the oncolytic virus, the second immunomodulator (including combination of immunomodulators), and the inactivated tumor cells) of the pharmaceutical composition. The one or more components in the polymer (e.g., hydrogel) formulation may delay the release of the component(s) by at least any of 1 minute, 5 minutes, 10 minutes, 30 minutes, 1 hour, 2 hours, 3 hours, 6 hours, or more at the administration site. The polymer (e.g., hydrogel) may comprise any of the suitable materials, such as naturally occurring, or synthetic polymers known in the art. In some embodiments, the polymers are biodegradable and biocompatible.

The components of the compositions (such as pharmaceutical compositions) described herein, including the oncolytic virus, the second immunomodulator (including combination of immunomodulators), and the plurality of inactivated tumor cells may be present at specific relative ratios with respect to each other. In some embodiments, the relative ratio of the oncolytic virus to the inactivated tumor cells is based on the multiplicity of infection (MOI) index calculated using the number of oncolytic virus particles to the number of the inactivated tumor cells alone or to the total number of live tumor cells including the inactivated tumor cells and the estimated number of live tumor cells at the administration site. In some embodiments, the MOI is at least about any one of 1, 2, 5, 10, 50, 100, 200, 500, 1000, 5000, $10^4$, $10^5$, $10^6$, or more. In some embodiments, the oncolytic virus is provided in an amount proportional to the volume of the estimated tumor sites. In some embodiments, the inactivated tumor cells are provided in an amount limited by preparations from tumor biopsy, tumor resection, tumor cell culture and other methods for isolating tumor cells known to the art. In some embodiments, the oncolytic virus is provided in the composition at about $1\times10^5$ particles to about $1\times10^{14}$ particles (for example, about $1\times10^{12}$ particles).

In some embodiments, the inactivated tumor cells are provided in the composition at about 1×10³ cells to about 1×10⁸ cells (for example, about 1×10⁵ inactivated tumor cells). In some embodiments, the second immunomodulator (including combination of immunomodulators) is provided in the composition at about 0.1 mg/Kg to about 100 mg/Kg of body weight (for example, about 1 mg/Kg of body weight).

In some embodiments, the total amount of the composition is enough for a full dosage for a single local administration (such as intratumoral injection or intravesical administration). In some embodiments, the total amount of the composition is enough for a split dosage for a single local administration (such as intratumoral injection) to one of a plurality of tumor sites. In some embodiments, the total amount of the composition is enough for multiple local administrations, including a combination of a single local administration (such as intratumoral injection) into one tumor site and multiple split-dosage administrations at multiple tumor sites.

Oncolytic Viruses

The methods and compositions described herein are related to oncolytic viruses, such as a viral vector, for example, oncolytic adenovirus. The oncolytic virus may be a genetically modified oncolytic virus, for example an attenuated oncolytic virus, and the oncolytic virus has additional favorable features (e.g., preferential replication in cancer cells, and encoding an immune-related molecule).

Exemplary viruses that are suitable for use in the present invention include, but are not limited to, adenovirus, for example, H101 (ONCOCRINE®), CG-TG-102 (Ad5/3-D24-GM-CSF), and CG0070; herpes simplex virus, for example, Talimogene laherparapvec (T-VEC) and HSV-1716 (SEPREHVIR®); reo virus, for example, REOLY-SIN®; vaccinia virus, for example, JX-594; Seneca valley virus, for example, NTX-010 and SVV-001; Newcastle disease virus, for example, NDV-NS1 and GL-ONC1; polio virus, for example, PVS-RIPO; measles virus, for example, MV-NIS; coxsackie virus, for example, CAVATAK™; vesicular stomatitis virus; maraba and rhabdoviruses; parvovirus and mumps virus.

In some embodiments, the oncolytic virus is genetically modified. In some embodiments, the oncolytic virus is attenuated (for example through multiple passages, inactivation or genetic modification). In some embodiments, the oncolytic virus is only a part, or parts of the wild type oncolytic virus that can cause infection, inflammation or infection-like effects.

In some embodiments, the oncolytic virus is replication competent. In some embodiments, the oncolytic virus preferentially replicates in a cancer cell. In some embodiments, the oncolytic virus preferentially replicates in a cancer cell that is defective in the Rb pathway.

The oncolytic virus (such as oncolytic adenovirus) comprises a viral vector comprising a tumor cell-specific promoter operably linked to a viral gene essential for replication of the virus. In some embodiments, the tumor-specific promoter is an E2F-1 promoter, such as a human E2F-1 promoter or an E2F-1 promoter comprising the nucleotide sequence set forth in SEQ ID NO: 1 as shown below. In some embodiments, the viral gene essential for replication of the virus is selected from the group consisting of E1A, E1B, and E4.

SEQ ID NO: 1
gggcccaaaattagcaagtgaccacgtggttctgaagccagtggcctaag
gaccacccttgcagaaccgtggtctccttgtcacagtctaggcagcctct
ggcttagcctctgtttctttcataaccttttctcagcgcctgctctgggcc
agaccagtgttgggaggagtcgctactgagctcctagattggcaggggag
gcagatggagaaaggagtgtgtgtggtcagcattggagcagaggcagca
gtgggcaatagaggaagtgagtaaatccttgggagggctccctagaagtg
atgtgttttctttttttgttttagagacaggatctcgctctgtcgcccag
gctggtgtgcagtggcatgatcatagctcactgcagcctcgacttctcgg
gctcaagcaatcctcccacctcagcctcccaagtagctgggactacgggc
acacgccaccatgcctggctaattttgtattttttgtagagatgggtct
tcaccatgttgatcaggctggtctcgaactcctgggctcatgcgatccac
cccgccagctgattacagggattccggtggtgagccaccgcgcccagacg
ccacttcatcgtattgtaaacgtctgttacctttctgttccctgtctac
tggactgtgagctccttagggccacgaattgaggatggggcacagagcaa
gctctccaaacgtttgttgaatgagtgagggaatgaatgagttcaagcag
atgctatacgttggctgttggagattttggctaaaatgggacttgcagga
aagcccgacgtcccctcgccatttccaggcaccgctcttcagcttgggc
tctggtgagcgggatagggctgggtgcaggattaggataatgtcatgggt
gaggcaagttgaggatggaagaggtggctgatggctgggctgtggaactg
atgatcctgaaaagaagaggggacagtctctggaaatctaagctgaggct
gttgggggctacaggttgagggtcacgtgcagaagagaggctctgttctg
aacctgcactatagaaaggtcagtgggatgcgggagcgtcggggcggggc
ggggcctatgttcccgtgtccccacgcctccagcaggggacgcccgggct
gggggcggggagtcagaccgcgcctggtaccatccggacaaagcctgcgc
gcgccccgccccgccattggccgtccgccccgccgccgcccccatcccg
cccctcgccgccgggtccggcgcgttaaagccaataggaaccgccgccgt
tgttcccgtcacggacggggcagccaattgtggcggcgctcggcggctcg
tggctctttcgcggcaaaaaggatttggcgcgtaaaagtggccgggactt
tgcaggcagcggcggccggggcggagcgggatcgagccctcgccgaggc
ctgccgccatgggcccgcgccgccgccgccgcctgtcacccgggccgcgc
gggccgtgagcgtcatg The viral vector of the oncolytic virus (such as oncolytic adenovirus) further comprises a heterologous gene encoding an immune-related molecule (such as cytokine or chemokine). In some embodiments, the heterologous gene is operably linked to a viral promoter. In some embodiments, the viral promoter is the E3 promoter.

In some embodiments, the oncolytic virus is an adenovirus serotype 5, wherein the endogenous E1a promoter of a native adenovirus is replaced by the human E2F-1 promoter and E3 19kD coding region of the native adenovirus is replaced by a nucleic acid encoding an immune-related molecule (such as cytokine or chemokine, for example, GM-CSF). In some embodiments, the tumor-specific promoter is a human E2F-1 promoter or an E2F-1 promoter comprising the nucleotide sequence set forth in SEQ ID NO: 1.

In some embodiments, the oncolytic virus is CG0070, an adenovirus serotype 5 which has an E2F promoter at the E1a gene and a GM-CSF expression at the E3 gene.

CG0070 is a conditionally replicating oncolytic adenovirus (serotype 5) designed to preferentially replicate in and kill Rb pathway-defective cancer cells. This vector is transcriptionally regulated by a promoter (e.g., E2F-1 promoter) that is up-regulated in Rb-pathway-detective tumor cells. In approximately 85% of all cancers, one or more genes of the Rb pathway, such as the tumor suppressor Rb gene, are mutated. In addition to its restricted propagation. CG0070 also encodes the human cytokine GM-CSF, which is expressed selectively in the infected tumor cells to stimulate immune responses against uninfected distant (such as metastases) and local tumor foci.

The genomic structure of the oncolytic adenoviral vector CG0070 is shown schematically in FIG. 1. Products of the adenoviral early E1A gene are essential for efficient expression of other regions of the adenoviral genome. CG0070 has been engineered to express the E1A gene under control of the human E2F-1 promoter, which provides tumor specificity to the E1A gene product. To protect from transcriptional read-through activating E1A expression, a polyadenylation signal (PA) was inserted 5' of the E2F-1 promoter. CG0070 includes the entire wild type E3 region except for the 19kD-coding region. A direct comparison of E3-containing to E3-deleted oncolytic adenovirus vectors showed superiority of E3-containing vectors in tumor spread and efficacy. In place of the 19kD gene, CG0070 carries the cDNA for human GM-CSF under the control of the endogenous E3 promoter (E3P). Since the E3 promoter is in turn activated by E1A, both viral replication and GM-CSF expression are ultimately under the control of the E2F-1 promoter. The rest of the viral vector backbone, including the E2, E4, late protein regions and inverted terminal repeats (ITRs), is identical to the wild type Ad5 genome.

CG0070 is manufactured in HeLa-S3 cells, and released from infected HeLa-S3 cells by detergent lysis. CG0070 is purified from the lysate by chromatography, and then formulated in 5% sucrose, 10 mM Tris, 0.05% polysorbate-80, 1% glycine, 1 mM magnesium chloride. pH 7.8.

CG0070 is supplied as a sterile, slightly opalescent, frozen liquid in stoppered glass vials. The particle concentration per mL (vp/mL) is stated on the Certificate of Analysis for each lot of CG0070.

CG0070 has additional potential anti-tumor activity in that it carries the cDNA for human GM-CSF, a key cytokine for generating long-lasting anti-tumor immunity. Thus, CG0070 is a selectively replicating oncolytic vector with the potential for attacking the tumor by two mechanisms: direct cytotoxicity as a replicating vector and induction of a host immune response. Summarized in the following sections are in vitro and in vivo studies conducted to characterize the tumor selectivity and anti-tumor activity and safety of CG0070.

Immunomodulators

The methods of the present invention in some embodiments comprise administration of an oncolytic virus with an immunomodulator (including combination of immunomodulators).

"Immunomodulator" refers to an agent that when present, alters, suppresses or stimulates the body's immune system. Immunomodulators can target specific molecules, such as the checkpoint molecules, or non-specifically modulate the immune response. Immunomodulators can include compositions or formulations that activate the immune system (e.g., adjuvants or activators), or downregulate the immune system. Adjuvants can include aluminum-based compositions, as well as compositions that include bacterial or mycobacterial cell wall components. Activators can include molecules that activate antigen presenting cells to stimulate the cellular immune response. For example, activators can be immunostimulant peptides. Activators can include, but are not limited to, agonists of toll-like receptors TLR-2, 3, 4, 6, 7, 8, or 9, granulocyte macrophage colony stimulating factor (GM-CSF); TNF; CD40L; CD28; FLT-3 ligand; or cytokines such as IL-1, IL-2, IL-4, IL-7, IL-12, IL-15, or IL-21. Activators can include agonists of activating receptors (including co-stimulatory receptors) on T cells, such as an agonist (e.g., agonistic antibody) of CD28. OX40, GITR. CD137, CD27, CD40, or HVEM. Activators can also include compounds that inhibit the activity of an immune suppressor, such as an inhibitor of the immune suppressors IL-10, IL-35, TGF-β, IDO, or cyclophosphamide, or inhibit the activity of an immune checkpoint such as an antagonist (e.g., antagonistic antibody) of CTLA-4. PD-1, PD-L1. PD-L2, LAG3, B7-1, B7-H3, B7-H4, BTLA, VISTA, KIR, A2aR, or TIM3. Activators can also include costimulatory molecules such as CD40, CD80, or CD86. Immunomodulators can also include agents that downregulate the immune system such as antibodies against IL-12p70, antagonists of toll-like receptors TLR-2, 3, 4, 5, 6, 8, or 9, or general suppressors of immune function such as cyclophosphamide, cyclosporin A or FK506. These agents (e.g., adjuvants, activators, or downregulators) can be combined to achieve an optimal immune response.

Immunomodulators of particular interest in the present invention include immune-stimulating agents and immune checkpoint inhibitors. As used herein, the term "immune checkpoint inhibitors," "checkpoint inhibitors," and the like refers to compounds that inhibit the activity of control mechanisms of the immune system. Immune system checkpoints, or immune checkpoints, are inhibitory pathways in the immune system that generally act to maintain self-tolerance or modulate the duration and amplitude of physiological immune responses to minimize collateral tissue damage. Checkpoint inhibitors can inhibit an immune system checkpoint by stimulating the activity of a stimulatory checkpoint molecule, or inhibiting the activity of an inhibitory checkpoint molecule in the pathway. Stimulatory checkpoint molecules are molecules, such as proteins, that stimulate or positively regulate the immune system. Inhibitory checkpoint molecules are molecules, such as proteins, that inhibit or negatively regulate the immune system. Immune system checkpoint molecules include, but are not limited to, cytotoxic T-lymphocyte antigen 4 (CTLA-4), programmed cell death 1 protein (PD-1), programmed cell death 1 ligand 1 (PD-L), programmed cell death 1 ligand 2 (PD-L2), lymphocyte activation gene 3 (LAG3), B7-1, B7-H3, B7-H4. T cell membrane protein 3 (TIM3). B- and T-lymphocyte attenuator (BTLA), V-domain immunoglobulin (Ig)-containing suppressor of T-cell activation (VISTA), Killer-cell immunoglobulin-like receptor (KIR), and A2A adenosine receptor (A2aR). As such, checkpoint inhibitors include antagonists of CTLA-4, PD-1, PD-L1, PD-L2, LAG3, B7-1, B7-H3, B7-H4, BTLA, VISTA, KIR. A2aR, or TIM3. For example, antibodies that hind to CTLA-4. PD-1. PD-L1, PD-L2. LAG3, B7-1. B7-H3, B7-H4, BTLA, VISTA. KIR, A2aR, or TIM3 and antagonize their function are checkpoint inhibitors. Moreover, any molecule (e.g., peptide, nucleic acid, small molecule, etc.) that inhibits the inhibitory function of an immune system checkpoint is a checkpoint inhibitor.

The immunomodulator can be of any one of the molecular modalities known in the art, including, but not limited to, aptamer, mRNA, siRNA, microRNA, shRNA, peptide, antibody, anticalin, Spherical nucleic acid, TALEN, Zinc Finger Nuclease, CRISPR/Cas9, and small molecule.

In some embodiments, the immunomodulator is an immune-stimulating agent. In some embodiments, the immune-stimulating agent is a natural or engineered ligand of an immune stimulatory molecule, including, for example, ligands of OX40 (e.g., OX40L), ligands of CD-28 (e.g., CD80, CD86), ligands of ICOS (e.g., B7RP1), ligands of 4-1BB (e.g., 4-1BBL. Ultra4-1 BBL), ligands of CD27 (e.g., CD70), ligands of CD40 (e.g., CD40L), and ligands of TCR (e.g., MHC class I or class II molecules, IMCgp100). In some embodiments, the immune-stimulating agent is an antibody selected from the group consisting of anti-CD28 (e.g., TGN-1412), anti-OX40 (e.g., MEDI6469, MEDI-0562), anti-ICOS (e.g., MEDI-570), anti-GITR (e.g., TRX518, INBRX-110, NOV-120301), anti-41-BB (e.g., BMS-663513. PF-05082566), anti-CD27 (e.g., BION-1402, Varlilumab and hCD27.15), anti-CD40 (e.g., CP870,893, BI-655064, BMS-986090, APX005, APX005M), anti-CD3 (e.g., blinatumomab, muromonab), and anti-HVEM. In some embodiments, the antibody is an agonistic antibody. In some embodiments, the antibody is a monoclonal antibody. In some embodiments, the antibody is an antigen-binding fragment selected from the group consisting of Fab, Fab', F(ab')$_2$, Fv, scFv, and other antigen-binding subsequences of the full length antibody. In some embodiments, the antibody is a human, humanized, or chimeric antibody. In some embodiments, the antibody is a bispecific antibody, a multispecific antibody, a single domain antibody, a fusion protein comprising an antibody portion, or any other functional variants or derivatives thereof.

In some embodiments, the immunomodulator is an immune checkpoint inhibitor. In some embodiments, the immune checkpoint inhibitor is a natural or engineered ligand of an inhibitory immune checkpoint molecule, including, for example, ligands of CTLA-4 (e.g., B7.1, B7.2), ligands of TIM3 (e.g., Galectin-9), ligands of A2a Receptor (e.g., adenosine, Regadenoson), ligands of LAG3 (e.g., MHC class I or MHC class II molecules), ligands of BTLA (e.g., HVEM, B7-H4), ligands of KIR (e.g., MHC class I or MHC class II molecules), ligands of PD-1 (e.g., PD-L1, PD-L2), ligands of IDO (e.g., NKTR-218, Indoximod, NLG919), ligands of CD47 (e.g., SIRP-alpha receptor), and ligands of CSF1R. In some embodiments, the immune checkpoint inhibitor is an antibody that targets an inhibitory immune checkpoint protein. In some embodiments, the immunomodulator is an antibody selected from the group consisting of anti-CTLA-4 (e.g., Ipilimumab, Tremelimumab, KAHR-102), anti-TIM3 (e.g., F38-2E2, ENUM005), anti-LAG3 (e.g., BMS-986016, IMP701, IMP321, C9B7W), anti-KIR (e.g., Lirilumab. IPH2101, IPH4102), anti-PD-1 (e.g., Nivolumab, Pidilizumab, Pembrolizumab, BMS-936559, atezolizumab, Lambrolizumab. MK-3475, AMP-224, AMP-514. STI-A1110, TSR-042), anti-PD-L1 (e.g., KY-1003 (EP20120194977). MCLA-145, atezolizumab, BMS-936559, MEDI-4736, MSB0010718C, AUR-012, STI-A1010, PCT/US2001/020964. MPDL3280A, AMP-224. Dapirolizumab pegol (CDP-7657), MEDI-4920), anti-CD73 (e.g., AR-42 (OSU-HDAC42, HDAC-42, AR42, AR 42, OSU-HDAC 42, OSU-HDAC-42, NSC D736012, HDAC-42, HDAC 42, HDAC42, NSCD736012, NSC-D736012), MEDI-9447), anti-B7-H3 (e.g., MGA271, DS-5573a, 8H9), anti-CD47 (e.g., CC-90002, TTI-621. VLST-007), anti-BTLA, anti-VISTA, anti-A2aR, anti-B7-1, anti-B7-H4, anti-CD52 (such as alemtuzumab), anti-IL-10, anti-IL-35, anti-TGF-β (such as Fresolumimab), anti-CSF1R (e.g., FPA008), anti-NKG2A (e.g., monalizumab), anti-MICA (e.g., IPH43), and anti-CD39. In some embodiments, the antibody is an antagonistic antibody. In some embodiments, the antibody is a monoclonal antibody. In some embodiments, the antibody is a monoclonal antibody. In some embodiments, the antibody is an antigen-binding fragment selected from the group consisting of Fab, Fab', F(ab')$_2$, Fv, scFv, and other antigen-binding subsequences of the full length antibody. In some embodiments, the antibody is a human, humanized, or chimeric antibody. In some embodiments, the antibody is a bispecific antibody, a multispecific antibody, a single domain antibody, a fusion protein comprising an antibody portion, or any other functional variants or derivatives thereof.

The immunomodulators can be used singly or in combination. For example, any number (such as any of 1, 2, 3, 4, 5, 6, or more) of immune checkpoint inhibitors can be used simultaneously or sequentially, or any number (such as any of 2, 3, 4, 5, 6, or more) of immune-stimulating agents can be used simultaneously or sequentially. Alternatively, any number (such as any of 1, 2, 3, 4, 5, 6, or more) of immune checkpoint inhibitors in combination with any number (such as any of 2, 3, 4, 5, 6, or more) of immune-stimulating agents can be used simultaneously or sequentially. Sequential administration of immunomodulators can be separated by hours, days or weeks. The administration route(s) for two or more immunomodulators can be the same or different. For example, one immunomodulator can be administered intratumorally, and a second immunomodulator can be administered intravenously; or two immunomodulators can be administered both intratumorally.

Exemplary immune checkpoint molecules and immunomodulators thereof are discussed below. It is understood that other suitable immune checkpoint molecules and immunomodulators known in the art are also within the scope of the present application.

CTLA-4

CTLA-4 is an immune checkpoint molecule, which is up-regulated on activated T-cells. An anti-CTLA-4 mAb can block the interaction of CTLA-4 with CD80/86 and switch off the mechanism of immune suppression and enable continuous stimulation of T-cells by DCs. Examples of anti-CTLA-4 antibodies are Ipilimumab (see U.S. Pat. Nos. 6,984,720, 7,452,535, 7,605,238, 8,017,114 and 8,142,778). Tremelimumab (see U.S. Pat. Nos. 668,736, 7,109,003, 7,132,281, 7,411,057, 7,807,797, 7,824,679 and 8,143,379) and other anti-CTLA-4 antibodies, including single chain antibodies (e.g., see U.S. Pat. Nos. 5,811,097, 6,051,227 and 7,229,628, and US Patent Publication No. US20110044953).

Two IgG mAb directed against CTLA-4, Ipilimumab and Tremelimumab, have been tested in clinical trials for a number of indications. Ipilimumab is approved by the FDA for the treatment of melanoma. e.g., for late stage melanoma patients. The complete prescribing information is fully described in the packaging insert of YERVOY® (Bristol Meyers). YERVOY® (Ipilimumab) comes in 50 mg single use vials.

Anticalins are engineered proteins that are able to recognize and bind specific targets with high affinity. They are antibody mimetics, but they are not structurally related to antibodies. Instead, they are derived from human lipocalins, which are a family of naturally binding proteins. Anticalins are being used in lieu of monoclonal antibodies, but are about eight times smaller than monoclonal antibodies with a size of about 180 amino acids and a mass of about 20 kDa. Anticalins have been described in U.S. Pat. No. 7,250,297. Anticalins that bind CTLA-4 with high affinity and specificity have been developed, which are described in, for example, International Patent Application Publication No. WO2012072806. Any of the CTLA-4-binding anticalins may be used in the present application. In some embodiments, the CTLA-4 binding anticalin is PRS-010 (Piers AG).
PD-1

PD-1 is a part of the B7/CD28 family of co-stimulatory molecules that regulate T-cell activation and tolerance, and thus antagonistic anti-PD-1 antibodies can be useful for overcoming tolerance. PD-1 has been defined as a receptor for B7-4. B7-4 can inhibit immune cell activation upon binding to an inhibitory receptor on an immune cell. Engagement of the PD-1/PD-L1 pathway results in inhibition of T-cell effector function, cytokine secretion and proliferation. (Turnis et al., OncoImmunology 1(7):1172-1174, 2012). High levels of PD-1 are associated with exhausted or chronically stimulated T cells. Moreover, increased PD-1 expression correlates with reduced survival in cancer patients.

Agents for down modulating PD-1, B7-4, and the interaction between B7-4 and PD-1 inhibitory signal in an immune cell resulting in enhancement of the immune response. Any of the anti-PD-1 antibodies known in the art may be used in the present invention, for example, see U.S. Pat. Nos. 7,101,550, 5,698,520, 6,808,710, 7,029,674, 7,794,710, 7,892,540, 8,008,449, 8,088,905, 8,163,503, 8,168,757, 8,354,509, 8,460,927, 8,609,089, 8,747,833, 8,779,105, 8,900,587, 8,952,136, 8,981,063, 8,993,731, 9,062,112, 9,067,999, 9,073,994, 9,084,776, 9,102,728, and 7,488,802; and U.S. Patent Publication Nos. US20020055139, US20140044738. For example, Nivolumab is a human mAb to PD-1 that is FDA approved for the treatment of unresectable or metastatic melanoma, as well as squamous non-small cell lung cancer.
PD-L1/PD-L2

PD-L1 (Programmed cell death-ligand 1) is also known as cluster of differentiation 274 (CD274) or B7 homolog 1 (B7-H1). PD-L serves as a ligand for PD-1 to play a major role in suppressing the immune system during particular events such as pregnancy, tissue allographs, autoimmune disease and other disease states such as hepatitis and cancer. The formation of PD-1 receptor/PD-L1 ligand complex transmits an inhibitory signal which reduces the proliferation of CD8+ T cells at the lymph nodes.

Any of the known anti-PD-L1 antibodies may be used in the present invention, see, for example, U.S. Pat. Nos. 7,943,743, 7,722,868, 8,217,149, 8,383,796, 8,552,154, and 9,102,725; and U.S. Patent Application Publication Nos. US20140341917, and US20150203580; and International Patent Application No. PCT/US2001/020964. For example, anti-PD-L1 antibodies that are in clinical development include BMS935559 (also known as MDX-1105), MPDL3280A, MEDI4736, Avelumab (also known as MSB0010718C). KY-1003, MCLA-145, RG7446 (also known as atezolizumab), and STI-A1010.

PD-L2 (Programmed cell death 1 ligand 2) is also known as B7-DC. PD-L2 serves as a ligand for PD-1. Under certain circumstances, PD-L2 and its inhibitor can be used as a substitute for PD-L1 and its inhibitor respectively.
CD40

CD40 (Cluster of differentiation 40) is a co-stimulatory protein found on antigen presenting cells and is required for their activation. Binding of CD40L (CD154) on $T_H$ cells to CD40 activates antigen presenting cells and includes a variety of downstream effects to stimulate immune response.

Agents that stimulate the activity of CD40 is useful as an immune-stimulating agent. Any of the known agonistic anti-CD40 antibodies may be used in the present invention, see, for example, U.S. Pat. Nos. 5,786,456, 5,674,492, 5,182,368, 5,801,227, 7,824,683, 6,843,989, 7,618,633, 7,537,763, 5,677,165, 5,874,082, 6,051,228, 6,312,693, 6,315,998, 6,413,514, 6,838,261, 6,843,989, 6,946,129, 7,063,845, 7,172,759, 7,193,064, 7,288,251, 7,338,660, 7,547,438, 7,563,442, 7,626,012, 8,778,345; and U.S. Pat. Publication Nos. US 2003059427, US 20020142358, and US20050136055; International Pat. Publication Nos. WO 02/088186, WO 01/56603, WO 88/06891, WO 94/04570, and WO05/63289; Schlossman et al., Leukocyte Typing, 1995, 1:547-556; and Paulie et al., 1984. Cancer Immunol. Immunother. 17:165-179. For example, agonistic anti-CD40 antibodies that are in clinical development include CP-870, 893, Dacetuzumab (also known as SGN-40), and ChiLob 7/4 or APX005M.
OX40

OX40, also known as CD134 and TNFRSF4, is a member of the TNFR-superfamily of receptors. OX40 is a co-stimulatory immune checkpoint molecule, expressed after 24 to 72 hours following activation of the T cells. The interaction of OX40L and OX40 will sustain T cell proliferation and immune response and memory beyond the first two days. Methods for enhancing the immune response to a tumor antigen by engaging the OX40 receptor on the surface of T-cells by an OX40 receptor binding agent, OX40L or an OX40 agonist during or shortly after priming of the T-cells by the antigen can be used in CLIVS as an immune checkpoint inhibitor.
LAG-3

The use of LAG-3 (Lymphocyte Activating Gene-3), and in a more general way, the use of MHC class II ligands or MHC class II-like ligands as adjuvants for vaccines, in order to boost an antigen specific immune response has been successful in pre-clinical models. Antibodies or agents directed against or modulate LAG-3 gene products may be helpful in the present invention. See U.S. Pat. No. 5,773,578, cited and referenced patents for details of LAG-3 related patents and claims.

Table 1 below summarizes examples of commercially available immunomodulators administered via systemic routes that have been approved by the FDA or are involved in clinical trial studies. Any of the immunomodulators in Table 1 may be used as the first, second, or third immunomodulator in any of the methods described herein, using the same or different administration routes, and/or dosages, and/or dosing frequency, and/or duration, and/or maintenance schedule as listed in Table 1.

TABLE 1

Examples of Systemic Administration of Exemplary Immunomodulators

| Immunomodulator | Generic name | Route | Dose | Frequency | Duration | Maintenance |
|---|---|---|---|---|---|---|
| anti-CTLA-4 Antibody | Ipilimumab | IV | 3 mg/kg or 10 mg/kg | Q3W | Up to 4 doses | Q12W, up to 3 years |
| anti-CTLA-4 Antibody | Tremelimumab (CP-675,206) | IV | 15 mg/kg | Q90D | Up to 4 doses | N/A |
| | | EV | 10 mg/kg | Q4W | 6 doses | Q12W |

TABLE 1-continued

Examples of Systemic Administration of Exemplary Immunomodulators

| Immunomodulator | Generic name | Route | Dose | Frequency | Duration | Maintenance |
|---|---|---|---|---|---|---|
| anti-PD-1 Antibody | Nivolumab (MDX-1105) | IV | 1-3 mg/kg | Q2W or Q3W | 4 doses | N/A |
| anti-PD-1 Antibody | Pembrolizumab (MK-3475) | IV | 2 mg/kg | Q3W | N/A | N/A |
| anti-PD-1 Antibody | Pidilizumab (CT-011) | IV | 1.5 mg/kg-6.0 mg/kg | Q2W | Up to 54 weeks | N/A |
| anti-PD-1 Antibody | PDR001 | IV | N/A | N/A | N/A | N/A |
| anti-PD-L1 Antibody | Atezolizumab (MPDL3280A) | IV | 1-20 mg/kg | Q2W, Q3W, or Q4W | Up to 1 year | N/A |
|  |  | IV | 750-1200 mg | Q2W or Q3W | 2 doses or up to 1 year | N/A |
| anti-PD-L1 Antibody | MDX-1105 | IV | 0.1-10 mg/kg | Q2W | Up to 2 years | N/A |
| anti-PD-L1 Antibody | Avelumab (MSB0010718C) | IV | 10 mg/kg | Q2W | N/A | N/A |
| anti-OX40 Antibody | MEDI6469 | IV | 0.4 mg/kg | N/A | 3 doses over 5-6 days | N/A |
| anti-OX40 Antibody | GSK3174998 | IV | 0.003-10.0 mg/kg | Q3W | Up to 48 weeks | N/A |
| anti-OX40 Antibody | KHK4083 | IV | N/A | N/A | 12 weeks | 40 weeks |
| anti-LAG3 Antibody | BMS-986016 | IV | 20-800 mg | Q2W | 12 eight week cycles | N/A |
| anti-LAG3 Antibody | IMP321 | subcutaneous | 0.05-30 mg | Q2W | 6 doses | N/A |
| anti-B7-H3 Antibody | Enoblituzumab (MGA271) | IV | 0.01-15 mg/kg | Q1W | 3 weeks out of every 4-week cycle | Weekly for 8 weeks up to 12 cycles |
| anti-B7-H3 Antibody | DS-5573a | IV | 0.1-30 mg/kg | N/A | N/A | N/A |
| anti-CD137 Antibody | Urelumab | IV | 0.1-15 mg/kg | Q3W | 12 weeks | N/A |
| anti-GITR Antibody | TRX518 | IV | N/A | Q1W | 21-days or 18 weeks | Q1W, 24 months |
| anti-CD47 Antibody | CC-90002 | IV | N/A | 42-day cycle | 4 cycles | 28-day cycles up to a maximum of 2 years |
| anti-B7.1 Antibody | Galiximab | IV | 500 mg/m² | Q1W | 4 doses | Q4W |
| anti-CD27 Antibody | Varlilumab (CDX-1127) | IV | 0.1-10.0 mg/kg | Q1W or Q3W | 4 doses | Q1W or Q3W |
| anti-CCR4 Antibody | Mogamulizumab (KW-0761) | IV | 0.1-1 mg/kg | Q1W | 8 weeks | Q1W for 8 weeks |
| anti-CD52 Antibody | Alemtuzumab | IV | 3-30 mg | three times per week | 12 weeks | N/A |
| anti-TGF-β Antibody | Fresolimumab (GC1008) | IV | 0.1-15 mg/kg | Q14D | up to 2.5 years | N/A |
| Anti-CSF1R Antibody | FPA008 | IV | N/A | Q2W | Up to 52 weeks | N/A |
| Anti-KIR Antibody | Lirilumab (BMS-986015) | IV | 0.1-3 mg/kg | Q4W | 8-96 weeks | Q4W |
| Anti-NKG2A | Monalizumab (IPH2201) | IV | 0.4-10 mg/kg | Q2W | N/A | N/A |

EXEMPLARY EMBODIMENTS

The invention provides the following embodiments:

1. A method of treating a solid or lymphatic tumor in an individual, comprising: a) locally administering to the site of the tumor an effective amount of an oncolytic virus; and b) systemically administering an effective amount of an immunomodulator, wherein the oncolytic virus comprises a viral vector comprising a tumor cell-specific promoter operably linked to a viral gene essential for replication of the virus, and a heterologous gene encoding an immune-related molecule.

2. The method of embodiment 1, wherein the oncolytic virus preferentially replicates in a cancer cell.

3. The method of embodiment 2, wherein the cancer cell is defective in the Rb pathway.

4. The method of embodiment 3, wherein the tumor-specific promoter is an E2F-1 promoter.

5. The method of embodiment 4, wherein the tumor-specific promoter is a human E2F-1 promoter.

6. The method of embodiment 5, wherein the E2F-1 promoter comprises the nucleotide sequence set forth in SEQ ID NO: 1.

7. The method of any one of embodiments 1-6, wherein the immune-related molecule is selected from the group consisting of GM-CSF, IL-2, IL-12, interferon, CCL4, CCL19, CCL21, CXCL13, TLR1, TLR2, TLR3, TLR4, TLR5, TLR6, TLR7, TLR8, TLR9, TLR10. RIG-I, MDA5, LGP2, and LTα3.

8. The method of embodiment 7, wherein the immune-related molecule is GM-CSF.

9. The method of any one of embodiments 1-8, wherein the heterologous gene is operably linked to a viral promoter.

10. The method of any one of embodiments 1-9, wherein the oncolytic virus is selected from the group consisting of adenovirus, herpes simplex virus, vaccinia virus, mumps virus. Newcastle disease virus, polio virus, measles virus, Seneca valley virus, coxsackie virus, reo virus, vesicular stomatitis virus, maraba and rhabdovirus, and parvovirus.

11. The method of embodiment 10, wherein the oncolytic virus is an oncolytic adenovirus.

12. The method of embodiment 11, wherein the viral gene essential for replication of the virus is selected from the group consisting of E1A. E1B, and E4.

13. The method of embodiment 11 or embodiment 12, wherein the heterologous gene is operably linked to an E1 promoter or an E3 promoter.

14. The method of any one of embodiment 1-13, wherein the oncolytic virus is an adenovirus serotype 5, wherein the endogenous E1a promoter of a native adenovirus is replaced by the human E2F-1 promoter, and the endogenous E3 19kD coding region of the native adenovirus is replaced by a nucleic acid encoding human GM-CSF.

15. The method of embodiment 14, wherein the oncolytic virus is CG0070.

16. The method of any one of embodiments 1-15, wherein the oncolytic virus is administered at a dose of about $1 \times 10^8$ to about $1 \times 10^{14}$ viral particles.

17. The method of any one of embodiments 1-16, wherein the oncolytic virus is administered weekly.

18. The method of any one of embodiments 1-17, wherein the oncolytic virus is administered for about 1 week to about 6 weeks.

19. The method of any one of embodiments 1-18, wherein the oncolytic virus is administered directly into the tumor.

20. The method of any one of embodiments 1-18, wherein the oncolytic virus is administered to the tissue having the tumor.

21. The method of any one of embodiments 1-20, wherein the immunomodulator is administered intravenously.

22. The method of any one of embodiments 1-21, wherein the oncolytic virus and the immunomodulator are administered sequentially.

23. The method of embodiment 22, wherein the oncolytic virus is administered prior to the administration of the immunomodulator.

24. The method of embodiment 22, wherein the oncolytic virus is administered after the administration of the immunomodulator.

25. The method of any one of embodiments 1-24, wherein the oncolytic virus and the immunomodulator are administered simultaneously.

26. The method of any one of embodiments 1-25, wherein the immunomodulator is a modulator of an immune checkpoint molecule selected from the group consisting of CTLA-4, PD-1, PD-L1. PD-L2, TIM3, B7-H3. B7-H4, LAG-3, KIR, and ligands thereof.

27. The method of embodiment 26, wherein the immunomodulator is an inhibitor of PD-L1.

28. The method of embodiment 27, wherein the inhibitor of PD-L1 is an anti-PD-L1 antibody.

29. The method of embodiment 28, wherein the anti-PD-L1 antibody is Atezolizumab.

30. The method of any one of embodiments 1-25, wherein the immunomodulator is an immune-stimulating agent.

31. The method of embodiment 30, wherein the immune-stimulating agent is an activator of a molecule selected from the group consisting of OX40, 4-1BB and CD40.

32. The method of embodiment 31, wherein the immune-stimulating agent is an activator of OX40.

33. The method of embodiment 32, wherein the immunomodulator is an agonist antibody of OX40.

34. The method of any one of embodiments 1-33, further comprising locally administering to the site of the tumor a second immunomodulator.

35. The method of embodiment 34, wherein the second immunomodulator is a modulator of an immune checkpoint molecule selected from the group consisting of CTLA-4, PD-1, PD-L1, PD-L2. TIM3, B7-H3. B7-H4, LAG-3, KIR, and ligands thereof.

36. The method of embodiment 35, wherein the second immunomodulator is an inhibitor of CTLA-4.

37. The method of embodiment 36, wherein the inhibitor of CTLA-4 is an anti-CTLA-4 antibody.

38. The method of embodiment 34, wherein the second immunomodulator is an immune-stimulating agent selected from the group consisting of activators of OX40, 4-1BB and CD40.

39. The method of any one of embodiments 34-38, wherein the second immunomodulator is administered directly into the tumor.

40. The method of any one of embodiments 34-38, wherein the second immunomodulator is administered to the tissue having the tumor.

41. The method of any one of embodiments 34-40, wherein the immunomodulator and the second immunomodulator are administered simultaneously.

42. The method of any one of embodiments 34-40, wherein the immunomodulator and the second immunomodulator are administered sequentially.

43. The method of embodiment 42, wherein the immunomodulator is administered prior to the administration of the second immunomodulator.

44. The method of embodiment 42, wherein the immunomodulator is administered after the administration of the second immunomodulator.

45. The method of any one of embodiments 34-44, further comprising administering a third immunomodulator.

46. The method of embodiment 45, wherein the third immunomodulator is administered systemically.

47. The method of embodiment 46, wherein the third immunomodulator is administered locally to the site of the tumor.

48. The method of embodiment 47, wherein the third immunomodulator is administered directly into the tumor.

49. The method of embodiment 47, wherein the third immunomodulator is administered to the tissue having the tumor.

50. The method of any one of embodiments 45-49, wherein the third immunomodulator is a modulator of an immune checkpoint molecule selected from the group consisting of CTLA-4, PD-1, PD-L1, PD-L2, TIM3, B7-H3. B7-H4, LAG-3, KIR, and ligands thereof.

51. The method of any one of embodiments 45-49, wherein the third immunomodulator is an immune-stimulating agent selected from the group consisting of activators of OX40, 4-1BB and CD40.

52. The method of any one of embodiments 45-51, wherein the second immunomodulator and the third immunomodulator are administered simultaneously.

53. The method of any one of embodiments 45-51, wherein the second immunomodulator and the third immunomodulator are administered sequentially.

54. The method of any one of embodiments 1-53, further comprising locally administering to the site of the tumor a pretreatment composition prior to the administration of the oncolytic virus.

55. The method of embodiment 54, wherein the pretreatment composition comprises a transduction enhancing agent.

56. The method of embodiment 55, wherein the transduction enhancing agent is N-Dodecyl-β-D-maltoside (DDM).

57. The method of any one of embodiments 1-56, wherein the individual is subject to a prior therapy prior to the administration of the oncolytic virus and the immunomodulator.

58. The method of embodiment 57, wherein the prior therapy is radiation therapy.

59. The method of embodiment 57, wherein the prior therapy comprises administration of a therapeutic agent.

60. The method of embodiment 59, wherein the therapeutic agent is an agent that increases the level of cytokines involved an immunogenic pathway.

61. The method of embodiment 59, wherein the therapeutic agent is an agent that causes dysfunction or damage to a structural component of a tumor.

62. The method of any one of embodiments 57-61, wherein the therapeutic agent is selected from the group consisting of an anti-VEGF antibody, a hyaluronidase. CCL21, and N-dodecyl-β-maltoside.

63. The method of any one of embodiments 57-62, wherein the prior therapy is provided at a dose that is insufficient to treat the tumor.

64. The method of any one of embodiments 1-63, further comprising locally administering to the site of the tumor an effective amount of inactivated tumor cells.

65. The method of embodiment 64, wherein the inactivated tumor cells are autologous.

66. The method of embodiment 64, wherein the inactivated tumor cells are allogenic.

67. The method of embodiment 64, wherein the inactivated tumor cells are from a tumor cell line.

68. The method of any one of embodiments 64-67, wherein the inactivated tumor cells are inactivated by irradiation.

69. The method of any one of embodiments 64-68, wherein the oncolytic virus and the inactivated tumor cells are administered simultaneously.

70. The method of embodiment 69, wherein the oncolytic virus and the inactivated tumor cells are administered as a single composition.

71. The method of embodiment 69 or embodiment 70, wherein the oncolytic virus and the inactivated tumor cells are admixed immediately prior to the administration.

72. The method of any one of embodiments 1-71, wherein the solid or lymphatic tumor is bladder cancer.

73. The method of embodiment 72, wherein the oncolytic virus is administered intravesically.

74. The method of embodiment 71 or embodiment 72, wherein the bladder cancer is muscle invasive bladder cancer.

75. The method of embodiment 71 or embodiment 72, wherein the bladder cancer is non-muscle invasive bladder cancer.

76. The method of any one of embodiments 1-75, wherein the individual has high expression of one or more biomarkers selected from PD-1, PD-L1, and PD-L2 in the tumor.

77. The method of any one of embodiments 1-76, wherein the individual has high expression of one or more biomarkers selected from CD80. CD83, CD86, and HLA-Class II antigens in tumor-derived mature dendritic cells.

78. The method of any one of embodiments 1-77, wherein the individual has high expression of one or more biomarkers selected from the group consisting of CXCL9, CXCL10, CXCL11. CCR7, CCL5. CCL8. SOD2. MT2A, OASL. GBP1. HES4, MTIB, MTIE, MTIG. MTIH, GADD45A, LAMP3 and miR-155.

79. The method of any one of embodiments 1-78, wherein the individual is a human individual.

80. A kit for treating a solid or lymphatic tumor in an individual, comprising: a) an oncolytic virus, b) an immunomodulator, and c) a device for locally administering the oncolytic virus to a site of tumor, wherein the oncolytic virus comprises a viral vector comprising a tumor cell-specific promoter operably linked to a viral gene essential for replication of the virus, and a heterologous gene encoding an immune-related molecule, and wherein the immunomodulator is formulated for systemic administration.

81. The kit of embodiment 80, wherein the immune-related molecule is selected from the group consisting of GM-CSF, IL-2, IL12, interferon, CCL4, CCL19, CCL21. CXCL13, TLR1, TLR2, TLR3, TLR4, TLR5, TLR6, TLR7, TLR8, TLR9, TLR10, RIG-I, MDA5, LGP2, and LTαβ.

82. The kit of embodiment 80 or embodiment 81, wherein the oncolytic virus is an oncolytic adenovirus.

83. The kit of embodiment 82, wherein the oncolytic virus is an adenovirus serotype 5, wherein the endogenous E1a promoter of a native adenovirus is replaced by the human E2F-1 promoter, and the endogenous E3 19kD coding region of the native adenovirus is replaced by a heterologous gene encoding human GM-CSF.

84. The kit of embodiment 83, wherein the oncolytic virus is CG0070.

85. The kit of any one of embodiments 80-84, wherein the immunomodulator is a modulator of an immune checkpoint molecule selected from the group consisting of: CTLA-4. PD-1, PD-L1, PD-L2. TIM3, B7-H3. B7-H4, LAG-3, KIR, and ligands thereof.

86. The kit of embodiment 85, wherein the immunomodulator is an inhibitor of PD-L1.

87. The kit of embodiment 86, wherein the inhibitor of PD-L is an anti-PD-L1 antibody.

88. The kit of embodiment 87, wherein the anti-PD-L1 antibody is atezolizumab.

89. The kit of any one of embodiments 80-88, wherein the immunomodulator is an immune-stimulating agent selected from the group consisting of activators of OX40, 4-1BB and CD40.

90. The kit of embodiment 89, wherein the immunomodulator is an agonist antibody of OX40.

91. The kit of any one of embodiments 80-90, further comprising a second immunomodulator formulated for local administration to the site of the tumor.

92. The kit of embodiment 91, further comprising a third immunomodulator.

93. The kit of any one of embodiments 80-92, further comprising a pretreatment composition comprising a transduction enhancing agent.

94. The kit of embodiment 93, wherein the transduction enhancing agent is N-Dodecyl-3-D-maltoside (DDM).

95. The kit of any one of embodiments 80-94, further comprising an immune-related molecule selected from the group consisting of GM-CSF, IL-2, IL12, interferon, CCL4, CCL19, CCL21, CXCL13, TLR1, TLR2, TLR3, TLR4, TLR5, TLR6, TLR7, TLR8, TLR9, TLR10, RIG-I, MDA5, LGP2, LTαβ, STING activators. PRRago. TLR stimulators, and RLR stimulators.

96. The kit of any one of embodiments 80-95, further comprising a plurality of inactivated tumor cells.

97. The kit of embodiment 96, further comprising instructions for admixing the oncolytic virus and the inactivated tumor cells prior to the administration.

98. The kit of embodiment 96 or embodiment 97, wherein the device for local administration is used for simultaneous administration of the plurality of inactivated tumor cells and the oncolytic virus.

99. The kit of any one of embodiments 80-98, wherein the device for local administration is for administrating the oncolytic virus directly into the tumor.

100. The kit of any one of embodiments 80-99, wherein the device for local administration is for administering the oncolytic virus to the tissue having the tumor.

EXAMPLES

The examples below are intended to be purely exemplary of the invention and should therefore not be considered to limit the invention in any way. The following examples and detailed description are offered by way of illustration and not by way of limitation.

Example 1: Clinical Study of Intratumoral or Intravesical Administration of CG0070 in Combination with Systemic Administration of One or More Immunomodulators Clinical studies are carried out to evaluate the efficacy and safety of combination therapy comprising local administration of CG0070 and systemic administration of an immunomodulator or a combination (such as 2) of immunomodulators to patients having a solid or lymphatic tumor. For patients having bladder cancer, the CG0070 is administered intravesically. In some cases of solid cancer, patients are administered CG0070 intratumorally.

A variety of immunomodulators are administered individually or in combination to the patients. Any one or more of the immunomodulators of Table 1 may be tested in the clinical studies. The routes of administration, doses, dosing frequencies, duration, and/or maintenance dosing scheme for systemic administration of the immunomodulator(s) can be the same or different from those listed in Table 1. Table 1 is presented here for examples only. Immunomodulators outside the scope of Table 1 can also be evaluated in the clinical studies.

Example 2: A Phase I/II Clinical Study of Intravesical Administration of CG0070 in Combination with Intravesical Administrator of a CTLA-4 Inhibitor and Intravenous Administration of an OX40 Activator in Patients with Muscle Invasive Bladder Cancer This example describes a clinical study of intravesical administration of CG0070 in combination with intravesical administration of an anti-CTLA-4 antibody, and intravenous administration of an OX40 activator in patients with muscle invasive bladder cancer (MIBC). Muscle invasive bladder cancer is chosen herein as an example because CG0070 has shown to be active in bladder cancer. Furthermore all muscle invasive bladder cancer patients need to have a cystectomy, thus providing a good tumor specimen to prepare the tumor cells needed for this vaccine system. In addition the prognosis of muscle invasive bladder cancer patients (T3-4) has been poor despite the use of neo-adjuvant chemotherapy. Most of these patients are over 60 years of age and few can undergo the serious side effects of chemotherapy. An effective agent that can minimize the risk of disease recurrence in this patient population is an unmet need.

This clinical study is a phase I/II, single-arm, open-label, interventional dose-escalation safety and efficacy study of intravesical CG0070 in combination with intravesical administration of a CTLA-4 inhibitor and intravenous administration of an OX40 activator as a neo-adjuvant therapy in patients with transitional cell muscle-invasive bladder cancer disease, who have been selected for radical cystectomy and pelvic lymphadenectomy. The primary safety objective of the study is to investigate whether CG0070 combined with CTLA 4 blockade and OX40 activation is safe and tolerable for the neo-adjuvant treatment of MIBC patients prior to cystectomy. The primary efficacy objective of the study is to measure tumor PD-L1 or PD-1 level changes after CG0070, CTLA-4 inhibitor, and OX40 activator neo-adjuvant treatment. Secondary study objectives include evaluation of 2-year Disease Free Survival (DFS), 2-year Progression Free Survival (PFS), Overall Survival (OS). Pathological Complete Response proportion at Cystectomy (p0 proportion), Pathological Down Staging Proportion at Cystectomy, and Organ Confined Disease Proportion at Cystectomy.

In the Phase I portion of the study, cohorts of (e.g., three to six) patients receive intravesical CG0070, intravesical CTLA4 inhibitor, and intravenous OX40 activator at one of four dose levels. The first dose level consists of CG0070 and CTLA4 inhibitor alone. Each patient receives 4 weekly installations of intravesical CG0070 (e.g., on Day 1 of each week), and 3 weekly installations of intravesical CTLA-4 inhibitor (e.g., Ipilimumab) from the second week (e.g., on Days 8, 15, and 22), and one installation of intravenous OX40 activator (e.g., GSK3174998) at one of four dose levels in the third week (e.g., on Day 22) with administration of the CTLA-4 inhibitor and the OX40 activator following CG0070.

Dose escalation follows a modified Fibonacci sequence in which the dose increments become smaller as the dose increases. For example, if none of the first three patients in a cohort experiences a dose-limiting toxicity, another three patients will be treated at the next higher dose level. However, if one of the first three patients experiences a dose-limiting toxicity, three more patients will be treated at the same dose level. The dose escalation continues until at least two patients among a cohort of three to six patients experience dose-limiting toxicities (i.e., ≥33% of patients with a dose-limiting toxicity at that dose level). The recommended dose for the next stage or phase of the trial is conventionally defined as the dose level just below this toxic dose level. Dose-limiting toxicity (DLT) is defined with the use of the Common Terminology Criteria for Adverse Events (CTCAE) version 4. A DLT is defined as a ≥Grade 3 drug-related Adverse Events (AE) from day 1 of week 1 to day 1 of week 4 of treatment, including any grade 3 or higher toxicity which requires interruption of study treatment for more than 3 consecutive weeks and/or permanent discontinuation of the drug(s) due to immune-related toxicities, but excluding Grade 3 AE of tumor flare (defined as local pain, irritation, or rash localized at sites of known or suspected tumor) and Grade 3 immune-mediated events of the skin (rash, pruritus) or endocrine systems (hypothyroidism, hyperthyroidism, hypopituitarism, adrenal insufficiency, hypogonadism and Cushingoid syndrome) that resolve to Grade 1 or baseline within 3 weeks with or without the administration of steroids. Hepatic immune toxicity is defined as Grade 3 or higher elevation in aspartate aminotransferase, alanine aminotransferase or total bilirubin. A significant D-dimer increase (20% increase with at least a 1 μg/mL from baseline) in combination with a >grade 2 change in INR, PT, PTT, platelets, or fibrinogen lasting for >7 days is considered a DLT. In addition, clinically significant thrombosis or bleeding related to CG0070 treatment is considered a DLT. Patients with a treatment delay extending beyond 21 days due to toxicity related to study treatment are considered as having a treatment related DLT. For reasons other than treatment related toxicity, patients with a treatment delay extending beyond 7 days or who withdraw from the study before 3 administrations are replaced within the cohort. The maximum tolerated dose (MTD) is the dose immediately preceding that resulting in 2 DLT. If the MTD is not defined, the highest dose administered without 2 DLT will be the Maximum Feasible Dose (MFD). Dose reduction for patients in this study is not allowed. However, if at least 2 out of 6 patients in dose level 1 experience a DLT, three patients will be enrolled at dose level 1. Furthermore, if at least 2 out of 6 patients in dose level 1 experience a DLT, three patients will be enrolled at dose level 2.

A suitable dosage of CG0070 is about $1 \times 10^{12}$ viral particles (vp) once weekly for four weeks. A suitable dosage of the intravesical CTLA-4 inhibitor (e.g., Ipilimumab) is about 0.1 mg/Kg to about 0.3 mg/Kg, but not exceeding 20 mg in total per dose, weekly for three weeks, starting from week 2 and ending on week 4. A suitable dosage of the intravenous OX40 activator (e.g., GSK3174998) is about 0.003 mg/kg to about 10 mg/kg once every three weeks, starting from week 3.

In the Phase II portion of the study, each patient is administered intravesically CG0070 in combination with intravesical administration of the CTLA-4 inhibitor and intravenous administration of the OX40 activator at a dose level determined in the Phase I portion of the study for a four-week treatment course. During both Phase I and Phase II portions of the study, prior to administration of the combination therapy, each patient is assessed for adverse events, and samples (such as blood and urine samples) are collected for laboratory assessment. For example, prior to the first intravesical administration of CG0070, blood and urine samples are collected from each patient to assess GM-CSF level, as well as CG0070 and wildtype adenovirus levels. Prior to each of the week 2, 3, and 4 administrations, samples from patients are collected to for laboratory assessment in hematology (such as CBC with differential, chemistry and coagulation), serum chemistry (such as sodium, potassium, chloride. BUN, creatinine, glucose, total protein, albumin, calcium, total bilirubin, direct bilirubin, alkaline phosphate, LDH, AST. ALT, and thyroid functions), and urinalysis. Vital signs, including blood pressure, pulse, respirations and temperature are recorded prior to each CG0070 treatment and every hour for 2 hours total during the treatment to ensure the patient is clinically stable.

CG0070 and the CTLA-4 inhibitor can be administered as follows. Patients are advised not to drink fluids for 4 hours before treatment and should empty their bladder prior to treatment administration. On the study day, each patient receives pretreatment with a transduction enhancing agent (DDM) administered intravesically via a catheter (Rusch 173430 Foley Catheter & BARD LUBRI-SIL Foley Catheter #70516SI). Pretreatment consists of an intravesical wash with 100 mL normal saline, followed by an intravesical wash with 75 mL of 0.1% DDM. The patient then receive intravesical instillation of 100 mL of 0.1% DDM, which is retained in the bladder for 12-15 minutes and subsequently rinsed with 100 mL of saline. If a patient is unable to tolerate at least 5 minutes of DDM pretreatment, further treatment with CG0070 and CTLA-4 inhibitor should be discontinued for that treatment. If the intravesical infusion of CG0070 is delayed for more than two hours after DDM pretreatment, the patient will not receive CG0070 and must be rescheduled for DDM and CG0070 treatment no sooner than 2 days later. If treatment is delayed for more than 2 weeks, patients must continue to meet eligibility criteria prior to retreatment. Following pretreatment with DDM, each patient receives a single intravesical instillation via catheter (e.g., Rusch 173430 Foley Catheter & BARD LUBRI-SIL Foley Catheter #70516SI) of 100 mL of CG0070 at a concentration of $1.0 \times 10^{10}$ vp/mL with a 45 to 50 minute dwell time. Treatment must occur at least 14 days following any prior bladder biopsy. Patients who experience bleeding during catheter insertion (traumatic catheterization) should not be treated with CG0070. While CG0070 is held in the bladder, the patient should be repositioned from left side to right side and also should lie upon the back and the abdomen to maximize bladder surface exposure to CG0070. The patient position is changed every 10-12 minutes for a total of 45 to 50 minutes. CG0070 is then be drained through the catheter into a disposal bag. As soon as the CG0070 solution has been drained from the bladder, the CTLA-4 inhibitor (for example, Ipilimumab, such as YERVOY®) at the appropriate dosage (e.g., Dose Level I of Phase I study does not include any CTLA-4) is diluted into 100 ml of normal saline, and is instilled into the bladder. After instillation, urethral catheter is then withdrawn and patient is asked to hold for another 45 min to 1 hour (or as long as possible) before emptying by urination.

After the 6-week treatment course in the Phase II portion of the study, each patient receives a cystectomy. Cystectomy is performed 10 to 14 days (e.g., about Day 40) after the last intravesical treatment or as soon as any treatment related toxicity has subsided and medical condition is suitable for surgery. After the cystectomy, tumor specimen is obtained from the patient and assessed in a pathology lab, and laboratory evaluation is performed to determine if the patient has responded to the treatment. This assessment includes pathological and immunological assessments of the resected tumor for: (1) tumor stage and grade, if present; (2) tumor immunological parameters, such as Treg, CD4. CD8 and other T cell subsets; (3) tumor PD-L1 expression status by immunohistochemistry methods; (4) lymph node involvement; (5) macroscopic photo comparison between pre- and post-treatment. Each patient is evaluated at months 3, 6, 12, 18, and 24 (plus or minus 2 weeks) from the date of cystectomy to monitor long-term response and toxicity of CG0070, disease recurrence or progression, and subsequent therapies and response. After 2 years, patients are contacted once a year for assessment of long-term toxicities related to gene therapy (such as new malignancies, autoimmune disease, neurologic and hematologic disorders, etc.), and survival for five years after the first intravesical CG0070 therapy. Patients are followed for up to 5 years in total post treatment with CG0070, or according to current FDA guidelines and the current standard of care.

Primary outcome measures of the study are determined as follows. Patients are followed throughout and upon completion of the study for assessment of AE, SAE, and SUSAR to determine safety and tolerability of the treatment. Additionally, at cystectomy, efficacy of the treatment is assessed by determining the rate of change in PD-L1 and PD-1 status, which is defined as the difference in proportions of patients that are PDL1 or PD1 positive before and after intervention for at least three or more completed intravesical instillations.

Secondary outcome measures of the study are determined as follows. At cystectomy. Pathological Complete Response Proportion at Cystectomy for each T stage (p0 proportion) is assessed by determining the proportion of patients with a pathological complete tumor response at the primary tumor site after intervention at cystectomy stratified further by T staging and for the whole group of patients. Also determined at the time of cystectomy are Pathological Down Staging Proportion at Cystectomy, defined as the proportion of patients with a downgrade of tumor stage or grade at the primary tumor site after intervention at cystectomy; and Organ Confined Disease Proportion at Cystectomy, defined as the proportion of patients with no positive lymph nodes found at cystectomy. Up to 2 years after the cystectomy, patients are followed to determine 2-year Disease Free Survival, defined as the number of months from the date of cystectomy to the earlier of disease recurrence or death (whatever the cause); and 2-year Progression Free Survival for patients with residual disease after cystectomy, defined as the number of months from the date of cystectomy to the earlier of disease progression or death (whatever the cause). Up to five years after the cystectomy, patients are followed to determine Overall Survival, defined as the number of months from the date of cystectomy to the date of death (whatever the cause).

Additionally, exploratory outcome measures to be assessed during the course of the study include, but are not limited to, changes in immune functions within the primary tumor site including assessment of changes in Treg (CD4+ CD25+Foxp3+), CD4, CD8, CD4RO45 and CD41COShigh etc. before and after intervention; macroscopic changes in the primary tumor site by photographs taken before and after intervention; systemic absolute lymphocyte counts; and systemic cytokine patterns in the patients.

Patients must meet all of the following conditions to be eligible for the study:
1. 18 years of age or older;
2. Pathologically diagnosed transitional cell (urothelial) bladder cancer patients; where radical cystectomy with curative intent is indicated for muscle invasive disease (i.e., American Joint Committee on Cancer (AJCC) stage T2-4a, $N_{x-1}$, M0). Patients must be able to enter into the study within five weeks of their most recent diagnostic procedure, which is usually a diagnostic biopsy, a transurethral resection of bladder tumor (TURBT) procedure or other diagnostic scanning such as CT, MRI and PET procedures:
3. Histopathologically confirmed, transitional cell (urothelial) carcinoma. Urothelial tumors with mixed histology (but with <50% variant) are eligible;
4. Ineligible to receive neo-adjuvant chemotherapy due to a medical condition that can be confirmed by the investigator. (For example, renal impairment can be based on a calculated creatinine clearance of about <60 ml/min OR hearing loss ≥25 dB by audiometry, averaged at 3 contiguous test frequencies in at least 1 ear; or other significant cardio dysfunction, vascular disease or chronic obstructive pulmonary disease etc.), or refuses to receive neo-adjuvant chemotherapy after a specific informed consent that addresses the increased risks of both recurrence and morbidity without neo-adjuvant chemotherapy;
5. Have an Eastern Cooperative Oncology Group (ECOG) performance status ≤2;
6. Not pregnant or lactating;
7. Agree to study informed consent and HIPAA authorization for release of personal health information;
8. Adequate baseline CBC and hepatic function, as defined as:
   a. WBC>3000 cells/mm3, ANC>1.000 cells/mm3, hemoglobin >9 g/dL, and platelet count >80,000/mm3;
   b. Bilirubin, AST and ALT less than 2.5× Upper Limit of Normal:
   c. Adequate coagulation with acceptable PT/INR. PTT, and fibrinogen (less than 1.5 of Upper Limit of Normal or according to institutional specifications);
   d. Absolute lymphocyte count ≥800/μL.

Patients who meet any of the following exclusion criteria are excluded from the study:
1. History of anaphylactic reaction following exposure to humanized or human therapeutic monoclonal antibodies, hypersensitivity to GM-CSF, clinically meaningful allergic reactions or any known hypersensitivity or prior reaction to any of the formulation excipients in the study drugs;
2. Known infection with HIV. HBV or HCV;
3. Anticipated use of chemotherapy or radiotherapy not specified in the study protocol while on study;
4. Any underlying medical condition that, in the Investigator's opinion, will make the administration of study drugs hazardous to the patient, would obscure the interpretation of adverse events, or surgical resection;
5. Systemic treatment on any investigational clinical trial within 28 days prior to registration:
6. Concurrent treatment with other immunosuppressive or immune-modulatory agents, including any systemic steroid (exception: inhaled or topically applied steroids, and acute and chronic standard dose NSAIDs, are permitted). Use of a short course (i.e., ≤1 day) of a glucocorticoid is acceptable to prevent a reaction to the IV contrast used for CT scans:
7. Immunosuppressive therapy, including: cyclosporine, antithymocyte globulin, or tacrolimus within 3 months of study entry;
8. History of stage III or greater cancer, excluding urothelial cancer. Basal or squamous cell skin cancers must have been adequately treated and the subject must be disease-free at the time of registration. Patients with a history of stage I or II cancer must have been adequately treated and have been disease-free for ≥2 years at the time of registration'
9. Concomitant active autoimmune disease (e.g., rheumatoid arthritis, multiple sclerosis, autoimmune thyroid disease, uveitis);
10. Progressive or current viral or bacterial infection. All infections must be resolved and the patient must remain afebrile for seven days without antibiotics prior to being placed on study.

Example 3: A Phase I/II Clinical Study of Intratumoral Administration of CG0070 in Combination with Intratumoral Administration of a CTLA-4 Inhibitor and Intravenous Administration of an OX40 Activator for Patients with Refractory Injectable Solid Tumors This example describes a Phase I/II clinical study of CG0070 in combination with a CTLA-4 inhibitor (such as an anti-CTLA-4 monoclonal antibody or blocker) and an OX40 activator (such as an anti-OX40 agonist antibody) for patients with refractory injectable solid tumors. This study is a multi-center, single-arm, open-label, interventional study aimed at evaluating the safety and efficacy of the combination therapy comprising intratumoral administration of CG0070, intratumoral administration of a CTLA-4 inhibitor, and intravenous administration of an OX40 activator in patients with solid tumor, including cutaneous or visceral lesions, such as head and neck squamous cell cancer, breast cancer, colorectal cancer, pancreatic adenocarcinoma, ovarian cancer, non-small cell lung cancer, prostate cancer, and melanoma. The CG0070 administration can include a pretreatment with a transducer, such as DDM.

In Phase I, each subject is administered a combination of CG0070 (e.g., with DDM pretreatment) and the CTLA-4 inhibitor via intratumoral injections weekly (e.g., on Day 1 of each week) for a 6 weeks. Additionally, the subject is administered intravenously an OX40 inhibitor (such as GSK3174998) once every three weeks starting in week 1 at one of three dose levels for 6 weeks. Dose escalation procedure is as described in Example 1. Once the MTD or MFD has been reached, the patients receive repeated 6-week treatment course at 3 month after the first injection and subsequent courses every 3 months until complete response, disappearance of all injectable tumors, confirmed disease progression or intolerance of study treatment, whichever occurs first. Patients who are in the dose escalation phase of the study can be enrolled in the repeat MTD or MFD courses study after a period of three months from the last intervention with full successful enrollment evaluation.

A suitable dosage of intratumoral injection of CG0070 (e.g., with DDM) is about $5 \times 10^{10}$ vp, $1 \times 10^{11}$ vp, $5 \times 10^{11}$ vp, or $1 \times 10^{12}$ vp weekly for four weeks. For example, the virus CG0070 is reconstituted in 0.1% of DDM in saline. The total volume of each dose is 2 mL. The concentration of the CG0070 solution is about $2.5 \times 10^{10}$ vp/ml for the lowest dose and about $5 \times 10^{11}$ vp/ml for the highest dose. If the patient has a single lesion, which must be greater than 2 cm, the total volume of the CG0070 solution is injected into the lesion. If there are two or more lesions, the maximum injection volume based on the lesion size as shown in Table 2 is followed. Any remaining volume is injected into the largest lesion, if the largest lesion is at least 2 cm. If the largest lesion is less than 2 cm, then the remaining volume is divided between the two larger lesions. The maximum number of lesions injected is 3. The total dose is given regardless the total number and size of the lesions.

TABLE 2

Injection volume per lesion based on tumor size

| Tumor Size (longest dimension) | Maximum Injection Volume |
|---|---|
| ≥5.0 cm | 2.0 mL |
| ≥2.0 cm to 5.0 cm | 1.0 mL |
| >0.5 cm to 2.0 cm | 0.5 mL |

A suitable dosage of intratumoral injection of the CTLA-4 inhibitor (e.g., Ipilimumab) is about 6 mg to about 18 mg, weekly for six weeks. Immediately after each CG0070 injection, the CTLA-4 inhibitor is administered. The total volume at each dose level, and the maximum injection volumes based on lesion sizes for more than two injected lesions are listed in Table 3 below. The maximum number of injected lesions is 3, and the total dose of the CTLA-4 inhibitor is given regardless the total number and size of the lesions. Any remaining volume of the CTLA-4 inhibitor is administered subcutaneously around the injected lesion(s). In case lesions completely resolved prior to the last planned treatment, both CG0070 and the CTLA-4 inhibitor (e.g., Ipilimumab) can be administered to a previously un-injected lesion. If all lesions are resolved before the end of the treatment course, the CTLA-4 inhibitor (e.g., Ipilimumab) alone can be injected in the subcutaneous area at or around the former lesion.

TABLE 3

Injection volume of immunomodulator per lesion based on tumor size

| Tumor Size (longest dimension) | Dose level | | | | | |
|---|---|---|---|---|---|---|
| | 6.0 mg | | 12 mg | | 18 mg | |
| | Max dose per lesion | Max Volume | Max dose per lesion | Max Volume | Max dose per lesion | Max Volume |
| ≥5.0 cm | 6.0 mg | 1.2 mL | 12 mg | 2.4 mL | 18 mg | 3.6 mL |
| ≥2.0 cm to 5.0 cm | 3.0 mg | 0.6 mL | 6.0 mg | 1.2 mL | 9 mg | 1.8 mL |
| >0.5 cm to 2 cm | 1.5 mg | 0.3 mL | 3.0 mg | 0.6 mL | 4.5 mg | 0.9 mL |

A suitable dosage of the intravenous OX40 activator (e.g., GSK3174998) is about 0.003 mg/kg to about 10 mg/kg once every three weeks, starting from week 1.

Dose escalation procedure is as described in Example 1, and MTD/MFD is designated as the study dose, which is used in Phase II.

For Phase II of the study, the cohort of patients first receive a once weekly intratumoral injection of the combination of CG0070 (e.g., with DDM) and the CTLA-4 inhibitor (e.g., Ipilimumab), and intravenous fusion of the OX40 inhibitor (e.g., GSK3174998) once every three weeks starting from week 1 at the study dose determined in Phase I for six weeks. Afterwards, the patients receive repeated 6-week treatment course at 3 month after the first injection and subsequent courses every 3 months until complete response, disappearance of all injectable tumors, confirmed disease progression or intolerance of study treatment, whichever occurs first. Patients who are in the dose escalation phase of Phase I can be enrolled in the Phase II study as long as there is a rest period of at least six weeks from the last dose. For each administration, GC0070 is first injected to the lesions, followed by the CTLA-4 inhibitor (e.g., Ipilimumab), followed by intravenous infusion of the OX40 activator (e.g., GSK3174998).

There are two primary outcome measures for this study: (1) safety and tolerability; and (2) efficacy. Efficacy is assessed by confirmed objective response rate (ORR) of the treatment. The secondary outcome measures of this study are as follows. Safety secondary outcomes are assessed from the beginning of each phase until 24 months following enrollment of the last subject at each phase. Safety secondary outcome measures include incidence of all Adverse Events (AEs), grade 3 or greater AEs, events requiring discontinuation of study drug(s), local effects on tumor, clinically significant laboratory changes and clinically significant changes in vital signs. The efficacy secondary outcomes are assessed from the beginning of each stage until 24 months following enrollment of the last subject at each stage. Efficacy secondary outcome measures include Best Overall Response Rate (BOR), Disease Control Rate (DCR). Durable Response Rate (DRR), Duration of Response (DOR). Time to Response (TTR), Progression Free Survival (PFS). Overall Survival Rate (OS), 1 year and 2 year Survival Rate.

Eligibility of patients of both genders for the study is determined based on the following inclusion criteria:
1. Patients must have histologically confirmed solid tumors that have failed standard therapies (surgery, chemotherapy, radiotherapy, or endocrine therapy) and for which no curative options exist, including, but not limited to: squamous cell carcinoma of the head and neck, squamous cell carcinoma of the skin, carcinoma of the breast, malignant melanoma, colorectal cancer, pancreatic adenocarcinoma, ovarian cancer, non-small cell lung cancer and prostate cancer;
2. Patients may have had any kind and number of prior cancer therapies;
3. Patients must have measurable lesions that are evaluable by the RECIST method;
4. The tumor mass to be treated must be adequate for injections (i.e., more than 2 cm away from major vascular structures) and measurement by RECIST:
5. Patients must be ≥18 years of age;
6. Patients must have a life expectancy of ≥12 weeks;
7. Patients must have an Eastern Cooperative Oncology Group (ECOG) performance status of 0, 1, or 2;
8. Patients must have adequate hepatic function, as defined as:
a. Total bilirubin levels ≤1.5× upper limit of normal (ULN); and
b. AST/ALT levels ≤2.5×ULN, or ≤5×ULN if liver metastases are present;
9. Patients must have adequate renal function as defined as serum creatinine ≤1.5×ULN or creatinine clearance (calculated) ≥60 mL/min/1.73 m2 for patients with creatinine >1.5×ULN;
10. Patients must have adequate bone marrow function, as defined as:
a. Absolute neutrophil count ≥1.200/µL; and
b. Platelet count ≥80,000/µL;
11. Patients must have no known bleeding diathesis or coagulopathy that would make intratumoral injection or biopsy unsafe;
12. Men and women of childbearing potential must agree to use adequate contraception prior to study entry and for up to six months;
13. Females of childbearing potential must have a negative urine or serum pregnancy test within one week prior to start of treatment; and
14. Patients must be able to understand and willing to sign a written informed consent document.

The following patients are excluded from the study:
1. Patients receiving chemotherapy, immunotherapy or radiotherapy within 4 weeks prior to screening, or adverse events >Grade 1, except alopecia, resulting from agents administered more than 4 weeks prior to screening;
2. Patients with a history of significant tumor bleeding, or coagulation or bleeding disorders;
3. Patients with target tumors that could potentially invade a major vascular structure(s) (e.g., innominate artery, carotid artery), based on unequivocal imaging findings, as determined by a radiologist;
4. Patients with Grade ≥1 pre-existing neurologic abnormalities (CTCAE version 4.0);
5. Patients who have been hospitalized for emergent conditions requiring inpatient evaluation, treatment or procedure during the 30 days prior to entry on study. In addition, emergent conditions requiring inpatient evaluation, treatment or procedure must have resolved or be medically stable and not severe for 30 days prior to entry on study;
6. Patients with clinically evident Human Immunodeficiency Virus (HIV), Hepatitis B Virus (HBV), Hepatitis C virus (HCV), or Epstein-Barr virus (EBV) infection. Patients are tested for HIV during pre-treatment screening
7. Patients receiving steroids or immunosuppressive agents, e.g., for rheumatoid arthritis;
8. Patients who have concurrent use of any other investigational agents;
9. Patients with presence or history of central nervous system metastasis;
10. Pregnant or breastfeeding women or women desiring to become pregnant within the timeframe of the study;
11. Patients with uncontrolled inter-current illness including, but not limited to, ongoing or active infection, symptomatic congestive heart failure, unstable angina pectoris, cardiac arrhythmia, or psychiatric illness/social situations that would limit compliance with study requirements.

Example 4: A Phase I/II Clinical Study of Intravesical Administration of CG0070 in Combination with Intravesical Administrator of a CTLA-4 Inhibitor and Intravenous Administration of a PD-L1 Inhibitor in Patients with Muscle Invasive Bladder Cancer This example describes a clinical study of intravesical administration of CG0070 in combination with intravesical administration of an anti-CTLA-4 antibody, and intravenous administration of a PD-L1 inhibitor in patients with muscle invasive bladder cancer (MIBC). Muscle invasive bladder cancer is chosen herein as an example because CG0070 has shown to be active in bladder cancer. Furthermore all muscle invasive bladder cancer patients need to have a cystectomy, thus providing a good tumor specimen to prepare the tumor cells needed for this vaccine system. In addition the prognosis of muscle invasive bladder cancer patients (T3-4) has been poor despite the use of neo-adjuvant chemotherapy. Most of these patients are over 60 years of age and few can undergo the serious side effects of chemotherapy. An effective agent that can minimize the risk of disease recurrence in this patient population is an unmet need.

This clinical study is a phase I/II, single-arm, open-label, interventional dose-escalation safety and efficacy study of intravesical CG0070 in combination with intravesical administration of a CTLA-4 inhibitor and intravenous administration of a PD-L inhibitor as a neo-adjuvant therapy in patients with transitional cell muscle-invasive bladder cancer disease, who have been selected for radical cystectomy and pelvic lymphadenectomy. The primary safety objective of the study is to investigate whether CG0070 combined with CTLA 4 and PD-L1 activation is safe and tolerable for the neo-adjuvant treatment of MIBC patients prior to cystectomy. The primary efficacy objective of the study is to measure tumor PD-L1 or PD-1 level changes after CG0070, CTLA-4 inhibitor, and PD-L inhibitor neo-adjuvant treatment. Secondary study objectives include evaluation of 2-year Disease Free Survival (DFS), 2-year Progression Free Survival (PFS), Overall Survival (OS), Pathological Complete Response proportion at Cystectomy (p0 proportion). Pathological Down Staging Proportion at Cystectomy, and Organ Confined Disease Proportion at Cystectomy.

In the Phase I portion of the study, cohorts of (e.g., three to six) patients receive intravesical CG0070, intravesical CTLA4 inhibitor, and intravenous PD-L1 inhibitor at one of four dose levels. The first dose level consists of CG0070 and CTLA4 inhibitor alone. Each patient receives 4 weekly installations of intravesical CG0070 (e.g., on Day 1 of each week), and 3 weekly installations of intravesical CTLA-4 inhibitor (e.g., Ipilimumab) from the second week (e.g., on Days 8, 15, and 22), and one installation of intravenous PD-L inhibitor (e.g., atezolizumab) at one of four dose levels in the third week (e.g., on Day 22) with administration of the CTLA-4 inhibitor and the PD-L inhibitor following CG0070.

Dose escalation follows a modified Fibonacci sequence in which the dose increments become smaller as the dose increases. For example, if none of the first three patients in a cohort experiences a dose-limiting toxicity, another three patients will be treated at the next higher dose level. However, if one of the first three patients experiences a dose-limiting toxicity, three more patients will be treated at the same dose level. The dose escalation continues until at least two patients among a cohort of three to six patients experience dose-limiting toxicities (i.e., ≥33% of patients with a dose-limiting toxicity at that dose level). The recommended dose for the next stage or phase of the trial is conventionally defined as the dose level just below this toxic dose level. Dose-limiting toxicity (DLT) is defined with the use of the Common Terminology Criteria for Adverse Events (CTCAE) version 4. A DLT is defined as a ≥Grade 3 drug-related Adverse Events (AE) from day 1 of week 1 to day 1 of week 4 of treatment, including any grade 3 or higher toxicity which requires interruption of study treatment for more than 3 consecutive weeks and/or permanent discontinuation of the drug(s) due to immune-related toxicities, but excluding Grade 3 AE of tumor flare (defined as local pain, irritation, or rash localized at sites of known or suspected tumor) and Grade 3 immune-mediated events of the skin (rash, pruritus) or endocrine systems (hypothyroidism, hyperthyroidism, hypopituitarism, adrenal insufficiency, hypogonadism and Cushingoid syndrome) that resolve to Grade 1 or baseline within 3 weeks with or without the administration of steroids. Hepatic immune toxicity is defined as Grade 3 or higher elevation in aspartate aminotransferase, alanine aminotransferase or total bilirubin. A significant D-dimer increase (20% increase with at least a 1 µg/mL from baseline) in combination with a >grade 2 change in INR, PT, PTT, platelets, or fibrinogen lasting for >7 days is considered a DLT. In addition, clinically significant thrombosis or bleeding related to CG0070 treatment is considered a DLT. Patients with a treatment delay extending beyond 21 days due to toxicity related to study treatment are considered as having a treatment related DLT. For reasons other than treatment related toxicity, patients with a treatment delay extending beyond 7 days or who withdraw from the study before 3 administrations are replaced within the cohort. The maximum tolerated dose (MTD) is the dose immediately preceding that resulting in 2 DLT. If the MTD is not defined, the highest dose administered without 2 DLT will be the Maximum Feasible Dose (MFD). Dose reduction for patients in this study is not allowed. However, if at least 2 out of 6 patients in dose level 1 experience a DLT, three patients will be enrolled at dose level 1. Furthermore, if at least 2 out of 6 patients in dose level 1 experience a DLT, three patients will be enrolled at dose level 2.

A suitable dosage of CG0070 is about $1 \times 10^{12}$ viral particles (vp) once weekly for four weeks. A suitable dosage of the intravesical CTLA-4 inhibitor (e.g., Ipilimumab) is about 0.1 mg/Kg to about 0.3 mg/Kg, but not exceeding 20 mg in total per dose, weekly for three weeks, starting from week 2 and ending on week 4. A suitable dosage of the intravenous PD-L1 inhibitor (e.g., atezolizumab) is about 1 mg/kg to about 20 mg/kg (such as about 750 mg to about 1200 mg) at a frequency of about once every two weeks to about once every three weeks, starting from week 3.

In the Phase II portion of the study, each patient is administered intravesically CG0070 in combination with intravesical administration of the CTLA-4 inhibitor and intravenous administration of the PD-L inhibitor at a dose level determined in the Phase I portion of the study for a four-week treatment course. During both Phase I and Phase II portions of the study, prior to administration of the combination therapy, each patient is assessed for adverse events, and samples (such as blood and urine samples) are collected for laboratory assessment. For example, prior to the first intravesical administration of CG0070, blood and urine samples are collected from each patient to assess GM-CSF level, as well as CG0070 and wildtype adenovirus levels. Prior to each of the week 2, 3, and 4 administrations, samples from patients are collected to for laboratory assessment in hematology (such as CBC with differential, chemistry and coagulation), serum chemistry (such as sodium, potassium, chloride. BUN, creatinine, glucose, total protein, albumin, calcium, total bilirubin, direct bilirubin, alkaline phosphate, LDH. AST. ALT, and thyroid functions), and urinalysis. Vital signs, including blood pressure, pulse, respirations and temperature are recorded prior to each CG0070 treatment and every hour for 2 hours total during the treatment to ensure the patient is clinically stable.

CG0070 and the CTLA-4 inhibitor can be administered as follows. Patients are advised not to drink fluids for 4 hours before treatment and should empty their bladder prior to treatment administration. On the study day, each patient receives pretreatment with a transduction enhancing agent (DDM) administered intravesically via a catheter (Rusch 173430 Foley Catheter & BARD LUBRI-SIL Foley Catheter #70516SI). Pretreatment consists of an intravesical wash with 100 mL normal saline, followed by an intravesical wash with 75 mL of 0.1% DDM. The patient then receive intravesical instillation of 100 mL of 0.1% DDM, which is retained in the bladder for 12-15 minutes and subsequently rinsed with 100 mL of saline. If a patient is unable to tolerate at least 5 minutes of DDM pretreatment, further treatment with CG0070 and CTLA-4 inhibitor should be discontinued for that treatment. If the intravesical infusion of CG0070 is delayed for more than two hours after DDM pretreatment, the patient will not receive CG0070 and must be rescheduled for DDM and CG0070 treatment no sooner than 2 days later.

If treatment is delayed for more than 2 weeks, patients must continue to meet eligibility criteria prior to retreatment. Following pretreatment with DDM, each patient receives a single intravesical instillation via catheter (e.g., Rusch 173430 Foley Catheter & BARD LUBRI-SIL Foley Catheter #70516SI) of 100 mL of CG0070 at a concentration of $1.0 \times 10^{10}$ vp/mL with a 45 to 50 minute dwell time. Treatment must occur at least 14 days following any prior bladder biopsy. Patients who experience bleeding during catheter insertion (traumatic catheterization) should not be treated with CG0070. While CG0070 is held in the bladder, the patient should be repositioned from left side to right side and also should lie upon the back and the abdomen to maximize bladder surface exposure to CG0070. The patient position is changed every 10-12 minutes for a total of 45 to 50 minutes. CG0070 is then be drained through the catheter into a disposal bag. As soon as the CG0070 solution has been drained from the bladder, the CTLA-4 inhibitor (for example, Ipilimumab, such as YERVOY®) at the appropriate dosage (e.g., Dose Level I of Phase I study does not include any CTLA-4) is diluted into 100 ml of normal saline, and is instilled into the bladder. After instillation, urethral catheter is then withdrawn and patient is asked to hold for another 45 min to 1 hour (or as long as possible) before emptying by urination.

After the 6-week treatment course in the Phase II portion of the study, each patient receives a cystectomy. Cystectomy is performed 10 to 14 days (e.g., about Day 40) after the last intravesical treatment or as soon as any treatment related toxicity has subsided and medical condition is suitable for surgery. After the cystectomy, tumor specimen is obtained from the patient and assessed in a pathology lab, and laboratory evaluation is performed to determine if the patient has responded to the treatment. This assessment includes pathological and immunological assessments of the resected tumor for: (1) tumor stage and grade, if present; (2) tumor immunological parameters, such as Treg, CD4. CD8 and other T cell subsets; (3) tumor PD-L1 expression status by immunohistochemistry methods; (4) lymph node involvement; (5) macroscopic photo comparison between pre- and post-treatment. Each patient is evaluated at months 3, 6, 12, 18, and 24 (plus or minus 2 weeks) from the date of cystectomy to monitor long-term response and toxicity of CG0070, disease recurrence or progression, and subsequent therapies and response. After 2 years, patients are contacted once a year for assessment of long-term toxicities related to gene therapy (such as new malignancies, autoimmune disease, neurologic and hematologic disorders, etc.), and survival for five years after the first intravesical CG0070 therapy. Patients are followed for up to 5 years in total post treatment with CG0070, or according to current FDA guidelines and the current standard of care.

Primary outcome measures of the study are determined as follows. Patients are followed throughout and upon completion of the study for assessment of AE. SAE, and SUSAR to determine safety and tolerability of the treatment. Additionally, at cystectomy, efficacy of the treatment is assessed by determining the rate of change in PD-L1 and PD-1 status, which is defined as the difference in proportions of patients that are PDL1 or PD1 positive before and after intervention for at least three or more completed intravesical instillations.

Secondary outcome measures of the study are determined as follows. At cystectomy. Pathological Complete Response Proportion at Cystectomy for each T stage (p0 proportion) is assessed by determining the proportion of patients with a pathological complete tumor response at the primary tumor site after intervention at cystectomy stratified further by T staging and for the whole group of patients. Also determined at the time of cystectomy are Pathological Down Staging Proportion at Cystectomy, defined as the proportion of patients with a downgrade of tumor stage or grade at the primary tumor site after intervention at cystectomy; and Organ Confined Disease Proportion at Cystectomy, defined as the proportion of patients with no positive lymph nodes found at cystectomy. Up to 2 years after the cystectomy, patients are followed to determine 2-year Disease Free Survival, defined as the number of months from the date of cystectomy to the earlier of disease recurrence or death (whatever the cause); and 2-year Progression Free Survival for patients with residual disease after cystectomy, defined as the number of months from the date of cystectomy to the earlier of disease progression or death (whatever the cause). Up to five years after the cystectomy, patients are followed to determine Overall Survival, defined as the number of months from the date of cystectomy to the date of death (whatever the cause).

Additionally, exploratory outcome measures to be assessed during the course of the study include, but are not limited to, changes in immune functions within the primary tumor site including assessment of changes in Treg (CD4+ CD25+Foxp3+), CD4, CD8, CD4RO45 and CD41COShigh etc. before and after intervention; macroscopic changes in the primary tumor site by photographs taken before and after intervention; systemic absolute lymphocyte counts; and systemic cytokine patterns in the patients.

Patients must meet all of the following conditions to be eligible for the study:
1. 18 years of age or older;
2. Pathologically diagnosed transitional cell (urothelial) bladder cancer patients; where radical cystectomy with curative intent is indicated for muscle invasive disease (i.e., American Joint Committee on Cancer (AJCC) stage T2-4a, $N_{X-1}$, M0). Patients must be able to enter into the study within five weeks of their most recent diagnostic procedure, which is usually a diagnostic biopsy, a transurethral resection of bladder tumor (TURBT) procedure or other diagnostic scanning such as CT, MRI and PET procedures:
3. Histopathologically confirmed, transitional cell (urothelial) carcinoma. Urothelial tumors with mixed histology (but with <50% variant) are eligible;
4. Ineligible to receive neo-adjuvant chemotherapy due to a medical condition that can be confirmed by the investigator. (For example, renal impairment can be based on a calculated creatinine clearance of about <60 ml/min OR hearing loss ≥25 dB by audiometry, averaged at 3 contiguous test frequencies in at least 1 ear; or other significant cardio dysfunction, vascular disease or chronic obstructive pulmonary disease etc.), or refuses to receive neo-adjuvant chemotherapy after a specific informed consent that addresses the increased risks of both recurrence and morbidity without neo-adjuvant chemotherapy;
5. Have an Eastern Cooperative Oncology Group (ECOG) performance status ≤2;
6. Not pregnant or lactating;
7. Agree to study informed consent and HIPAA authorization for release of personal health information;
8. Adequate baseline CBC and hepatic function, as defined as:
   a. WBC>3000 cells/mm3, ANC>1.000 cells/mm3, hemoglobin >9 g/dL, and platelet count >80,000/mm3;
   b. Bilirubin, AST and ALT less than 2.5× Upper Limit of Normal;

c. Adequate coagulation with acceptable PT/INR. PTT, and fibrinogen (less than 1.5 of Upper Limit of Normal or according to institutional specifications);

d. Absolute lymphocyte count ≥800/μL.

Patients who meet any of the following exclusion criteria are excluded from the study:
1. History of anaphylactic reaction following exposure to humanized or human therapeutic monoclonal antibodies, hypersensitivity to GM-CSF, clinically meaningful allergic reactions or any known hypersensitivity or prior reaction to any of the formulation excipients in the study drugs;
2. Known infection with HIV. HBV or HCV;
3. Anticipated use of chemotherapy or radiotherapy not specified in the study protocol while on study;
4. Any underlying medical condition that, in the Investigator's opinion, will make the administration of study drugs hazardous to the patient, would obscure the interpretation of adverse events, or surgical resection;
5. Systemic treatment on any investigational clinical trial within 28 days prior to registration;
6. Concurrent treatment with other immunosuppressive or immune-modulatory agents, including any systemic steroid (exception: inhaled or topically applied steroids, and acute and chronic standard dose NSAIDs, are permitted). Use of a short course (i.e., ≤1 day) of a glucocorticoid is acceptable to prevent a reaction to the IV contrast used for CT scans:
7. Immunosuppressive therapy, including: cyclosporine, antithymocyte globulin, or tacrolimus within 3 months of study entry;
8. History of stage III or greater cancer, excluding urothelial cancer. Basal or squamous cell skin cancers must have been adequately treated and the subject must be disease-free at the time of registration. Patients with a history of stage I or II cancer must have been adequately treated and have been disease-free for ≥2 years at the time of registration'
9. Concomitant active autoimmune disease (e.g., rheumatoid arthritis, multiple sclerosis, autoimmune thyroid disease, uveitis);
10. Progressive or current viral or bacterial infection. All infections must be resolved and the patient must remain afebrile for seven days without antibiotics prior to being placed on study.

Example 5: A Phase I/II Clinical Study of Intratumoral Administration of CG0070 in Combination with Intratumoral Administration of a CTLA-4 Inhibitor and Intravenous Administration of a PD-L1 Inhibitor for Patients with Refractory Injectable Solid Tumors This example describes a Phase I/II clinical study of CG0070 in combination with a CTLA-4 inhibitor (such as an anti-CTLA-4 monoclonal antibody or blocker) and a PD-L1 inhibitor (such as an anti-PD-L1 antagonist antibody) for patients with refractory injectable solid tumors. This study is a multi-center, single-arm, open-label, interventional study aimed at evaluating the safety and efficacy of the combination therapy comprising intratumoral administration of CG0070, intratumoral administration of a CTLA-4 inhibitor, and intravenous administration of a PD-L1 inhibitor in patients with solid tumor, including cutaneous or visceral lesions, such as head and neck squamous cell cancer, breast cancer, colorectal cancer, pancreatic adenocarinoma, ovarian cancer, non-small cell lung cancer, prostate cancer, and melanoma. The CG0070 administration can include a pretreatment with a transducer, such as DDM.

In Phase I, each subject is administered a combination of CG0070 (e.g., with DDM pretreatment) and the CTLA-4 inhibitor via intratumoral injections weekly (e.g., on Day 1 of each week) for a 6 weeks. Additionally, the subject is administered intravenously a PD-L1 inhibitor (such as atezolizumab) about once every two weeks to about once every three weeks starting in week 1 at one of three dose levels for 6 weeks. Dose escalation procedure is as described in Example 1. Once the MTD or MFD has been reached, the patients receive repeated 6-week treatment course at 3 month after the first injection and subsequent courses every 3 months until complete response, disappearance of all injectable tumors, confirmed disease progression or intolerance of study treatment, whichever occurs first. Patients who are in the dose escalation phase of the study can be enrolled in the repeat MTD or MFD courses study after a period of three months from the last intervention with full successful enrollment evaluation.

A suitable dosage of intratumoral injection of CG0070 (e.g., with DDM) is about $5\times10^{10}$ vp, $1\times10^{11}$ vp, $5\times10^{11}$ vp, or $1\times10^{12}$ vp weekly for four weeks. For example, the virus CG0070 is reconstituted in 0.1% of DDM in saline. The total volume of each dose is 2 mL. The concentration of the CG0070 solution is about $2.5\times10^{10}$ vp/ml for the lowest dose and about $5\times10^{11}$ vp/ml for the highest dose. If the patient has a single lesion, which must be greater than 2 cm, the total volume of the CG0070 solution is injected into the lesion. If there are two or more lesions, the maximum injection volume based on the lesion size as shown in Table 2 is followed. Any remaining volume is injected into the largest lesion, if the largest lesion is at least 2 cm. If the largest lesion is less than 2 cm, then the remaining volume is divided between the two larger lesions. The maximum number of lesions injected is 3. The total dose is given regardless the total number and size of the lesions.

A suitable dosage of intratumoral injection of the CTLA-4 inhibitor (e.g., Ipilimumab) is about 6 mg to about 18 mg, weekly for six weeks. Immediately after each CG0070 injection, the CTLA-4 inhibitor is administered. The total volume at each dose level, and the maximum injection volumes based on lesion sizes for more than two injected lesions are listed in Table 3 below. The maximum number of injected lesions is 3, and the total dose of the CTLA-4 inhibitor is given regardless the total number and size of the lesions. Any remaining volume of the CTLA-4 inhibitor is administered subcutaneously around the injected lesion(s). In case lesions completely resolved prior to the last planned treatment, both CG0070 and the CTLA-4 inhibitor (e.g., Ipilimumab) can be administered to a previously un-injected lesion. If all lesions are resolved before the end of the treatment course, the CTLA-4 inhibitor (e.g., Ipilimumab) alone can be injected in the subcutaneous area at or around the former lesion.

A suitable dosage of the intravenous PD-L1 inhibitor (e.g., atezolizumab) is about 1 mg/kg to about 20 mg/kg (such as about 750 mg to about 1200 mg) at a frequency of about once every two weeks to about once every three weeks, starting from week 1.

Dose escalation procedure is as described in Example 1, and MTD/MFD is designated as the study dose, which is used in Phase II.

For Phase II of the study, the cohort of patients first receive a once weekly intratumoral injection of the combination of CG0070 (e.g., with DDM) and the CTLA-4 inhibitor (e.g., Ipilimumab), and intravenous fusion of the PD-L1 inhibitor (e.g., atezolizumab) about once every two weeks to about once every three weeks starting from week 1 at the study dose determined in Phase I for six weeks. Afterwards, the patients receive repeated 6-week treatment course at 3 month after the first injection and subsequent courses every 3 months until complete response, disappearance of all injectable tumors, confirmed disease progression or intolerance of study treatment, whichever occurs first. Patients who are in the dose escalation phase of Phase I can be enrolled in the Phase II study as long as there is a rest period of at least six weeks from the last dose. For each administration, GC0070 is first injected to the lesions, followed by the CTLA-4 inhibitor (e.g., Ipilimumab), followed by intravenous infusion of the PD-L1 inhibitor (e.g., atezolizumab).

There are two primary outcome measures for this study: (1) safety and tolerability; and (2) efficacy. Efficacy is assessed by confirmed objective response rate (ORR) of the treatment. The secondary outcome measures of this study are as follows. Safety secondary outcomes are assessed from the beginning of each phase until 24 months following enrollment of the last subject at each phase. Safety secondary outcome measures include incidence of all Adverse Events (AEs), grade 3 or greater AEs, events requiring discontinuation of study drug(s), local effects on tumor, clinically significant laboratory changes and clinically significant changes in vital signs. The efficacy secondary outcomes are assessed from the beginning of each stage until 24 months following enrollment of the last subject at each stage. Efficacy secondary outcome measures include Best Overall Response Rate (BOR), Disease Control Rate (DCR), Durable Response Rate (DRR), Duration of Response (DOR), Time to Response (TTR). Progression Free Survival (PFS), Overall Survival Rate (OS), 1 year and 2 year Survival Rate.

Eligibility of patients of both genders for the study is determined based on the following inclusion criteria:
1. Patients must have histologically confirmed solid tumors that have failed standard therapies (surgery, chemotherapy, radiotherapy, or endocrine therapy) and for which no curative options exist, including, but not limited to: squamous cell carcinoma of the head and neck, squamous cell carcinoma of the skin, carcinoma of the breast, malignant melanoma, colorectal cancer, pancreatic adenocarcinoma, ovarian cancer, non-small cell lung cancer and prostate cancer;
2. Patients may have had any kind and number of prior cancer therapies;
3. Patients must have measurable lesions that are evaluable by the RECIST method;
4. The tumor mass to be treated must be adequate for injections (i.e., more than 2 cm away from major vascular structures) and measurement by RECIST;
5. Patients must be ≥18 years of age;
6. Patients must have a life expectancy of ≥12 weeks;
7. Patients must have an Eastern Cooperative Oncology Group (ECOG) performance status of 0, 1, or 2;
8. Patients must have adequate hepatic function, as defined as:
   a. Total bilirubin levels ≤1.5× upper limit of normal (ULN); and
   b. AST/ALT levels ≤2.5×ULN, or ≤5×ULN if liver metastases are present;
9. Patients must have adequate renal function as defined as serum creatinine ≤1.5×ULN or creatinine clearance (calculated) ≥60 mL/min/1.73 m2 for patients with creatinine >1.5×ULN;
10. Patients must have adequate bone marrow function, as defined as:
    a. Absolute neutrophil count ≥1,200/μL; and
    b. Platelet count ≥80,000/μL;
11. Patients must have no known bleeding diathesis or coagulopathy that would make intratumoral injection or biopsy unsafe;
12. Men and women of childbearing potential must agree to use adequate contraception prior to study entry and for up to six months;
13. Females of childbearing potential must have a negative urine or serum pregnancy test within one week prior to start of treatment; and
14. Patients must be able to understand and willing to sign a written informed consent document.

The following patients are excluded from the study:
1. Patients receiving chemotherapy, immunotherapy or radiotherapy within 4 weeks prior to screening, or adverse events >Grade 1, except alopecia, resulting from agents administered more than 4 weeks prior to screening;
2. Patients with a history of significant tumor bleeding, or coagulation or bleeding disorders;
3. Patients with target tumors that could potentially invade a major vascular structure(s) (e.g., innominate artery, carotid artery), based on unequivocal imaging findings, as determined by a radiologist;
4. Patients with Grade ≥1 pre-existing neurologic abnormalities (CTCAE version 4.0);
5. Patients who have been hospitalized for emergent conditions requiring inpatient evaluation, treatment or procedure during the 30 days prior to entry on study. In addition, emergent conditions requiring inpatient evaluation, treatment or procedure must have resolved or be medically stable and not severe for 30 days prior to entry on study;
6. Patients with clinically evident Human Immunodeficiency Virus (HIV), Hepatitis B Virus (HBV), Hepatitis C virus (HCV), or Epstein-Barr virus (EBV) infection. Patients are tested for HIV during pre-treatment screening
7. Patients receiving steroids or immunosuppressive agents, e.g., for rheumatoid arthritis;
8. Patients who have concurrent use of any other investigational agents;
9. Patients with presence or history of central nervous system metastasis;
10. Pregnant or breastfeeding women or women desiring to become pregnant within the timeframe of the study;
11. Patients with uncontrolled inter-current illness including, but not limited to, ongoing or active infection, symptomatic congestive heart failure, unstable angina pectoris, cardiac arrhythmia, or psychiatric illness/social situations that would limit compliance with study requirements.

What is claimed is:

1. A method of treating a solid or lymphatic tumor in an individual, comprising: a) intravesically administering an effective amount of an oncolytic virus, wherein the oncolytic virus is CG0070; and b) intravenously administering an effective amount of an immunomodulator, wherein the immunomodulator is pembrolizumab, and wherein the solid or lymphatic tumor is bladder cancer.

2. The method of claim 1, further comprising locally administering to the site of the tumor a pretreatment composition prior to the administration of the oncolytic virus.

3. The method of claim 2, wherein the pretreatment composition comprises a transduction enhancing agent.

4. The method of claim 1, wherein the individual is subject to a prior therapy prior to the administration of the oncolytic virus and the immunomodulator.

5. The method of claim 4, wherein the prior therapy comprises administration of a therapeutic agent.

6. The method of claim 4, wherein the prior therapy is provided at a dose that is insufficient to treat the tumor.

7. The method of claim 4, wherein the prior therapy is treatment with *Bacillus* Calmette-Guerin (BCG).

8. The method of claim 4, wherein the individual is resistant to the prior therapy.

9. The method of claim 4, wherein the individual has recurrent bladder cancer after the prior therapy.

10. The method of claim 1, wherein the bladder cancer is non-muscle invasive bladder cancer.

11. The method of claim 10, wherein the non-muscle invasive bladder cancer comprises carcinoma in situ.

12. The method of claim 11, wherein the non-muscle invasive bladder cancer further comprises Ta, T1, or a combination thereof.

13. The method of claim 7, wherein:
a. the individual is resistant to treatment of bladder cancer with BCG;
b. the individual is initially responsive to treatment of bladder cancer with BCG but has progressed after treatment; or
c. the individual has recurrent bladder cancer after treatment with BCG.

14. The method of claim 1, wherein the oncolytic virus is administered weekly for 6 weeks.

15. The method of claim 1, wherein the immunomodulator is administered once every 6 weeks.

16. The method of claim 3, wherein the transduction enhancing agent is N-Dodecyl-β-D-maltoside (DDM).

17. The method of claim 1, wherein the method comprises intravenous administration of a single immunomodulator.

\* \* \* \* \*